United States Patent
Cali et al.

(10) Patent No.: US 10,077,244 B2
(45) Date of Patent: *Sep. 18, 2018

(54) LUMINOGENIC AND FLUOROGENIC COMPOUNDS AND METHODS TO DETECT MOLECULES OR CONDITIONS

(71) Applicant: Promega Corporation, Madison, WI (US)

(72) Inventors: James J. Cali, Verona, WI (US);
William Daily, Santa Maria, CA (US);
Erika Hawkins, Madison, WI (US);
Dieter Klaubert, Arroyo Grande, CA (US); Jianquan Liu, Fremont, CA (US); Poncho Meisenheimer, San Luis Obispo, CA (US); Michael Scurria, San Luis Obispo, CA (US); John W. Shultz, Verona, WI (US); James Unch, Arroyo Grande, CA (US); Michael P. Valley, Fitchburg, WI (US); Keith V. Wood, Mt. Horeb, WI (US); Wenhui Zhou, Santa Maria, CA (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/553,445

(22) Filed: Nov. 25, 2014

(65) Prior Publication Data

US 2016/0176830 A1    Jun. 23, 2016

Related U.S. Application Data

(63) Continuation of application No. 13/913,919, filed on Jun. 10, 2013, now abandoned, which is a continuation of application No. 12/217,494, filed on Jul. 3, 2008, now Pat. No. 8,476,450, which is a continuation of application No. 11/444,145, filed on May 31, 2006, now Pat. No. 7,951,550.

(60) Provisional application No. 60/790,455, filed on Apr. 7, 2006, provisional application No. 60/692,925, filed on Jun. 22, 2005, provisional application No. 60/693,034, filed on Jun. 21, 2005, provisional application No. 60/685,957, filed on May 31, 2005.

(51) Int. Cl.
| | | |
|---|---|---|
| C07D 417/04 | (2006.01) |
| C07D 417/14 | (2006.01) |
| C07D 277/66 | (2006.01) |
| C07D 311/16 | (2006.01) |
| C07D 493/10 | (2006.01) |
| C12Q 1/66 | (2006.01) |
| C07D 277/68 | (2006.01) |
| C09B 11/24 | (2006.01) |
| C09B 19/00 | (2006.01) |
| C09B 57/00 | (2006.01) |
| C09B 57/02 | (2006.01) |
| C07F 9/6558 | (2006.01) |

(52) U.S. Cl.
CPC ......... *C07D 277/66* (2013.01); *C07D 277/68* (2013.01); *C07D 311/16* (2013.01); *C07D 417/04* (2013.01); *C07D 417/14* (2013.01); *C07D 493/10* (2013.01); *C07F 9/65583* (2013.01); *C09B 11/24* (2013.01); *C09B 19/00* (2013.01); *C09B 57/00* (2013.01); *C09B 57/02* (2013.01); *C12Q 1/66* (2013.01); *G01N 2500/00* (2013.01)

(58) Field of Classification Search
CPC ........................... C07D 417/04; C07D 417/14
See application file for complete search history.

(56) References Cited

U.S. PATENT DOCUMENTS

| | | |
|---|---|---|
| 4,612,302 A | 9/1986 | Szabo et al. |
| 4,655,022 A | 4/1987 | Michihiro et al. |
| 4,665,022 A | 5/1987 | Schaeffer et al. |
| 4,684,620 A | 8/1987 | Hruby et al. |
| 4,826,989 A | 5/1989 | Batz et al. |
| 4,853,371 A | 8/1989 | Coy et al. |
| 4,992,531 A | 2/1991 | Patroni et al. |
| 5,035,999 A | 7/1991 | Geiger et al. |
| 5,098,828 A | 3/1992 | Geiger et al. |
| 5,114,704 A | 5/1992 | Spanier et al. |
| 5,283,179 A | 2/1994 | Wood |
| 5,283,180 A | 2/1994 | Zomer et al. |
| 5,290,684 A | 3/1994 | Kelly |
| 5,374,534 A | 12/1994 | Zomer et al. |
| 5,498,523 A | 3/1996 | Tabor et al. |
| 5,641,641 A | 6/1997 | Wood |
| 5,650,135 A | 7/1997 | Contag et al. |

(Continued)

FOREIGN PATENT DOCUMENTS

| | | |
|---|---|---|
| EP | 0411912 | 2/1991 |
| JP | 63-501571 | 6/1988 |

(Continued)

OTHER PUBLICATIONS

Chemical Abstracts Registry No. 760162-40-1, indexed in the Registry file on STN CAS Online Oct. 11, 2004.*

(Continued)

*Primary Examiner* — Laura L. Stockton
(74) *Attorney, Agent, or Firm* — Michael Best & Friedrich LLP

(57) ABSTRACT

A method to detect the presence of amount of at least one molecule in a sample which employs a derivative of luciferin or a derivative of a fluorophore is provided. Compounds and compositions for carrying out the methods of the invention are also provided.

16 Claims, 49 Drawing Sheets

(56) References Cited

U.S. PATENT DOCUMENTS

| | | | |
|---|---|---|---|
| 5,650,289 | A | 7/1997 | Wood |
| 5,726,041 | A | 3/1998 | Chrespi et al. |
| 5,744,320 | A | 4/1998 | Sherf et al. |
| 5,756,303 | A | 5/1998 | Sato et al. |
| 5,780,287 | A | 7/1998 | Kraus et al. |
| 5,814,471 | A | 9/1998 | Wood |
| 5,876,946 | A | 3/1999 | Burbaum et al. |
| 5,976,825 | A | 11/1999 | Hochman |
| 6,143,492 | A | 11/2000 | Makings et al. |
| 6,217,847 | B1 | 4/2001 | Contag et al. |
| 6,291,164 | B1 | 9/2001 | Blakesley |
| 6,299,858 | B1 | 10/2001 | Serbedzija et al. |
| 6,376,208 | B1 | 4/2002 | Kajiyama |
| 6,420,130 | B1 | 7/2002 | Makings et al. |
| 6,514,687 | B1 | 2/2003 | Makings et al. |
| 6,602,677 | B1 | 8/2003 | Wood et al. |
| 6,638,713 | B2 | 10/2003 | Makings et al. |
| 7,118,878 | B1 | 10/2006 | Hawkins et al. |
| 7,524,876 | B2 | 4/2009 | Takakura et al. |
| 7,692,022 | B2 | 4/2010 | Cali et al. |
| 8,476,450 | B2 | 7/2013 | Cali et al. |
| 8,765,969 | B2 | 7/2014 | Cali et al. |
| 9,816,127 | B2 * | 11/2017 | Huang ................... C12Q 1/48 |
| 2002/0076777 | A1 | 6/2002 | Merkulov et al. |
| 2003/0211560 | A1 | 11/2003 | O'Brien et al. |
| 2003/0225036 | A1 | 12/2003 | Kolesnikov et al. |
| 2003/0237103 | A1 | 12/2003 | Jacob et al. |
| 2004/0146959 | A1 | 7/2004 | Graham et al. |
| 2004/0248225 | A1 | 12/2004 | Heindl et al. |
| 2005/0004103 | A1 | 1/2005 | Koshio et al. |
| 2005/0009098 | A1 | 1/2005 | Reymonds et al. |
| 2005/0026171 | A1 | 2/2005 | Hawkins et al. |
| 2005/0118257 | A1 | 6/2005 | Bova |
| 2005/0153306 | A1 | 7/2005 | Harris |
| 2007/0015790 | A1 | 1/2007 | Cali et al. |
| 2007/0155806 | A1 | 7/2007 | Takakura et al. |
| 2008/0194522 | A1 | 8/2008 | Chen et al. |
| 2010/0062470 | A1 | 3/2010 | Corona et al. |
| 2011/0003316 | A1 | 1/2011 | Cali et al. |
| 2012/0058501 | A1 * | 3/2012 | Huang ................... C12Q 1/48 435/15 |
| 2014/0154716 | A1 | 6/2014 | Cali et al. |
| 2014/0380514 | A1 | 12/2014 | Cali et al. |

FOREIGN PATENT DOCUMENTS

| | | |
|---|---|---|
| JP | 01-502431 | 8/1989 |
| JP | 08-059686 | 3/1996 |
| JP | 2000-505086 | 4/2000 |
| JP | 2000-270894 | 10/2000 |
| JP | 2002080476 | 3/2002 |
| JP | 2006219381 | 8/2006 |
| RU | 2242471 | 12/2004 |
| WO | WO 87/02667 | 5/1987 |
| WO | WO 88/05434 | 7/1988 |
| WO | WO 96/31206 | 10/1996 |
| WO | WO 97/36885 | 10/1997 |
| WO | WO 99/60096 | 11/1999 |
| WO | WO 00/16763 | 3/2000 |
| WO | WO 00/34506 | 6/2000 |
| WO | WO 00/35900 | 6/2000 |
| WO | WO 01/20002 | 3/2001 |
| WO | WO 03/040100 | 5/2003 |
| WO | WO 03/066611 | 8/2003 |
| WO | WO 03/096980 | 11/2003 |
| WO | WO 2004/027378 | 4/2004 |
| WO | WO 2006/130551 | 12/2006 |
| WO | WO 2010/021686 | 2/2010 |

OTHER PUBLICATIONS

Sano et al., CA 133:263204, 2000.*
Chemical Abstracts Registry No. 882674-32-0, indexed in the Registry file on STN CAS Online dated May 3, 2006.*
"5' Labeling—fluorescein and cyanine dyes, biotin," Glen Report, http://www.glenres.com/GlenReports/GR8-2.pdf (Published online by Glen Research, Sterling, VA), (Dec. 1995) 8(2):8 pages.
"Amplex Red monoamine oxidase assay kit (A12214)," Molcular Probes (Oct. 1, 2004) 4 pages, retrieved from the Internet: http://probes.invitrogen.com/media/pis/mp12214.pdf.
Abyshev, A.Z. et al., "Preparation and antiviral effect of benzopyran-2-one derivatives," Khimiko-Farmatsevticheskii Zhurnal (1996) 30(7):17-19; Database CA Accession No. 125:237748.
Allen, T. et al., "Cloning and expression fo the adenine phophoribosyltransferase gene from Leishmania donovani," Mol. Biochem. Parasitology (1995) 74:99-103.
Amess, R. et al., "Synthesis of luciferin glycosides as substrates for novel ultrasensitive enzyme assays," Carbohydrate Research (1990) 205:225-233.
Aparna, M.V.L. et al., "Synthesis and 5-HT2A antagonist activity of some 7-(3-aminopropoxy)-4-methyl-chromen-2-ones," Indian J. Pharm. Sci. (2005) 67(4):467-472; Database CA Accession No. 145:62752.
Beilstein Registry No. 1007132, Database Crossfire Beilstein, White, E.H. et al., J. Org. Chem. (1966) 31:1484-1488 (2 pages).
Beilstein Registry No. 1034055, Database Crossfire Beilstein, (McCapra, F. et al., Chem. Commun., 1968) 22-23, 1 page).
Beilstein Registry No. 1041968, Database Crossfire Beilstein, White et al., Bioorg. Chem. (1971) 1:92-116 (2 pages).
Beilstein Registry No. 1119094, Database Crossfire Beilstein, Benkoe, et al., Montsh. Chem. (1975) 106:1027-1032 (3 pages).
Beilstein Registry No. 1119095, Database Crossfire Beilstein, Benkoe, A. et al., Monatsh. Chem. (1975) 106:1027-1032 (2 pages).
Beilstein Registry No. 1126922, Databsase Crossfire Beilstein, Benkoe et al., Monatsh. Chem. (1975) 106:1027-1032 (3 pages).
Beilstein Registry No. 1129927, Database Crossfire Beilstein, Benkoe et al., Monatsh. Chem. (1975) 106:1027-1032 ( 2 pages).
Beilstein Registry No. 30484, Database Crossfire Beilstein, White et al., J. Am. Chem. Soc. (1963) 85:337-343 (12 pages).
Beilstein Registry No. 3984932, Database Crossfire Beilstein, White et al., J. Org. Chem. (1965) 30:2344-2348 (2 pages).
Beilstein Registry No. 4240164, Database Crossfire Beilstein, Arness, R. et al., Carbohydr. Res. (1990) 1(1):225-233 (2 pages).
Beilstein Registry No. 926292, Database Crossfire Beilstein, White et al., J. Org. Chem. (1965) 30:2344-2348 (2 pages).
Benet, L.Z. et al., "Pharmacokinetics The Dynamics of drug absorption, distribution and elimination," Introduction and Chapter 1 of The Pharmacological Basis of Therapeutics, 9th Edition, McGraw Hill (1996) 1-27.
Ben-Shlomo, Y. et al., "Using monoamine oxidase Type B inhibitors in Parkinson's disease," BMJ (2004) 329:581-582.
Binda, C. et al., "Structure-function relationships in flavoenzyme-dependent amine oxidations—a comparison of polyamine oxidase and monoamine oxidase," J. Biol. Chem. (2002) 277(27):23973-23976.
Black, S.D. et al., "P-450 cytochromes: structure and function," Adv. Enzymol. Relat. Areas Mol. Biol. (1987) 60:35-87.
Bowie, L.J. et al., "Synthesis of a new substrate analog of firefly luciferin," Biochemistry (1973) 12(10):1845-1852.
Branchini, B.R., "Naphtyl- and quinolylluciferin: green and red light emitting firefly luciferin analogues," Photochem. Photobiol. (1989) 49(5):689-695.
Cali et al., "Characterization of Human Sterol 27-Hydroxylase. A Mitochondrial Cytochrome P-450 That Catalyzes Multiple Oxidation Reactions in Bile Acid Biosynthesis," J. Biol. Chem., 266:12, 7774-7778 (1991).
Cali et al., "Screen for Cytochrome P450 Activity Using a Luminescent Assay," Cell Notes, 13 (2005) pp. 8-10.
Cali, "Bioluminescent P450 assays that use D-luciferin derivatives as substrates for CYPIAI. JA2. JBI, 2C8, 2C9, 2J2, 3A4, 3A7, 4AJ I, 4F3B. 4F1 2 and 19," Proc. 14th Int. Conf Cytochromes P450, Medimond Int. Proc. (2005).
Cali, "Screen for CYP450 Inhibitors Using P450-GLO™ Luminescent Cytochrome P450 Assays," Cell Notes.7: 2-4 (2003).
Carlile, D.J. et al., "In vivo clearrance of ethoxycoumarin and its prediction from in vitro systems," Drug Metabolism and Disposition (1998) 26(3):216-221.

(56) References Cited

OTHER PUBLICATIONS

Chandran et al., "Latent Fluorophore Based on the Trimethyl Lock," J. Am. Chem. Soc., 127:1652-1653 (2005).
Charng, Y. et al., "Molecular cloning and expression of the gene encoding ADP-glucose phrophosphorylase from the *cyanobacterium anabaena* sp. strain PCC 7120," Plant Mol. Biol. (1992) 20:37-47.
Chemistry 2131: organic Chemistry for the Life Sciences (3), http://www.mta.ca/~acockshu/c2131elimination.html (Mount Allison University), observed Dec. 17, 2004 (3 pages).
Chen, K. et al., "R1, a novel repressor of the human monoamine oxidase A," J. Biol. Chem. (2005) 280(12):11552-11559.
Craig, F.F. et al., "Membrane-permeable luciferin esters for assay of firefly luciferase in live intact cells," Biochem. J. (1991) 276(3):637-641.
Database Accession No. 4240164, Database Crossfire Beilstein, Beilstein Institute zur Foerderung der chemischen Wissenschafter, Frankfurt am Main, Germany (1991) 2 pages.
Demir, B. et al., "Platelet monoamine oxidase activity in alcoholism subtypes: relationship to personality traits and executive functions," Alcohol & Alcoholism (2002) 37(6):597-602.
Dukhovich, A. et al., "Time course of luciferyl adenylate synthesis in the firefly luciferase reaction," FEBS Lett. (1996) 395(2-3):188-190.
Ellis et al., "Evidence That Aspartic Acid 301 Is a Critical Substrate-Contact Residue in the Active Site of Cytochrome P450 2D6," J. Biol Chem., 270:49, 29055-29058 (1995).
Eriksson, J. et al., "Method for real time detectino of inorganic pyrophosphatase activity," Anal. Biochem. (2001) 293(1):67-70.
Farace, C. et al., "Synthesis and characterization of a new substrate of photinus pyralis luciferase: 4-methyl-D-luciferin," J. Clin. Chem. Clin. Biochem. (1990) 28(7):471-474.
Feldmann, R. et al., "Decreased metabolism and viability of mycoplasma hominis induced by monoclonal antibody-mediated agglutination," Infection and Immunity (1992) 60(1):166-174.
Flickinger, B., "Using metabolism data in early development," Drug. Disc. Dev. (2001) 4(():53-56.
Gabelova, A. et al., "Mutagenicity of 7H-dibenzo[c,g]carbazole and its tissue specific derivatives in genetically engineered chinese hamster V79 cell lines stably expressing cytochrome P450," Mutation Research (2002) 517:135-145.
Gandelman, O. et al., "Cytoplasmic factors that affect the intensity and stability of bioluminescence from firefly luciferase in living mammalian cells," J. Biolum. Chemilumin. (1994) 9(6):363-371.
Garrido-Hernandez, H. et al., "Design and synthesis of phosphotyrosine peptidomimetic prodrugs," J. Med. Chem. (2006) 49:3368-3376.
Geiger, R. et al., "A new ultrasensitive bioluminogenic enzyme substrate for beta-galactosidase," Biol. Chem. Hoppe-Seyler (1992) 373:1187-1191.
Gomez-Lechon, M. et al., "Expression and induction of a large set of drug-metabolizing enzymes by the highly differentiated human hepatoma cell line BC2," Eur. J. Biochem. (2001) 268:1448-1459.
Graham-Lorence, S. et al., "P450s: structural similarities and functional differences," FASEB J. (1996) 10:206-214.
Greene, T.W.; Wutz, P.G.M. "Protecting Groups in Organic Svnthesis," 3rd edition, John Wiley & Sons, Inc., New York (1999).
Greenwald et al., "Controlled Release of Proteins from Their Poly(Ethylene Glycol) Conjugates: Drug Delivery Systems Employing 1,6-Elimination," Bioconjugate Chem., 14:395-403 (2003).
Greenwald et al., "Drug Delivery Systems Employing 1,4- or 1,6-Elimination: Poly(ethylene glycol) Prodrugs of Amine-Containing Compounds," J. Med. Chem., 42:3657-3667 (1999).
Guengerich, F.P., "Common and uncommon cytochrome P-450 reactions related to metabolism and chemical toxocity," Chem. Res. Tox. (2001) 14(6):611-650.
Gutierrez, M.C. et al., "The first fluorogenic assay for detecting a baeyer-villigerase activity in microbial cells," Org. Biomol. Chem. (2003) 1:3500-3506.

Hawkins, E.M. et al., "Coelenterazine derivatives for improved sollution stability," Luminescene, Proceedings of the International Symposium on Bioluminescence and Chemiluminescence, (2002) 17:91-92 (Abstract only).
Holt, A., "Imidazoline binding sites on receptors and enzymes: emerging targets for novel antidepressant drugs?" J. Psychiatry Neurosci. (2003) 28(6):409-414.
Huffman, et al., "Lithium Alkoxides of Cinchona Alkaloids as Chiral Controllers for Enantioselective Acetylide Addition to Cyclic N-Acyl Ketimines," J. Org. Chem. 1995, 60, 1590-1594.
Hynson, R.M.G. et al., "Conformational changes in monoamine oxidase A in response to ligand binding or reduction," Biochimica et Biophysica Acta (2004) 1672:60-66.
Inouye, S. et al., "The use of renilla luciferase, oplophorus luciferase, and apoaequorin as bioluminscent reporter rpotein in the presence of coelenterazine analogues as substrate," Biochem. Biophys. Res. Comm. (1997) 233:349-353.
International Union of Pure and Applied Chemistry, "Definitive Rules for Nomenclature of Organic Chemistry," J. Am. Chem. Soc. 1960, 82, 5566.
Jagadeeswaran, P. et al., "Nucleotide sequence and analysis of deletion mutants of the *Escherichia coli* gpt gene in plasmid pSV2 gpt," Gene (1996) 31:309-313.
Jiang, Y. et al., "Crithidia fasciculata: isolation, sequencing and expression of the hypoxanthine-guanine phosphoribosyltransferase gene," Exp. Parasitology (1996) 82:73-75.
Kalmar, G. et al., "Cloning and expression of rat liver CTP:phosphocholine cytidylyltransferase: a ampipathetic protein that controls phophatidylcholine synthesis," Proc. Natl. Acad. Sci. USA (1990) 87:6029-6033.
Katz, I.R. et al., "Monoamine oxidase, an intracellular probe of oxygen pressure in isolated cardiac myocytes," J. Biol. Chem. (1984) 259(12):7504-7509.
Kelly, J.H. et al., "A fluorescent cell-based assay for cytochrome P-450 isozyme 1A2 induction and inhibition," J. Biomol. Screening (2000) 5(4):249-253.
Kim, D. et al., "Molecular cloning of cucumber phosphoenolpyruvate carboxykinase and development regulation of gene expression," Plant Mol. Biol. (1994) 26:423-434.
Kim, J.J. et al., "Selective enhancement of emotional, but not motor, learning in monoamine oxidase A-deficient mice," Proc. Natl. Acad. Sci. USA (1997) 94:5929-5933.
Ladror, U. et al., "Cloning, sequencing and expressino of pyrophosphate-dependent phosphofructokinase from propionibacterium freudenreichii," J. Biol. Chem. (1991) 266(25):16550-16555.
Lee et al., "Synthesis of 7'-[123I]iodo-d-luciferin for in vivo studies of firefly luciferase gene expression," Bioorg. Med. Chem. Lett. 2004, v.14, pp. 1161-1163.
Leemann, T. et al., "Cytochrome P450TB (CYP2C): a major monooxygenase catalyzing diclofenac 4'-hydroxylation in human liver," Life Sci. (1993) 52(1):29-34.
Lembert, N., "Firefly luciferase can use L-luciferin to produce light," Biochem. J. (1996) 317(Pt. 1):273-277.
Leyh, T. et al., "The sulfate activation locus of *Escherichia coli* K12: cloning, genetic, and enzymatic characterization," J. Biol. Chem. (1988) 263(5):2409-2416.
Li, A.P., "Evaluation of luciferin-isopropyl acetal as a CYP3A4 substrate for human hepatocytes: effects of organic solvents, cytochrome P450 (P450) inhibitors, and P450 inducers," Drug Metabolism and Disposition (2009) 37(8):1598-1603.
Ludin, K. et al., "The Ade4 gene of schizosaccharomyces pombe: cloning, sequence and regulation," Curr. Genet. (1994) 25:465-468.
Madan et al., "Effects of Prototypical Microsomal Enzyme Inducers on Cytochrome P450 Expression in Cultured Human Hepatocytes," Drug Metab. Dispos., 31:421-431 (2003).
Mancy, A. et al., "Diclofenac and its derivatives as tools for studying human cytochromes P450 active sites: particular efficiency and regioselectivity of P450 2Cs," Biochem. (1999) 38:14264-14270.
March, "Advanced Organic Chemistry," 4th ed. Wiley-Interscience, John Wiley and Sons, New York, 1992.

(56) References Cited

OTHER PUBLICATIONS

Markaglou, N. et al., "Immobilized enzyme reactors based upon the flavoenzymes monamine oxidase A and B," J. Chromatog. B (2004) 804:295-302.
Marolda, C. et al., "Identification, expression and DNA sequence of the GDP-mannose biosynthesis genes encoded by the 07 rfb gene cluster of strain VW 187 (*Escherichia coli* 07:k1)," J. Bacteriol. (1993) 175(1):148-158.
Masuda-Nishimura, I. et al., "Development of a rapid postive/abstent test for coliforms using sensitive bioluminescence assay," Lett. Appl. Microbiol. (2000) 30(2):130-135.
Mazeas et al., "Synthesis of New Melatoninergic Ligands Including Azaindole Moiety," Heterocycles, 50:1065-1080 (1999).
Miller, V.P. et al., "Fluorometric high-throughput screenign for inbitors of cytochrome P450," Ann. NY Acad. Sci. (2000) 919:26-32.
Miska, w. et al., "A new type of ultrasensitive bioluminogenic eynzyme substrates, I. Enzyme substrates with D-luciferin as leaving group," Biol. Chem. Hoppe-Seyler (1998) 369(5):407-411.
Miska, W. et al., "Evaluation of the bioluminescence-enhanced zona binding assay," Biolum. Chemilum.: Mol. Reporting with Protons, Proceedings fo the International Symposium on Bioluminescence and Chemiluminescence, Oct. 4-8, 1996, pp. 315-318.
Miska, W. et al., "Synthesis and characterization of luciferin derivatives for use in bioluminescence enhanced enzyme immunoassays," J. Clin. Chem. Clin. Biochem. (1987) 25:23-30.
Mitani, M. et al., "Chemiluminescent assay of beta-D-galactosidase using cypridina luciferin analogue: 3-(Beta-D-galactopyranosyloxy)-6-(4-methoxyphenyl)-2-methyl-imidazol[1,2-alpha]pyrazine," Anal. Sci. (1994) 10(50:813-814.
Monsees, T. et al., "A novel bioluminogenic assay for alpha-chymotrypsin," J. Biolumin. Chemilumin. (1995) 10(4):213-218.
Monsees, T. et al., "Synthesis and characterization of a bioluminogenic substrate for alpha-chymotrypsin," Anal. Biochem. (1994) 221(2):329-334.
Muller-Rober, B. et al., "Isolation and expression analysis of cDNA clones encoding a small and a large subunit of ADP-glucose pyrophosphorylase from sugar beet," Plant Mol. Biol. (1995) 27:191-197.
Nakagawa, S. et al., "Nucleotide sequence of the FAD synthetase gene from corynebacterium ammoniagenes and its expression in *Escherichia coli*," Biosci. Biotech. Biochem. (1995) 59(4):694-702.
Nelson, D.R. et al., "P450 superfamily: update on new sequences, gene mappin, accession numbers and nomenclature," Pharmacogenetics (1996) 6:1-42.
Nicolaus, B.J., "Symbiotic approach to drug design," Decision making in Drug Research (1983) 173-186.
O'Brien, M.A. et al., "Homogeneous, bioluminescent protein assays: caspase-3 as a model," J. Biomol. Screen. (2005) 10(2):137-148.
Paquette, Leo A.; "Principles of Modern Heterocyclic Chemistry," (W.A. Benjamin, New York, 1968).
Phillips, I.R. et al., "Preface: Cytochrome P450 protocols," Methods in Mol. Biol. (1998) 107:v-vi.
Pla, J. et al., "Cloning of the candida albicans H1S1 gene by direct complementation of a C. albicans histidine auxotroph using an improved double-ARS shuttle vector," Gene (1995) 165:115-120.
Promega Corporation, "P450-Glo™ Assays," Technical Bulletin No. 325, Madison, Wisconsin (Jun. 2003) 19 pages.
Rahman, A. et al., "Selective biotransformation of taxol to 6 alpha-hydroxytaxol by human cytochrome P450 2C8," Cancer Res. (1994) 54(21):5543-5546.
Rendic, "Summary of Information on Human CYP Enzymes: Human P450 Metabolism Data," Drug Metab. Rev. 34: 83-448 (2002).
Renwick, A.B. et al., "Evaluation of 7-benzyloxy-4-trifluoromethyl-coumarin, some other 7-hydroxy-4-trifluoro-methylcoumarin derivatives and 7-benzyloxyquinoline as fluorescent substrates for rat hepatic cytochrome P450 enzymes," Xenobiotica (2001) 31(12):861-878.
Rose, A. et al., "A phosphoribosylanthranilate transferase gene is defective in blue fluorescent *arabidopsis thaliana* tryptophan mutants," Plant Physiol. (1992) 100:582-592.
Sai, Y. et al., "Assessment of specificity of eight chemical inhibitors using cDNA-expressed cytochrome P450," Xenobiotica (2000) 30(4):327-343.
Salles, C. et al., "Biochemical characteristics of liver and brain monoamine oxidase from pacu," J. Fish Biol. (2001) 58:1301-1310.
Sasson et al., "From Azides to Nitriles. A Novel Fast Transformation Made Possible by BrF3," Org Lett., 7:11, 2177-2179 (2005).
Shanmugam, K. et al., "Purification and characterization of a tRNA nucleotidyltransferase from lipinus albus and fucntional complementation of a yeast mutation by the corresponding cDNA," Plant Mol. Biol. (1996) 30:281-295.
Shimada et al., "Oxidation of Xenobiotics by Recombinant Human Cytochrome P450 1B1," Drug Metab. Dispos., 29:5, 617-622 (1997).
Shimomura, O. et al., "Semi-synthetic aequorins with improved sensitivity to Ca2+ ions," Biochem. J. (1989) 261:913-920.
Shinde, N.D. et al., "Synthesis of some sulfonamido and amino alkanes and their antifungal activity," Asian J. Chem. (1996) 8(1):85-90, Database CA Accession No. 124:232194.
Shou, M. et al., "A kinetic model for the metabolic interaction of two substrates at the active site of cytochrome P450 3A4," J. Biol. Chem. (2001) 276(3):2256-2262.
Stevens et al., "Developmental Expression of the Major Human Hepatic CYP3A Enzymes," J. Pharm. Exp. Ther., 307:2, 573-582 (2003).
Stresser, D.M. et al., "Cytochrome P450 flourometric substrates: identification of isoform-selective probes for rat CYP2D2 and human CYP3A4," Drug and Disposition (2002) 30(7):845-852.
Sussman, H.E. et al., "Choosing the best reporter assay," The Scientist (Jul. 23, 2001) 25-27 (retrieved from the Internet, http:www.the-scientist.com/article/display/12529/profile2_010723.html.
Takahashi et al., "Heteroaromatic N-Oxides. X. 1) Synthesis and Reactions of Benzothiazole 3-Oxide," Chem & Pharm. Bull., 18:6, 1176-1184 (1970).
Takahashi, S. et al., "Benzimidazole N-oxide. VIII. The reactivity of ethyl 1-methyl-2-benzimidazolecarboxylate 3-oxide and related compounds," Chem. Pharm. Bull. (1968) 16(3):527-538.
Tassaneeyakul, W. et al., "Specificity of substrate and inhibitor probes for human cytochromes P450 1A1 and 1A2," J. Pharmacol. Exp. Ther. (1993) 265(1):401-407.
Teranishi, K. et al., "Coelenterazine analogs as chemiluminescent probe for superoxide anion," Anal. Biochem. (1997) 249:37-43.
Toya, Y. et al., "Improved synthetic methods of firefly luciferin derivatives for use in bioluminescent analysis of hydrolytic enzymes: carboxylyic esterase and alkaline phosphatase," Bulletin of the Chemical Society of Japan (1992) 65(10):2604-2610.
Tucker, et al., "Synthesis of a Series of 4-(Arylethynyl)-6-chloro-4-cyclopropyl-3,4-dihydroquinazolilHn-)2-(o nes as Novel Non-nucleoside HIV-1 Reverse Transcriptase Inhibitors," J. Med. Chem. 1994, 37, 2437-2444.
Ubeaud, G. et al., "Estimation of flavin-containing monooxygenase activity in intact hapatoxyte monolayers or rat, hamster, rabbit, dog and human by using N-oxidation of benzydamine," Eur. J. Pharm. Sci. (1999) 8:255-260.
Van Vleet, T. et al., "Metabolism and cytotoxicity of aflatoxin B1 in cytochrome P-450-expressing human lung cells," J. Toxicolog. Environ. Health (2002) 65:853-867.
Vinitsky, A. et al., "Cloning and nucleic acid sequence of the *Salmonella typhimurium* pncB gene and structur of nicotinate phosphoribosyitransferase," J. Bacteriol. (1991) 173(2):536-540.
Vonstein, V. et al., "Molecular cloning of the pyrE gene from the extreme thermophile thermus flavus," J. Bacteriol. (1995) 177(8):4540-4543.
Wahler, d. et al., "Enzyme fingerprints of activity, and stereo- and anantionselectivity from fluorogenic and chromogenic substrate arrays," Chem. A European Journal. (2002) 8(14):3211-3228.
Wang et al., "Synthesis of a Novel Esterase-Sensitive Cyclic Prodrug System for Peptides That Utilizes a "Trimethyl Lock"—Facilitated Lactonization Reaction," J. Org. Chem., 62:1363-1367 (1997).

(56) References Cited

OTHER PUBLICATIONS

Wei et al., "Activation of Antibacterial Prodrugs by Peptide Deformylase," Bioorg. Med. Chem. Lett., 10, 1073-1076 (2000).
Weissberger, "The Chemistry of Heterocyclic Compounds, A Series of Monographs," John Wiley & Sons, New York, 1950.
White, E.H. et al, "Analogues of firefly luciferin, III," J. Org. Chem. (1966) 31:1484-1488.
White, E.H. et al., "Amino analogs of firefly luciferin and biological activity thereof," J. Amer. Chem.. Soc. (1966) 88(9):2015-2018.
White, E.H. et al., "Analogs of firefly luciferin," J. Org. Chem. (1965) 30:2344-2348.
Wood, K.A., "Engineering luciferase enzymes and substrates for novel assay capabilities," Proceedings of SPIE—Microarrays and Combinatorial Techniques: Design, Fabrication and Analysis II (Jun. 2004) 5328:69-77.
Wrighton, S.A. et al., "The human hepatic cytochromes P450 involved in drug metabolism," Crit. Rev. Toxicol. (1992) 22(1):1-21.
Yang, J. et al., "An easily synthesized photolyzable luciferase for in vivo luciferase activity measurement," Biotechniques (1993) 15(5):848-850.
Yang, X. et al., "Homogeneous enzyme immunoassay modified for application to luminescence-based biosensors," Anal. Biochem. (2005) 336:102-107.
Yoshitomi, S. et al., "Establishment of the transformants expressing human cytochrome P450 subtypes in HepG2, and their applications on drug metabolism and toxicology," Toxicology in Vitro (2001) 15:245-256.
Youdin, M.B. et al., "Novel substrates and products of amine oxidase-catalysed reactions," Biochem. Soc. Trans. (1990) 19:224-228.
Yun, B-S et al., "Coumarins with monamine oxidase inhibitory activity and antioxidative coumarino-lignans from hibiscus syriacus," J. Natl. Prod. (2001) 64(9):1238-1240.
Yun, C-H. et al., "Rate-determining steps in phenacetin oxidations by human cytochrome P450 1A2 and selected mutants," Biochem. (2000) 39:11319-11329.
Zapata, G. et al., "Sequence of the cloned *Escherichia coli* K1 CMP-N-acetylneuraminic acid synthetase gene," J. Biol. Chem. (1989) 264(25):14769-14774.
Zhou, G. et al., "Platelet monoamine oxidase B and plasma beta-phenylethylamine in Parkinson's disease," J. Neurol. Neurosurg. Psychiatry (2001) 70:229-231.
Zhou, M. et al., "A one-step fluorometric method for the continuous measurement of monoamine oxidase activity," Anal. Biochem. (1997) 253:169-174.
Zhou, M. et al., "A stable nonfluorescent derivative of resorufin for the fluorometric determination of trace hydrogen perioxide: applications in detecting the activity of phagocyte NADPH oxidase and other oxidases," Anal. Biochem. (1997) 253:162-168.
Zhou, W. et al., "New bioluminogenic substrates for monoamine oxidase assays," J. Am. Chem. Soc. (2006) 128(10):3122-3123.
Xiao-Hua, L. et al., "Design and Synthesis of a Novel Fluorescein-based Flourescent Probe for Labeling of Histidine in Human Serum" Chemical Journal of Chinese Universities (1986) vol. 24, No. 11 (3 pages with English Abstract).
Australian Application Serial No. 2003267245 Notice of Acceptance dated Jun. 29, 2007 (3 pages).
Australian Application Serial No. 2003267245, Examiner's first Report dated Nov. 29, 2006 (1 page).
Canadian Patent Office Action for Application No. 2497560 dated Feb. 3, 2009 (2 pages).
Canadian Patent Office Action for Application No. 2,497,560 dated Dec. 21, 2009 (2 pages).
European Patent Office Examination Report for Application No. 03749715.3 dated Apr. 4, 2008 (6 pages).
European Patent Office Examination Report for Application No. 03749715.3 dated Feb. 24, 2009 (5 pages).
European Patent Office Supplemental Search Report for Application No. 03749715.3 dated Jun. 14, 2007 (4 pages).
European Patent Office Action for Application No. 03749715.3 dated Jan. 20, 2010 (3 pages).
European Patent Office Action for Application No. 06771475.8 dated Jun. 12, 2008 (5 pages).
European Patent Office Examination Report for Application No. 06771475.8 dated Oct. 23, 2009 (3 pages).
European Patent Office Action for Application No. 06771475.8 dated Dec. 14, 2010 (3 pages).
European Patent Office Action for Application No. 06771475.8 dated Jun. 4, 2012 (4 pages).
European Patent Office Action for Application No. 06771475.8 dated Oct. 18, 2011 (3 pages).
European Patent Office Action for Application No. 06771475.8 dated Aug. 20, 2013 (4 pages).
European Patent Office Action for Application No. 08151520.7 dated May 20, 2009 (2 pages).
European Patent Office Search Report for Application No. 08151520.7 dated Jun. 5, 2008 (10 pages).
European Patent Office Action for Application No. 08151520.7 dated Dec. 17, 2010 (8 pages).
European Patent Office Action for Application No. 08151520.7 dated Dec. 1, 2011 (7 pages).
European Patent Office Action for Application No. 08151520.7 dated Feb. 19, 2013 (8 pages).
European Patent Office Extended Search Report for Application No. 10075500.8 dated Dec. 10, 2010 (8 pages).
European Patent Office Action for Application No. 10075500.8 dated Jan. 11, 2012 (4 pages).
European Patent Office Extended Search report for Application No. 10075501.6 dated Dec. 9, 2010 (5 pages).
European Patent Office Action for Application No. 10075501.6 dated Jan. 11, 2012 (3 pages).
European Patent Office Extended Search Report for Application No. 10075502.4 dated Dec. 17, 2010 (9 pages).
European Patent Office Action for Application No. 10075502.4 dated Jan. 11, 2012 (4 pages).
European Patent Office Action for Application No. 10075502.4 dated Dec. 14, 2012 (4 pages).
European Patent Office Action for Application No. 10075502.4 dated Dec. 16, 2013 (3 pages).
European Patent Office Action for Application No. 10075501.6 dated Dec. 21, 2012 (3 pages).
European Patent Office Examination Report for Application No. 09789154.3 dated Nov. 14, 2012 (6 pages).
European Patent Office Action for Application No. 10075502.4 dated Apr. 23, 2014 (4 pages).
European Search Report for Application No. 14172029.2 dated Jul. 16, 2014 (5 pages).
European Patent Office Action for Application No. 10075502.4 dated Jul. 17, 2014 (4 pages).
European Patent Office Action for Application No. 06771475.8 dated Jul. 28, 2014 (4 pages).
International Preliminary Examination Report for Application No. PCT/US03/29078 dated Oct. 19, 2006 (6 pages).
International Preliminary Report on Patentability for Application No. PCT/US06/020731 dated Sep. 12, 2007 (8 pages).
International Search Report for Application No. PCT/US03/29078 dated Oct. 8, 2004 (4 pages).
International Search Report and Written Opinion for Application No. PCT/US2006/020731 dated Mar. 13, 2007 (17 pages).
Partial International Search Report for Application No. PCT/US2006/020731 dated Oct. 2, 2006 (6 pages).
International Search Report and Written Opinion for Application No. PCT/US2009/004696 dated Nov. 19, 2009 (13 pages).
Japanese Appeal Brief for Application No. 2004-537859 dated Dec. 3, 2008 (3 pages).
Japanese Patent Office Action for Application No. 2008-514754 dated Jan. 12, 2012 (12 pages) with English translation.
Japanese Patent Office Action for Application No. 2008-514754 dated Sep. 6, 2012 (3 pages—English Translation).
Japanese Patent Office Action for Application No. 2008-514754 dated Apr. 3, 2013 (3 pages—English Translation).

(56) References Cited

OTHER PUBLICATIONS

Japanese Patent Office Action for Application No. 2004-537859 dated Aug. 5, 2008 (5 pages) with English translation.
Japanese Patent Office Action for Application No. 2004537859 dated Feb. 5, 2008 (8 pages) with translation.
Japanese Patent Office Action for Application No. 2004-537859 dated Mar. 2, 2010 (18 pages) with translation.
Japanese Patent Office Action for Application No. 2008-146920 dated Jul. 7, 2011 (7 pages) with translation.
United States Patent Office Action for U.S. Appl. No. 10/665,314 dated Jan. 15, 2009 (6 pages).
United States Patent Office Action for U.S. Appl. No. 10/665,314 dated Jul. 18, 2008 (14 pages).
United States Patent Office Action for U.S. Appl. No. 10/665,314 dated Mar. 19, 2008 (5 pages).
United States Patent Office Action for U.S. Appl. No. 10/665,314 dated May 15, 2009 (6 pages).
United States Patent Office Action for U.S. Appl. No. 10/665,314 dated Oct. 11, 2007 (16 pages).
United States Patent Office Action for U.S. Appl. No. 10/665,314 Advisory Action dated Jun. 6, 2008 (3 pages).
United States Patent Office Action for U.S. Appl. No. 11/444,145 dated Apr. 28, 2009 (15 pages).
United States Patent Office Action for U.S. Appl. No. 11/444,145 dated Mar. 24, 2008 (16 pages).
United States Patent Office Action for U.S. Appl. No. 11/444,145 dated Oct. 15, 2008 (16 pages).
United States Patent Office Action for U.S. Appl. No. 11/444,145 dated Dec. 3, 2009 (27 pages).
United States Patent Office Action for U.S. Appl. No. 11/444,145 dated Jul. 20, 2010 (14 pages).
United States Patent Office Notice of Allowance for U.S. Appl. No. 11/444,145 dated Jan. 24, 2011 (19 pages).
United States Patent Office Action for U.S. Appl. No. 12/217,494 dated Dec. 16, 2009 (18 pages).
United States Patent Office Action for U.S. Appl. No. 12/217,494 dated Jun. 28, 2010 (10 pages).
United States Patent Office Action for U.S. Appl. No. 12/217,494 dated Jan. 26, 2012 (14 pages).
United States Patent Office Action for U.S. Appl. No. 12/217,494 dated Aug. 7, 2012 (17 pages).
United States Patent Office Action for U.S. Appl. No. 12/217,494 dated Nov. 16, 2012 (3 pages).
United States Patent Office Action for U.S. Appl. No. 12/217,494 dated Jan. 14, 2013 (3 pages).
United States Patent Office Notice of Allowance for U.S. Appl. No. 12/217,494 dated Feb. 21, 2013 (5 pages).
United States Patent Office Action for U.S. Appl. No. 12/217,374 dated Jul. 28, 2010 (8 pages).
United States Patent Office Action for U.S. Appl. No. 12/217,374 dated Dec. 17, 2010 (9 pages).
United States Patent Office Action for U.S. Appl. No. 12/217,374 dated May 24, 2011 (8 pages).
United States Patent Office Action for U.S. Appl. No. 12/217,374 dated May 7, 2013 (12 pages).
United States Patent Office Notice of Allowance for U.S. Appl. No. 12/217,374 dated Nov. 25, 2013 (9 pages).
United States Patent Office Action for U.S. Appl. No. 12/754,164 dated May 13, 2011 (5 pages).
United States Patent Office Notice of Allowance for U.S. Appl. No. 12/754,164 dated Sep. 21, 2011 (5 pages).
United States Patent Office Action for U.S. Appl. No. 12/543,376 dated Jan. 26, 2012 (7 pages).
United States Patent Office Notice of Allowance for U.S. Appl. No. 12/543,376 dated Jul. 9, 2012 (10 pages).
United States Patent Office Action for U.S. Appl. No. 13/913,919 dated Mar. 26, 2014 (24 pages).
European Patent Office Action for Application No. 06771475.8 dated Nov. 4, 2015 (3 pages).
European Patent Office Action for Application No. 06771475.8 dated Jul. 12, 2016 (6 pages).
European Patent Office Action for Application No. 14172029.2 dated Aug. 11, 2016 (4 pages).
United States Patent Office Action for U.S. Appl. No. 14/319,219 dated Mar. 31, 2016 (11 pages).
United States Patent Office Notice of Allowance for U.S. Appl. No. 14/319,219 dated Oct. 6, 2016 (8 pages).
European Patent Office Extended Search Report for Application No. 17186149.5 dated Mar. 7, 2018 (6 pages).

* cited by examiner

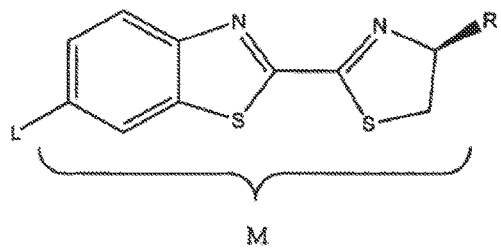

| L | M | R | Target enzyme |
|---|---|---|---|
| HO- | Luciferin | CH₂OH | Alcohol dehydrogenase |
| Boc-Orn(Ac)O- | Luciferin | CO₂H | Histone deacetylase |
| Boc-Lys(Ac)-HN- | Luciferin | CO₂H | Histone deacetylase |
| Suc-LLVY-HN- | Luciferin | CO₂H | Proteasome and Calpain substrate |
| Z-KKR-SEVNLDAEFR-HN- | Luciferin | CO₂H | B-secretase substrate |
| AAF-HN- | Luciferin | CO₂H | Protease release assay |
| Z-FR-HN- | Luciferin | CO₂H | Cathepsin B, L assay |
| Z-GGR-HN- | Luciferin | CO₂H | Thrombin assay |
| Z-GPR-HN- | Luciferin | CO₂H | Thrombin assay |
| Z-IEPD-HN- | Luciferin | CO₂H | Cytotoxic response CTL, Granzyme B |
| HO- | N-Acetyl-2,3-dihydroluciferin | CO₂H | HRP substrate |
| HO- | Luciferin | CO₂-Amino acid | Mycoplasma |

*FIG. 2*

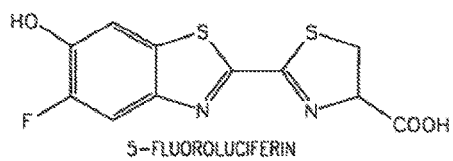

5-FLUOROLUCIFERIN

| # | Name | Type | Structure |
|---|------|------|-----------|
| 1 | 6-(2,4,6-trimethylbenzyl)-luciferin (908-74-2707s) | 1A | 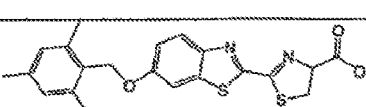 |
| 2 | 6-*p*-chlorophenolthiol methoxyluciferin | 1A | 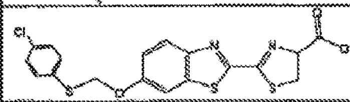 |
| 3 | 6-phenylpiperizinexylyl-luciferin | 1A | 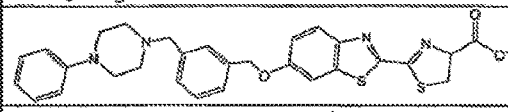 |
| 4 | 6-*o*-trifluoromethylbenzylluciferin | 1A | 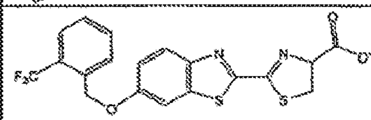 |
| 5 | 6-(2,3,4,5,6 pentafluorobenzyloxy)-luciferin | 1A | 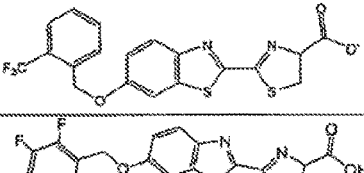 |
| 6 | 6-phenyl-piperizine-2,4,5,6-quatrafluoroxylyl-luciferin | 1A | 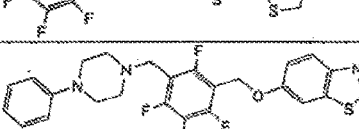 |
| 7 | bis-luciferin-methylenediether | 1A | 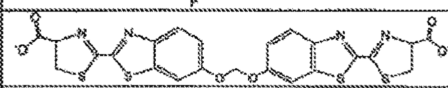 |
| 8 | Bis-luciferin-xylyldiether | 1A | 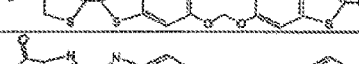 |
| 9 | luciferin-6-isobutylcarbonate | 1A | 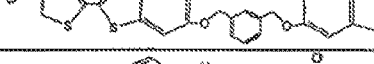 |
| 10 | luciferin-6-ditrifluoromethylbenzylether | 1A | 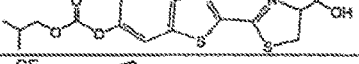 |
| 11 | 4-methyl-6-(O-methyl)-luciferin | 2A | 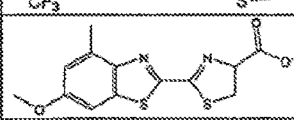 |
| 12 | 4-(O-methyl)-6-(O-methyl)-luciferin | 2A | 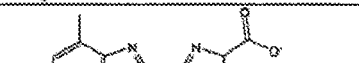 |
| 13 | 5-fluoro-6-methoxy luciferin | 2A | 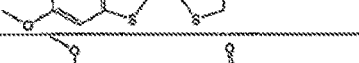 |

FIG. 19A

| # | Name | Type | Structure |
|---|---|---|---|
| 14 | 5-6-dimethoxy-luciferin | 2A | 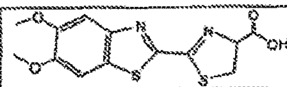 |
| 15 | Quinolylluciferin-6-methyl ether | 1A, 1B | 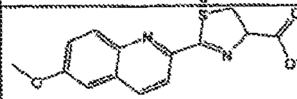 |
| 16 | Quinolylluciferin-6-benzyl ether | 1A, 1B | 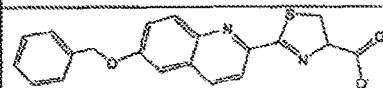 |
| 17 | 6-(p-aminophenyloxy)-quinolylluciferin | 1A, 1B, Ester | 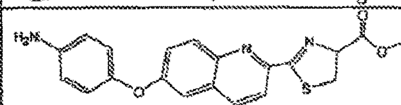 |
| 18 | 6-benzyloxymethoxy-quinolylluciferin | 1A, 1B, ester | 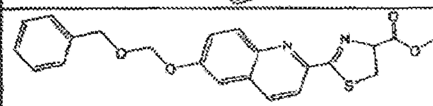 |
| 19 | naphthylluciferin 6-methyl ether | 1A, 1B | 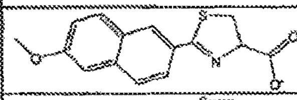 |
| 20 | quinoxalylluciferin methyl ether | 1A, 1B | 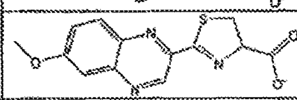 |
| 21 | N,N-Bis-benzyl-aminoluciferin | 1ANH | 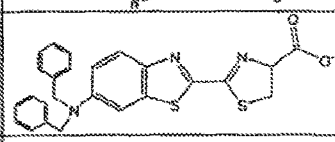 |
| 22 | N-Benzyloxycarbonyl-aminoluciferin | 1ANH | 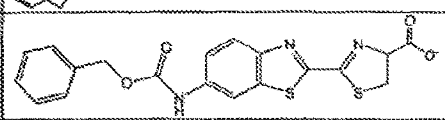 |
| 23 | N-isobutoxycarbonyl-aminoluciferin | 1ANH | 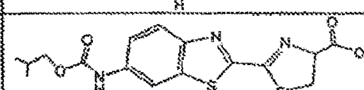 |
| 24 | luciferin-H ethylene glycol ester | 1A, Ester | 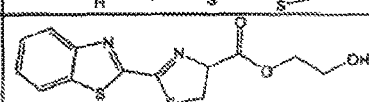 |
| 26 | Lucifern-H methyl ester | 1A, Ester | 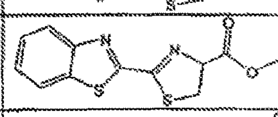 |
| 27 | Luciferin-6-methylether picolinyl ester | 1A, Ester | 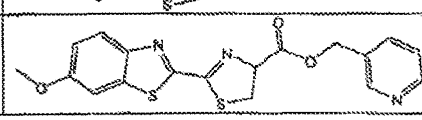 |

FIG. 19B

| 28 | 6-*m*-picolinyl luciferin methyl ester | 1A Ester | 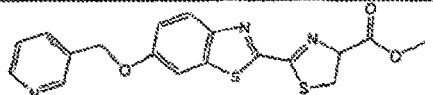 |
| 30 | 6-*p*-picolinyl luciferin methyl ester | 1A Ester | 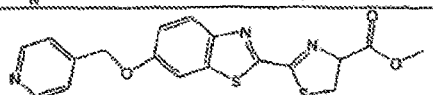 |
| 32 | Luciferin-H picolinyl ester | 1A Ester | 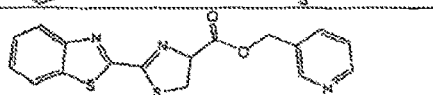 |
| 33 | Luciferin-6-methylether methyl ester | 1A Ester |  |
| 34 | Luciferin-6-methylether propanol ester | 1A Ester | 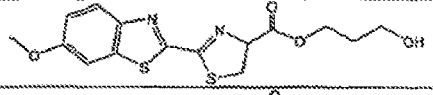 |
| 36 | Luciferin-6-methylether ethylene glycol ester | 1A Ester |  |
| 37 | Quinolylluciferin-6-methylether methyl ester | 1A 1B Ester | 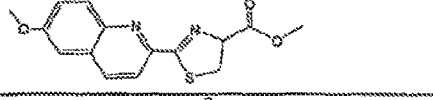 |
| 38 | quinolylluciferin-H ethyleneglycol ester | 1A 1B Ester | 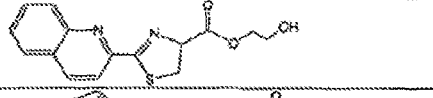 |
| 40 | Luciferin-6-methylether hydrazide | 1A Hydrazide |  |
| 41 | luciferin-6-methylether-N-methoxylamide | 1A Methoxamide | 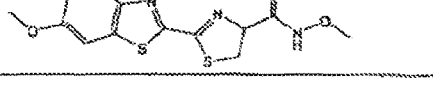 |

FIG. 19C

3A4 PPXE assays for inhibition by nifedipine

| uM nifedipi | PPXE | PPXE | PPXE | | |
|---|---|---|---|---|---|
| 200 | 8584 | 8236 | 7914 | 8244.667 | 335.0841 |
| 100 | 13594 | 12898 | 12378 | 12956.67 | 610.1191 |
| 50 | 22014 | 21868 | 23056 | 22312.67 | 647.8714 |
| 25 | 33136 | 33182 | 32656 | 32991.33 | 291.3166 |
| 12.5 | 49210 | 47340 | 48470 | 48340 | 941.7537 |
| 6.25 | 82042 | 77646 | 81388 | 80358.67 | 2371.887 |
| 3.125 | 91596 | 86630 | 89658 | 89294.67 | 2502.858 |
| 0 | 136742 | 125432 | 129692 | 130622 | 5712.066 |

*FIG. 50*

Cambrex human hepatocytes; donor is 11yr old male
48 Hour induction with 10uM Rifampicin
3 hr incubation with 50uM 5FBE keto

| luciferin-5FBE | | | | | ave |
|---|---|---|---|---|---|
| vehicle | 3174 | 3847 | 2900 | 5211 | 3783 |
| vehicle+ke | 835 | 1099 | 1197 | 621 | 938 |
| 10uM rifan | 36371 | 39351 | 34085 | 33834 | 35910.25 |
| Rifamp.+k | 1199 | 1097 | 941 | 965 | 1050.5 |

*FIG. 51*

Cambrex human hepatocytes; donor is 11 yr old male
48 Hour induction with 10uM Rifampicin
3 hr incubation with 50uM PPXE

| luciferin-PPXE | | | | | ave | sd |
|---|---|---|---|---|---|---|
| vehicle | 1297 | 1641 | 1863 | 2367 | 1792 | 448.5131 |
| vehicle+ke | 20 | 196 | 238 | 224 | 169.5 | 101.1846 |
| 10oM rifan | 9311 | 8468 | 6355 | 10540 | 8668.5 | 1761.42 |
| rifamp.+ke | 428 | 578 | 356 | 592 | 488.5 | 115.382 |

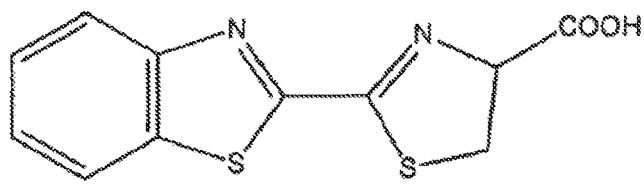
6' deoxyluciferin
Luciferin H
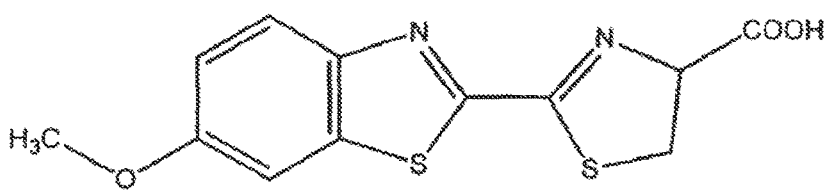
Luciferin 6' methyl ether (Luciferin-ME)
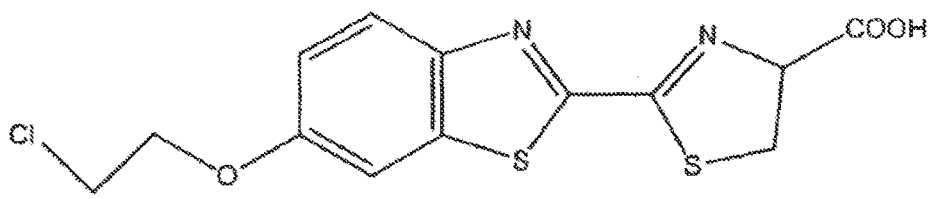
Luciferin 6' chloroethyl ether (Luciferin-CEE)
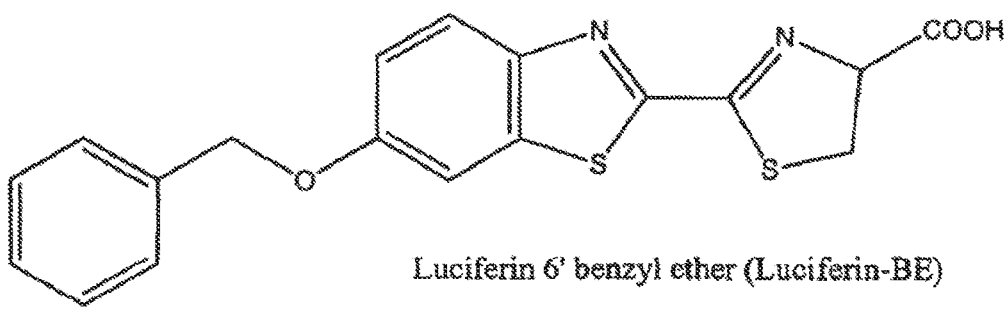
Luciferin 6' benzyl ether (Luciferin-BE)
*FIG. 54*

LUMINOGENIC AND FLUOROGENIC COMPOUNDS AND METHODS TO DETECT MOLECULES OR CONDITIONS

CROSS-REFERENCE TO RELATED APPLICATIONS

This application is a continuation of U.S. application Ser. No. 13/913,919, filed Jun. 10, 2013, which is a continuation of U.S. application Ser. No. 12/217,494, filed Jul. 3, 2008, now U.S. Pat. No. 8,476,450, which is a continuation of U.S. patent application Ser. No. 11/444,145, filed May 31, 2006, now U.S. Pat. No. 7,951,550, which application claims the benefit of the filing date of U.S. Application Ser. No. 60/685,957, filed May 31, 2005, U.S. Application Ser. No. 60/693,034, filed Jun. 21, 2005, U.S. Application Ser. No. 60/692,925, filed Jun. 22, 2005 and U.S. Application Ser. No. 60/790,455, filed Apr. 7, 2006, the disclosures of which are incorporated by reference herein.

BACKGROUND

Luminescence is produced in certain organisms as a result of a luciferase-mediated oxidation reaction. Luciferase genes from a wide variety of vastly different species, particularly the luciferase genes of *Photinus pyralis* and *Photuris pennsylvanica* (fireflies of North America), *Pyrophorus plagiophthalamus* (the Jamaican click beetle), *Renilla reniformis* (the sea pansy), and several bacteria (e.g., *Xenorhabdus luminescens* and *Vibrio* spp), are extremely popular luminescence reporter genes. Firefly luciferase is also a popular reporter for determining ATP concentrations, and, in that role, is widely used to detect biomass. Luminescence is also produced by other enzymes when those enzymes are mixed with certain synthetic substrate, for instance, alkaline phosphatase and adamantyl dioxetane phosphate, or horseradish peroxidase and luminol.

Luciferase genes are widely used as genetic reporters due to the non-radioactive nature, sensitivity, and extreme linear range of luminescence assays. For instance, as few as $10^{-20}$ moles of firefly luciferase can be detected. Consequently, luciferase assays of gene activity are used in virtually every experimental biological system, including both prokaryotic and eukaryotic cell cultures, transgenic plants and animals, and cell-free expression systems. Similarly, luciferase assays used to determine ATP concentration are highly sensitive, enabling detection to below $10^{-16}$ moles.

Luciferases can generate light via the oxidation of enzyme-specific substrates, e.g., luciferins. For firefly luciferase and all other beetle luciferases, light generation occurs in the presence of luciferin, magnesium ions, oxygen, and ATP. For anthozoan luciferases, including *Renilla* luciferase, only oxygen is required along with the substrate coelentrazine. Generally, in luminescence assays to determine genetic activity, reaction substrates and other luminescence activating reagents are introduced into a biological system suspected of expressing a reporter enzyme. Resultant luminescence, if any, is then measured using a luminometer or any suitable radiant energy-measuring device. The assay is very rapid and sensitive, and provides gene expression data quickly and easily, without the need for radioactive reagents.

Because most enzymatic reactions do not generate outputs that are as ideal as luciferase, the availability of a luciferase mediated assay for enzymatic reactions useful in cellular analysis and high-throughput screening applications would be desirable to those working in this field. The development of such a luciferase mediated reaction as the basis for such enzymatic or biological assays has, however, been limited. Luciferase mediated reactions have been employed to detect numerous other molecules, e.g., ATP or lactate dehydrogenase. For some of those reactions, a derivative of the naturally occurring substrate is employed. Native firefly luciferin, a polytherocyclic organic acid, D-(−)-2-(6'hydroxy-2'-benzothiazolyl)-$\Delta^2$-thiazolin-4-carbozylic acid, is shown in FIG. 1. For instance, methods for using luciferin derivatives with a recognition site for an enzyme such as a protease as a prosubstrate were described by Miska et al. (*Journal of Clinical Chemistry and Clinical Biochemistry*, 25:23 (1987)). The heterogenous assays were conducted by incubating the luciferin derivative with the appropriate enzyme, e.g., a protease, for a specified period of time, then transferring an aliquot of the mixture to a solution containing luciferase. Masuda-Nishimura et al. (*Letters in Applied Microbio.*, 30:130 (2000)) reported the use of a single tube (homogenous) assay which employed a galactosidase substrate-modified luciferin. In these luciferin derivatives, the portion of the derivative functioning as the reactive group for the nonluciferase enzyme activity was coupled to the D-luciferin or aminoluciferin backbone such that upon the action of the nonluciferase enzyme, a D-luciferin or aminoluciferin molecule was produced as the direct product of the reaction to serve as the substrate for luciferase. A primary obstacle to broadly applying luciferase mediated reactions for other enzymatic assays has been the belief that to modify the luciferin molecule to function as a substrate for a nonluciferase enzyme, the activity of the nonluciferase enzyme must directly yield a D-luciferin or aminoluciferin molecule to retain its function as a substrate for luciferase.

There is, therefore, a need in the field of biological assays to expand the utility of luciferase mediated reactions for nonluciferase enzymes by identifying derivatives of luciferin that function in a substrate for a nonluciferase enzyme or other biological molecule of interest and as a prosubstrate for luciferase regardless of whether D-luciferin or aminoluciferin is released as a direct result of the nonluciferase enzymatic reaction.

SUMMARY OF THE INVENTION

The present invention provides derivatives of luciferin and methods for using such derivatives in enzyme activity assays or non-enzymatic biological assays where the luciferin derivative serves as a substrate for a desired enzyme and is a prosubstrate for luciferase or wherein the luciferin derivative is a molecule which is modified by a molecule of interest, which modified molecule is a substrate for luciferase. Surprisingly, many of the luciferin derivatives also have activity as substrates for luciferase in a light generating assay. Thus, by providing luciferin derivatives having a particular enzyme recognition site (reactive chemical group in a molecule referred to as a substrate for a particular enzyme) for a desired nonluciferase enzyme coupled to the luciferin backbone (or other chemical moiety constituting a suitable substrate for luciferase), such as derivatives with modifications at the 6' hydroxy site of luciferin or the 6' amino site of aminoluciferin, yielding a substrate for a desired nonluciferase enzyme and a prosubstrate of luciferase, numerous nonluciferase enzymes may be measured in a bioluminescent assay.

Modifications of luciferin within the scope of the derivatives of this invention include one or more substitutions of a ring atom, one or more substitutions of a substituent (atom or group) attached to a ring atom, and/or addition of one or more atoms to the ring, e.g., expansion or addition of rings, or a combination thereof. Numbering for some of the ring atoms in D-luciferin is shown in FIG. 1. Native firefly luciferin has three linked rings, a 6 membered ring having an OH group at position 6 ("ring A" or "A ring" hereinafter), a 5 membered thiazole ring linked to the 6 membered ring ("ring B" or "B ring" hereinafter), and a 5 membered thiazole ring that is modified with a carboxyl group at position 5 ("ring C" or "C ring" hereinafter). For instance, a luciferin derivative with a A ring modification may have a substitution of a C atom in the A ring with another atom, addition of a ring, a substitution of a substituent attached to a ring atom with a different atom or group, or any combination thereof. A luciferin derivative with a B ring modification may have an addition to or substitution of an atom in the five membered ring, e.g., insertion of one or more atoms, thereby expanding the ring, for instance, to a six membered ring, substitution of N or S in the ring with a different atom, e.g., a C or O, substitution of a substituent atom or group attached to a ring atom, or any combination thereof. A luciferin derivative with a C ring modification may have a substitution of an atom in the ring with another atom, a substitution of a substituent attached to a ring atom, with a different atom or group, or any combination thereof. In one embodiment, a derivative of the invention is one which is modified at more than one position, for instance, the derivative has two (or more) A ring modifications, two (or more) B ring modifications, two (or more) C ring modifications, or any combination thereof. In one embodiment, one modification is the substitution of a substituent on one of the rings of D-luciferin with a substrate for a nonluciferase enzyme, or a linker and a substrate for the nonluciferase enzyme.

Exemplary derivatives with A ring modifications may be a substrate for a reductase, such as a cytochrome P450 reductase, monoamine oxidase (MAO), flavin monooxygenase (FMO), glutathione S transferase (GST), dealkylase, deacetylase, deformylase, phosphatide, e.g., alkaline phosphatase (AP), sulfatase, beta-lactamase, alcohol dehydrogenase, protease e.g., proteosome, cathepsin, calpain, beta secretase, thrombin, or granzyme, luciferase, or useful to detect reactive oxygen species (ROS), peroxidase e.g., horseradish peroxidase (HRP), and redox conditions. Exemplary molecules or conditions to be detected with derivatives having at least a B ring modification include but are not limited to dealkylase, GST or luciferase, or redox conditions. Exemplary molecules to be detected with those derivatives include a cytochrome P450 enzyme, esterase, e.g., acetylcholinesterase, OH radicals, demethylase, deacetylase, deformylase, or mycoplasma carboxypeptidase. Exemplary molecules to be detected with derivatives having C ring modifications include but are not limited to esterases.

In one embodiment, derivatives of luciferin or aminoluciferin have the following structure; L-X-M-Y-R (compound of formula IV), wherein L, if present, may be a substrate for an enzyme or another molecule which interacts with the enzyme; X may be O, NH, or a linker, e.g., a self-cleavable linker which spontaneously cleaves to yield M-Y-R after L has been removed from L-X-M-Y-R; M may be luciferin, quinolinyl luciferin or naphthyl luciferin, or aminoluciferin or aminoquinolinyl luciferin, Y is O (ester), NH (amide), NH—NH (hydrazide), or S (thioester), and R, if present, may be alkyl, an aromatic molecule, a peptide, an oligonucleotide, or a self-cleavable linker attached to a substrate for an enzyme.

In one embodiment, the invention provides a compound of formula I:

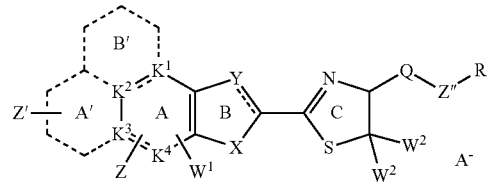

wherein

Y is N, N-oxide, N—($C_1$-$C_6$)alkyl, or CH;

when Y is N, then X is not S;

X is S, O, CH=CH, N=CH, or CH=N;

when X is S, then Y is not N;

Z and Z' are independently H, OR, NHR, or NRR;

Z" is O, S, NH, NHR, or N=N;

Q is carbonyl or $CH_2$;

$W^1$ is H, halo, ($C_1$-$C_6$)alkyl, ($C_2$-$C_{20}$)alkenyl, hydroxyl, or ($C_1$-$C_6$)alkoxy; or $W^1$ and Z are both keto groups on ring A, and at least one of the dotted lines denoting optional double bonds in ring A is absent;

each $W^2$ is independently H, halo, ($C_1$-$C_6$)alkyl, ($C_2$-$C_4$) alkenyl, hydroxyl, or ($C_1$-$C_6$)alkoxy;

each of $K^1$, $K^2$, $K^3$, and $K^4$ are independently CH, N, N-oxide, or N—($C_1$-$C_6$)alkyl, and the dotted lines between $K^1$ and $K^2$, and $K^3$ and $K^4$, denote optional double bonds;

A' and B' are optional aromatic rings fused to ring A, only one of which is present in the compound, so as to form a fused tricyclic system; and when B' is present, the group Z is present, and when A' is present, the group Z is absent; and the dotted line in ring B is an optional double bond;

each R is independently H, ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{12}$)alkoxy, ($C_6$-$C_{30}$)aryl, heteroaryl, heterocycle, ($C_1$-$C_{20}$)alkylsulfoxy, ($C_6$-$C_{30}$)arylsulfoxy, heteroarylsulfoxy, ($C_1$-$C_{20}$)alkylsulfonyl, ($C_6$-$C_{30}$)arylsulfonyl, heteroarylsulfonyl, ($C_1$-$C_{20}$) alkylsulfinyl, ($C_6$-$C_{30}$)arylsulfinyl, heteroarylsulfinyl, ($C_1$-$C_{20}$)alkoxycarbonyl, amino, NH($C_1$-$C_6$)alkyl, N(($C_1$-$C_6$) alkyl)$_2$, tri($C_1$-$C_{20}$)ammonium($C_1$-$C_{20}$)alkyl, heteroaryl($C_1$-$C_{20}$)alkyl, heteroaryl having quaternary nitrogen, heteroarylcarbonyl having quaternary nitrogen, ($C_6$-$C_{30}$) arylthio, ($C_1$-$C_{20}$)alkylphosphate, ($C_1$-$C_{20}$)alkylphosphonate, ($C_6$-$C_{30}$)arylphosphate, ($C_6$-$C_{30}$)arylphosphonate, phosphate, sulfate, saccharide, or $M^+$ optionally when Z" is oxygen, wherein M is an alkali metal;

or when Z or Z' is $NR^1R^1$, $R^1R^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from ($C_1$-$C_{20}$)alkyl, ($C_2$-$C_{20}$)alkenyl, ($C_2$-$C_{20}$)alkynyl, ($C_3$-$C_{20}$) cycloalkyl, ($C_1$-$C_{20}$)alkoxy, ($C_1$-$C_{20}$)alkylcarbonyl, ($C_1$-$C_{20}$)alkylcarboxyl, halo, hydroxyl, —COOR$^x$, —SO$_2$R$^x$, —SO$_3$R$^x$, nitro, amino, ($C_1$-$C_{20}$)alkyl-S(O)—, ($C_1$-$C_{20}$) alkyl-SO$_2$—, phosphate, ($C_1$-$C_{20}$)alkylphosphate, ($C_1$-$C_{20}$) alkylphosphonate, NH($C_1$-$C_6$)alkyl, NH($C_1$-$C_6$)alkynyl, N(($C_1$-$C_6$)alkyl)$_2$, N(($C_1$-$C_6$)alkynyl)$_2$, mercapto, ($C_1$-$C_{20}$) alkylthio, ($C_6$-$C_{30}$)aryl, ($C_6$-$C_{30}$)arylthio, trifluoromethyl, =O, heteroaryl, and heterocycle, and each substituent is optionally substituted with one to three R groups;

$R^x$ is H, $(C_1-C_6)$alkyl, or $(C_6-C_{30})$aryl;

when Z or Z' composes a nitrogen moiety, one or both of the hydrogens of the Z or Z' nitrogen moiety may be replaced by $(C_1-C_{20})$alkyl or the group L, wherein L is an amino acid radical, a peptide radical having up to 20 ammo acid moieties, or any other small molecule that is a substrate for a nonluciferase; with the proviso that when L is an amino acid radical or a peptide radical, at least one $W^2$ is not H;

when Z is a hydroxyl group or a nitrogen moiety, H of the hydroxyl or nitrogen moiety may be replaced by $(HO)_2P(O)—OCH_2—$, sulfo, $—PO_3H_2$, or by a cephalosporanic acid attached to the group Z via a carbon chain of one to about 12 carbon atoms; with the proviso that when ring B is a thiazole ring, the sulfo or the $—PO_3H_2$ group is attached to the hydroxyl oxygen via a $(C_1-C_6)$alkylene group;

when Z or Z' is a hydroxyl group or a nitrogen moiety, or when Z"—R is a hydroxyl group, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds, linker is attached to L' via an oxygen atom or an NH group at one terminus of the linker and the other terminus of the linker forms an ether, ester, or amide linkage with a group Z, Z' or Z"—R;

when Z is OR, formula I is optionally a dimer connected at the two A rings via a linker comprising a $(C_1-C_{12})$alkyl diradical that is optionally interrupted by one to four O atoms, N atoms, or an optionally substituted aryl, heteroaryl, or heterocycle group to form a bridge between the dimer of formula I, and the R group of each Z group connecting the dimer of formula I is replaced by the bridge;

$A^-$ is an anion, present when a quaternary nitrogen is present;

or a salt thereof,
provided that:
when rings A and B form a naphthalene or quinoline ring system, then $W^1$ is not hydrogen;

when a ring A substituent is OH, then -Q-R"—R is not $—C(O)—NH—NH_2$;

when Y is N or CH and X is CH=CH and $W^1$ is H, then Z is not OH attached to $K^3$; and when Y is N or CH and X is CH=CH and Z is H, then $W^1$ is not OH attached to $K^3$.

In another embodiment, the invention provides a compound of formula IA:

Z is H, OR, NHR, or NRR;
Z" is O, S, NH, NHR, or N=N;
$W^1$ is H halo, hydroxyl, $(C_1-C_6)$alkyl, or $(C_1-C_6)$alkoxy;
the dotted line in ring B is an optional double bond;

each R is independently H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, heteroaryl, heterocycle, $(C_1-C_{20})$alkylsulfoxy, $(C_6-C_{30})$arylsulfoxy, heteroarylsulfoxy, $(C_1-C_{20})$alkylsulfonyl, $(C_6-C_{30})$arylsulfonyl, heteroarylsulfonyl, $(C_1-C_{20})$alkylsulfinyl, $(C_6-C_{30})$arylsulfinyl, heteroarylsulfinyl, $(C_1-C_{20})$alkoxycarbonyl, amino $NH(C_1-C_6)$alkyl, $N((C_1-C_6)$alkyl$)_2$, tri$(C_1-C_{20})$ammonium$(C_1-C_{20})$alkyl, heteroaryl$(C_1-C_{20})$alkyl, heteroaryl having quaternary nitrogen, heteroarylcarbonyl having quaternary nitrogen $(C_6-C_{30})$arylthio, $(C_1-C_{20})$alkylphosphate, $(C_1-C_{30})$alkylphosphonate, $(C_6-C_{30})$arylphosphate, $(C_6-C_{30})$arylphosphonate, phosphate, sulfate, saccharide, or $M^+$ optionally when Z" is oxygen, wherein M is an alkali metal;

or when Z or Z' is $NR^1R^1$,$R^1R^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_3-C_{20})$alkylcarboxyl, halo, hydroxyl, $—COOR^x$, $—SO_2R^x$, $—SO_3R^x$, nitro, amino, $(C_1-C_{20})$alkyl-S(O)—, $(C_1-C_{20})$alkyl-SO$_2$—, phosphate, $(C_1-C_{20})$alkylphosphate, $(C_1-C_{20})$alkylphosphonate, $NH(C_1-C_6)$alkyl, $NH(C_1-C_6)$alkynyl, $N((C_1-C_6)$alkyl$)_2$, $N((C_1-C_6)$alkynyl$)_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

$R^x$ is H, $(C_1-C_6)$alkyl, or $(C_6-C_{30})$aryl;

$A^-$ is an anion, present when a quaternary nitrogen is present;

or a salt thereof,
provided that:
when rings A and B form a naphthalene or quinoline ring system, then $W^1$ is not hydrogen.

when a ring A substituent is OH, then -Q-Z"—R is not $—C(O)—NH—NH_2$;

when Y is N or CH and X is CH=CH and $W^1$ is H, then Z is not OH attached to carbon-6 of ring A (carbon 6 as shown in FIG. 1); and when Y is N or CH and X is CH=CH and Z is H, then $W^1$ is not OH attached to carbon-6 of ring A.

In another embodiment, the invention provides a compound of formula II:

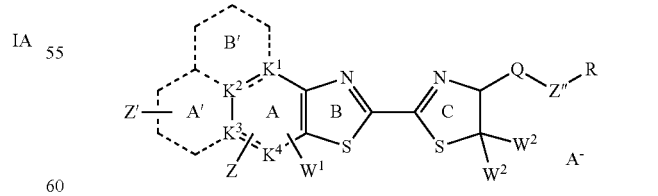

wherein
Z and Z' are independently $OR^1$, $NHR^1$, or $NR^1R^1$;
Z" is O, S, NH, NHR, r N=N;
Q is carbonyl or $CH_2$.
$W^1$ is H, halo, $(C_1-C_6)$alkyl, $(C_2-C_{20})$alkenyl, hydroxyl, or $(C_1-C_6)$alkoxy; or

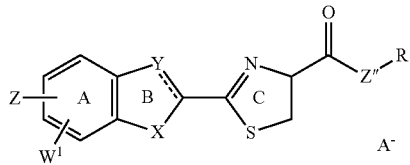

wherein
Y is N, N-oxide, N—$(C_1-C_6)$alkyl, or CH;
when Y is N, then X is not S;
X is S, O, CH=CH, N=CH, or CH=N;
when X is S, then Y is not N;

W¹ and Z are both keto groups on ring A, and at least one of the dotted lines denoting optional double bonds in ring A is absent;

each $W^2$ is independently H, halo, $(C_1-C_6)$alkyl, $(C_2-C_4)$alkenyl, hydroxyl, or $(C_1-C_6)$alkoxy;

each of $K^1$, $K^2$, $K^3$, and $K^4$ are independently CH, N, N-oxide, or N—$(C_1-C_6)$alkyl, and the dotted lines between $K^1$ and $K^2$, and $K^3$ and $K^4$, denote optional double bonds;

A' and B' are optional aromatic rings fused to ring A, only one of which is present in the compound, so as to form a fused tricyclic system; and when B' is present, the group Z is present, and
when A' is present, the group Z is absent; and R is H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, heteroaryl, heterocycle, $(C_1-C_{20})$alkylsulfoxy, $(C_6-C_{30})$arylsulfoxy, heteroarylsulfoxy, $(C_1-C_{20})$alkoxycarbonyl, amino, NH$(C_1-C_6)$alkyl, N$((C_1-C_6)$alkyl$)_2$, tri$(C_1-C_{20})$ammonium $(C_1-C_{20})$alkyl, heteroaryl$(C_1-C_{20})$alkyl, heteroaryl having quarternary nitrogen, heteroarylcarbonyl having quaternary nitrogen, saccharide, of $M^+$ optionally when Z" is oxygen, wherein M is an alkali metal;

$R^1$ is $(C_6-C_{30})$aryl, heteroaryl, heterocycle, $(C_1-C_{20})$alkylthio, $(C_1-C_{20})$alkyl-S(O)—, $(C_1-C_{20})$alkyl-SO$_2$, —SO$_3(C_1-C_{20})$alkyl, saccharide, $(C_1-C_{20})$alkylphosphate, $(C_1-C_{20})$alkylphosphonate, $(C_6-C_{30})$arylthio, $(C_6-C_{30})$aryl-S(O)—, $(C_6-C_{30})$aryl-SO$_2$, —SO$_3(C_6-C_{30})$aryl, $(C_6-C_{30})$arylphosphate, $(C_6-C_{30})$arylphosphonate, or $R^1$ is $(C_1-C_{20})$alkyl substituted by $R^2$;

$R^2$ is $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, hydroxyl, —COOR$^x$, —SO$_3$R$^x$, $(C_1-C_{20})$alkylthio, $(C_6-C_{30})$arylthio, $(C_1-C_{20})$alkyl-S(O)—, $(C_1-C_{20})$alkyl-SO$_2$—, nitro, amino, NH$(C_1-C_6)$alkyl, NH$(C_1-C_6)$alkynyl, N$((C_1-C_6)$alkyl$)_2$, or N$((C_1-C_6)$alkynyl$)_2$, mercapto, saccharide, or trifluoromethyl;

or when Z or Z' is NR$^1$R$^1$, R$^1$R$^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substitutes selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —COOR$^x$, —SO$_2$R$^x$, —SO$_3$R$^x$, $(C_1-C_{20})$alkyl-S(O)—, $(C_1-C_{20})$alkyl-SO$_2$—, phosphate, $(C_1-C_{20})$alkylphosphate, $(C_1-C_{20})$alkylphosphonate, nitro, amino, NH$(C_1-C_6)$alkyl, NH$(C_1-C_6)$alkynyl, N$((C_1-C_6)$alkyl$)_2$, N$((C_1-C_6)$alkynyl$)_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

$R^x$ is H or $(C_1-C_6)$alkyl;

when Z or Z" comprises a nitrogen moiety, a hydrogen of the Z or Z' nitrogen moiety may be replaced by the group L, wherein L is an amino acid radical, a peptide radical having up to 20 amino acid moieties, or any other small molecule that is a substrate for a nonluciferase; with the proviso that when L is an amino acid radical or a peptide radical, at least one of W¹ or a $W^2$ is not H;

when Z is a hydroxyl group or a nitrogen moiety, H of the hydroxyl or nitrogen moiety may be replaced by (HO)$_2$P(O)—OCH$_2$—, sulfo, —PO$_3$H$_2$, or by a cephalosporanic acid attached to the group Z via a carbon chain of one 10 about 12 carbon atoms; with the proviso that the sulfo or the —PO$_3$H$_2$ group is attached to the hydroxyl oxygen via a $(C_1-C_6)$alkylene group;

when Z or Z' is a hydroxyl group or a nitrogen moiety, or when Z"—R is a hydroxyl group, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds, linker is attached to L' via an oxygen atom or an NH group it one terminus of the linker and the other terminus of the linker forms an ether, ester, or amide linkage with a group Z, Z', or Z"—R;

when Z is OR¹, formula II is optionally a dimer connected at the two A rings via linker comprising a $(C_1-C_{12})$alkyl diradical that is optionally interrupted by one to four O atoms, N atoms, or an optionally substituted aryl, heteroaryl, or heterocycle group to form a bridge between the dimer of formula II, and the R¹ group of each Z group connecting the dimer of formula II is replaced by the bridge;

provided that a saccharide is not directly attached to $K^3$;

A⁻ is an anion, present when a quaternary nitrogen is present;

or a salt thereof.

In yet another embodiment, the invention provides a compound of formula IIA:

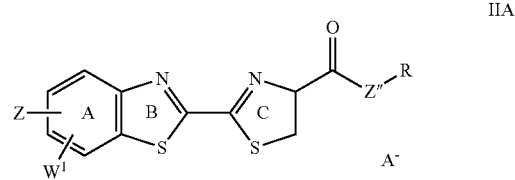

IIA wherein
Z is OR¹, NHR¹, or NR¹R¹;
Z" is O, S, NH, NHR, or N=N;
W¹ is H, halo, hydroxyl, $(C_1-C_6)$alkyl, or $(C_1-C_6)$alkoxy;
R is H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, heteroaryl, heterocycle, $(C_1-C_{20})$alkylsulfoxy, $(C_6-C_{30})$arylsulfoxy, heteroarylsulfoxy, $(C_1-C_{20}$alkoxycarbonyl, amino NH$(C_3-C_6)$alkyl, N$((C_1-C_6)$alkyl$)_2$, tri$(C_1-C_{20})$ammonium $(C_1-C_{20})$alkyl, heteroaryl$(C_1-C_{20})$alkyl, heteroaryl having quaternary nitrogen, heteroarylcarbonyl having quaternary nitrogen, saccharide, or $M^+$ optionally when is oxygen, wherein M is in alkali metal;

$R^1$ is $(C_6-C_{30})$aryl, heteroaryl, heterocycle, $(C_1-C_{20})$alkylthio, $(C_1-C_{20})$alkyl-S(O)—, $(C_1-C_{20})$alkyl-SO$_2$, —SO$_3(C_1-C_{20})$alkyl, saccharide, $(C_1-C_{20})$alkylphaphate, $(C_1-C_{20})$alkylphosphonate, $(C_6-C_{30})$arylthio, $(C_6-C_{30})$aryl-S(O)—, $(C_6-C_{30})$aryl-SO$_2$, —SO$_3(C_6-C_{30})$aryl, $(C_6-C_{30})$arylphosphate, $(C_6-C_{30})$arylphosphonate, or $R^1$ is $(C_1-C_{20})$alkyl substituted by $R^2$;

$R^2$ is $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, hydroxyl, —COOR$^x$, —SO$_3$R$^x$, $(C_1-C_{20})$alkylthio, $(C_6-C_{30})$arylthio, $(C_1-C_{20})$alkyl-S(O)—, $(C_1-C_{20})$alkyl-SO$_2$—, nitro, amino, NH$(C_1-C_6$-alkyl, NH$(C_1-C_6)$alkynyl, N$((C_1-C_6)$alkyl$)_2$, or N$((C_1-C_6)$alkynyl$)_2$, mercapto, saccharide, or trifluoromethyl;

or when Z or Z' is NR¹R¹, R¹R¹ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —COOR$^x$, —SO$_2$R$^x$, —SO$_3$R$^x$, $(C_1-C_{20})$alkyl-S(O)—, $(C_1-C_{20})$alkyl-SO$_2$—, phosphate, $(C_1-C_{20})$alkylphosphate, $(C_1-C_{20})$alkylphosphonate, nitro, amino NH$(C_1-C_6)$alkyl, NH$(C_1-C_6)$alkynyl, N$((C_1-C_6)$alkyl$)_2$, N$((C_1-C_6)$alkynyl$)_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

R$^x$ is H or $(C_1-C_6)$alkyl;

when Z is OR$^1$, formula IIA is optionally a dimer connected at the two A rings via linker comprising a $(C_1-C_{12})$ alkyl diradical that is optionally interrupted by one to four O atoms, N atoms, or an optionally substituted aryl, heteroaryl, or heterocycle group to form a bridge between the dimer of formula IIA, and the R$^1$ group of each Z group connecting the dimer of formula II is replaced by the bridge;

provided that a saccharide is not directly attached to K$^3$;

A$^-$ is an anion, present when a quaternary nitrogen is present;

or a salt thereof.

Other deriviates and their use in luminogenic assays is described hereinbelow.

The use of the luciferin derivatives described herein can result in an assay which produces a measurable change in optical properties upon interaction with a nonluciferase molecule, which interaction may alter the structure of the luciferin derivative. As described herein, the product of a reaction between a luciferin derivative and a nonluciferase enzyme or other molecule of interest need not be D-luciferin or aminoluciferin. For example, a luciferin derivative may include a substrate that includes a reactive chemical group for a nonluciferase enzyme linked to luciferin or aminoluciferin via a chemical linker. Transformation of the reactive chemical group of the derivative by the nonluciferase enzyme may yield a product that contains (retains) a portion of the substrate, a portion of the chemical linker, the chemical linker, or a portion of the substrate and the chemical linker, and that product is a substrate for luciferase. Also provided are luciferin derivatives which, after interaction with a nonluciferase enzyme or other molecule, may yield a product that optionally undergoes one or more further reactions, e.g., β-elimination, to yield a suitable substrate for luciferase. Luciferin derivatives in which the backbone of luciferin is further modified in its ring structure, e.g., a quinolyl or napthyl luciferin, are provided, as well as advantageously providing modifications at the carboxy position of the thiazole ring, to provide improved characteristics to the luciferin derivative. Derivatives with certain modifications provide for or improve assays for certain nonluciferase enzymes or molecules. For instance, as described hereinbelow, a pH insensitive derivative of luciferin was identified that is useful in biological assays that may be run at a pH other than physiological pH, i.e., less than about pH 7.0 and greater than about 7.9. Thus, bioluminescent methods that employ a luciferin derivative of the invention may be used to detect one or more molecules, e.g., an enzyme, a cofactor for an enzymatic reaction such as ATP, an enzyme substrate, an enzyme inhibitor, an enzyme activator, or OH radicals, or one or more conditions, e.g., redox conditions.

In one embodiment, the methods employ a compound of formula III:

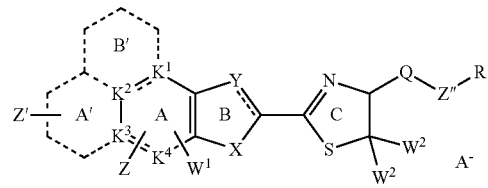

III wherein

Y is N, N-oxide, N—$(C_1-C_6)$alkyl, or CH;

X is S, O, CH=CH, N=CH, or CH=N;

Z and Z' are independently H, OR, NHR, or NRR;

Z'' is O, S, NH, NHR, or N=N;

Q is carbonyl or CH$_2$;

W$^1$ is H, halo, $(C_1-C_6)$alkyl, $(C_2-C_{20})$alkenyl, hydroxyl, or $(C_1-C_6)$alkoxy; or W$^1$ and Z are both keto groups on ring A, and at least one of the dotted lines denoting optional double bonds in ring A is absent;

each W$^2$ is independently H, halo, $(C_1-C_6)$alkyl, $(C_2-C_4)$alkenyl, hydroxyl, or $(C_1-C_6)$alkoxy;

each of K$^1$, K$^2$, K$^3$, and K$^4$ are independently CH, N, N-oxide, or N—$(C_1-C_6)$alkyl and the dotted lines between K$^1$ and K$^2$, and K$^3$ and K$^4$, denote optional double bonds;

A' and B' are optional aromatic rings fused to ring A, only one of which is present in the compound, so as to form a fused tricyclic system; and when B' is present, the group Z is present, and when A' is present, the group Z is absent, and the dotted line in ring B is an optional double bond;

each R is independently H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, heteroaryl, heterocycle, $(C_1-C_{20})$alkylsulfoxy, $(C_6-C_{30})$arylsulfoxy, heteroarylsulfoxy, $(C_1-C_{20})$alkylsulfonyl, $(C_6-C_{30})$arylsulfonyl, heteroarylsulfonyl, $(C_1-C_{20})$alkylsulfinyl, $(C_6-C_{30})$arylsulfinyl, heteroarylsulfinyl, $(C_1-C_{20})$alkoxycarbonyl, amino, NH$(C_1-C_6)$alkyl; N$((C_1-C_6)$alkyl$)_2$, tri$(C_1-C_{20})$ammonium$(C_1-C_{20})$alkyl, heteroaryl$(C_1-C_{20})$alkyl, heteroaryl having quaternary nitrogen, heteroarylcarbonyl having quaternary nitrogen, $(C_6-C_{30})$arylthio, $(C_1-C_{20})$alkylphosphate, $(C_1-C_{20})$alkylphosphonate, $(C_6-C_{30})$arylphosphate, $(C_6-C_{30})$arylphosphonate, phosphate, sulfate, saccharide, or M' optionally when Z'' is oxygen, wherein M is an alkali metal;

or when Z or Z' is NR$^1$R$^1$,R$^1$R$^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —COOR$^x$, —SO$_2$R$^x$, —SO$_3$R$^x$, nitro, amino, $(C_1-C_{20})$alkyl-S(O)—, $(C_1-C_{20})$alkyl-SO$_2$—, phosphate, $(C_1-C_{20})$alkylphosphate, $(C_1-C_{20})$alkylphosphonate, NH$(C_1-C_6)$alkyl, NH$(C_1-C_6)$alkynyl, N$((C_1-C_6)$alkyl$)_2$, N$((C_1-C_6)$alkynyl$)_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

R$^x$ is H, $(C_1-C_6)$alkyl, or $(C_6-C_{30})$aryl;

when Z or Z' comprises a nitrogen moiety, one or both of the hydrogens of the Z or Z' nitrogen moiety may be replaced by (CH$_1$—C$_{20}$)alkyl or the group L, wherein L is an amino acid radical, a peptide radical having up to 20 amino acid moieties, or any other small molecule that is a substrate for a nonluciferase; with the proviso that when L is an amino acid radical or a peptide radical, at least one $W^2$ is not H;

when Z is a hydroxyl group or a nitrogen moiety, H of the hydroxyl or nitrogen moiety may be replaced by $(HO)_2P(O)$—$OCH_2$—, sulfo, —$PO_3H_2$, or by a cephalosporanic acid attached to the group Z via a carbon chain of one to about 12 carbon atoms; with the proviso that when ring B is a thiazole ring, the sulfo or the —$PO_3H_2$ group is attached to the hydroxyl oxygen via a $(C_1-C_6)$alkylene group;

when Z or Z' is a hydroxyl group or a nitrogen moiety, or when Z"—R is a hydroxyl group, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds, linker is attached to L' via an oxygen atom or an NH group at one terminus of the linker and the other terminus of the linker forms an ether, ester, or amide linkage with a group Z, Z', or Z"—R;

when Z is OR, formula III is optionally a dimer connected at the two A rings via a linker comprising a $(C_1-C_{12})$alkyl diradical that is optionally interrupted by one to four O atoms, N atoms, or an optionally substituted aryl, heteroaryl, or heterocycle group to form a bridge between the dimer of formula III, and the R group of each Z group connecting the dimer of formula III is replaced by the bridge;

A' is an anion, present when a quaternary nitrogen is present;

or a salt thereof;

provided that the compound of formula III is not aminoluciferin that has been modified to include a protease substrate via a peptide bond at the amino group which optionally also has a protected carboxyl group at position 5 on ring C, or any of luciferin 6'-methyl ether, luciferin 6'-chloroethyl ether, 6'-deoxyluciferin, 6'-luciferin-4-trifluoromethyl benzylether, luciferin 6'-phenytethylether, luciferin 6'-geranyl ether, luciferin 6'-ethyl ether, 6'-luciferin prenyl ether, 6'-luciferin 2-picolinylether, 6'-luciferin 3-picolinylether, 6'-luciferin 4-picolinyl ether, luciferin 6'-benzyl ether, D-luciferin-O-β-galacto-pyranoside, D-luciferin-O-sulfate, D-luciferin-O-phosphate, D-luciferyl-L-phenylalanine, and D-luciferyl-L-N'-arginine; or not a substrate for one or more cytochrome P450 enzymes but optionally may be a substrate for a non-cytochrome P450 enzyme.

In one embodiment, a bioluminescent assay method to detect one or more nonluciferase enzymes is provided. The method includes contacting a sample suspected of having one or more nonluciferase enzymes, a substrate or a co-factor for the reaction, with a corresponding reaction mixture that includes a derivative of luciferin or a derivative of aminoluciferin that is a substrate for the nonluciferase enzyme. In one embodiment, the derivative is one having a modification in the benzene ring of D-luciferin that includes a recognition site for the nonluciferase enzyme, e.g., for a monoamine oxidase. In another embodiment, the derivative is one having a modification in the thiazole ring (ring B) of D-luciferin which derivative is a substrate for luciferase and optionally a substrate for a nonluciferase enzyme. In another embodiment, the derivative is one having a modification in the thiazole ring (ring C) of luciferin that includes a recognition site for on enzyme of interest, e.g., acetylcholinesterase. In another embodiment, the derivative is one having a modification to one of the rings that includes a recognition site for the enzyme of interest, as well as a further modification to that ring or one or more of the other rings.

Previously, enzymes that could be tested with luciferin derivatives were those that interacted well close to aromatic structures (D-luciferin or aminoluciferin) and interacted with a recognition site (substrate) that was stable close to aromatic structures. As described herein, luciferin derivatives that are substrates for nonluciferase enzymes that do not necessarily react with structures close to aromatic rings or those with recognition sites that are more stable when attached to an aryl chain than an aromatic structure, were identified. For example, an assay which employed previously described luciferin derivatives with a phosphate group attached through the hydroxyl group on the benzene ring, i.e., a substrate for alkaline phosphatase, was limited by high background because the phosphate spontaneously hydrolyzed. Attaching the phosphate to an aryl chain is likely stabilizing, which may allow for a derivative that is a substrate for alkaline phosphatase and may reduce the background. Thus, the sensitivity and utility of a phosphatase assay such as an alkaline phosphatase assay is increased employing a luciferin derivative of the invention.

Generally, luciferase substrates have a free hydroxyl (luciferin) or free amino group (amino luciferin) on the benzene ring. Alternate backbones for luciferin, like quinolinyl luciferin or napthyl luciferin, with free hydroxyl or free amino groups, are luciferase substrates. To expand the scaffolding upon which modifications can be made to luciferin and result in a luciferase substrate, luciferin derivatives with aryl or other chains attached through the oxygen or nitrogen on the A ring of luciferin were prepared. Derivatives with nitrogen on the A ring were utilized by beetle luciferase to generate bright luminescence. Moreover, HPLC verified that luciferin derivatives with aryl or alkyl chains decreased in concentration when acted upon by a thermostable luciferase (as opposed to wild-type luciferin contamination causing the light and decreasing in concentration). Such luciferin derivatives are also shown herein to be utilized by other luciferases. Moreover, those scaffolds, e.g., luciferase substrates that have groups attached through the oxygen or nitrogen on the A ring of luciferin, may be modified to include a substrate for an enzyme, a binding site for another molecule, or any reactive group useful to measure a molecule such as a cellular bioactive molecule, including second messengers, e.g., a cAMP binding site, for instance, to measure cAMP, calmodulin, e.g., to measure calcium, or to measure IP3.

In one embodiment, a method to detect luciferase employs a compound of formula IIIA:

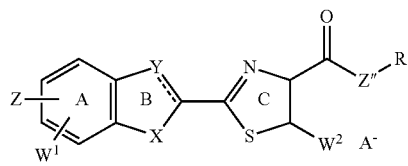

IIIA wherein

Y is N, N-oxide. N—$(C_1-C_6)$alkyl, or CH;

X is S, O, CH=CH, N=CH, or CH=N;

Z is H, OR, NHR, or NRR;

Z" is O, S, NH, NHR, or N=N;

W¹ is H, halo, hydroxyl, $(C_1-C_6)$alkyl, $(C_2-C_{20})$alkenyl, $(C_1-C_6)$alkoxy;

W² is H, F, or methyl;

the dotted line in ring B is an optional double bond;

each R is independently H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, heteroaryl, heterocycle, $(C_1-C_{20})$alkylsulfoxy, $(C_6-C_{30})$arylsulfoxy, heterarylsulfoxy, $(C_1-C_{20})$alkylsulfonyl, $(C_6-C_{30})$arylsulfonyl, heteroarylsulfonyl, $(C_1-C_{20})$alkylsulfinyl, $(C_6-C_{30})$arylsulfinyl, heteroarylsulfinyl, $(C_1-C_{20})$alkoxycarbonyl, amino, NH$(C_1-C_6)$alkyl, N$((C_1-C_6)$alkyl$)_2$, tri$(C_1-C_{20})$ammonium$(C_1-C_{20})$alkyl, heteroaryl$(C_1-C_{20})$alkyl, heteroaryl having quaternary nitrogen, heteroarylcarbonyl having quaternary nitrogen, $(C_6-C_{30})$arylthio, $(C_1-C_{20})$alkylphosphate, $(C_1-C_{20})$alkylphosphonate, $(C_6-C_{30})$arylphosphate, $(C_6-C_{30})$arylphosphonate, phosphate, sulfate, saccharide, or M⁺ optionally when Z" is oxygen, wherein M is an alkali metal;

or when Z or Z' is NR¹R¹, R¹R¹ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —COOR$^x$, —SO$_2$R$^x$, —SO$_3$R$^x$, nitro, amino, $(C_1-C_{20})$alkyl-S(O)—, $(C_1-C_{20})$alkyl-SO$_2$—, phosphate, $(C_1-C_{20})$alkylphosphate, $(C_1-C_{20})$alkylphosphonate, NH$(C_1-C_6)$alkyl, NH$(C_1-C_6)$alkynyl, N$((C_1-C_6)$alkyl$)_2$, N$((C_1-C_6)$alkynyl$)_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

R$^x$ is H, $(C_1-C_6)$alkyl, or $(C_6-C_{30})$aryl;

when Z is OR, formula III is optionally a dimer connected at the two A rings via a linker comprising a $(C_1-C_{12})$alkyl diradical that is optionally interrupted by one to four O atoms, N atoms, an optionally substituted aryl, heteroaryl, or heterocycle group, or a combination thereof, to form a bridge between the dimer of formula III, and the R group of each Z group connecting the dimer of formula III is replaced by the bridge;

A⁻ is an anion, present when a quaternary nitrogen is present;

or salt thereof, provided that the compound of formula III is not aminoluciferin that has been modified to include a protease substrate via a peptide bond at the amino group which optionally also has a protected carboxyl group at position 5 on ring C, or any of luciferin 6'-methyl ether, luciferin 6'-chloroethyl ether, 6'-deoxyluciferin, 6'-luciferin-4-trifluoromethyl benzylether, luciferin 6'-phenylethylether, luciferin 6'-geranyl ether, luciferin 6'-ethyl ether, 6'-luciferin prenyl ether, 6'-luciferin 2-picolinylether, 6'-luciferin 3-picolinylether, 6'-luciferin 4-picolinyl ether, luciferin 6'-benzyl ether, D-luciferin-O-β-galacto-pyranoside, D-luciferin-O-sulfate, D-luciferin-O-phosphate, D-luciferyl-L-phenylalanine, and D-luciferyl-L-N'-arginine; or not a substrate for one or more cytochrome P450 enzymes but optionally may be a substrate for a non-cytochrome P450 enzyme.

Furthermore, the inclusion of a thiol compound with a luciferin derivative in a luciferase-mediated assay may effectively stabilize the luminescence of the reaction, thereby providing for "glow" kinetics, i.e., luminescent intensity of the luciferase-mediated reaction is relatively constant overtime after addition of the derivative. Such compounds may be also be used in bioluminogenic assays monitoring the presence or activity of nonluciferase enzymes or a nonenzymatic biological reaction.

For derivatives that function directly as a substrate for luciferase, as well as optionally a substrate of a nonluciferase enzyme or other molecules, the derivative may be employed to directly detect luciferase, or a co-factor, inhibitor, or activator of the luciferase reaction. If the derivative is a prosubstrate for luciferase, i.e., the product of a reaction between the derivative and the nonluciferase enzyme is a substrate for luciferase, sequential or concurrent reactions for the nonluciferase enzyme and the luciferase may be conducted. For instance, an assay for a nonluciferase enzyme that includes a luciferin derivative that is a prosubstrate for luciferase may be conducted in a single reaction vessel and a beetle luciferase reaction mixture added to that vessel. In another embodiment, a reaction mixture for an assay for a nonluciferase enzyme that includes a luciferin derivative that is a prosubstrate for luciferin may be conducted in a single reaction vessel and a portion of that reaction added to a different vessel having a beetle luciferase reaction mixture. Alternatively, the nonluciferase and luciferase reactions may be conducted simultaneously in the same vessel.

The invention thus provides in an embodiment a method to detect or determine the presence or amount of a molecule for a nonluciferase enzyme-mediated reaction in a sample. The method includes contacting a sample, a first reaction mixture for a nonluciferase enzyme-mediated reaction, and a derivative of luciferin which is a substrate for the nonluciferase enzyme, so as to yield a first mixture comprising a luminogenic product that is a substrate for a luciferase. In one embodiment, the derivative is a compound of formula I. In another embodiment, the derivative is a compound of formula II. At least a portion of the first mixture is contacted with a second reaction mixture for a luciferase-mediated reaction, so as to yield a second mixture. Then luminescence in the second reaction is detected or determined, thereby detecting or determining the presence or amount of a molecule for the nonluciferase enzyme-mediated reaction in the sample, e.g., compared to a control. In one embodiment, the derivative is a substrate for a transferase, e.g. glutathione S transferase (GST). Exemplary derivatives useful to detect GST are shown in FIG. 12. In some embodiments, a second nonluciferase enzyme may be used to further chemically transform the product of the first nonluciferase enzyme-mediated reaction to yield a substrate for a luciferase. For example, the sample, nonluciferase reaction mixture or luciferase reaction mixture may include an esterase, or the esterase may be added separately.

In one embodiment, derivatives of luciferin having on ester modification are employed in methods of the invention, such as those to detect nonluciferase enzymes including P450 enzymes or monoamine oxidases (MAOs), or other enzymes such as flavin monoamine oxidases (FMOs), glutathione S transferases (GSTs), phosphatases, e.g., alkaline phosphatases (AP), or sulfatases, as those derivatives may have improved properties as a non luciferase enzyme substrate. In particular, as shown herein, the addition of an ester group at the carboxy position of the thiazole ring of a luciferin derivative provided a substrate that was recognized by two P450 enzymes, 2D6 and 2C19, that did not react with previously described luciferin derivatives that are substrates of cytochrome P450 enzymes (see U.S. published application 20040171099).

In an alternate embodiment, a method to detect or determine the presence or amount of a molecule for a first nonluciferase enzyme-mediated reaction in a sample is provided wherein the method includes contacting a sample, a reaction mixture for a nonluciferase-mediated enzyme reaction and a luciferase-mediated reaction, and a derivative of luciferin which is a substrate for the nonluciferase enzyme yielding a mixture. A reaction between the nonluciferase enzyme and the derivative yields a luminogenic product that is a substrate for the luciferase. Luminescence in the mixture is detected or determined, thereby detecting or determining the presence or amount of a molecule for the nonluciferase-mediated reaction in the sample.

The invention also provides an embodiment directed to a method to detect the presence or amount of a non-enzymatic molecule in a sample. The method includes contacting a sample, a first reaction mixture for a nonenzyme-mediated reaction and a derivative of luciferin which in the presence of the molecule yields a luminogenic product that is a substrate for a luciferase, and contacting a portion of the first reaction and a second reaction mixture for a luciferase-mediated reaction, to yield a second reaction, then luminescence in the second reaction is detected or determined, thereby detecting or determining the presence or amount of the molecule. For instance, a mixture is provided having a sample, a first reaction mixture for a nonenzyme-mediated reaction and a derivative of luciferin which in the presence of the molecule yields a a luminogenic product that is a substrate for a beetle luciferase. At least a portion of the first mixture and a second reaction mixture for a beetle luciferase-mediated reaction are mixed, to yield a second mixture, and then luminescence in the second mixture is detected or determined, thereby detecting or determining the presence or amount of the molecule.

For the biolumingenic assays described herein which employ luciferin derivatives with a lower background luminescence than D-luciferin or aminoluciferin, those assays can use lower amounts, e.g., because small changes in luminescence can be detected, or higher amounts, e.g., in reactions that are improved by increased amounts of substrate, of the derivative, and those derivatives may have improved reactivity, e.g., with a nonluciferase enzyme. In addition, for any of the bioluminogenic assays described herein, other reagents may be added to reaction mixtures, including but not limited to those that inhibit or prevent inactivation of luciferase, or otherwise extend or enhance signal.

Also provided is a method to identify a modulator of a nonluciferase enzyme-mediated reaction. The method includes contacting one or more agents, a first reaction mixture for a nonluciferase enzyme-mediated reaction, and a derivative of luciferin which is a substrate for the nonluciferase enzyme, so as to yield a first mixture, or providing such a mixture. The first mixture in the absence of the one or more agents includes a luminogenic product that is a substrate for a beetle luciferase. At least a portion of the first mixture and a second reaction mixture for a beetle luciferase-mediated reaction are mixed, so as to yield a second mixture. Luminescence in the second mixture is compared with a control mixture, thereby identifying whether one or more of the agents modulates the nonluciferase enzyme-mediated reaction.

In a further embodiment of the present invention, luciferin derivatives that retain activity directly as a substrate for luciferase may be utilized to inactivate or inhibit the luciferase enzyme, e.g., by covalent modification thereof, or as a competitive or noncompetitive inhibitor thereof. This embodiment provides a method to screen for compounds that prevent the inactivation of luciferase. Also provided is a method to identify a modulator of a luciferase-mediated reaction using a luciferin derivative of the present invention.

The invention further provides a fluorogenic method which employs a derivative of a fluorophore that is modified to detect one or more molecules, e.g., an enzyme, a cofactor for an enzymatic reaction such as ATP, an enzyme substrate, an enzyme inhibitor, an enzyme activator, or OH radicals, or one or more conditions, e.g., redox conditions. The invention thus provides for bioluminogenic and fluorogenic assays to detect the amount, activity or presence of a molecule in a sample.

The invention also provides further embodiments directed to fluorogenic assays and derivatives of fluorophores which are a substrate for a nonluciferase nonproteolytic enzyme. Thus, a method to detect or determine the presence or amount of a molecule for a nonprotease enzyme-mediated reaction in a sample by a fluorescent method is provided. The method includes contacting a sample, a first reaction mixture for a nonluciferase, nonproteolytic enzyme-mediated reaction, and a derivative of a fluorophore which includes a substrate for the enzyme, so as to yield a first mixture, wherein if the molecule is present in the sample, the first mixture composes a hydroxy fluorescent product. The interaction between the enzyme and the derivative optionally produces an minimum and/or aldehyde intermediate which optionally undergoes a noncatalytic β-elimination to yield the hydroxy fluorescent product. Fluorescence in the mixture is detected or determined, thereby detecting or determining the presence or amount of a molecule for the nonprotease enzyme mediated reaction in the sample. The invention also provides for methods of using fluorophore derivatives of the invention to identify inhibitor, activators, substrates or co-factors for enzymatic reactions.

The invention provides compositions or kits having one or more luciferin derivatives and/or fluorophore derivatives of the invention. The kits may optionally contain other reagents, e.g., enzyme, reaction mixtures, and the like. The bioluminogenic reaction mixtures, compositions and kits of the invention may optionally include an agent that slows the reaction rate, e.g., amino methyl benzothiazole (AMBT) or aminophenyl methyl benzothiazol (APMBT), see U.S. published application 20040171099, yielding glow kinetics and/or an agent that stabilizes light production, e.g., a thiol or coenzyme A.

BRIEF DESCRIPTION OF THE FIGURES

FIG. 2. Exemplary luciferin derivatives for enzymes.

FIG. 3. Structures of 5'-fluoroluciferin.

FIGS. 5A-8. Exemplary substrates.

FIG. 6. Redox substrates.

FIG. 17. RLU for a series of luciferin derivatives and each of a panel of P450 enzymes.

FIG. 18. RLU for a series of luciferin derivatives and each of a panel of P450 enzymes.

FIGS. 19A-19C. Structures of exemplary derivatives useful to detect P450 enzymes.

FIG. 50. Inhibition of CYP3A4 activity by nifedipine in a reaction with luciferin-PPXE (6'-((4-phenylpiperazin-1-yl)methyl)benzyloxy)-luciferin.

FIG. 51. CYP3A4 activity in human hepatocytes hepatocytes after treatment with rifampicin, ketoconazole, or rifampicin and ketoconazole, in a reaction with luciferin-PPXE.

FIG. 54. Structures of derivatives of luciferin which may be a substrate for different luciferases.

DETAILED DESCRIPTION OF THE INVENTION

I. Definitions

Figure 1:
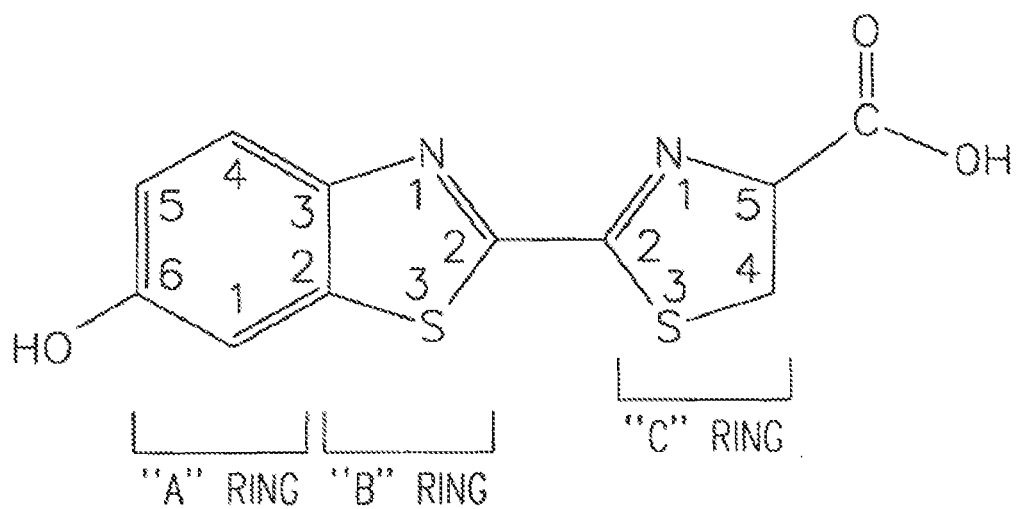
FIG. 1. Numbering of ring atoms in the six membered ring ("A ring" or "ring A"), five mannered center ring ("B ring" or "ring B"), and other five membered ring ("C ring" or "ring C") of beetle luciferin (D-luciferin).

As used herein, the following terms and expressions have the indicated meanings. It will be appreciated that the compounds of the present invention contain asymmetrically substituted carbon atoms, and may be isolated in optically active or racemic forms. It is well known to the art how to prepare optically active forms, such as by resolution of racemic forms or by synthesis from optically active starting materials. All chiral, diastereomeric, racemic forms and all geometric isomeric forms of a structure are part of this invention.

Specific values listed below for radicals, substituents, and ranges, are for illustration only; they do not exclude other defined values or other values within defined ranges for the radicals and substituents.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, the suitable indicated groups can include, e.g.; —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR —S(=O)$_2$O$^-$, —S(=O)$_2$OH, —S(=O)$_2$R, —OS(=O)$_2$OR, —S(=O)$_2$NR, —S(=O)R, —OP(=O)O$_2$RR, —P(=O)O$_2$RR —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(O)SR, —C(S)SR, —C(O)NRR, —C(S)NRR, —C(NR)NRR, where each X is independently a halogen ("halo"): F, Cl, BR, or I; and each R is independently H, alkyl, aryl, heteroaryl, heterocycle, a protecting group or prodrug moiety. As would be readily understood by one skilled in the art, when a substituent is keto (=O) or thioxo (=S), or the like, then two hydrogen atoms on the substituted atom are replaced.

"Stable compound" and "stable structure" are meant to indicate a compound that is sufficiently robust to survive isolation to a useful degree of purity from a reaction mixture. Only stable compounds are contemplated by and claimed in the present invention, however, certain unstable compounds, for example, those that cannot easily be isolated, can be employed in the methods described herein.

One diastereomer may display superior properties or activity compared with another. When required, separation of the racemic material can be achieved by HPLC using a chiral column or by a resolution using a resolving agent such as camphonic chloride as described by Thomas S. Tucker, et al., *J. Med. Chem.* 1994, 37,2437-2444. A chiral compound may also be directly synthesized using a chiral catalyst or a chiral ligand, e.g. Mark A. Huffman, et al., *J. Org. Chem.* 1995, 60, 1590-1594.

As used herein, the term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylate).

The term "alkenyl" refers to a monoradical branched or unbranched partially unsaturated hydrocarbon chain (i.e. a carbon-carbon, sp$^2$ double bond). In one embodiment, an alkenyl group can have from 2 to 10 carbon atoms, or 2 to 6 carbon atoms. In another embodiment, the alkenyl group has from 2 to 4 carbon atoms Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In one embodiment, alkoxy groups include, e.g., methoxy, ethoxy, n-propoxy, iso-propoxy, n-butoxy, sec butoxy, n-pentoxy, n-hexoxy, 1,2-dimethylbutoxy, and the like. The alkoxy can be unsubstituted or substituted.

As used herein, "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In one embodiment, the haloalkyl can be substituted with 1, 2, 3, 4, or 5 halo groups. In another embodiment, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-20 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrroloyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide, oxygen, sulfur, and N(Z) wherein Z is absent or is H, O, alkyl, aryl, or $(C_1-C_6)$ alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) or a thioxo group attached to the ring. Non-limiting examples of heterocycle groups, include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine. piperazinyl, piperidine, piperidyl, pyrazolidino, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W. A. Benjamin, New York, 1968), particularly Chapters 1, 3,4,6, 7, and 9; *"The Chemistry of Heterocyclic Compounds A Series of Monographs"* (John Wiley & Sons, New York, 1950 to present), in particular Volumes 13, 14, 16, 19, and 28; and *J. Am. Chem. Soc.* 1960, 82, 5566. In one embodiment, "heterocycle" includes a "carbocycle" as defined herein, wherein one or more (e.g. 1, 2, 3, or 4) carbon atoms have been replaced with a heteroatom (e.g. O, N, or S).

Examples of heterocycles, by way of example and not limitation, include, dihydroypyridyl, tetrahydropyridyl (piperidyl), thiazolyl, tetrahydrothiophenyl, sulfur oxidized tetrahydrothiophen, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded hetetocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 10 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarboxy" refers to —O—C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —NH$_2$. The amino group can be optionally substituted as defined herein for the term "substituted". The term "alkylamino" refers to —NR; wherein at least one R is alkyl and the second R is alkyl or hydrogen. The term "acylamino" refers to N(R)C(=O)R, wherein each R is independently hydrogen, alkyl, or aryl.

The term "amino acid," includes a residue of a natural amino acid (e.g. Ala, Arg, Asn, Asp, Cys, Glu, Gln, Gly, His, Hyl, Hyp, He, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine) The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example. Greene, T. W.; Wutz, P. G. M. *Protecting Groups In Organic Synthesis*. $2^{nd}$ edition, John Wiley & Sons, Inc., New York (1991) and references cited therein).

The term "peptide" describes a sequence of 2 to 35 amino acids (e.g. as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids. Peptide derivatives can be prepared as disclosed in U.S. Pat. Nos. 4,612,302; 4,853,371; and 4,684,620, or as described in the Examples herein below. Peptide sequences specifically recited herein are written with the amino terminus on the left and the carboxy terminus on the right.

The term "saccharide" refers to a sugar or other carbohydrate, especially a simple sugar. The saccharide can be a $C_6$-polyhydroxy compound, typically $C_6$-pentahydroxy, and often a cyclic glycal. The term includes the known simple sugars and their derivatives, as well as polysaccharides with two or more monosaccaride residues. The saccharide can include protecting groups on the hydroxyl groups, as described above in the definition of amino acids. The hydroxy groups of the saccharide can be replaced with one or more halo or amino groups. Additionally, one or more of the carbon atoms can be oxidized, for example to keto or carboxyl groups.

The term "interrupted" indicates that another group is inserted between two adjacent carbon atoms (and the hydrogen atoms to which they are attached (e.g., methyl ($CH_3$) (methylene ($CH_2$) or methine (CH))) of a particular carbon chain being referred to in the expression using the term "interrupted, provided that each of the indicated atoms" normal valency is not exceeded, and that the interruption results in a stable compound. Suitable groups that can interrupt a carbon chain include, e.g., with one or more non-peroxide oxy (—O—), thio(—S—), imino (—N(H)—), methylene dioxy (—OCH$_2$O—), carbonyl (—C(=O)—), carboxy (—C(=O)O—), carbonyldioxy (—OC(=O)—), carboxylato (—OC(=O)—), imine (C=NH), sulfinyl (SO) and sulfonyl ($SO_2$). Alkyl groups can be interrupted by one ore more (e.g., 1, 2, 3, 4, 5, or about 6) of the aforementioned suitable groups. The site of interruption can also be between a carbon atom of an alkyl group and a carbon atom to which the alkyl group is attached.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in an claim of the invention, the total number will be determined as set forth above.

The term "linker" as used herein is a carbon chain that covalently attaches two chemical groups together and optionally can self-cleave or if covalently bonded to a substrate for an enzyme, may be cleaved by that enzyme or another molecule, which chain is optionally interrupted by one or more nitrogen atoms, oxygen atoms, carbonyl groups, (substituted) aromatic rings, or peptide bonds.

The term "luciferase," unless specified otherwise, refers to a naturally occurring or mutant luciferase. The luciferase, if naturally occurring, may be obtained easily by the skilled from an organism. If the luciferase is one that occurs naturally or is a mutant, which retains activity in the luciferase-luciferin reaction, of a naturally occurring luciferase, it can be obtained readily from a culture of bacteria, yeast, mammalian cells, insect cells, plant cells, or the like, transformed to express a cDNA encoding the luciferase, or from an in vitro cell-free system for making the luciferase from a nucleic acid encoding same. Luciferases are available from Promega Corporation. Madison, Wis.

As used herein, a "fluorophore" includes a molecule which is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelengths that the fluorophore releases energy or fluoresces.

As used herein, a "bioluminogenic assay" or "bioluminogenic reaction" includes a reaction in which a product of a reaction between a nonluciferase enzyme and a derivative of luciferin or aminoluciferin is a substrate of luciferase or a product of a nonenzymatic reaction having a derivative of luciferin or aminoluciferin is a substrate for luciferase, or a reaction between a luciferase and a derivative of luciferin or aminoluciferin, is bioluminogenic, i.e., produces a measurable amount of light.

As used herein, "bioluminescence" is light produced as a result of a reaction between an enzyme and a substrate that generates light. Examples of such enzymes (bioluminescent enzymes) include firefly luciferase, click beetle luciferase. Renilla luciferase, cypridina luciferase, Aequorin photoprotein, obelin photoprotein and the like.

As used herein, a "bioluminogenic assay reagent" may include a substrate, as well as a cofactor(s) or other molecule(s) such as a protein, e.g., an enzyme, for a bioluminogenic reaction.

A "reaction mixture" may contain all reagents for a particular reaction, or may lack at least one of the reagents for the reaction. For example, a luciferase reaction mixture may contain reagents for the reaction except for a substrate for the luciferase, e.g., a reaction mixture useful to determine whether a test sample has a luciferase substrate. A reaction mixture for a nonluciferase enzyme may include all reagents for that reaction except for a molecule to be detected, e.g., the mixture contains all reagents except for a cofactor for the nonluciferase enzyme, and so the mixture is useful to detect the presence of the cofactor in a test sample.

As used herein a "derivative of luciferin" or a "derivative of aminoluciferin" is a molecule that is a substrate for a nonluciferase enzyme and a prosubstrate of a luciferase, a substrate for a luciferase, a substrate for a nonluciferase enzyme and a substrate for a luciferase, or is useful to detect molecules generated in nonenzymatic reactions. The derivatives of the invention have one or more modifications to one or more of the three rings and/or substituents attached to one or more of the rings of the D-luciferin or aminoluciferin backbone (see FIG. 1).

A "fluorogenic assay" or "fluorogenic reaction" includes a reaction in which a product of a reaction between a nonluciferase, nonproteolytic enzyme and a derivative of a fluorophore is fluorescent. A "fluorogenic assay reagent" may include a substrate, as well as a cofactor(s) or other molecule(s) such as a protein, e.g., an enzyme, for a fluorogenic reaction. Thus, the invention provides a method to detect or determine the presence or amount of a molecule for a nonprotease enzyme-mediated reaction in a sample.

II. Methods of the Invention

The invention provides a bioluminogenic or fluorogenic method which employs a derivative of luciferin or aminoluciferin or a derivative of a fluorophore to detect one or more molecules, e.g., an enzyme, a cofactor for an enzymatic reaction such as ATP, an enzyme substrate, an enzyme inhibitor, an enzyme activator, or OH radicals, or one or more conditions, e.g., redox conditions. The invention thus provides for bioluminogenic and fluorogenic assays to detect the amount, activity or presence of a molecule in a sample.

The methods may be used, for example, to determine the presence or amount of at least one molecule, e.g., a nonluciferase enzyme, a regulator of a nonluciferase enzyme, a nonluciferase enzyme substrate, and/or cofactors of the reaction, or a condition in a sample including but not limited to an animal, e.g., vertebrate, physiological fluid, e.g., blood, plasma, urine, mucous secretions and the like, a cell, cell lysate, cell supernatant, or purified fraction of a cell (e.g., a subcellular fraction). In one embodiment, the methods according to the present invention provide a rapid method for detecting one or more molecules in a single sample such as an aliquot of cells or a lysate thereof. In one embodiment, the method includes quantifying the presence, amount or specific activity of a molecule such as an enzyme, substrate or cofactor in a bioluminogenic assay or quantifying the presence or amount of an enzyme, substrate or cofactor in a fluorogenic assay. The intensity of the bioluminogenic or fluorogenic signal is a function of the presence or amount of the respective molecule. In addition, the reaction may contain one or more test agents. e.g., enzyme inhibitors or activators, and/or different concentrations of inhibitors or activators. In one embodiment, the method employs at least two different reactions, where the first reaction is a nonluciferase enzyme-mediated reaction and the second reaction is a beetle luciferase-mediated reaction. In another embodiment, the first reaction is a nonenzymatic reaction and the second reaction is a beetle luciferase-mediated reaction. In yet another embodiment, the method employs a single reaction, e.g., a beetle luciferase-mediated reaction or a fluorogenic reaction.

Thus, a bioluminogenic assay may directly or indirectly detect, e.g., measure, the amount, presence, or specific activity of, for example, a cofactor for an enzyme-mediated reaction, and enzyme, an enzyme substrate, an inhibitor of the enzyme, an activator of the enzyme, or a condition. For instance, in one embodiment, a beetle luciferase and a derivative of luciferin that is a substrate of the beetle luciferase may be employed in a bioluminogenic assay to detect ATP concentration. In another embodiment, a derivative of luciferin which is a substrate for a nonluciferase enzyme, for instance, a derivative which is a substrate of a monoamine oxidase, yields a product which is a substrate for a beetle luciferase, and so may be employed in a bioluminogenic assay to detect the oxidase. In one embodiment, the derivative is a prosubstrate of a beetle luciferase, which yields a product that is a substrate of luciferase but does not itself yield a substantial amount of light in a reaction with the beetle luciferase. In some embodiments, the derivative is a substrate for a nonluciferase enzyme or useful to detect another molecule, and a substrate for luciferase which yields a substantial amount of light. In this embodiment, the derivative is altered by luciferase but is generally inefficient in a light generating reaction.

In one embodiment, the invention provides a bioluminescent assay method to detect one or more nonluciferase enzymes. The method includes contacting a sample suspected of having one or more nonluciferase enzymes, or a substrate or a co-factor for the nonluciferase-mediated reaction, with a corresponding reaction mixture that includes a derivative of luciferin or a derivative of aminoluciferin that is a substrate for the nonluciferase enzyme. In one embodiment, the derivative is one having a modification in the A ring of D-luciferin that includes a recognition site for the nonluciferase enzyme, e.g., for a phosphatase. In another embodiment, the derivative is one having a modification in the B ring of D-luciferin which derivative is a substrate for luciferase or a prosubstrate for luciferase. In another embodiment, the derivative is one having a modification in the C ring of luciferin that includes a recognition site for an enzyme of interest, e.g., acetylcholinesterase. In another embodiment, the derivative is one having a modification in one of the rings that includes a recognition site for the enzyme of interest, as well as a further modification in that ring or one or more of the other rings.

For derivatives that are a substrate for luciferase, as well as optionally a substrate of a nonluciferase enzyme or other molecules, the derivative may be employed to detect luciferase, or a co-factor, inhibitor, or activator of the luciferase reaction. If the derivative is a prosubstrate for luciferase, i.e., the product of a reaction between the derivative and the nonluciferase enzyme is a substrate for luciferase, sequential or concurrent reactions for the nonluciferase enzyme and the luciferase may be conducted. For instance, a reaction for a nonluciferase enzyme that contains the prosubstrate may be conducted in a single well and a beetle luciferase reaction mixture added to that well. In another embodiment, a reaction mixture for a nonluciferase enzyme that contains the prosubstrate is conducted in a single well and a portion of that reaction added to a different well having a beetle luciferase reaction mixture. Alternatively, reactions may be conducted simultaneously in the same well.

The invention thus provides a method to detect or determine the presence or amount of a molecule for a nonluciferase enzyme-mediated reaction in a sample. The method includes contacting a sample, a first reaction mixture for a nonluciferase enzyme-mediated reaction, and a derivative of luciferin which is a substrate for the nonluciferase enzyme, so as to yield a first mixture or providing such a first mixture comprising a luminogenic product that is a substrate for a luciferase, or providing such a first mixture. In one embodiment, the derivative is a compound of formula I. In another embodiment, the derivative is a compound of formula II. At least a portion of the first mixture is contacted with a second reaction mixture for a beetle luciferase-mediated reaction, so as to yield a second mixture. Then luminescence in the second mixture is detected or determined, thereby detecting or determining the presence or amount of a molecule for the nonluciferase enzyme-mediated reaction in the sample. In some embodiments, the nonluciferase reaction mixture or luciferase reaction mixture may include an esterase, e.g., if the product of the reaction between the derivative and the nonluciferase enzyme has an ester group and that product is a proluciferase substrate. The esterase may be included with the first reaction mixture, added prior to initiation of the luciferase reaction mixture, or included in the luciferase reaction mixture. In some embodiments, e.g., a derivative with a picolinyl ester, the product of the reaction between the derivative and the nonluciferase enzyme is a substrate for luciferase in the absence of an exogenously added esterase. In one embodiment, derivatives of luciferin having an ester modification are employed in methods of the invention, such as those to detect nonluciferase enzymes including cytochrome P450 enzymes, as those derivatives may have improved properties as a nonluciferase substrate. Although not intending to be bound by any mechanism, the inclusion of the ester modification at position 5 in ring C may block negative charges or add a lipophilic quality to the derivative, rendering it an improved substrate.

Further provided is a method to detect or determine the presence or amount of a molecule for a nonluciferase enzyme-mediated reaction in a sample. The method includes contacting a sample, a reaction mixture for a nonluciferase-mediated enzyme reaction and for a luciferase-mediated reaction, and a derivative of luciferin which is a substrate for the nonluciferase enzyme, yielding a mixture. A reaction between the nonluciferase enzyme and the derivative yields a luminogenic product that is a substrate for the luciferase. In one embodiment, the derivative is a compound of formula I. In another embodiment, the derivative is a compound of formula II. Luminescence in the mixture is detected or determined, thereby detecting or determining the presence or amount of a molecule for the nonluciferase-mediated reaction in the sample.

The invention further provides a method to detect or determine the presence or amount of a molecule for a luciferase-mediated reaction in a sample. The method includes contacting a sample, a reaction mixture for a beetle luciferase, and a derivative of luciferin which is a substrate for the luciferase, to yield a reaction.

The invention also provides a method to detect the presence or amount of a molecule in a sample. The method includes contacting a sample, a first reaction mixture for a nonenzyme-mediated reaction and a derivative of luciferin which in the presence of the molecule yields a luminogenic product that is a substrate for a luciferase, and then contacting at least a portion of the first reaction and a second reaction mixture for a luciferase-mediated reaction, to yield a second reaction. Luminescence in the second reaction is detected or determined, thereby detecting or determining the presence or amount of the molecule. For instance, a mixture is provided having a sample, a first reaction mixture for a nonenzyme-mediated reaction and a derivative of luciferin which in the presence of the molecule yields a a luminogenic product that is a substrate for a beetle luciferase. At least a portion of the first mixture and a second reaction mixture for a beetle luciferase-mediated reaction are mixed, to yield a second mixture, and then luminescence in the second mixture is detected or determined, thereby detecting or determining the presence or amount of the molecule.

For the biolumingenic assays described herein which employ luciferin derivatives with a lower background, those assays can use lower (or higher) amounts of the derivative, and those derivatives may have improved reactivity, e.g., with a nonluciferase enzyme. In addition, for any of the bioluminogenic assays described herein, other reagents may be added to reaction mixtures, including but not limited to those that inhibit or prevent inactivation of luciferase, or otherwise extend or enhance luminescent signal.

Also provided is a method to identify or measure the potency of a modulator of a nonluciferase enzyme-mediated reaction. The method includes contacting one or more agents, a first reaction mixture for a nonluciferase enzyme-mediated reaction, and a derivative of luciferin which is a substrate for the nonluciferase enzyme, so as to yield a first mixture, or providing such a mixture, wherein the derivative includes an A or B ring modification relative to D-luciferin. The first mixture in the absence of the one or more agents includes a luminogenic product that is a substrate for a beetle luciferase. At least a portion of the first mixture and a second reaction mixture for a beetle luciferase-mediated reaction are mixed, so as to yield a second mixture. Luminescence in the second mixture is compared with a control mixture, thereby identifying whether one or more of the agents modulates the nonluciferase enzyme-mediated reaction and/or to what extent and with what potency.

In one embodiment of the invention, test compounds can be screened and evaluated for their activities as substrates or cofactors of, or regulators, either inhibitors or activators, of an enzymatic or nonenzymatic reaction by using the luciferin and fluorophore derivatives of the present invention. A candidate compound may be determined to be regulator or a substrate of a reaction by contacting a reaction mixture with a derivative and the test compound, under conditions that would, in the absence of the test compound, yield bioluminescence, fluorescence, or a bioluminogenic product.

In one aspect of the invention, a method is provided to distinguish between a substrate and an inhibitor of a reaction. For example, the compound is incubated with at least one enzyme under conditions which allow for metabolism of the compound prior to providing a luciferin derivative under conditions that, in the absence of an inhibitor or substrate of the enzyme, would be suitable for interaction between the luciferin derivative and the enzyme. In one embodiment, the product of that reaction is a substrate of luciferase and in the presence of luciferase yields a light emitting second reaction. The resulting light emitting reaction is compared to the one obtained from contacting the enzyme with the compound and the derivative, under conditions that would, in the absence of an inhibitor of the enzyme, be suitable for interaction between the luciferin derivative and the enzyme. Metabolism of the compound by the enzyme reduces its concentration the assay medium and may lead to an apparent loss of inhibitory activity compared to conditions without metabolism of the compound which would indicate it was a substrate for the enzyme. An inhibitory compound that was not metabolized would show equal potency, irrespective of the time of addition of the substrate.

In one aspect of the invention, the compound is preferably contacted first with the enzyme for a first predetermined time period. Thereafter, the mixture is contacted with a luciferin derivative and bioluminescent enzyme, e.g., luciferase, simultaneously or contemporaneously, and the mixture is allowed to incubate for a second predetermined time period.

In another aspect of the invention, the compound is incubated with the enzyme for a first predetermined time period to form a first mixture. Thereafter, the first mixture is contacted with the luciferin derivative, to form a second mixture that is allowed to incubate for a second predetermined time period. The second mixture is then contacted with a bioluminescent enzyme, e.g., luciferase, to form a third mixture, which is allowed to incubate for a third predetermined time period. Thereafter, the activity resulting from the interaction of the enzyme with the compound is determined by measuring luminescence during and/or after the third predetermined time period relative to a control (e.g., no compound) reaction. In this way, for example, mechanism based inhibitors of the first enzyme can be identified and distinguished from nonmechanism based inhibitors because the first incubation with the test compound but without the luciferin derivative will lead to a more profound inhibition by a mechanism based inhibitor than would be observed without the first incubation or substrates of the first reaction will show reduced inhibition.

In another embodiment of the invention, a cell-based method is provided for screening a compound to determine its effect on enzyme activity of the cell. The test compound is contacted with a cell having the enzyme, either naturally or via recombinant expression, the luciferin derivative, and bioluminescent enzyme, e.g., luciferase, or contacted with a cell having the enzyme and luciferase, and the derivative, for a predetermined period of time. Thus, in one embodiment, a cell that either transiently or stably expresses a recombinant enzyme such as a bioluminescent enzyme, e.g., luciferase, may be employed. Any conventional method for creating transient or stable transfected cells may be used. In one embodiment, a luciferin derivative is contacted with and diffuses into a cell and, if the appropriate molecule is present, yields a product, which is a substrate for luciferase. If a luciferase is present in the cell, luminescence can be detected. Alternatively, in a cell which lacks luciferase, the product passes out of the cell into the medium and that medium is added to a luciferase reaction mixture. Thereafter, the activity resulting from the interaction of the cell with the compound is determined by measuring luminescence of the reaction mixture relative to a control (minus test compound) reaction mixture.

In one aspect of the invention, the compound is preferably contacted first with the cell for a predetermined time period. Thereafter, the cell is contacted with the luciferin derivative and luciferase simultaneously or contemporaneously and the mixture allowed to incubate for a second predetermined time period. Enzyme activity is determined by measuring the amount of luminescence generated from the reaction mixture relative to a control reaction mixture (e.g., minus test compound). In another aspect of the invention, the test compound is preferably contacted first with the cell for a predetermined time period. Thereafter, the exposed cell is then contacted with the luciferin derivative and incubated for a second predetermined time period. The cell is then contacted with luciferase to form a third mixture which is allowed to incubate for a third predetermined time period.

Thereafter, the activity of the cell resulting from the interaction of the cell with the test compound(s) is determined by measuring luminescence of the reaction mixture relative to a control reaction mixture (e.g., minus test compound). Detergent addition can rupture the cells and release cell content.

A cell-based luminescence detection assay for molecules present in the cell medium, e.g., molecules which actively or via inactive mechanisms are present in the cell medium, can include adding a reaction mixture with the luciferin derivative to the cell medium, or adding the cell medium to a reaction mixture with the luciferin derivative, and detecting luminescence.

In yet another embodiment of the cell-based assay of the invention, the cells may be lysed in an appropriate lysis buffer. For animal cells, a buffet with 0.1-1.0% non-ionic detergents such as Triton X 100 or Tergitol is typically sufficient. Bacteria, plant, fungal or yeast cells are usually more difficult to lyse. Detergents, freeze/thaw cycles, hypotonic buffers, sonication, cavitation or combinations of these methods may be used. The method of lysis that produces a lysate is compatible with luciferase or other enzyme activity, or the detection of other molecules or conditions.

The presence or activity of nonluciferase enzymes may be measured in cells grown in culture medium or in cells within animals, e.g., living animals. For measurements in cells in animals, a luciferin derivative may be administered to the animal, e.g., injected into the animal or added to an aqueous solution, e.g., water, or food consumed by the animal. Conversion of the derivative to a product that is a luciferase substrate may be detected by luminescence mediated by luciferase expressed in cells in the animal, e.g., transgenic cells, by luciferase administered to the animal, e.g., injected into the animal, or by collecting physiological fluids, e.g., blood, plasma, urine, and the like, or tissue samples, and combining those with a luciferase reagent.

In one embodiment, the derivative employed in the methods is not aminoluciferin which is modified to include a protease substrate via a peptide bond at the amino group which optionally also has a protected carboxyl group at position 5 in the C ring, or any of luciferin 6' methyl ether, luciferin 6' chloroethyl ether, 6' deoxyluciferin, 6' luciferin 4-trifluoromethyl benzylether, luciferin 6' phenylethylether, luciferin 6" geranyl ether, luciferin 6' ethyl ether, 6' luciferin prenyl ether, 6' luciferin 2-picolinylether, 6' luciferin 3-picolinylether, 6' luciferin 4-picolinyl ether, luciferin 6' benzyl ether, D-luciferin-O-β-galactopyranoside, D-luciferin-O-sulfate, D-luciferin-O-phosphate, D-luciferyl-L-phenylalanine, and D-luciferyl-L-N'-arginine. In one embodiment, the derivative employed in the methods is not a luciferin derivative disclosed in U.S. published application 20040171099, the disclosure of which is incorporated by reference herein.

Assays which employ two reactions may be conducted simultaneously (one step) or sequentially (two step) to detect one or more moieties including proteins (peptides or polypeptides), e.g., enzymes, substrates, cofactors, inhibitors or activators for enzymatic reactions, or conditions, e.g., redox conditions. A sequential reaction may be conducted in the same vessel, e.g., a well of a multiwell plate. For a two step assay, the first reaction mixture may contain all of the reagents or less than all of the reagents for a nonluciferase enzyme-mediated reaction, where one of the reagents that is absent is the one to be detected in a sample, e.g., a cell lysate. For instance, a nonluciferase enzyme-mediated reaction is performed under conditions effective to convert a luciferin derivative that is a substrate for the nonluciferase and a prosubstrate of luciferase, to a product that is a substrate of luciferase. The first reaction may be quenched at the time, or prior to addition, of a luciferase reaction mixture. For instance, a quencher of the first reaction may be present in the luciferase reaction mixture. The luciferase reaction mixture preferably substantially lacks a substrate for the luciferase, e.g., the only source of substrate for the luciferase is provided by a reaction between the non-luciferase enzyme and the derivative. When all the reagents for the first reaction are present in the first reaction mixture, the assay may be employed in identify moieties that alter the reaction, e.g., inhibitors or enhancers of the reaction. After performing the reactions, either simultaneously or sequentially, the presence or amount of one or more molecules, or one or more inhibitors or activators of the reaction(s) is/are detected or determined and/or to what extent and with what potency.

For a one step assay, a reaction mixture may contain reagents for two reactions, such as reagents for a nonluciferase enzyme-mediated reaction and a luciferase-mediated reaction or for a nonenzymatic reaction and a luciferase-mediated reaction, or a reaction mixture for a single reaction, e.g., for a reaction between a derivative of a fluorophore which is a substrate for an enzyme and the enzyme or a luciferase-mediated reaction, e.g., a luciferase is suspected in a sample to be tested.

For assays which employ two reactions, the order of adding the molecules for the assays can vary if initiated and conducted sequentially (whether in the same vessel or not), adjustments to reaction conditions, e.g., reagent concentration, temperatures or additional reagents, may be performed. For instance, a quenching agent or enhancing agent may be added between reactions (see, e.g., U.S. Pat. Nos. 5,774,320 and 6,586,196, the disclosures of which are specifically incorporated by reference herein). In one embodiment, the two or more reactions are carried out simultaneously in a single reaction mixture. Optionally, the assays are a homogeneous assay, e.g., the components are mixed prior to adding the mixture to the sample. Results may be read without additional transfer of reagents.

The assays of the present invention thus allow the detection of one or more molecules or conditions in a sample, e.g., a sample which includes eukaryotic cells, e.g., yeast, avian, plant, insect or mammalian cells, including but not limited to human, simian, murine, canine, bovine, equine, feline, ovine, caprine or swine cells. or prokaryotic cells, or cells from two or more different organisms, or cell lysates or supernatants thereof, or a sample which includes a purified form of the molecule, e.g., purified nonluciferase enzyme which is useful to prepare a standard curve. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule.

The present methods can be employed to detect a molecule for an enzyme-mediated reaction, a nonenzymatic-mediated reaction or condition. For instance, molecules or conditions to be detected by the method include but are not limited to enzymes, e.g., demethylases, oxidases (e.g., a MAO), deacetylases, deformylases, proteases (proteosome, calpain, beta-secretase, cathepsin, calpain, thrombin, granzyme B). phosphatases, kinases, peroxidases, transferases, e.g., GST, sulfotases, beta-lactamases, cytochrome P450 enzymes, esterase, e.g., acetylcholinesterase, dehydrogenase, luciferase, substrates, inhibitors, co-factors, activators of enzyme mediated reactions, reactive oxygen species, reducing conditions and transcriptional regulators or regulators of gene transcription. The enzymes employed in the methods, either enzymes to be detected or enzymes which are useful to detect a substrate or cofactor, can be selected from any combination of enzymes including recombinant and endogenous (native) enzymes. In one embodiment, the enzyme to be detected is an endogenous enzyme. In another embodiment, the enzyme is a recombinant enzyme. Other combinations apparent to one of ordinary skill in the art can be used in the present assays and methods according to the teachings herein. The enzymes include but are not limited to proteases, phosphatases, peroxidases, sulfatases, peptidases, oxidases, dealkylases, deformylases and glycosidases. The enzyme may be a hydrolase, oxidoreductase, lyase, transferase, e.g., glutathione S transferase, isomerase, ligase, or synthase. Of particular interest are classes of enzymes that have physiological significance. These enzymes include protein peptidases, esterases, protein phosphatases, glycosylases, proteases, dehydrogenases, oxidases, oxygenases, reductases, methylases and the like. Exemplary cleavage sites for some proteases are set forth in FIG. 2. Enzymes of interest include those involved in making or hydrolyzing esters, both organic and inorganic, glycosylating, and hydrolyzing amides. In any class, there may be further subdivisions.

In particular, enzymes that are useful in the present invention include any protein that exhibits enzymatic activity, e.g., lipases, phospholipases, sulphatases, ureases, peptidases, proteases and esterases, including acid phosphatases, glucosidases, glucuronidases, galactosidases, carboxylesteraes, and luciferases. In one embodiment, the enzyme is a hydrolytic enzyme. Examples of hydrolytic enzymes include alkaline and acid phosphatases, esterases, decarboxylases, phospholipase D,P-xylosidase, β-fucosidase, thioglucosidase, β-D-galactosidase, α-D-galactosidase, α-D-glucosidase, β-D-glucosidase, β-D-glucuronidase, α-D-mannosidase, β-D-mannosidase, β-D-fructofuranosidase, and β-D-glucosiduronase.

In one embodiment, the invention provides the use of a compound of formula III or IIIA as described herein.

In one embodiment, an enzyme, for instance a nonproteolytic enzyme, is detected using a substrate which is covalently linked to a fluorophore. In one embodiment, the substrate includes a recognition site for the enzyme. In the absence of the appropriate enzyme or cofactor, a mixture including such a substrate generates minimal light at the emission wavelength as the fluorescent properties of the fluorophore are quenched, e.g., by the proximity of the quenching group. In the presence of the appropriate enzyme, cleavage of the conjugate yields the fluorophore.

III. Luciferin Derivatives

In one embodiment, derivatives of luciferin or aminoluciferin have the following structure; L-X-M-Y-R (compound of formula IV). wherein L, if present, may be a substrate for an enzyme or another molecule which interacts with the enzyme; X may be O, NH, or a linker, e.g., a self-cleavable linker which spontaneously cleaves to yield M-Y-R after L has been removed from L-X-M-Y-R; M may be luciferin, quinolinyl luciferin or naphthyl luciferin (X=O), or aminoluciferin or aminoquinolinyl luciferin (X=NH); Y is O (ester), NH (amide), NH—NH (hydrazide), or S (thioester); and R, if present, may be alkyl, an aromatic molecule, a peptide, an oligonucleotide, or a self-cleavable linker attached to a substrate for an enzyme. In one embodiment, the derivative may be modified at L or R to include a substrate for an enzyme such as a P450 enzyme, protease, MAO, FMO, or GST. In one embodiment, a derivative of the invention is a substrate for luciferase, including 6-aminoquinolinyl luciferin, which is a substrate of luciferase having substantial light output.

Bioluminescent substrates according to the present invention are derivatives of luciferin or aminoluciferin, i.e., are luminescent substrates other than luciferin or aminoluciferin, and include compounds having the general formulas described below including, e.g., formulas I and II.

In one embodiment, the invention provides a compound of formula I:

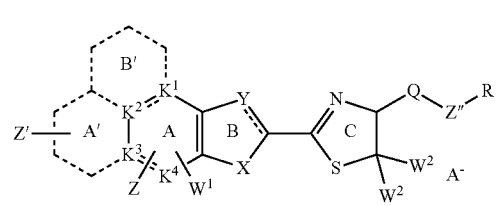

wherein
Y is N,N-oxide, N—($C_1$-$C_6$)alkyl, or CH;
when Y is N, then X is not S;
X is S, O, CH=CH, N=CH, or CH=N.
when X is S, then Y is not N;
Z and Z' are independently H, OR, NHR, or NRR;
Z" is O, S, NH, NHR, N=N;
Q is carbonyl or $CH_2$;
$W^1$ is H, halo, ($C_1$-$C_6$)alkyl, ($C_2$-$C_{20}$)alkenyl, hydroxyl, or ($C_1$-$C_6$)alkoxy; or
$W^1$ and X are both keto groups on ring A, and at least one of the dotted lines denoting optional double bonds in ring A is absent;
each $W^2$ is independently H, halo, ($C_1$-$C_6$)alkyl, ($C_2$-$C_4$)alkenyl, hydroxyl, or ($C_1$-$C_6$)alkoxy;
each of $K^1$, $K^2$, $K^3$, and $K^4$ are independently CH, N, N-oxide, or N—($C_1$-$C_6$)alkyl, and the dotted lines between $K^1$ and $K^2$, and $K^3$ and $K^4$, denote optional double bonds;
A' and B' are optional aromatic rings fused to ring A, only one of which is present in the compound, so as to form a fused tricyclic system; and
when B' is present, the group Z is present, and
when A' is present, the group Z is absent; and
the dotted line in ring B is an optional double bond;
each R is independently H, ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{12}$)alkoxy, ($C_6$-$C_{30}$)aryl, heteroaryl, heterocycle, ($C_1$-$C_{20}$)alkylsulfoxy, ($C_6$-$C_{30}$)arylsulfoxy, heteroarylsulfoxy, ($C_1$-$C_{20}$)alkylsulfonyl, ($C_6$-$C_{30}$)arylsulfonyl, heteroarylsulfonyl, ($C_1$-$C_{20}$)alkylsulfinyl, ($C_6$-$C_{30}$)arylsulfinyl, heteroarylsulfinyl, ($C_1$-$C_{20}$)alkoxycarbonyl, amino, NH($C_1$-$C_6$)alkyl, N(($C_1$-$C_6$)alkyl)$_2$, tri($C_1$-$C_{20}$)ammonium($C_1$-$C_{20}$)alkyl, heteroaryl($C_1$-$C_{20}$)alkyl, heteroaryl having quaternary nitrogen, heteroarylcarbonyl having quaternary nitrogen, ($C_6$-$C_{30}$)arylthio, ($C_1$-$C_{20}$)alkylphosphate, ($C_1$-$C_{20}$)alkylphosphonate, ($C_6$-$C_{30}$)arylphosphate, ($C_6$-$C_{30}$)arylphosphonate, phosphate, sulfate, saccharide, or M⁺ optionally when Z" is oxygen, wherein M is an alkali metal;

or when Z or Z' is NR¹R¹, R¹R¹ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —COOR$^x$, —SO$_2$R$^x$, —SO$_3$R$^x$, nitro, amino, $(C_1-C_{20})$alkyl-S(O)—, $(C_1-C_{20})$alkyl-SO$_2$—, phosphate, $(C_1-C_{20})$alkylphosphate, $(C_1-C_{20})$alkylphosphonate, NH$(C_1-C_6)$alkyl, NH$(C_1-C_6)$alkynyl, N$((C_1-C_6)$alkyl)$_2$, N$((C_1-C_6)$alkynyl)$_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

R$^x$ is H, $(C_1-C_6)$alkyl, or $(C_6-C_{20})$aryl;

when Z or Z' comprises a nitrogen moiety, one or both of the hydrogens of the Z or Z' nitrogen moiety may be replaced by $(C_1-C_{20})$alkyl or the group L, wherein L is an ammo acid radical, a peptide radical having up to 20 amino acid moieties, or any other small molecule that is a substrate for a nonluciferase; with the proviso that when L is an amine acid radical or a peptide radical, at least one W² is not H;

when Z is a hydroxyl group or a nitrogen moiety, H of the hydroxyl or nitrogen moiety may be replaced by (HO)₂P(O)—OCH₂—, sulfo, —PO₃H₂, or by a cephalosporanic acid attached to the group Z via a carbon chain of one to about 12 carbon atoms; with the proviso that when ring B is a thiazole ring, the sulfo or the —PO₃H₂ group is attached to the hydroxyl oxygen via a $(C_1-C_6)$alkylene group;

when Z or Z' is a hydroxyl group or a nitrogen moiety, or when Z"—R is a hydroxyl group, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds, linker is attached to L' via an oxygen atom or an NH group at one terminus of the linker and the other terminus of the linker forms an ether, ester, or amide linkage with a group Z, Z', or Z"—R;

when Z is OR, formula I is optionally a dimer connected at the two A rings via a linker comprising a $(C_1-C_{12})$alkyl diradical that is optionally interrupted by one to four O atoms, N atoms, or an optionally substituted aryl, heteroaryl, or heterocycle group to form a bridge between the dimer of formula I, and the R group of each Z group connecting the dimer of formula I is replaced by the bridge;

A⁻ is an anion, present when a quaternary nitrogen is present;

or a salt thereof;
provided that:
when rings A and B form a naphthalene or quinoline ring system, then W¹ is not hydrogen;
when a ring A substituent is OH, then -Q-Z"—R is not —C(O)—NH—NH₂;
when Y is N or CH and X is CH=CH and W¹ is H, then Z is not OH attached to K³; and
when Y is N or CH and X is CH—CH and Z is H, then W¹ is not OH attached to K³.

In another embodiment, the invention provides a compound of formula IA:

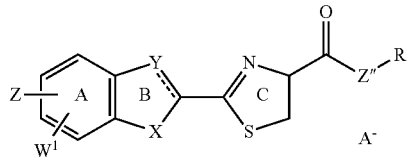

wherein
Y is N, N-oxide, N—$(C_1-C_6)$alkyl, or CH;
when Y is H, then X is not S;
X is S, O, CH=CH, N=CH, or CH=N;
when X is S, then Y is not N;
Z is H, OR, NHR, or NRR;
Z" is O, S, NH, NHR, or N=N:
W¹ is H, halo, hydroxyl, $(C_1-C_6)$alkyl, or $(C_1-C_6)$alkoxy;
the dotted line in ring B is an optional double bond;
each R is independently H, $(C_1-C_{20})$alkyl, $(C_2-C_{20})$alkenyl, $(C_2-C_{20})$alkynyl, $(C_3-C_{20})$cycloalkyl, $(C_1-C_{12})$aryl, heteroaryl, heterocycle, $(C_1-C_{20})$alkylsulfoxy, $(C_6-C_{30})$arylsulfoxy, heteroarylsulfoxy, $(C_1-C_{20})$alkylsulfonyl, $(C_6-C_{30})$arylsulfonyl, heteroarylsulfonyl, $(C_1-C_{20})$alkylsulfinyl, $(C_6-C_{30})$arylsulfinyl, heteroarylsulfinyl, $(C_1-C_{20})$alkoxycarbonyl, amino, NH$(C_1-C_6)$alkyl, N$((C_1-C_6)_2$, tri$(C_1-C_{20})$ammonium$(C_1-C_{20})$alkyl, heteroaryl$(C_1-C_{20})$alkyl, heteroaryl having quaternary nitrogen, heteroarylcarbonyl having quaternary nitrogen, $(C_6-C_{30})$arylthio, $(C_1-C_{20})$alkylphosphate, $(C_1-C_{20})$alkylphosphonate, $(C_6-C_{30})$arylphosphate, $(C_6-C_{30})$arylphosphonate, phosphate, sulfate, saccharide, or M⁺ optionally when Z" is oxygen, wherein M is an alkali metal;

or when Z or Z' is NR¹R¹, R¹R¹ together with the N to which they are attached forms a heteroaryl or heterocycle group;

wherein any alkyl, alkenyl, alkynyl, cycloalkyl, alkoxy, amino, aryl, heteroaryl, or heterocyclic group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —COOR$^x$, —SO$_2$R$^x$, —SO$_3$R$^x$, nitro, amino, $(C_1-C_{20})$alkyl-S(O)—, $(C_1-C_{20})$alkyl-SO$_2$—, phosphate, $(C_1-C_{20})$alkylphosphate, $(C_1-C_{20})$alkylphosphonate, NH$(C_1-C_6)$alkyl, NH$(C_1-C_6)$alkyl, N$((C_1-C_6)$alkyl)$_2$, N$((C_1-C_6)$alkynyl)$_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

R$^x$ is H, $(C_1-C_6)$alkyl, or $(C_6-C_{30})$aryl;

A⁻ is an anion, present when a quaternary nitrogen is present;

or a salt thereof;
provided that
when rings A and B form a naphthalene or quinoline ring system, then W¹ is not hydrogen;
when a ring A substituent is OH, then -Q-Z"—R is not —C(O)—NH—NH₂;
when Y is N or CH and X is CH=CH and W¹ is H, then Z is not OH attached to carbon-6 of ring A; and
when Y is N or CH and X is CH—CH and Z is H, then W¹ is not OH attached to carbon-6 of ring A.

As illustrated by formulas I and IA, the core structure of rings A and B can be a number of different ring systems. Modification of ring B allows the core structure to include benzofuran, benzothiophene, benzoaxazole, naphthalene, quinoline, isoquinoline, quinazoline, and quinoxyline ring systems, including the corresponding N-oxide and N-alkyl derivatives. Ring B modification also allows for access to N-oxide and N-alkyl derivatives of benzo[d]thiazole. Furthermore, by substituting a carbon atom of ring A in formula I with N,N-oxide, or N-alkyl (e.g., substituting one value of $K^1$, $K^2$, $K^3$, or $K^4$ for another value), other ring systems can be obtained, such as 1,8-naphthyridine, 1,7-naphthyridine-1,6-naphthyridine, and 1,5-naphthyridine ring systems; pyrido[3,2-b]pyrazine, pyrido[4,3-b]pyrazine, pyrido[3,4-b]pyrazine, and pyrido[2,3-b]pyrazine ring systems; pyrido[2,3-d]pyrimidine, pyrido[3,4-d]pyrimidine, pyrido[4,3-d]pyrimidine, and pyrido[3,2-d]pyrimidine ring systems; benzo[d]oxazole, oxazole[4,5-b]pyridine, oxazolo[4,5-c]pyridine, oxazolo[5,4-c]pyridine, and oxazole[5,4-b]pyridine ring systems; and thiazolo[4,5-b]pyridine, thiazolo[4,5-c]pyridine, thiazolo[5,4-c]pyridine, and thiazolo[5,4-b]pyridine ring systems.

Formula I also illustrates that by substituting a second carbon atom of ring A with N,N-oxide, or N-alkyl, the corresponding pyrazine, pyramidine, and pyridazine ring A analogs can be obtained for each of the above described ring systems. The substitution of a third carbon atom in ring A of formula I with N, N-oxide, or N-alkyl provides access to the corresponding 1,2,4-triazine ring system derivatives.

Formulas I and IA further include the various dihydro, tetrahydro, and hexahydro derivatives of each of its ring systems.

In another embodiment, the invention provides a compound of formula II:

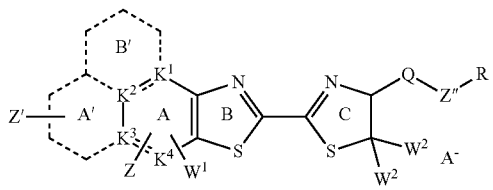

wherein
Z and Z' are independently $OR^1$, $NHR^1$, or $NR^1R^1$;
Z" is O, S, NH, NHR, or N=N;
Q is carbonyl or $CH_2$;
$W^1$ is H, halo, $(C_1-C_6)$alkyl, $(C_2-C_{20})$alkenyl, hydroxyl, or $(C_1-C_6)$alkoxy; or
$W^1$ and Z are both keto groups on ring A, and at least one of the dotted lines denoting optional double bonds in ring A is absent;
each $W^2$ is independently H, halo, $(C_1-C_6)$alkyl, $(C_2-C_4)$alkenyl, hydroxyl, or $(C_1-C_6)$alkoxy;
each of $K^1$, $K^2$, $K^3$, and $K^4$ are independently CH, N, N-oxide, or N—$(C_1-C_6)$alkyl, and the dotted lines between $K^1$ and $K^2$, and $K^3$ and $K^4$, denote optional double bonds;
A' and B' are optional aromatic rings fused to ring A, only one of which is present in the compound, so as to form a fused tricyclic system; and
when B' is present, the group Z is present, and
when A' is present, the group Z is absent; and
R is H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, heteroaryl, heterocycle, $(C_1-C_{20})$alkylsulfoxy, $(C_6-C_{30})$arylsulfoxy, heteroarylsulfoxy, $(C_1-C_{20})$alkoxycarbonyl, amino, $NH(C_1-C_6)$alkyl, $N(((C_1-C_6)$alkyl)_2$, tri$(C_1-C_{20})$ammonium $(C_1-C_{20})$alkyl, heteroaryl$(C_1-C_{20})$alkyl, heteroaryl having quaternary nitrogen, heteroarylcarbonyl having quaternary nitrogen, saccharide, or $M^+$ optionally when Z" is oxygen, wherein M is an alkali metal;
$R^1$ is $(C_6-C_{30})$aryl, heteroaryl, heterocycle, $(C_1-C_{20})$alkylthio, $(C_1-C_{20})$alkyl-S(O)—, $(C_1-C_{20})$alkyl-$SO_2$, —$SO_3(C_1-C_{20})$alkyl, saccharide, $(C_1-C_{20})$alkylphosphate, $(C_1-C_{20})$alkylphosphonate, $(C_6-C_{30})$arylthio, $(C_6-C_{30})$aryl-S(O)—, $(C_6-C_{30})$aryl-$SO_2$, —$SO_3(C_6-C_{30})$aryl, $(C_6-C_{30})$arylphosphate, $(C_6-C_{30})$arylphosphonate, or $R^1$ is $(C_1-C_{20})$alkyl substituted by $R^2$;
$R^2$ is $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, hydroxyl, —$COOR^x$, —$SO_3R^x$, $(C_1-C_{20})$alkylthio, $(C_6-C_{20})$arylthio, $(C_1-C_{20})$alkyl-S(O)—, $(C_1-C_{20})$alkyl-$SO_2$—, nitro, amino, $NH(C_1-C_6)$alkyl, $NH(C_1-C_6)$alkynyl, $N((C_1-C_6)$alkyl)_2$, or $N((C_1-C_6)$alkynyl)_2$, mercapto, saccharide, or trifluoromethyl;
or when Z or Z' is $NR^1R^1$, $R^1R^1$ together with the N to which they are attached forms a heteroaryl or heterocycle group;
wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —COOR', —$SO_2R^x$, —$SO_3R^x$, $(C_1-C_{20})$alkyl-S(O)—, $(C_1-C_{20})$alkyl-$SO_2$—, phosphate, $(C_1-C_{20})$alkylphosphate, $(C_1-C_{20})$alkylphosphonate, nitro, amino, $NH(C_1-C_6)$alkyl, $NH(C_1-C_6)$alkynyl, $N((C_1-C_6)$alkyl)_2$, $N((C_1-C_6)$alkynyl)_2$, mercapto, $(C_1-C_{20})$alkylthio, $(C_6-C_{30})$aryl, $(C_6-C_{10})$arylthio, trifluoromethyl, =O, heteroaryl, and heterocycle, and each substituent is optionally substituted with one to three R groups;
$R^x$ is H or $(C_1-C_6)$alkyl;
when Z or Z' comprises a nitrogen moiety, a hydrogen of the Z or Z' nitrogen moiety may be replaced by the group L, wherein L is an amino acid radical, a peptide radical having up to 20 amino acid moieties, or any other small molecule that is a substrate for a nonluciferase; with the proviso that when L is an amino acid radical or a peptide radical, at least one of $W^1$ or a $W^2$ is not H;
when Z is a hydroxyl group or a nitrogen moiety, H of the hydroxyl or nitrogen moiety may be replaced by $(HO)_2P(O)—OCH_2$—, sulfo, —$PO_3H_2$, or by a cephalosporanic acid attached to the group Z via a carbon chain of one to about 12 carbon atoms; with the proviso that the sulfo or the —$PO_3H_2$ group is attached to the hydroxyl oxygen via a $(C_1-C_6)$alkylene group;
when Z or Z' is a hydroxyl group or a nitrogen moiety, or when Z"—R is a hydroxyl group, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds,
linker is attached to L' via an oxygen atom or an NH group at one terminus of the linker and the other terminus of the linker forms an ether, ester, or amide linkage with a group Z, Z', or Z"—R,
when Z is $OR^1$, formula II is optionally a dimer connected at the two A rings via linker comprising a $(C_1-C_{12})$alkyl diradical that is optionally interrupted by one to four O atoms, N atoms, or an optionally substituted aryl, heteroaryl, or heterocycle group to form a bridge between the dimer of formula II, and the $R^1$ group of each Z group connecting the dimer of formula II is replaced by the bridge;

provided that a saccharide is not directly attached to $K^3$;

$A^-$ is an anion, present when a quaternary nitrogen is present;

or a suit thereof.

In yet another embodiment, the invention provides a compound of formula IIA:

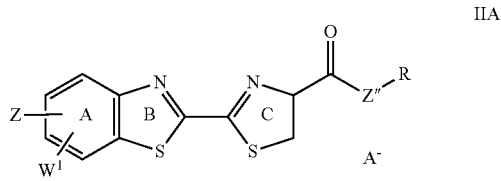

IIA wherein

Z is $OR^1$, $NHR^1$, or $NR^1R^1$;

Z" is O, S, NH, NHR, or N═N;

$W^1$ is H, halo, hydroxyl, $(C_1-C_6)$alkyl, or $(C_1-C_6)$alkoxy;

R is H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, heteroaryl, heterocycle, $(C_1-C_{20})$alkylsulfoxy, $(C_6-C_{30})$arylsulfoxy, heteroarylsulfoxy, $(C_1-C_{20})$alkoxycarbonyl, amino $NH(C_1-C_6)$alkyl, $N((C_1-C_6)$alkyl$)_2$, tri$(C_1-C_{20})$ammonium $(C_1-C_{20})$alkyl heteroaryl $(C_1-C_{20})$alkyl, heteroaryl having quaternary nitrogen, heteroarylcarbonyl having quaternary nitrogen, saccharide, or $M^+$ optionally when Z" is oxygen, wherein M is an alkali metal;

$R^1$ is $(C_6-C_{30})$aryl, heteroaryl, heterocycle, $(C_1-C_{20})$alkylthio, $(C_1-C_{20})$alkyl-S(O)—, $(C_1-C_{20})$alkyl-$SO_2$, —$SO_3(C_1-C_{20})$alkyl, saccharide, $(C_1-C_{20})$alkylphosphate, $(C_1-C_{20})$alkylphosphonate, $(C_6-C_{30})$arylthio, $(C_6-C_{30})$aryl-S(O)—, $(C_6-C_{30})$aryl-$SO_2$, —$SO_3(C_6-C_{30})$aryl, $(C_6-C_{30})$arylphosphate, $(C_6-C_{30})$arylphosphonate, or $R^1$ is $(C_1-C_{20})$alkyl substituted by $R^2$;

$R^2$ is $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, hydroxyl, —$COOR^x$, —$SO_3R^x$, $(C_1-C_{20})$alkylthio, $(C_6-C_{30})$arylthio, $(C_1-C_{20})$alkyl-S(O)—, $(C_1-C_{20})$alkyl-$SO_2$—, nitro, amino, $NH(C_1-C_6)$alkyl, $NH(C_1-C_6)$alkynyl, $N((C_1-C_6)$alkyl$)_2$, or $N((C_1-C_6)$alkynyl$)_2$, mercapto, saccharide, or trifluoromethyl;

or when Z or Z' is $NR^1R^1$, $R^1R^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —$COOR^x$, —$SO_2R^x$, —$SO_3R^x$, $(C_1-C_{20})$alkyl-S(O)—, $(C_1-C_{20})$alkyl-$SO_2$—, phosphate, $(C_1-C_{20})$alkylphosphate, $(C_1-C_{20})$alkylphosphonate, nitro, amino, $NH(C_1-C_6)$alkyl, $NH(C_1-C_6)$alkynyl, $N((C_3-C_6)$alkyl$)_2$, $N((C_1-C_6)$alkynyl$)_2$, mercapto, $(C_1-C_{20})$alkylthio, $(C_6-C_{30})$aryl, $(C_6-C_{30})$arylthio, trifluoromethyl, ═O, heteroaryl, and heterocycle, and each substituent is optionally substituted with one to three R groups;

$R^x$ is H or $(C_1-C_6)$alkyl;

when Z is $OR^1$, formula IIA is optionally a dimer connected at the two A rings via linker comprising a $(C_1-C_{12})$ alkyl diradical that is optionally interrupted by one to four O atoms, N atoms, or an optionally substituted aryl, heteroaryl, or heterocycle group to form a bridge between the dimer of formula IIA, and the $R^1$ group of each Z group connecting the dimer of formula II is replaced by the bridge;

provided that a saccharide is not directly attached to $K^3$;

$A^-$ is an anion, present when a quaternary nitrogen is present;

or a salt thereof.

As illustrated by formulas II and IIA, the core structure of rings A and B can also be a variety of ring systems. In addition to benzo[d]thiazole, substituting a carbon atom of ring A of formula II with N,N-oxide, or N-alkyl allows access to thiazolo[4,5-b]pyridine, thiazolo[4,5-c]pyridine, thiazole[5,4-c]pyridine, and thiazolo[5,4-b]pyridine ring systems, and their corresponding N-oxides and N-alkyl derivatives.

Formula II also illustrates that by substituting a second carbon atom of ring A with N,N-oxide, or N-alkyl, the corresponding pyrazine, pyramidine, and pyridazine ring A analogs can be obtained for each of the above described ring systems. The substitution of a third carbon atom in ring A of formula II provides access to the corresponding 1,2,4-triazine derivatives.

Formulas II and IIA include the various dihydro and tetrahydro derivatives of each of its ring systems.

All ring systems described above can be substituted as illustrated in the formulas described herein, for example, formulas I and/or II. Each of the above-described individual ring systems and their derivatives, substituted as described in the formulas herein, are separate embodiments of the invention.

Other deriviates and their use in luminogenic assays is described hereinbelow.

The use of the luciferin derivatives described herein can result in an assay which produces a measurable change in optical properties upon interaction with a nonluciferase molecule, which interaction may alter the structure of the luciferin derivative. As described herein, the product of a reaction between a luciferin derivative and a nonluciferase enzyme or other molecule of interest need not be D-luciferin or aminoluciferin. For example, a luciferin derivative may include a substrate that includes a reactive chemical group (or a nonluciferase enzyme linked to luciferin or aminoluciferin via a chemical linker. Transformation of the reactive chemical group of the derivative by the nonluciferase enzyme may yield a product that contains (retains) a portion of the substrate, a portion of the chemical linker, the chemical linker, or a portion of the substrate and the chemical linker, and that product is a substrate for luciferase. Also provided are luciferin derivatives which, after interaction with a nonluciferase enzyme or other molecule, may yield a product that optionally undergoes one or more further reactions, e.g., β-elimination, to yield a suitable substrate for luciferase. Luciferin derivatives in which the backbone of luciferin is further modified in its ring structure, e.g., a quinolyl or naphthyl luciferin, are provided, an well as advantageously providing modifications at the carboxy position of the thiazole ring, to provide improved characteristics to the luciferin derivative. Derivatives with certain modifications provide for or improve assays for certain nonluciferase enzymes or molecules. For instance, a described hereinbelow, a pH insensitive derivative of luciferin was identified that is useful in biological assays that may be run at a pH other than physiological pH, i.e., less than about pH 7.0 and greater than about pH 7.8. Thus, bioluminescent methods that employ a luciferin derivative of the invention may be used to detect one or more molecules, e.g., an enzyme, a cofactor for an enzymatic reaction such as ATP, an enzyme substrate, an enzyme inhibitor, an enzyme activator, or OH radicals, or one or more conditions, e.g., redox conditions.

In one embodiment, the invention provides a compound of formula (V):

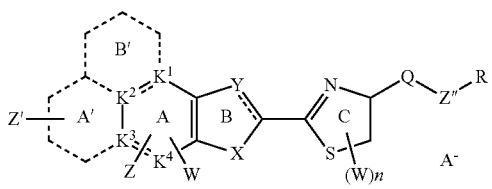

wherein
Y is N,N-oxide, N-loweralkyl, or CH;
X is S, CH=CH, or N=C,
Z and Z' are H, OR, NHR, of NRR,
Z" is O, S, NH, NHR, or N=N,
each W is independently H, halo, $C_{1-6}$-alkyl, $C_{2-20}$alkenyl, hydroxyl, or
$C_{1-6}$alkoxy; or
W and Z on ring A are both keto groups;
each of $K^1$, $K^2$, $K^3$, and $K^4$ are independently CH, N,N-oxide, or N-loweralkyl;
R is H, $C_{1-20}$alkyl, substituted $C_{1-20}$alkyl, $C_{2-20}$alkenyl, substituted $C_{2-20}$alkenyl, halogenated $C_{2-20}$alkenyl, substituted halogenated $C_{2-20}$alkenyl, $C_{3-20}$alkynyl, substituted $C_{3-20}$alkynyl, $C_{2-20}$alkenyl$C_{1-20}$alkyl, substituted $C_{2-20}$alkenyl$C_{1-20}$alkyl, $C_{3-20}$alkynyl$C_{2-20}$alkenyl, substituted $C_{1-20}$alkynyl$C_{2-20}$alkenyl, $C_{3-20}$cycloalkyl, substituted $C_{3-20}$cycloalkyl, $C_{6-30}$aryl, heteroaryl, $C_{6-30}$aryl$C_{1-20}$alkyl, substituted $C_{6-30}$aryl, substituted heteroaryl, substituted $C_{6-30}$aryl$C_{1-20}$alkyl, alkylsulfoxy$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{1-20}$ammonium$C_{1-20}$alkyl, heteroaryl$C_{1-20}$alkyl, substituted heteroaryl$C_{1-20}$alkyl, heteroaryl having quaternary nitrogen, heteroarylcarbonyl having quaternary nitrogen, and N-methyltetrahydropyridinyl; and $M^+$ when Z" is oxygen, wherein M is an alkali metal; wherein the alkyl, cycloalkyl, alkenyl, and/or alkynyl groups may be optionally substituted by one or more $C_{1-20}$alkyl, halo, hydroxyl, acetyl, amino, lower alkylamino, lower alkynylamino, imidazolinylmethylamino, di-lower lower alkylamino, di-lower alkynylamino, piperidino, pyrrolidine, azetidino, aziridino,
di-imidazolinylmethylamino, mercapto, $C_{1-20}$alkylthio, $C_{6-30}$arylthio, or trifluoromethyl groups, substituted $C_{6-30}$aryl$C_{1-20}$alkyl carbonyl; and each group R is defined independently if more than one is present;
W is $(C=O)_n$ or $(CH_2)_n$;
n is 0, 1, or 2;
and wherein
when Z or Z" is amino, one or both of the hydrogens may be replaced by $C_{1-20}$alkyl, or the group L, wherein
L is an amino acid radical, a peptide radical having up to 20 amino acid moieties, or may be any other small molecule that is a substrate for a nonluciferase; with the proviso that when L is an amino acid radical or a peptide radical, W is not H;
and wherein
when Z is hydroxyl or amino, H may be replaced by $(HO)_2P(O)$—$OCH_2$—, sulfo, or —$PO_3H_2$, or by cephalosporanic acid attached to the group Z via a carbon chain of one or more carbon atoms; with the proviso that when ring B is a thiazole ring, the sulfo or the —$PO_3H_2$ group is attached to the hydroxyl oxygen via a lower alkylene chain; and when Z is hydroxyl or amino or when Z"—R is hydroxyl, H may be replaced by the group L'- linker, wherein L' is a group removable by an enzyme to free the linker, and the linker is a carbon chain that may optimally self-cleave, optionally interrupted by one or more nitrogen atoms, oxygen atoms, carbonyl groups, (substituted) aromatic rings, or peptide bonds, and linker is attached to L' via an oxygen atom or an NH group at one terminus of the linker and the other terminus of the linker forms an ether, ester, or amide linkage with the group Z; and when Z is hydroxyl, formula V includes a luciferin dimer connected at the two A rings via an —$OCH_2O$— bridge; and wherein A' and B' are optional aromatic rings fused to ring A, only one of which may be present at a time, so as to form a fused tricyclic system; and when B' is present, the group Z is present, and
when A' is present, the group Z is absent, and wherein one carbon of ring A may be replaced by an N-oxide moiety;

the dotted line in ring B is an optional double bond;
if X is N=C, ring C is attached at the carbon atom of the N=C moiety, and $A^-$ is an anion, present when a quaternary nitrogen is present; or a salt thereof, with the proviso that W is not hydrogen when the compound to which W is attached is luciferin, luciferin methyl ester, or aminoluciferin or when rings A and B form a naphthalene or quinoline ring system.

Further derivatives of luciferin or aminoluciferin have the general formula VI.

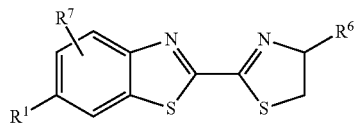

wherein
$R^1$ represents hydrogen, hydroxyl, amino, $C_{1-20}$alkoxy, substituted $C_{1-20}$alkoxy, $C_{2-20}$alkenyloxy, substituted $C_{2-20}$alkenyloxy, halogenated $C_{1-20}$alkoxy, substituted halogenated $C_{1-20}$alkoxy, $C_{3-20}$alkynyloxy, substituted $C_{3-20}$alkynyloxy, $C_{3-20}$cycloalkoxy, substituted $C_{3-20}$cycloalkoxy, $C_{3-20}$cycloalkylamino, substituted $C_{3-20}$cycloalkylamino, $C_{1-20}$alkylamino substituted $C_{1-20}$alkylamino, di$C_{1-20}$alkylamino, substituted di$C_{1-20}$alkylamino, $C_{2-20}$alkenylamino, substituted $C_{2-20}$alkenylamino, di$C_{2-20}$alkenylamino, substituted di$C_{2-20}$alkenylamino, $C_{2-20}$alkenyl$C_{1-20}$alkylamino, substituted $C_{2-20}$alkenyl$C_{1-20}$alkylamino, $C_{3-20}$alkynylamino, substituted $C_{3-20}$alkynylamino, di$C_{3-20}$alkynylamino, substituted di$C_{3-20}$alkynylamino, $C_{3-20}$alkynyl $C_{2-20}$alkenylamino,
or substituted $C_{3-20}$alkynyl$C_{2-20}$alkenylamino;
$R^6$ represents $CH_2OH$; $COR^{11}$ wherein $R^{11}$ represents H, OH, $C_{1-20}$alkoxide, $C_{2-20}$alkenyl, or $NR^{12}R^{13}$ wherein $R^{12}$ and $R^{13}$ are independently H or $C_{1-20}$alkyl; or —$OM^+$ wherein $M^+$ is an alkali metal; or a salt; and $R^7$ represents H, $C_{1-6}$alkyl, $C_{2-20}$alkenyl, halogen, or $C_{1-6}$alkoxide, with the proviso that when $R^1$ is OH or $NH_2$, $R^7$ is not H, $R^6$ is not $COR^{11}$ wherein $R^{11}$ is OH or OMe formula VI does not include luciferin, luciferin methyl ester, and aminoluciferin.

Further derivatives of luciferin or aminoluciferin have the general formula VII;

VII wherein
Y is N-oxide, N-loweralkyl, or CH;
X is S or CH=CH; or
Y is N and X is N=C or CH=CH;
Z and Z' are H, OR, NHR, or NRR; or
Z is a cyclic dietherified dihydroxyborane group attached to ring A via the boron atom;
Z" is O, S, NH, NHR, or N=N;
each W is independently H, halo, $C_{1-6}$alkyl, $C_{2-20}$alkenyl, hydroxyl, or $C_{1-6}$alkoxy;
each of $K^1$, $K^2$, $K^3$, and $K^4$ are independently CH, N, N-oxide, or N-loweralkyl;
R is H, $C_{1-20}$alkyl, substituted $C_{1-20}$alkyl, $C_{2-20}$alkenyl, substituted $C_{2-20}$alkenyl, halogenated $C_{2-20}$alkenyl, substituted halogenated $C_{2-20}$alkenyl, $C_{2-20}$alkenyl$C_{1-30}$alkyl, substituted $C_{2-20}$alkenyl$C_{1-20}$alkyl, $C_{3-20}$alkynyl, substituted $C_{3-20}$alkynyl, $C_{3-20}$alkynyl$C_{2-20}$alkenyl, substituted $C_{3-20}$alkynyl$C_{2-20}$alkenyl, $C_{3-20}$cycloalkyl, substituted $C_{3-20}$cycloalkyl, $C_{6-30}$aryl, heteroaryl, $C_{6-30}$aryl$C_{1-20}$alkyl, substituted $C_{6-30}$aryl substituted heteroaryl, substituted $C_{6-30}$aryl$C_{1-20}$alkyl, $C_{1-20}$alkoxycarbonyl, $C_{6-10}$aryl $C_{1-20}$alkoxycarbonyl, $C_{6-30}$arylthio$C_{1-20}$alkyl, hydroxy $C_{1-20}$alkyl, tri$C_{1-20}$ammonium$C_{1-20}$alkyl, heteroaryl $C_{1-20}$alkyl, substituted heteroaryl$C_{1-20}$alkyl, heteroaryl having quaternary nitrogen, heteroarylcarbonyl having quaternary nitrogen, N-methyl-tetrahydropyridinyl, pentafluorophenylsulphonyl, and $M^+$ when Z" is oxygen, wherein M is an alkali metal; wherein the alkyl, cycloalkyl, alkenyl, and/or alkynyl groups may be optionally substituted by one more $C_{1-20}$alkyl, halo, hydroxyl, acetyl, amino, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, or trifluoromethyl groups; and each group R is defined independently if more than one is present;
Q is $(C=O)_n$ or $(CH_2)_n$,
n is 0, 1, or 2;
and wherein
when Z is amino, one or both of the hydrogens may be replaced by $C_{1-20}$alkyl, or the group L, wherein
L is an amino acid radical, a peptide radical having up to 20 amino acid moieties, or may be any other small molecule that is a substrate for a nonluciferase;
and wherein
when Z is hydroxyl or amino, H may be replaced by $(HO)_2P(O)—OCH_2—$, sulfo or —$PO_3H_2$, or by a cephalosporanic acid attached to the group Z via a carbon chain of one or more carbon atoms; and
when Z is hydroxyl or amino or when Z"—R is hydroxyl, H may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted)aromatic rings, or peptide bonds, and
linker is attached to L' via an oxygen atom or an NH group at one terminus of the linker and the other terminus of the linker forms an ether, ester, or amide linkage with the group Z; and
when Z is hydroxyl, formula VII includes a luciferin dimer connected at the two A rings via an —$OCH_2O$— bridge; and
wherein
A' and B' are optional aromatic rings fused to ring A, only one of which may be present at a time, so as to form a fused tricyclic system; and
when B' is present, the group Z is present, and
when A' is present, the group Z is absent; and
wherein
one carbon of ring A may be replaced by an N-oxide moiety;
the dotted line in ring B is an optional double bond;
if X is N=C, ring C can optionally be attached at the carbon atom of the N=C moiety; and
$A^-$ is an anion, present when a quaternary nitrogen is present; or a salt thereof; with the proviso that W is not hydrogen when rings A and B form a naphthalene ring system.

Other derivatives include a compound of formula VIII:

VIII wherein
n=0 or 1 and when
n+0, then X=S, and ⚌ is a single bond; or when
n=1, then X=CH, and ⚌ is a double bond;
$R_1$=H, F, or OH:
$R_2$=H, methyl, ethyl, propyl, butyl, benzyl, hydroxyethyl, or an ester of hydroxyethyl;
$R_3$ and $R_4$ are independently H, methyl, ethyl, propyl, allyl, imidazolinylmethyl, or
$R_3$ and $R_4$ together with the nitrogen atom to which they are attached form a piperidino, pyrrolidino, azetidino, or aziridino ring;
$R_5$ and $R_6$ are independently H or methyl;
$R_7$ is H or methyl;
$R_8$ is H, methyl, hydroxyl, or acetyl; and
$R_9$ is H or methyl, Compounds of formula VIII may be useful as MAO substrates.

Yet other derivatives include a compound of formula IX:

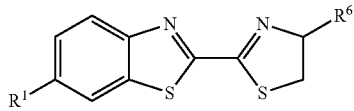

wherein $R^1$ is H, OR, NH—C(O)—O-benzyl, or NH—O-iso-butyl;

R is lower alkyl, benzyl, 2,4,6-trimethylbenzyl, phenylpiperazinobenzyl, 6-trifluoromethylbenzyl, or 3-picolinyl;

$R^6$ is a carboxyl group esterified by lower alkyl, 3-picolinyl, ethylene glycol when $R^1$ is H or OR, or $R^6$ is carboxyl when $R^1$ is NH—C(O)—O-benzyl or NH—O-iso-butyl or when $R^1$ is OR wherein R is 2,4,6-trimethylbenzyl, phenylpiperazinobenzyl, o-trifluoromethylbenzyl. Such derivatives may be useful as P450 substrates.

Also provided is a compound of formula X:

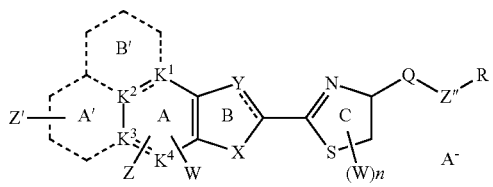

wherein

Y is N, N-oxide, N-loweralkyl, or CH;

X is S, CH═CH, or N═C,

Z and Z' are independently H, OR, NHR, or NRR.

Z" is O, S, NH, NHR, or N═N;

each W is independently H, halo, $C_{1-6}$alkyl, $C_{2-20}$alkenyl, hydroxyl, or $C_{1-6}$alkoxy; or W and Z are both keto groups on ring A, and the dotted lines in ring A are absent;

each of $K^1$, $K^2$, $K^3$, and $K^4$ are independently CH, N, N-oxide, or N-loweralkyl, and the dotted lines between $K^1$ and $K^2$, and $K^3$ and $K^4$ denote optional double bonds;

R is H, amino, $C_{1-20}$alkyl, $C_{2-20}$alkenyl, halogenated $C_{2-20}$alkenyl, $C_{3-20}$alkynyl, $C_{2-20}$alkenyl$C_{1-20}$alkyl, $C_{3-20}$alkynyl$C_{2-20}$alkenyl, $C_{3-20}$cycloalkyl, $C_{6-30}$aryl, heteroaryl, $C_{6-30}$aryl$C_{1-20}$alkyl, $C_{1-12}$alkoxy, $C_{1-20}$alkylsulfoxy, $C_{6-30}$arylsulfoxy$C_{1-20}$alkyl, $C_{1-20}$alkylsulfoxy$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{3-20}$ammonium$C_{1-20}$alkyl, heteroarylsulfoxy, heteroaryl$C_{1-20}$alkyl, heteroaryl having quarternary nitrogen, heteroarylcarbonyl having quaternary nitrogen, N-methyl-tetrahydropyridinyl; or $M^+$ and Z" is oxygen, wherein M is an alkali metal;

wherein any alkyl, alkenyl, alkynyl, cycloalkyl, alkoxy, aryl, or heteroaryl groups of R can be optionally substituted by one or more, e.g., 1, 2, 3, 4, or 5, $C_{1-20}$alkyl, halo, hydroxyl, acetyl, —COO$R^1$, —SO$_3R^1$, amino, nitro, lower alkylamino, lower alkynylamino, imidazolinylmethylamino, di-lower alkylamino, di-lower alkynylamino, piperidino, pyrrolidino, azetidino, aziridino, di-imidazolinylmethyl-amino, mercapto, $C_{1-20}$alkylthio, $C_{6-30}$arylthio, trifluoromethyl, $C_{1-20}$alkylcarboxyl, $C_{6-30}$aryl, substituted $C_{6-30}$aryl, $C_{6-30}$aryl$C_{1-20}$alkoxyl, heterocycle $C_{1-20}$alkyl, substituted $C_{6-30}$aryl$C_{1-20}$alkoxyl, $C_{6-30}$aryl$C_{1-20}$alkyl carbonyl, substituted $C_{6-30}$aryl$C_{1-20}$alkyl carbonyl or additional unsubstituted R groups; and wherein each group R is defined independently if more than one is present;

wherein heterocycle $C_{1-20}$alkyl is optionally substituted with one or more, e.g., 1, 2, 3, 4, or 5, R groups;

$R^1$ is hydrogen or $C_{1-6}$alkyl;

Q is C(═O) or CH$_2$, n is 0, 1, or 2;

and wherein when Z or Z" is amino, one or both of the hydrogens of the amino group may be replaced by $C_{1-20}$alkyl, or the group L, wherein L is an amino acid radical, a peptide radical having up to 20 amino acid moieties, or any other small molecule that is a substrate for a nonluciferase; with the proviso that when L is an amino acid radical or a peptide radical, W is not H;

and wherein when Z is hydroxy; or amino, H of the hydroxyl or amino may be replaced by (HO)$_2$P(O)—OCH$_2$—, sulfo, —PO$_3$H$_2$, or by a cephalosporanic acid attached to the group Z via a carbon chain of one or more carbon atoms; with the proviso that when ring B is a thiazole ring, the sulfo or the —PO$_3$H$_2$ group is attached to the hydroxyl oxygen via a loweralkylene chain; and when Z or Z' is hydroxyl or amino or when Z"—R is hydroxyl, one H of the hydroxyl or amino may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted) aromatic rings, or peptide bonds, and linker is attached to L' via an oxygen atom or an NH group at one terminus of the linker and the other terminus of the linker forms an ether, ester, or amide linkage with the group Z, Z', or Z"—R; and when Z is OR, formula X can optionally be a dimer connected at the two A rings via a CH$_2$ or CH$_2$—C$_6$H$_4$—CH$_2$ bridge, and the R group of each Z group connecting the dimer of formula X is replaced by the bridge; and wherein A' and B' are optional aromatic rings fused to ring A, only one of which may be present at a time, so as to form a fused tricyclic system; and when B' is present, the group Z is present, and when A' is present, the group Z is absent; and wherein one carbon of ring A may be replaced by an N-oxide moiety;

the dotted line in ring B is an optional double bond;

if X is N═C, ring C can optionally be attached at the carbon atom of the N═C moiety; and $A^-$ is an anion, present when a quaternary nitrogen is present; or a salt thereof, with the proviso that W is not hydrogen when the compound to which W is attached is luciferin, luciferin methyl ester, or aminoluciferin or when rings A and B form a naphthalene or quinoline ring system, with the proviso that -Q-Z"—R is not —C(O)—NH—NH$_2$ when a ring A substituent is OH.

In one embodiment, the W group attached to ring C is absent (i.e., the value of "n" is 0). In another embodiment, the W group attached to ring C is H or F.

Further provided is a compound of formula XI:

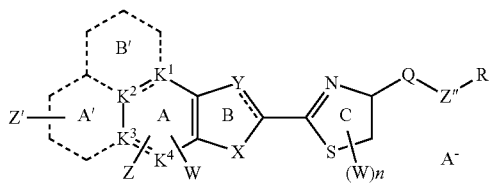

wherein
Y is N-oxide, N-loweralkyl, or CH;
X is S or CH═CH; or
Y is N and X is N═C or CH═CH;
Z and Z' are H, OR, NHR, or NRR; or
Z is a cyclic dietherified dihydroxyborane group attached to ring A via the boron atom;
Z" is O, S, NH, NHR, or N═N;
each W is independently H, halo, $C_{1-6}$alkyl, $C_{2-20}$alkenyl, hydroxyl, or $C_{1-6}$alkoxy;
each of $K^1$, $K^2$, $K^3$, and $K^4$ are independently CH, N, N-oxide, or N-loweralkyl, and the dotted lines between $K^1$ and $K^2$, and $K^3$ and $K^4$, denote optional double bonds;
R is H, $C_{1-20}$alkyl, $C_{2-20}$alkenyl, halogenated $C_{2-20}$alkenyl, $C_{3-20}$alkynyl, $C_{2-20}$alkenyl$C_{1-20}$alkyl, $C_{3-20}$alkynyl $C_{2-20}$alkenyl, $C_{3-20}$cycloalkyl, $C_{6-30}$aryl, heteroaryl, $C_{6-30}$aryl$C_{1-20}$alkyl, $C_{1-20}$alkylsulfoxy, $C_{6-30}$arylsulfoxy, $C_{6-30}$arylsulfoxy$C_{1-20}$alkyl, $C_{1-20}$alkylsulfoxy$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{1-20}$ammonium$C_{1-20}$alkyl, heteroaryl-sulfoxy, heteroaryl$C_{1-20}$alkyl, heteroaryl having quaternary nitrogen, heteroarylcarbonyl having quaternary nitrogen, N-methyl-tetrahydropyridinyl; or $M^+$ when Z" is oxygen, wherein M is an alkali metal;
wherein the alkyl, alkenyl, alkynyl, cycloalkyl, aryl, and heteroaryl groups of R can be optionally substituted by one or more, e.g., 1, 2, 3, 4, or 5, $C_{1-20}$alkyl, halo, hydroxyl, acetyl, —COOR$^1$, —SO$_3$R$^1$, amino, nitro, lower alkylamino, lower alkynylamino, imidazolinylmethylamino, di-lower alkylamino, di-lower, alkynylamino, piperidino, pyrrolidino, azetidino, aziridino, di-imidazolinylmethyl-amino, mercapto, $C_{1-20}$alkylthio, $C_{6-30}$arylthio, trifluoromethyl, substituted $C_{6-30}$aryl, $C_{1-20}$alkylcarboxyl, substituted $C_{6-30}$aryl, substituted $C_{6-30}$aryl$C_{1-20}$alkoxyl, substituted $C_{6-30}$aryl$C_{1-20}$alkyl carbonyl or additional unsubstituted R group; and each group R is defined independently if more than one is present;
$R^1$ is hydrogen or $C_{1-6}$alkyl;
Q is C(═O) or CH$_2$;
each n is independently 0, 1, or 2;
and wherein
when Z is amino, both of the hydrogens of the amino group may be replaced by $C_{1-20}$alkyl, or the group L, wherein
L is an amino acid radical, a peptide radical having up to 20 amino acid moieties, or may be any other small molecule that is a substrate for a nonluciferase;
and wherein
when Z or Z' is hydroxyl or amino, H of the hydroxyl or amino may be replaced by (HO)$_2$P(O)—OCH$_2$—, sulfo, —PO$_3$H$_2$, or by a cephalosporanic acid attached to the group Z via a carbon chain of one or more carbon atoms; and
when Z is hydroxyl or amino or when Z"—R is hydroxyl, one H of the hydroxyl or amino may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted) aromatic rings, or peptide bonds, and
linker is attached to L' via an oxygen atom or an NH group at one terminus of the linker and the other terminus of the linker forms an ether, ester, or amide linkage with the group Z, Z', or Z"—R; and
when Z is hydroxyl, formula XI includes a luciferin dimer connected at the two A rings via an —OCH$_2$O— bridge, and
wherein
A' and B' are optional aromatic rings fused to ring A, only one of which may be present at a time, so as to form a fused tricyclic system; and
when B' is present, the group Z is present, and
when A' is present, the group Z is absent; and
wherein
the dotted line in ring B is an optional double bond;
if X is N═C, ring C can optionally be attached at the carbon atom of the N═C moiety; and
$A^-$ is an anion, present when a quaternary nitrogen is present; or a salt thereof; with the proviso that W is not hydrogen when rings A and B form a naphthalene ring system. In one embodiment, the W group attached to ring C is absent (i.e., the value of "n" is 0). In another embodiment the W group attached to ring C is H or F.
Also provided is a compound of formula XII:

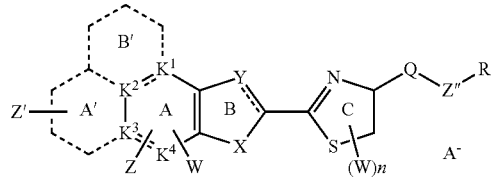

wherein
Y is N, N-oxide, N-loweralkyl, or CH;
X is S, CH═CH, or N═C,
Z and Z' are independently H, OR, NHR, or NRR;
Z" is O, S, NH, NHR, or N═N;
each W is independently H, halo, $C_{1-6}$alkyl, $C_{2-20}$alkenyl, hydroxyl, or $C_{1-6}$alkoxy; or
W and Z are both keto groups on ring A, and the dotted lines in ring A are absent;
each of $K^1$, $K^2$, $K^3$, and $K^4$ are independently CH, N, N-oxide, or N-loweralkyl, and the dotted lines between $K^1$ and $K^2$, and $K^3$ and $K^4$, denote optional double bonds;
R is H, $C_{1-20}$alkyl, $C_{2-20}$alkenyl, halogenated $C_{2-20}$alkenyl, $C_{3-20}$alkynyl, $C_{2-20}$alkenyl$C_{1-20}$alkyl, $C_{3-20}$alkynyl $C_{2-20}$alkenyl, $C_{3-20}$cycloalkyl, $C_{6-30}$aryl, heteroaryl, heterocyclic, substituted heterocyclic, $C_{6-30}$aryl$C_{1-20}$alkyl, $C_{1-20}$alkylsulfoxy, $C_{6-30}$arylsulfoxy, $C_{6-30}$arylsulfoxy $C_{1-20}$alkyl, $C_{1-20}$alkylsulfoxy$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{1-20}$ammonium$C_{1-20}$alkyl, heteroarylsulfoxy, heteroaryl$C_{1-20}$alkyl, heteroaryl having quaternary nitrogen, heteroarylcarbonyl having quaternary nitrogen, N-methyl-tetrahydropyridinyl; or $M^+$ when Z" is oxygen, wherein M is an alkali metal;
wherein the alkyl, alkenyl, alkynyl, cycloalkyl, aryl, and heteroaryl groups of R can be optionally substituted by one or more, e.g., 1, 2, 3, 4, or 5, $C_{1-20}$alkyl, halo, hydroxyl, acetyl, —COOR¹, —SO₃R¹, amino, nitro, lower alkylamino, lower alkynylamino, imidazolinylmethylamino, di-lower alkylamino, di-lower alkynylamino, piperidino, pyrrolidino, azetidino, aziridino, di-imidazolinylmethyl-amino, mercapto, $C_{1-20}$alkylthio, $C_{6-30}$arylthio, trifluoromethyl, $C_{1-20}$alkylcarboxyl, $C_{6-30}$aryl, substituted $C_{6-30}$aryl, $C_{6-30}$aryl$C_{1-20}$alkoxyl, substituted $C_{6-30}$aryl$C_{1-20}$alkoxyl, $C_{6-30}$aryl$C_{1-20}$alkyl carbonyl, substituted $C_{6-30}$aryl $C_{1-20}$alkyl carbonyl or additional unsubstituted R groups; and wherein each group R is defined independently if more than one is present;

wherein substituted aryl groups are substituted with one or alkyl, alkenyl, alkynyl, cycloalkyl, aryl, heterocyclic, substituted heterocyclic, and heteroaryl groups of R can be optionally substituted by one or more $C_{1-20}$alkyl, $C_6$-$C_{10}$aryl, halo, hydroxyl, acetyl, —COOR¹, amino, nitro, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, or trifluoromethyl groups;

R¹ is hydrogen or $C_{1-6}$alkyl;
Q is C(=O) or CH₂;
n is 0, 1, or 2;
and wherein when Z or Z" is amino, one or both of the hydrogens of the amino group may be replaced by $C_{1-20}$alkyl, or the group L, wherein L is an amino acid radical, a peptide radical having up to 20 amino acid moieties, or any other small molecule that is a substrate for a nonluciferase; with the proviso that when L is an amino acid radical or a peptide radical, W is not H;
and wherein when Z is hydroxyl or amino, H may be replaced by (HO)₂P(O)—OCH₂—, sulfo, or —PO₃H₂, or by a cephalosporanic acid attached to the group Z via a carbon chain of one or more carbon atoms; with the proviso that when ring B is a thiazole ring, the sulfo or the —PO₃H₂ group is attached in the hydroxyl oxygen via a lower alkyl chain; and when Z or Z' is hydroxyl or amino or when Z"—R is hydroxyl, one H may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted) aromatic rings, or peptide bonds, and linker is attached to L' via an oxygen atom or an NH group at one terminus of the linker and the other terminus of the linker forms an ether, ester, or amide linkage with the group Z, Z', or Z"—R; and when Z is hydroxyl, formula XII includes a luciferin dimer connected at the two A rings via an —OCH₂O— bridge; and wherein A' and B' are optional aromatic rings fused to ring A, only one of which may be present at a time, so as to form a fused tricyclic system; and when B' is present, the group Z is present, and
when A' is present, the group Z is absent; and
wherein the dotted line in ring B is an optional double bond;
if X is N=C, ring C can optionally be attached at the carbon atom of the N=C moiety; and A⁻ is an anion, present when a quaternary nitrogen is present; or a salt thereof, with the proviso that W is not hydrogen when the compound to which W is attached is luciferin, luciferin methyl ester, or aminoluciferin or when rings A and B form a naphthalene or quinoline ring system.

In one embodiment, the W group attached to ring C is absent (i.e., the value of "n" is 0). In another embodiment, the W group attached to ring C is H or F.

IV. Exemplary Luciferin Derivatives

Derivatives having a six membered B ring include:

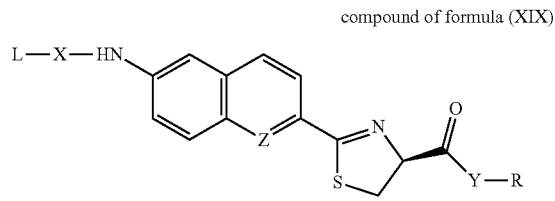

compound of formula (XIX)

wherein L may be any structure for an enzyme, such as a peptide sequence or small molecules: X is O, NH, or a self-cleavable linker; Z is N (aminoquinolinyl luciferin) or CH (naphthyl luciferin), Y is O (ester), NH (amide), NH—NH (hydrazide), or S (thioester); and R may be alkyl, aromatic, a peptide, an oligonucleotide, or a self-cleavable linker attached to a substrate for an enzyme.

In one embodiment, a derivative may be employed to detect N-dealkylation, e.g., by cytochrome (CYP) P450 isozymes. In the case of an ester (R=alkyl chain), an esterase may be added after the dealkylation reaction is commenced, or at the time the dealkylation reaction is initiated, and before a luciferase-mediated reaction is initiated.

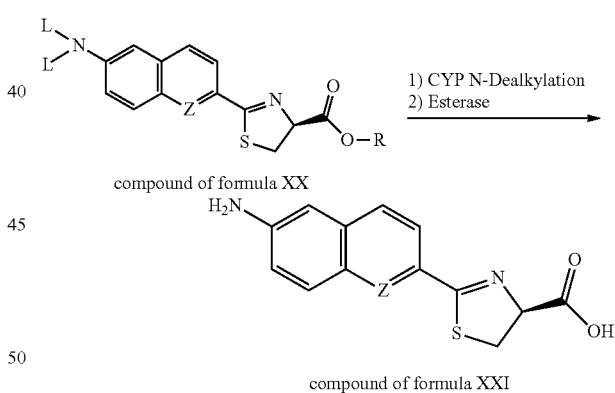

L = alkyl
Z = N or CH
R = H or alkyl

Although light output with 6-aminoquinolinyl luciferin (formula V) is pH sensitive, reactions including control reactions may be conducted at the same pH. Alternatively, 6-aminoquinolinyl luciferin may be modified so as to alter electron density distribution of the aromatic ring, for example, with halogenation.

Derivatives of the invention include fluorinated luciferin, quinolinyl luciferin, aminoquinolinyl luciferin, and naphthyl luciferin. For instance, the optical properties of fluorinated derivatives of aminoquinolinyl luciferin may be altered due to the electron withdrawing power of fluorine. Fluorinated derivatives include compound of formula XXII and XXIII:

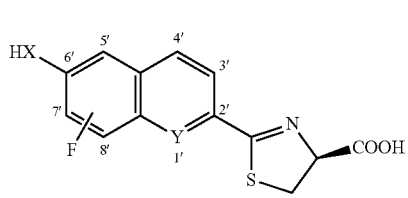

XXII

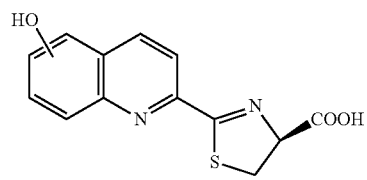

wherein X=O or NH; Y=N or CH; and F may be at 3', 4', 5', 7', or 8'

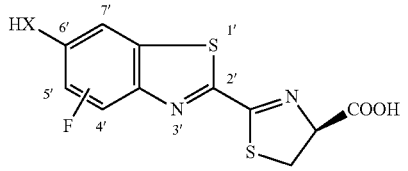

XXIII wherein X=O or NH; and F may be at 4', 5', or 7'.

An exemplary fluorinated derivative is 5-fluoro-6-amino-luciferin (FIG. 3).

In one embodiment, the invention provides for quinolinyl derivatives (compounds of formula XXIV-XXVI):

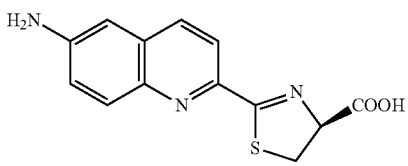

wherein OH is at positions 6' and/or 8'

Derivatives of the invention may be employed as sensors for reactive oxygen species (ROS) or a redox sensor for horseradish peroxidase (HRP) and other enzymes. Those derivatives include compounds of formula XXVII-XXXII:

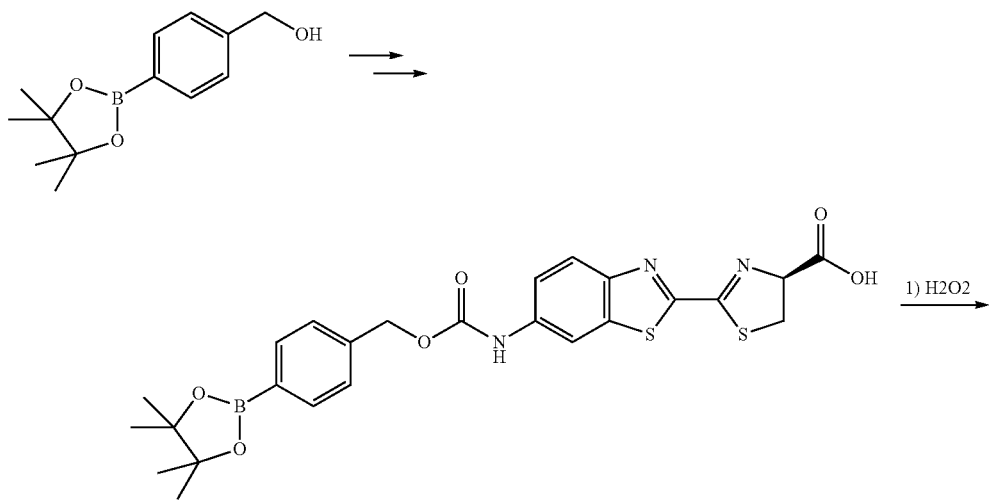

compound of formula XXVII

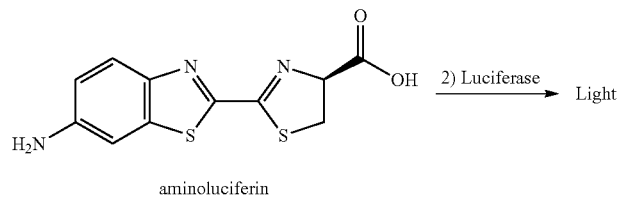

aminoluciferin

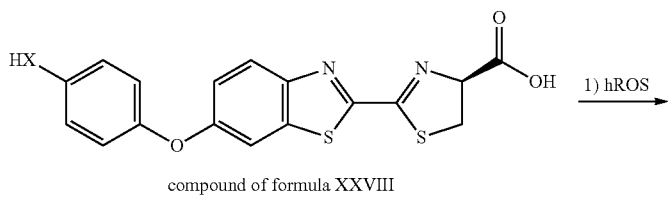

compound of formula XXVIII

-continued
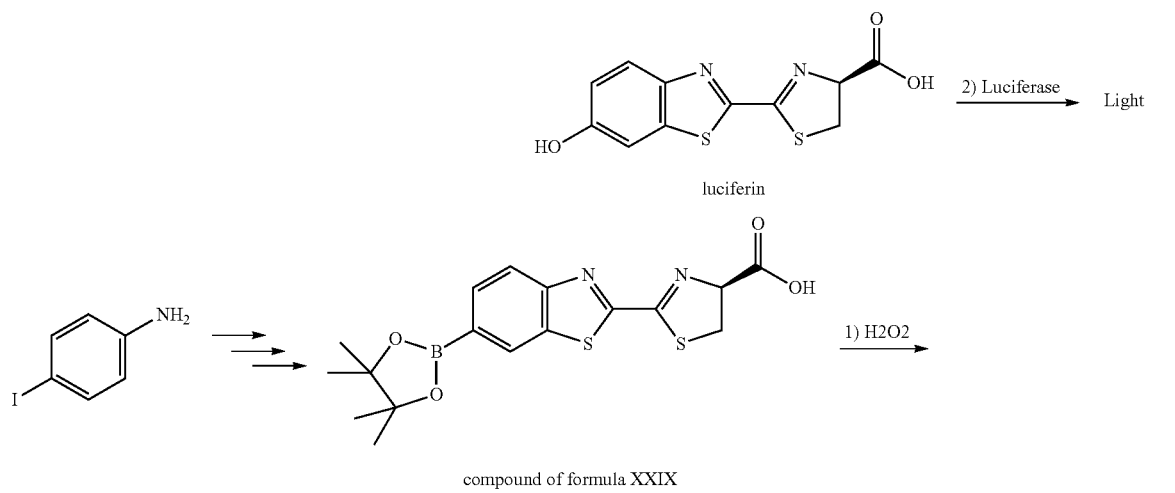
compound of formula XXIX
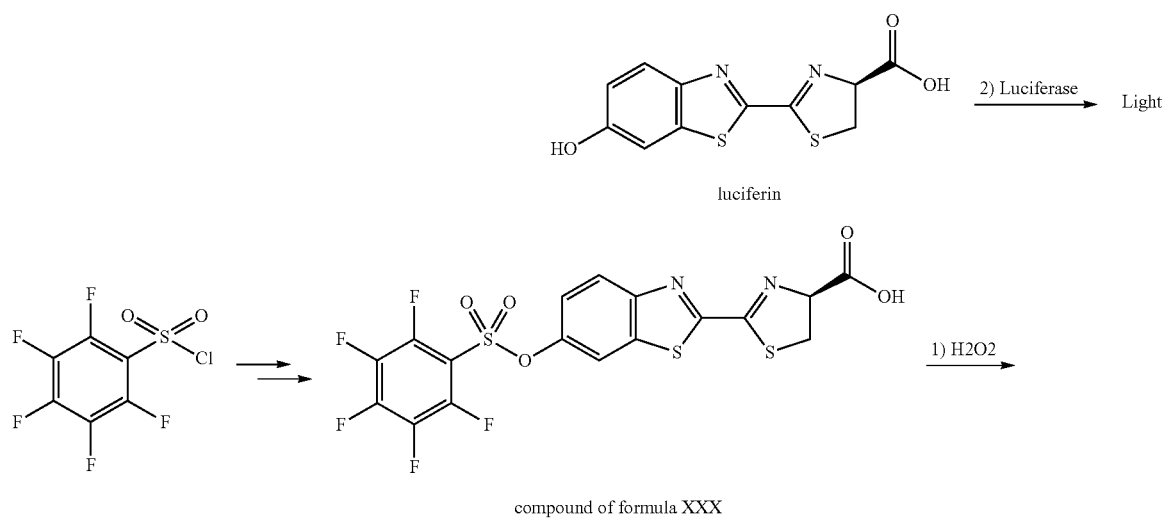
compound of formula XXX
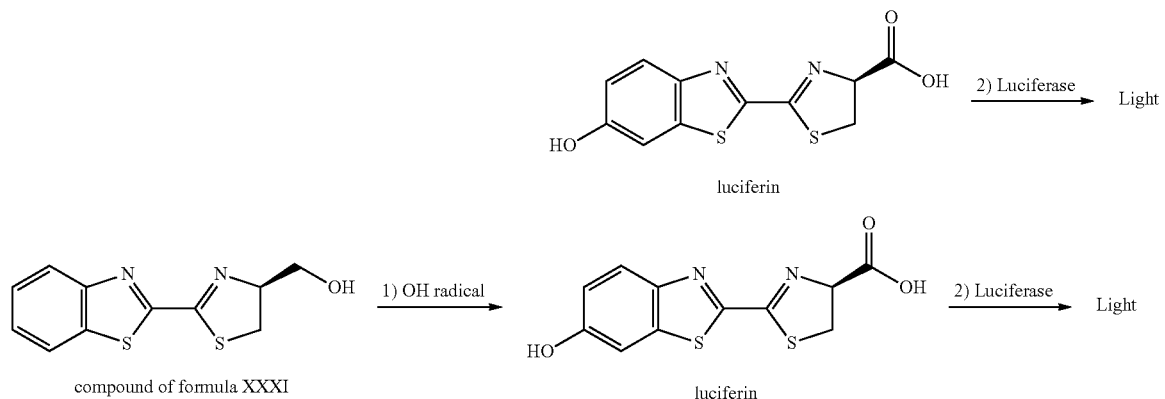
compound of formula XXXI
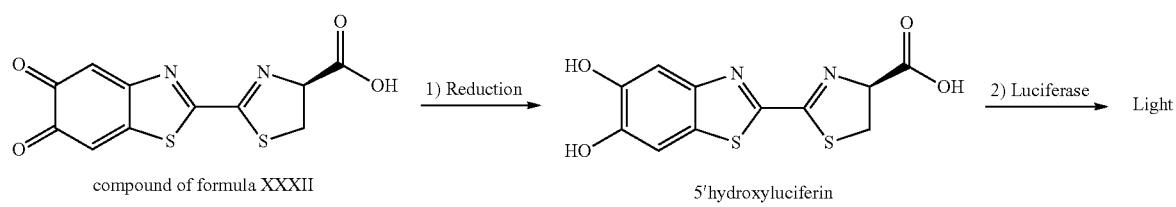
compound of formula XXXII    5′hydroxyluciferin Exemplary bioluminogenic MAO substrates include:

compound of formula XXXIII

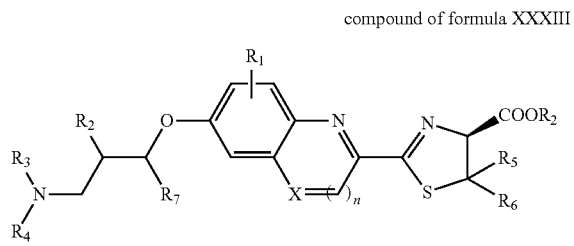

wherein n=0 and X=S or n=1 and X=CH;
wherein $R_1$=H, F, or OH;
wherein $R_2$=, $CH_3$, $CH_2CH_3$, $CH_2CH_2CH_3$, $CH_2CH(CH_3)_2$, $CH_2Ar$, $CH_2CH_2OH$, or any ester;
wherein $R_3$=H, $CH_3$, $CH_2CH_3$, $CH_2CH_2CH_3$, —$H_2C$—C=CH, —$H_2C$

or $R_3$=$(CH_2)_mR_4$:$R_3$=$R_4$=$CH_2$ and n+0, 1, 2, or 3;
wherein $R_5$ and $R_6$ are independently H or $CH_3$;
wherein $R_7$=H or $CH_3$;
wherein $R_8$=H, $CH_3$, OH, or $COCH_3$.

Exemplary bioluminogenic FMO substrates include formula XXXIV

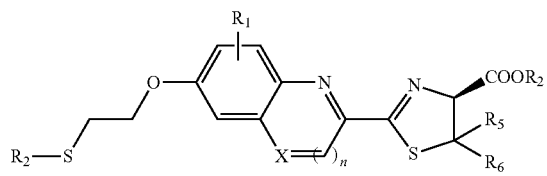

wherein n=0 and X=S or wherein n=1 and X=CH;
wherein $R_1$=H, F, or OH;
wherein $R_2$=H, $CH_3$, $CH_2CH_3$, $CH_2CH_2CH_3$, $CH_2CH_2CH(CH_3)_2$, $CH_2Ar$, $CH_2CH_2OH$, or any ester;
wherein $R_3$=H, $CH_3$, $CH_2CH_3$, $CH_2CH_2CH_3$, any alkyl chain,
or

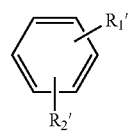

wherein $R_1'$, $R_2'$, H, F, Cl, Br, CN, $NO_2$, $CH_3$, $OCH_3$, $NH_2$, or $N(CH_3)_2$;
wherein $R_5$ and $R_6$ are independently H or $CH_3$.

The A ring of D-luciferin may also be modified to include another ring structure (compound of formulas XXXV-XXXVI):

compound of formula XXXV

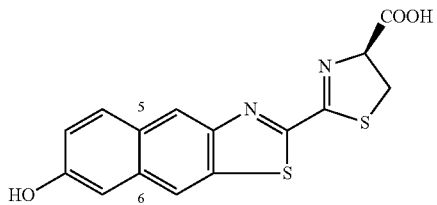

compound of formula XXXVI

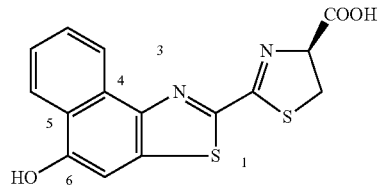

Other A ring modifications include a stable substrate for phosphatase which may also be a luciferase substrate (compound of formula XXXVII):

compound of formula XXXVII

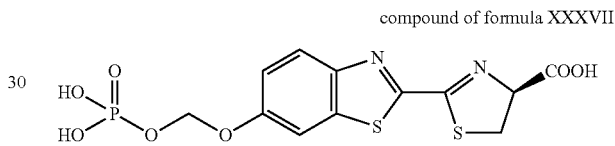

The C ring of luciferin may be modified to include a substrate for acetylcholinesterase (ACh), which optionally has a modified A ring or a modified C and A ring. ACh has a very high turnover number (25,000 $s^{-1}$) and has attained kinetic perfection as indicated by its $k_{cat}/K_M$ value of $2 \times 10^8$ $M^{-1}S^{-1}$. Two types of derivatives which are substrates for ACh include (compounds of formula XXXIX-XXXX):

compound of formula XXXVIII

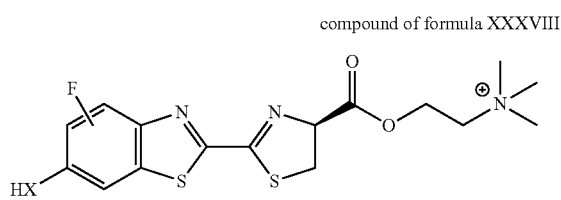

wherein X=O or NH compound of formula XXXIX

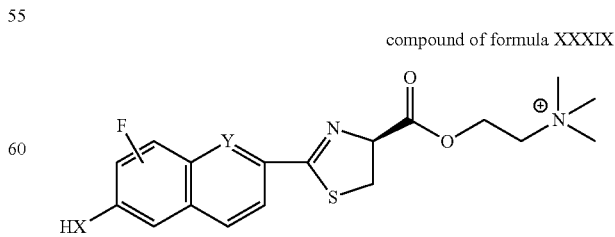

wherein X=O or NH, and
Y=N or CH

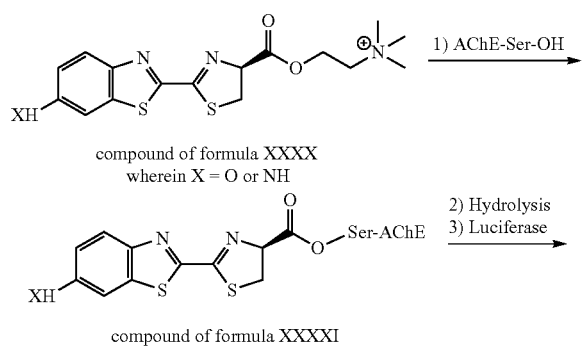

compound of formula XXXX
wherein X = O or NH

1) AChE-Ser-OH

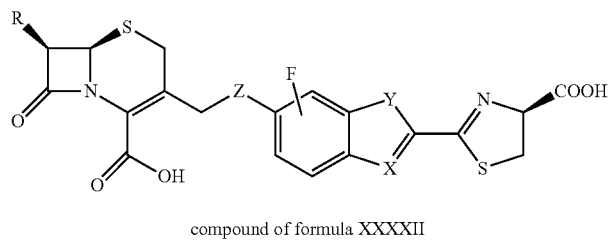

compound of formula XXXXI

2) Hydrolysis
3) Luciferase

Light

Derivatives useful to detect β-lactamase-mediated reactions include quinolinyl luciferin, aminoquinolinyl luciferin and naphthyl luciferin derivatives, optionally also modified with a halogen, e.g., a A ring modification that replaces a H linked to a C ring atom with a F.

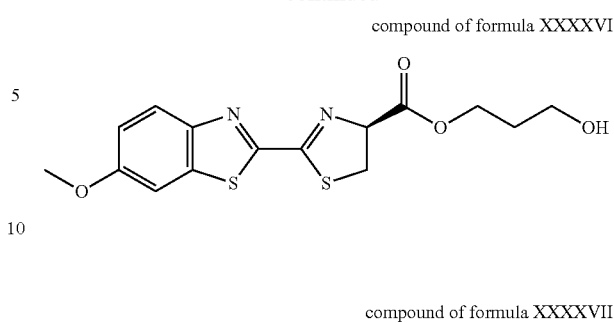

compound of formula XXXXII beta-lactamase

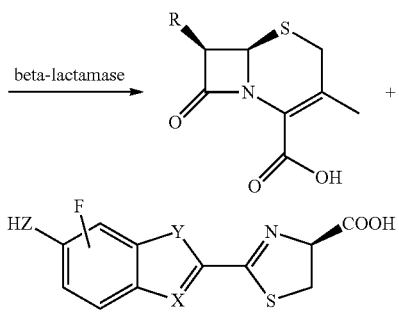

compound of formula XXXXIII wherein R=different group, X=N or CH, Y=S or CH=CH, and
Z=O or NH Derivatives which include esters of luciferin (a C ring modification) optionally with a A ring modification or a B ring modification, or a A and a C ring modification, include compound of formulas XXXXIV-LVIII:

compound of formula XXXXIV

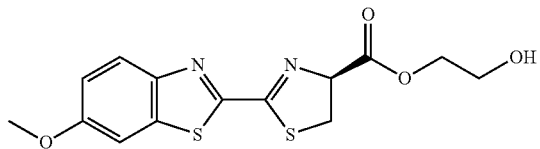

compound of formula XXXXV

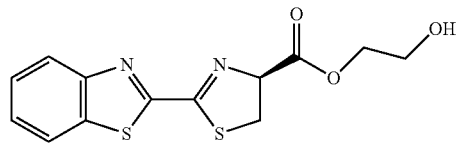

-continued compound of formula XXXXVI compound of formula XXXXVII compound of formula XXXXVIII

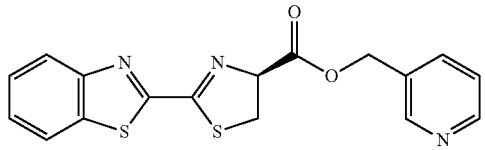

compound of formula XXXXIX

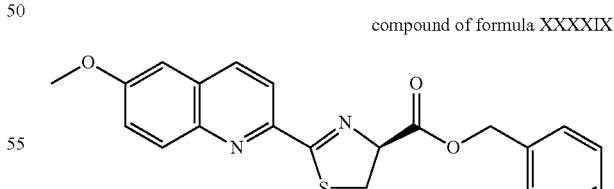

compound of formula L

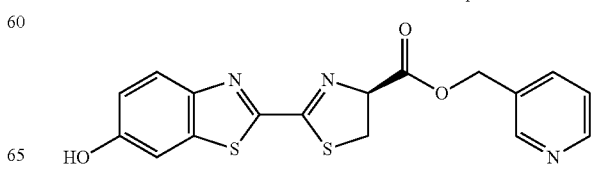

compound of formula LI

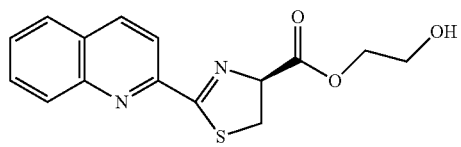

compound of formula LII

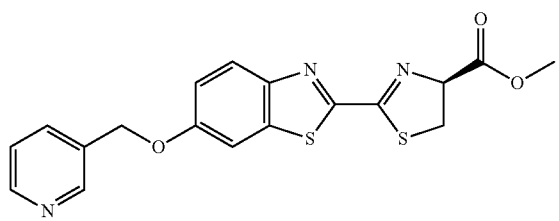

compound of formula LIII

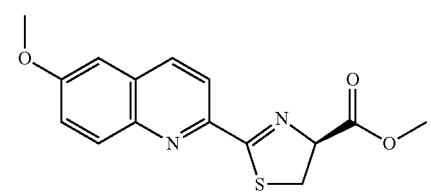

compound of formula LIV

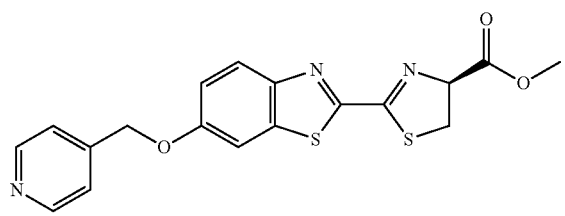

compound of formula LV

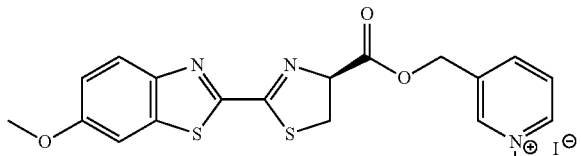

compound of formula LVII

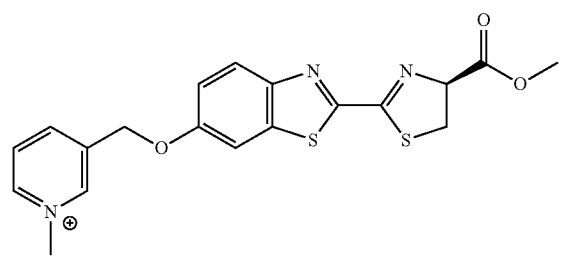

compound of formula LVIII

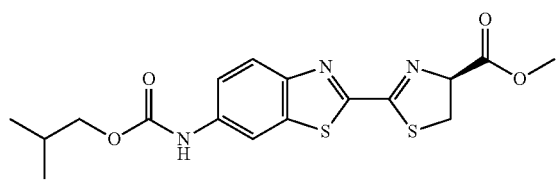

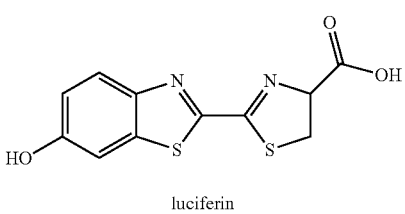

L-luciferin methyl ester

To prepare esters for a derivative of luciferin that are substrates for enzymes including P450, MAO and GST, a cyclization procedure, may be employed with TCEP to reduce ethylene glycol ester D-cysteine before adding to a cyano-containing molecule, is utilized. For instance, to a solution of D-cysteine ester neutralized with potassium bicarbonate, add TECP. After a few minutes, add the solution to the appropriate nitrile dissolved in methanol. Also, methyl ester luciferin derivatives are made by direct cyclization of benzothiole derivatives with methyl ester D-cyteine or methylation of carboxylic acids of luciferin with diazomethane.

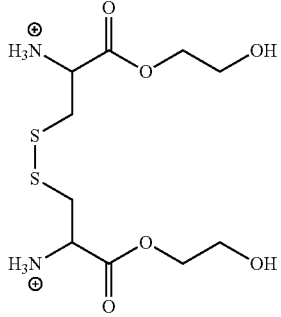

luciferin formula LIX

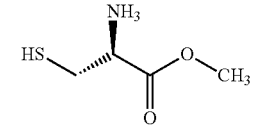

formula LX

Derivatives of luciferin with A, B and/or C ring modifications include:

(compounds of formula LXI-LXX below)

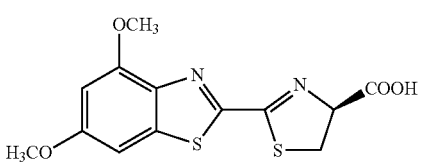

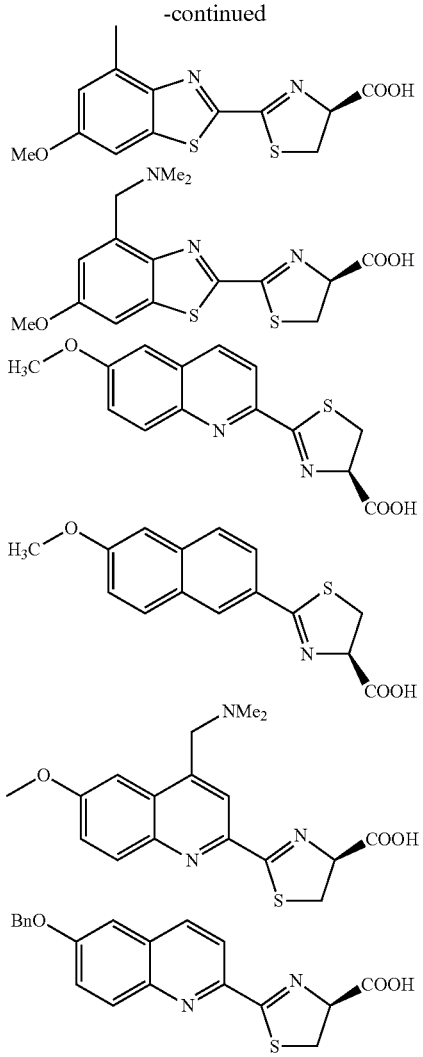
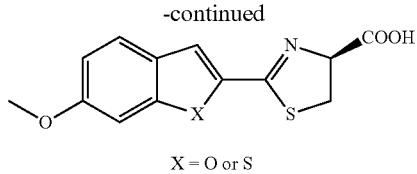
X = O or S
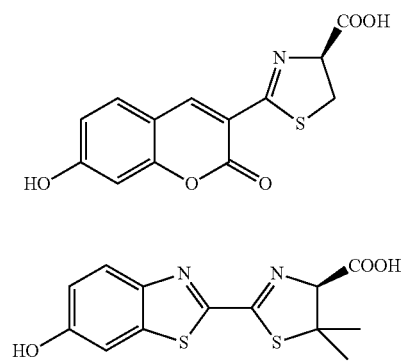
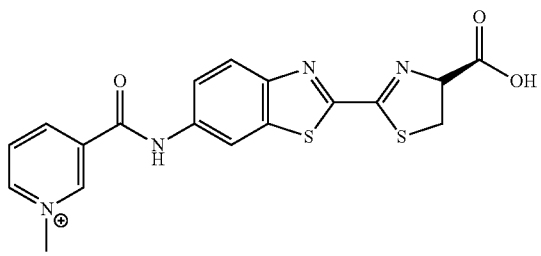
Yet further derivatives include compounds of formula LXXI, LXXII and LXXIII (below)
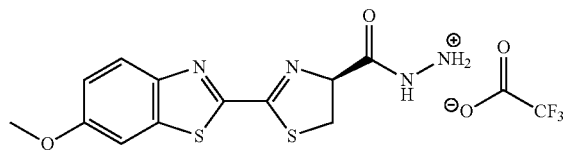
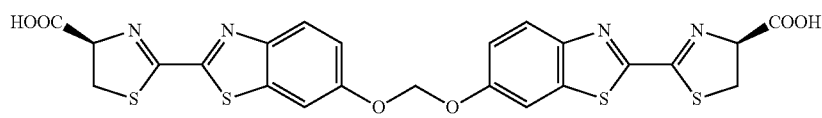
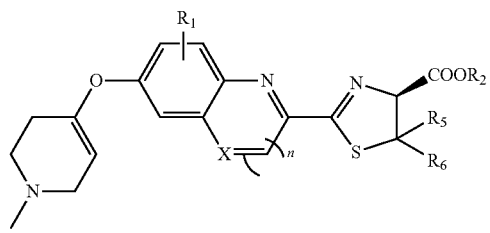

wherein $R_1$=H, F, or OH;

wherein $R_5$ and $R_6$ are independently H or $CH_3$.

In one embodiment, the derivative is a GST substrate (formula LXXIV-LXXV)

LXXIV

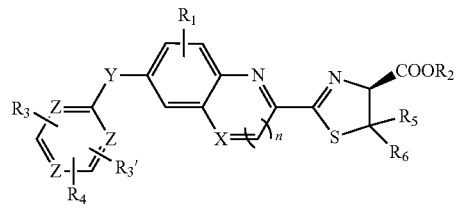

GST/GSH →

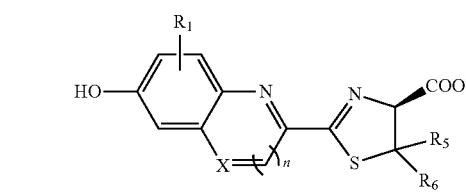

+

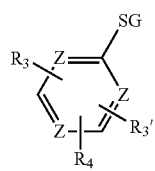

n = 0, X = S
n = 1, X = CH
Y = O, —OSO$_2$—, —OP(O)OR
(R = any alkyl or aromatic ester)
$R_1$ = H, F, OH
$R_2$ = H, CH$_3$, CH$_2$CH$_3$, CH$_2$CH$_2$CH$_3$, CH$_2$CH(CH$_3$)$_2$, CH$_2$Ar, CH$_2$CH$_2$OH, or any ester
$R_3$ = $R_3'$, $R_4$ = NO$_2$, CF$_3$, H
$R_5$, $R_6$ = H, CH$_3$
Z = CH, N wherein n=0 and X=S or n=1 and X=CH;

wherein $R_1$=H, F, or OH;

wherein $R_2$=H, $CH_3$, $CH_2CH_3$, $CH_2CH_2CH_3$, $CH_2CH(CH_3)_2$, $CH_2Ar$; $CH_2CH_2OH$, or any ester;

wherein $R_3$, $R_3'$, $R_4$ independently =NO$_2$, CF$_3$, or H.

LXXV

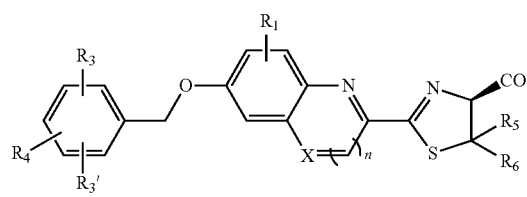

wherein n=0 and X=S or n=1 and X=CH;

wherein $R_1$=H, F, or OH;

wherein $R_2$=H, $CH_3$, $CH_2CH_3$, $CH_2CH_2CH_3$, $CH_2CH(CH_3)_2$, $CH_2Ar$, $CH_2CH_2OH$, or any ester;

wherein $R_3$, $R_3'$ or $R_4$ independently =NO$_2$, CF$_3$, or H.

LXXVIII

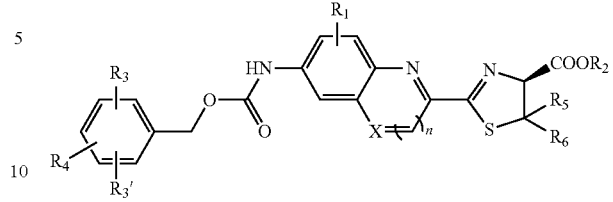

wherein n=0 and X=S or n=1 and X=CH;

wherein $R_1$=H, F, or OH;

wherein $R_2$=H, $CH_3$, $CH_2CH_3$, $CH_2CH_2CH_3$, $CH_2CH(CH_3)_2$, $CH_2$, Ar, $CH_2CH_2OH$, or any ester;

wherein $R_3$, $R_3'$, $R_4$ independently are NO$_2$, CF$_3$, or H.

LXXIX

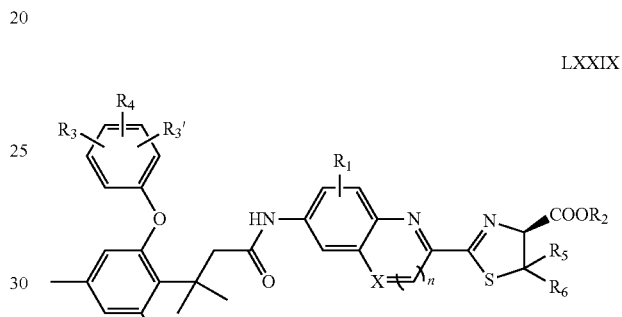

wherein n=0 and X=S or n=1 and X=CH;

wherein $R_1$=H, F, or OH;

wherein $R_2$=H, $CH_2CH_3$, $CH_2CH_2CH_3$, $CH_2CH(CH_3)_2$, $CH_2Ar$, $CH_2CH_2OH$, or any ester;

wherein $R_3$, $R_3'$, $R_4$ are independently NO$_2$, CF$_3$, or H

Exemplary phosphatase and sulfatase substrates include formulas LXXX-LXXXIII:

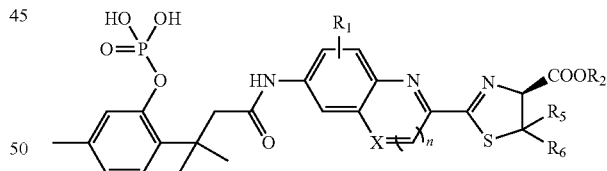

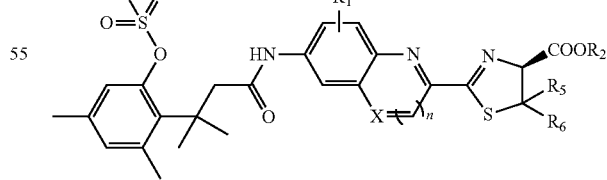

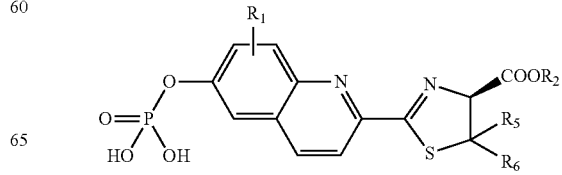

wherein n=0 and X=S or n=1 and X=CH;
wherein $R_1$=H, D, or OH;
wherein $R_2$=H, $CH_3$, $CH_2CH_3$, $CH_2CH_2CH_3$, $CH_2CH(CH_3)_2$, $CH_2Ar$, $CH_2CH_2OH$, or any ester.

wherein n=0 and X=S or n=1 and X=CH;
wherein $R_1$=H, F, or OH;
wherein $R_2$=H, $CH_3$, $CH_2CH_3$, $CH_2CH_2CH_3$, $CH_2CH(CH_3)_2$, $CH_2Ar$, $CH_2CH_2OH$, or any ester;
wherein $R_3$=H, F, Cl, Br, CN, $NO_2$, $CH_3$, $OCH_3$, $NH_2$, or $N(CH_3)_2$; or
wherein $R_5$ and $R_6$ are independently H or $CH_3$.

Derivatives for use in redox or dealkylase bioluminescent assays include compounds of formulas LXXXX-LXXXXI:

Other derivatives of the invention include compounds of formula LXXXVIII-LXXXIX:

Specific derivatives useful as reduction sensors or a dealkylase sensor include compounds of formula LXXXXII-LXXXXVI:

for Redox sensor;
Z = O
for dealkylase;
Z = Me

Y = OH, $NH_2$

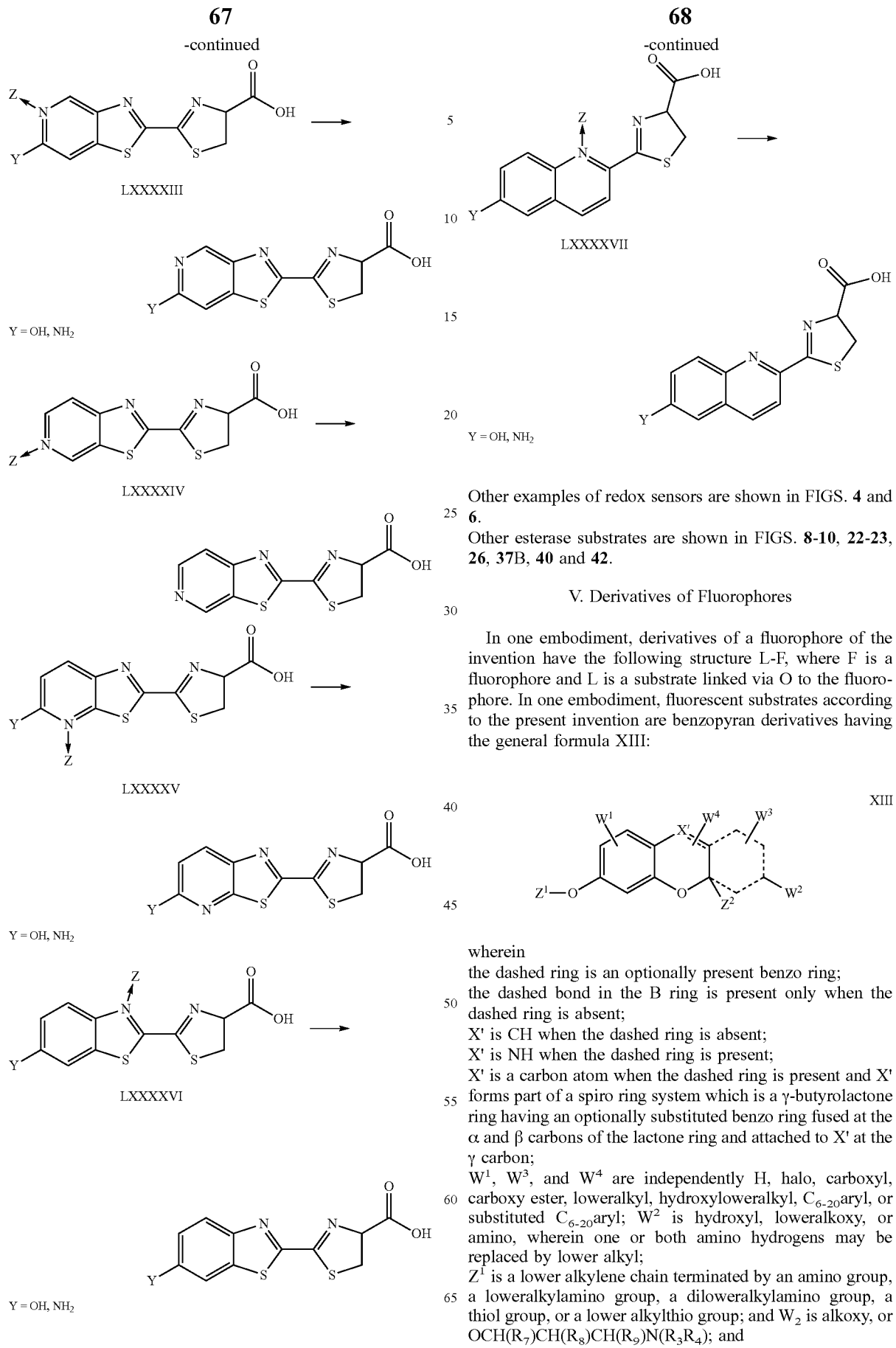

Figure 4A:
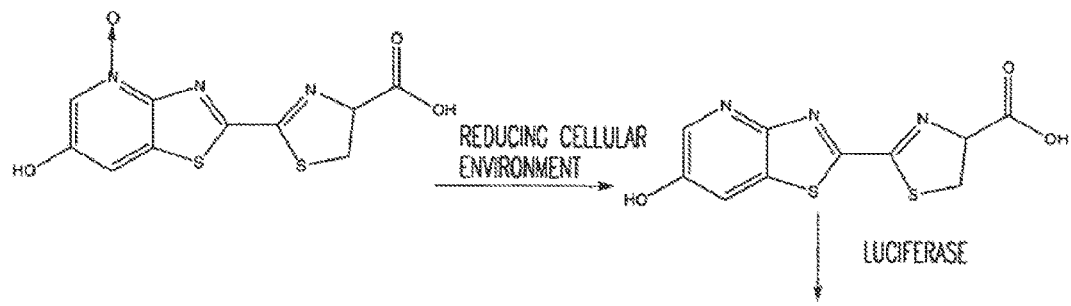
FIGS. 4A-B. Derivatives of luciferin useful as a redox sensor.
Figure 4B:
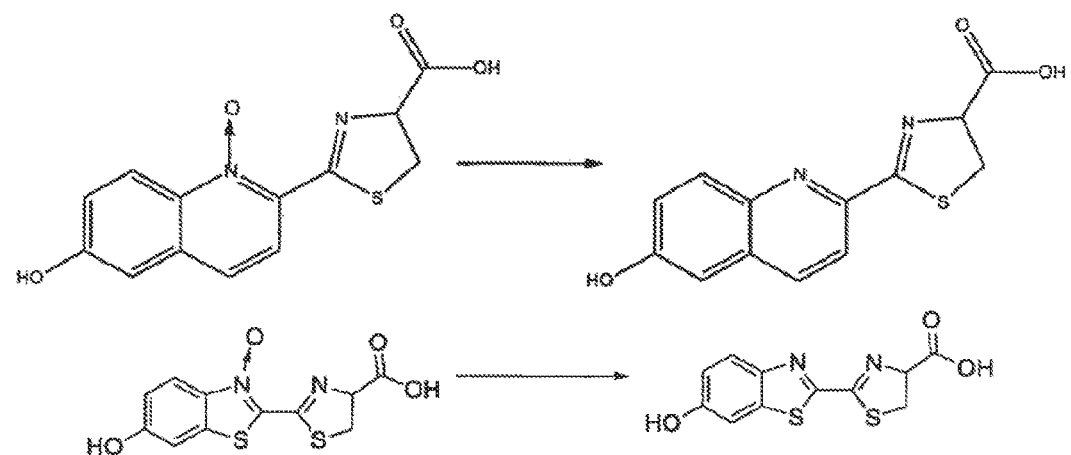
Figure 6:
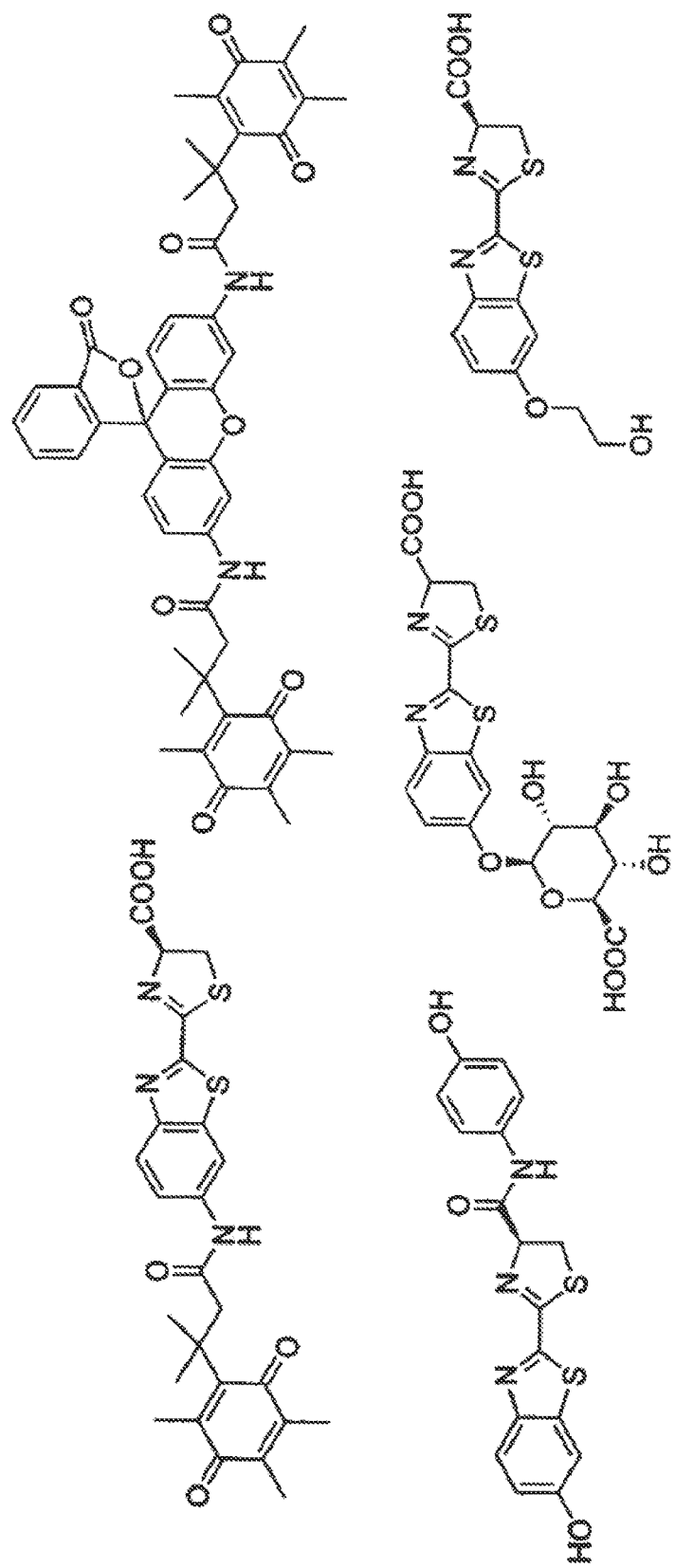

Other examples of redox sensors are shown in FIGS. 4 and 6.

Other esterase substrates are shown in FIGS. 8-10, 22-23, 26, 37B, 40 and 42.

V. Derivatives of Fluorophores

In one embodiment, derivatives of a fluorophore of the invention have the following structure L-F, where F is a fluorophore and L is a substrate linked via O to the fluorophore. In one embodiment, fluorescent substrates according to the present invention are benzopyran derivatives having the general formula XIII:

wherein
the dashed ring is an optionally present benzo ring;
the dashed bond in the B ring is present only when the dashed ring is absent;
X' is CH when the dashed ring is absent;
X' is NH when the dashed ring is present;
X' is a carbon atom when the dashed ring is present and X' forms part of a spiro ring system which is a γ-butyrolactone ring having an optionally substituted benzo ring fused at the α and β carbons of the lactone ring and attached to X' at the γ carbon;
$W^1$, $W^3$, and $W^4$ are independently H, halo, carboxyl, carboxy ester, loweralkyl, hydroxyloweralkyl, $C_{6-20}$aryl, or substituted $C_{6-20}$aryl; $W^2$ is hydroxyl, loweralkoxy, or amino, wherein one or both amino hydrogens may be replaced by lower alkyl;
$Z^1$ is a lower alkylene chain terminated by an amino group, a loweralkylamino group, a diloweralkylamino group, a thiol group, or a lower alkylthio group; and $W_2$ is alkoxy, or $OCH(R_7)CH(R_8)CH(R_9)N(R_3R_4)$; and $Z^2$ is a keto group present only when the benzo ring is absent.

Exemplary fluorogenic MAO substrates include formulas LXXXXVIII-C:

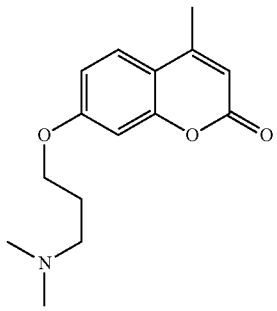

LXXXXVIII

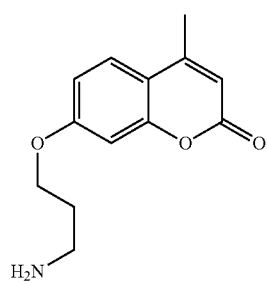

LXXXXIX

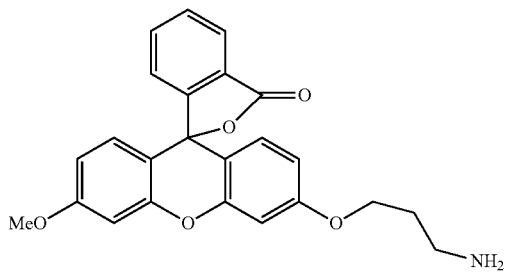

C

Fluorogenic FMO substrates include formulas CI-CIII:

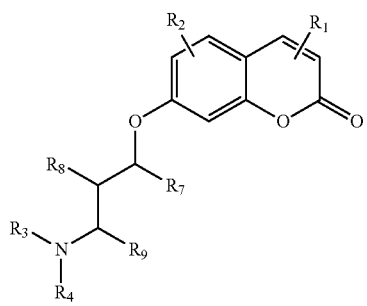

CI

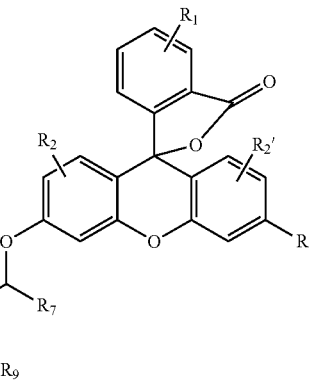

CII

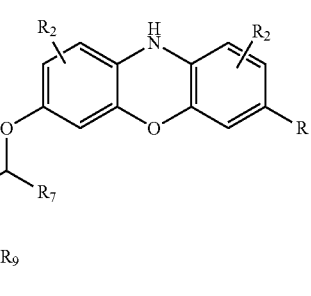

CIII $R_1$, $R_2$, $R_2'$=H, F, Cl, Br, I, COOH, COOR (any ester)
$R_3$, $R_4$=H, $CH_3$, $CH_2CH_3$, $CH_2CH_2CH_3$, —$H_2C$≡CH,

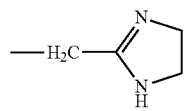

or $R_3(C_2)_nR_4 R_3$=$R_4$=$CH_2$, n=0, 1, 2, 3,
$R_7$=H, $CH_3$
$R_8$=H, $CH_3$, OH, $COCH_3$
$R_9$=H, $CH_3$
R=Alkoxyl (any), or symetric chain OCH(R7)CH(R8)CH(R9)N(R3R4)

Figure 5A:
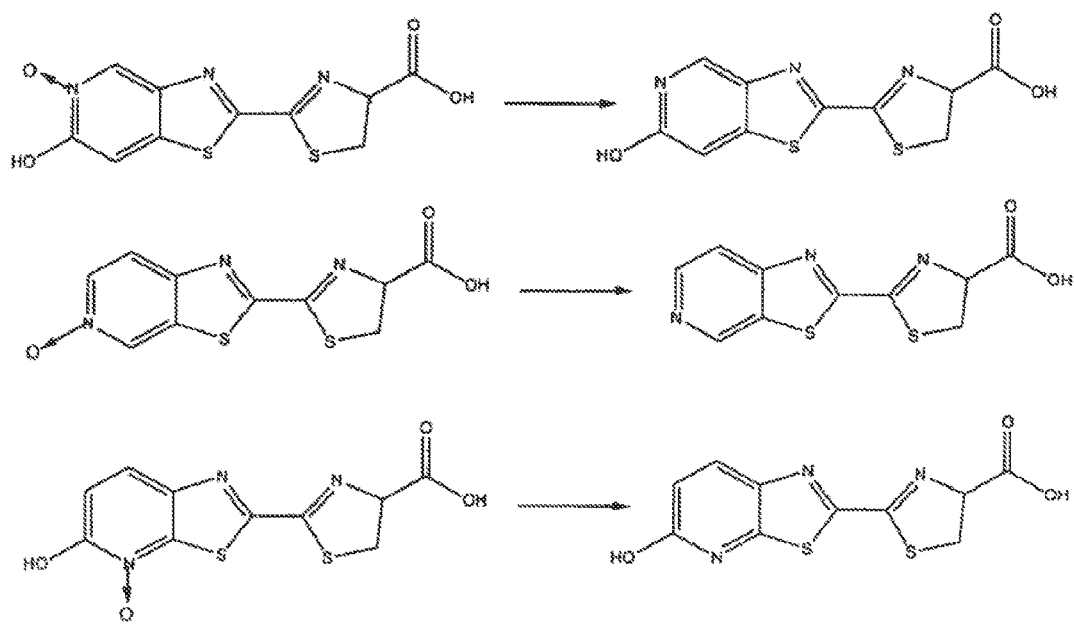
Figure 5B:
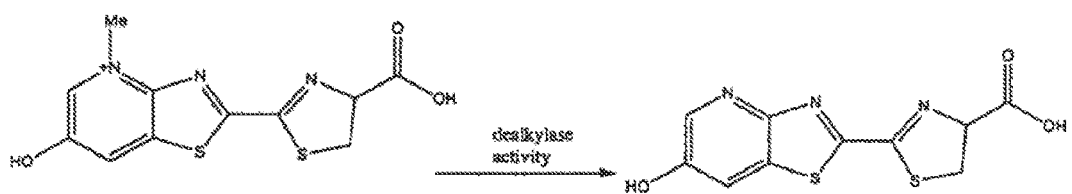
Figure 11:
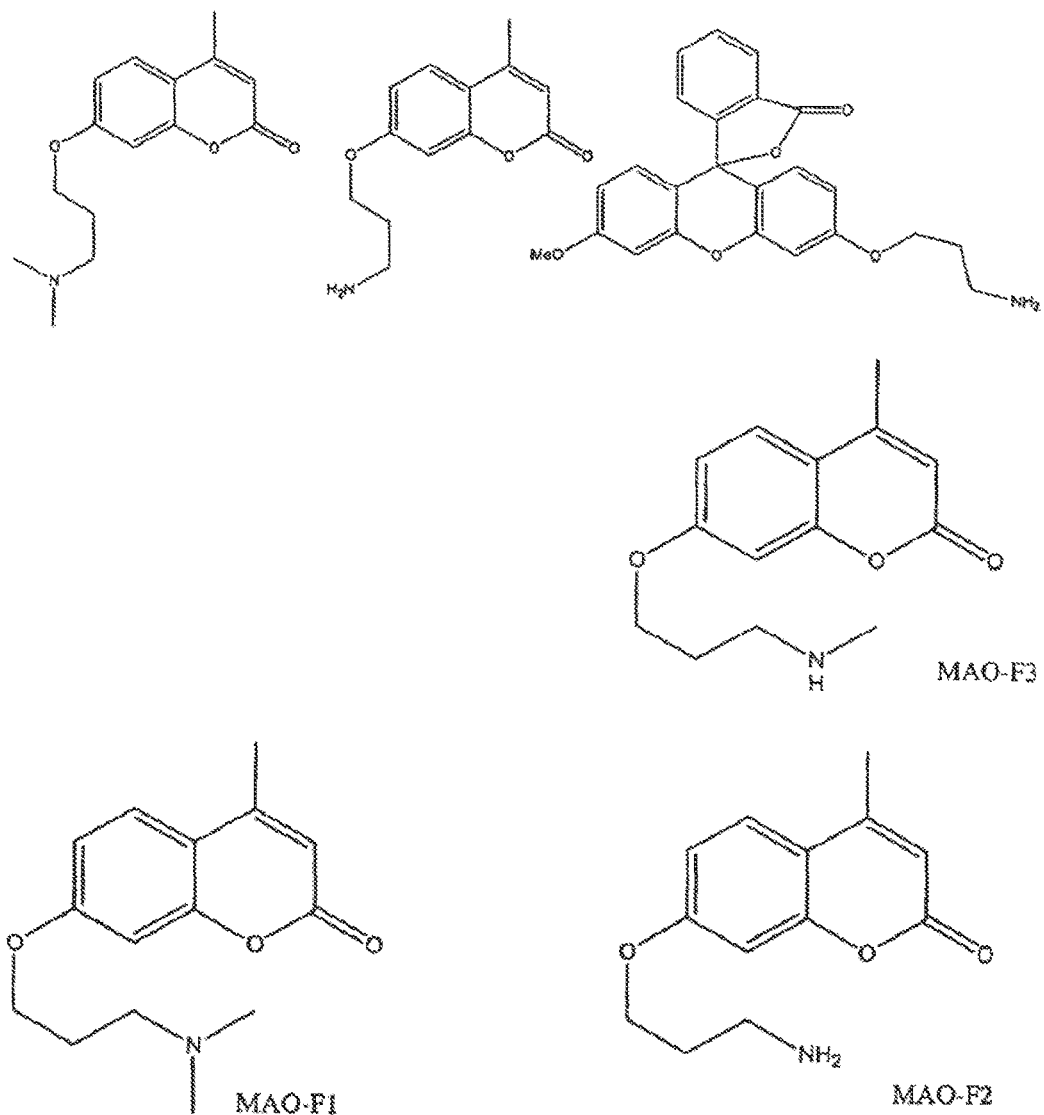
FIG. 11. A graphical representation of derivatives of fluorogenic derivatives useful us monoamine oxide (MAO) substrates.

See FIGS. 5 and 11 for exemplary fluorogenic substrates for redox and MAO reactions.

Any fluorophore may be employed to prepare a fluorogenic substrate, fluorophores including but not limited to fluorescein, Texas Red, DAPI, PI, acridine orange, Alexa fluors, e.g., Alexa 350, Alexa 405 or Alexa 488, cyanine dyes, e.g., Cy3, coumarin, ethidium bromide, fluorescein, BODIPY, a rhodol, Rox, 5-carboxyfluorescein, 6-carboxyfluorescein, and anthracene, 2-amino-4-methoxynaphthalene, a phenalenone, an acridone, fluorinated xanthene derivatives, α-naphtol, β-napthol, 1-hydroxypyrene, coumarins, e.g., 7-amino-4-methylcoumarin (AMC) or 7-amino-4-trifluoromethylcoumarin (AFC), rhodamines, e.g., tetramethylrhodamine, rhodamine-110, or carboxyrhodamine, cresyl violet, or resorufin, as wells as fluorophores disclosed in U.S. Pat. No. 6,420,130, the disclosure of which is incorporated by reference herein.

VI. Linkers

A linker strategy may be employed for either the A or C ring modified luciferins, or with fluorophore containing derivatives, to introduce a substrate for an enzyme of interest such as a deocetylase, deformylase, demethylase or other enzyme that can remove the L group of formula I (a substrate for that enzyme) to free the linker, yielding a substrate of luciferase, or a prosubstrate, where the remaining linker may optionally be removed by a nonenzymatic reaction.

Linkers can be alkyl or alkoxy chains, such as ($C_1$-$C_6$) alkyl or ($C_1$-$C_6$)alkoxy groups. The chain can have one or more election withdrawing group substituents R, such is an aldehyde, acetyl, sulfoxide, sulfone, nitro, cyano group, or a combination thereof. Other linkers include trimethyl lock, quinine methide and diketopiperazine linkers, and their derivatives. A trimethyl lock linker can be illustrated as follows:

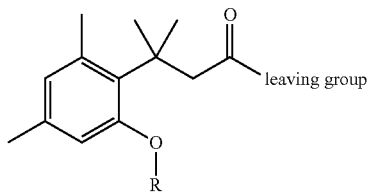

CIV wherein R is as defined for any one of formulas I-III or V-XII, which is a group removable by an enzyme, e.g., an enzyme that is being assayed; the trimethyl lock linker replaces a hydrogen atom of one of the groups Z, Z", or Z"—R, and 'leaving group' is the remainder of the structure of formula I-III or V-XII. See Wang et al., *J. Org. Chem.*, 62:1363 (1997) and Chandran et al, *J. Am. Chem. Soc.* 127:1652 (2005) for the use of trimethyl lock linkers.

A quinine methide linker can be illustrated as follows:

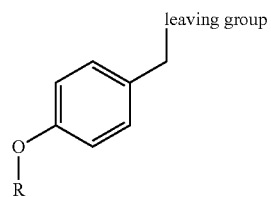

CV wherein R is as defined for any one of formulas I-III or V-XII, which is a group removable by an enzyme, e.g., an enzyme that is being assayed; the quinine methide linker replaces a hydrogen atom of one of the groups Z, Z", or Z"—R; and 'leaving group' is the remainder of the structure of formula I-III or V-XII. See Greenwald et al., *J. Med. Chem.* 42:3657 (1999) and Greenwald et al., *Bioconjugate Chem.*, 14:395 (2003) for the use of quinine methide linkers.

A diketopiperazine linker can be illustrated as follows

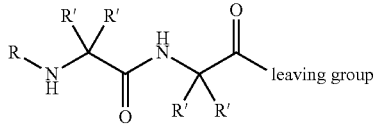

CVI wherein R is as defined for any one of formulas I-III or V-XII which is a group removable by an enzyme, e.g., an enzyme that is being assayed; each R' of the diketopiperazine linker is independently H or an alkyl chain optionally interrupted by O, S, or NH, preferably a methyl group, the diketopiperazine linker replaces a hydrogen atom of one of the groups Z, Z', or Z"—R; and 'leaving group' is the remainder of structure of formula I-III or V-XII. See Wei et al, *Bioorg. Med. Chem. Lett.*, 10: 1073 (2000) for the use of diketopiperazine linkers.

Other linker containing derivatives include:

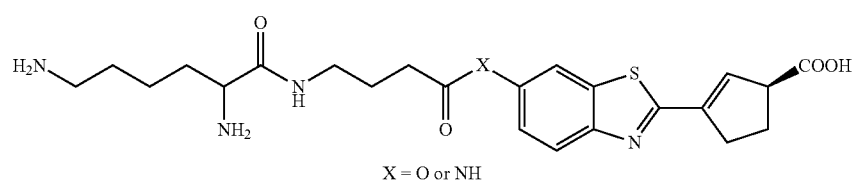

compound of formula CVII

X = O or NH

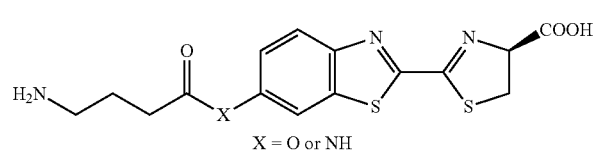

compound of formula CVIII

X = O or NH compound of formula CIX

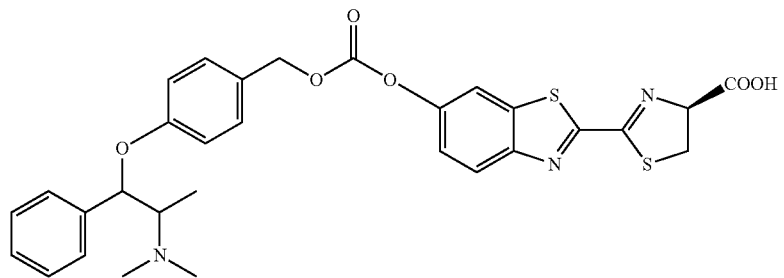

compound of formula CX

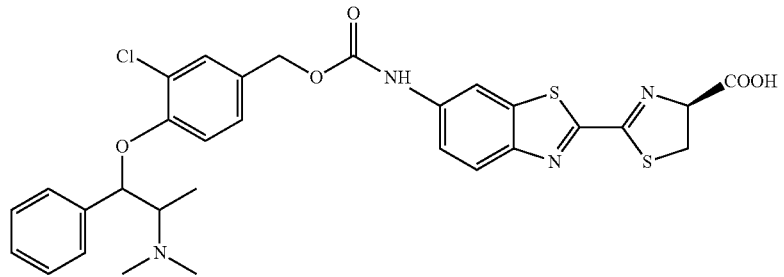

β-elimination of a product of a bioluminogenic or fluorogenic reaction with a substrate having a group R that in the product is an electron withdrawing group R, such as aldehyde, acetyl, sulfoxide, sulfone, nitro, or cyano, may yield a substrate for luciferase or a fluorophore.

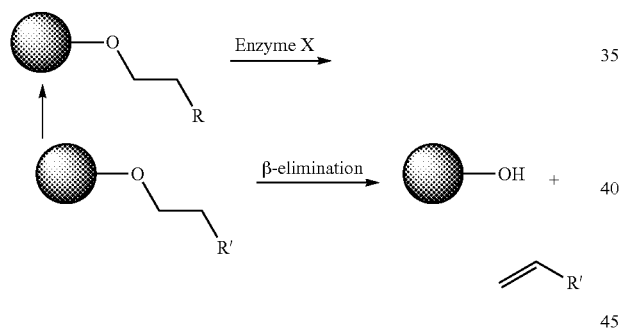

Any fluorogenic chromophore or luminophore

For instance,to detect MAO, the derivative may undergo the following reaction.

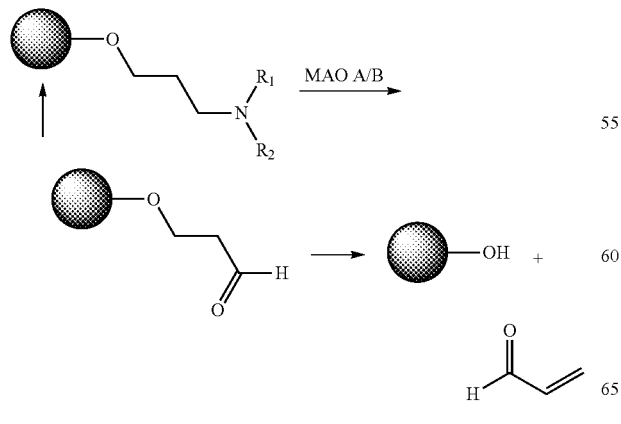

Any fluorogenic chromophore or luminophore

To detect FMO, the derivative may undergo the following reaction:

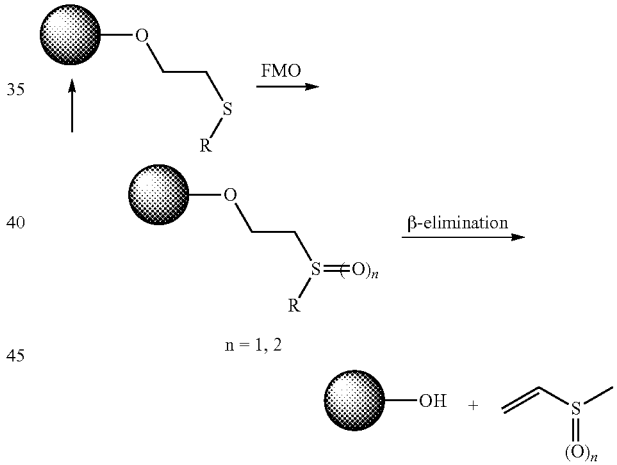

Any fluorogenic chromophore or luminophore

Specific embodiments of reactions and derivatives having formulas CXI-CXV which employ a linker include:

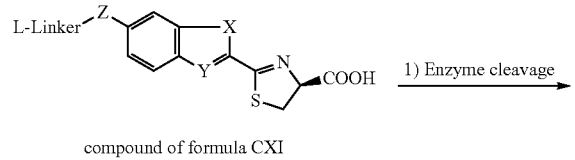

compound of formula CXI

75

-continued

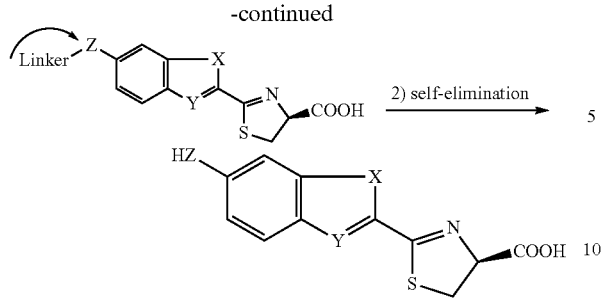

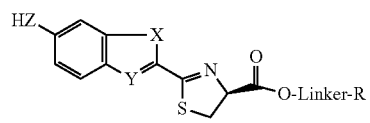

compound of formula CXII wherein L=Me for demethylase, Ac for deacetylase, or CHO for deformylase,
X=S or CH=CH, Y=N or CH, and Z=O or NH;

76

-continued

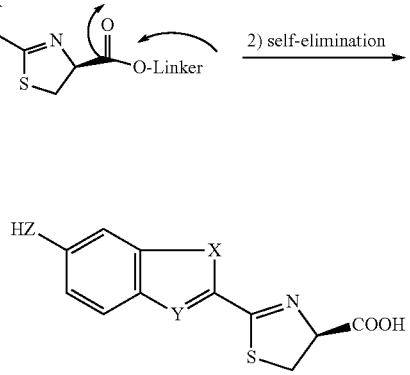

wherein R=Me for demethylase, Ac for deacetylase, or CHO for deformylase, X=S or CH=CH, Y=N or CH, and Z=O or NH

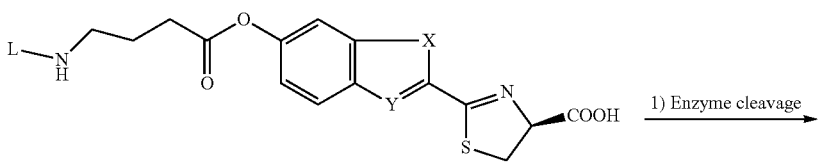

compound of formula CXIII

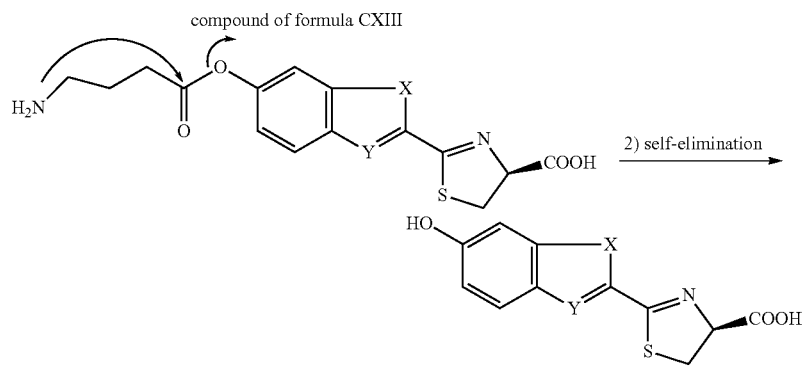

wherein L=Me for demethylase, Ac for deacetylase, or CHO for deformylase, X=S or CH=CH, and Y=N or CH;

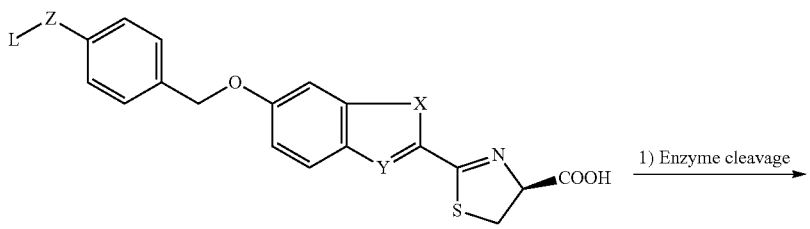

compound of formula CXIV

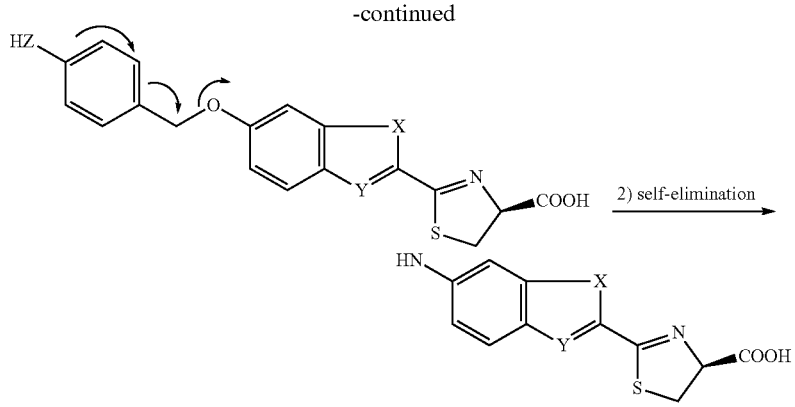

wherein L=Me for demethylase, Ac for deacetylase, or CHO for deformylase, X=S or CH=CH, Y=N or CH, and Z=O or NH; or

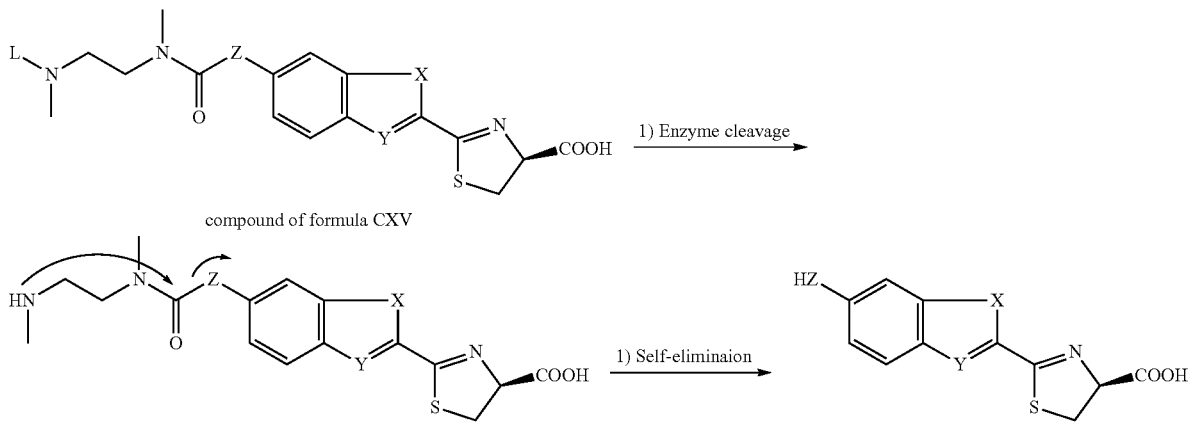

wherein L=Me for demethylase, Ac for deacetylase, or CHO for deformylase, X=S or CH=CH, Y=N or CH, and Z=O or NH.

VII. Agents Useful to Stabilize Light Production in Luciferase-Mediated Reactions Agents useful to stabilize light production in a luciferase-mediated reaction include organic compounds (i.e., compounds that comprise one or more carbon atoms). Such an agent may be added prior to, at the initiation of and/or during a nonluciferase enzyme-mediated reaction or a luciferase-mediated reaction. Suitable organic compounds can comprise a carbon-sulfur bond or a carbon-selenium bond, for example suitable organic compounds can comprise a carbon-sulfur double bond (C=S), a carbon selenium double bond (C=Se), a carbon-sulfur single bond (C—S), or carbon-selenium single bond (C—Se). Suitable organic compounds can also comprise a carbon bound mercapto group (C—SH) or a sulfur atom bound to two carbon atoms (C—S—C). In one embodiment, compounds are lipophilic in nature.

Suitable compounds that comprise a carbon sulfur double bond or a carbon selenium double bond include for example compounds of formula (XIV):

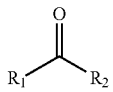

XIV wherein X is S or Se; $R_1$ and $R_2$ are each independently hydrogen, $(C_1-C_{20})$alkyl, $(C_3-C_8)$cycloalkyl, $(C_1-C_{20})$alkoxy, $(C_2-C_{20})$alkenyl, $(C_2-C_{20})$alkynyl, aryl, heteroaryl, or $NR_aR_b$; or $R_1$ and $R_2$ together with the carbon to which they are attached form a 5, 6, 7, or 8 membered saturated or unsaturated ring comprising carbon and optionally comprising 1, 2, or 3 heteroatoms selected from oxy (—O—), thio (—S—), or nitrogen (—$NR_c$)—, wherein said ring is optionally substituted with 1, 2, or 3 halo, hydroxy, oxo, thioxo, carboxy, $(C_1-C_{20})$alkyl, $(C_3-C_8)$cycloalkyl, $(C_1-C_{20})$alkoxy, $(C_1-C_{20})$alkanoyl, $(C_1-C_{20})$alkoxycarbonyl, $(C_2-C_{20})$alkenyl, $(C_2-C_{20})$alkynyl, aryl, or heteroaryl; and $R_a$, $R_b$ and $R_c$ are each independently hydrogen, $(C_1-C_{20})$alkyl, $(C_3-C_8)$ cycloalkyl, $(C_2-C_{20})$alkenyl, $(C_1-C_{20})$alkanoyl, $(C_1-C_{20})$ alkoxycarbonyl, $(C_2-C_{20})$alkynyl, aryl, heteroaryl; wherein any $(C_1-C_{20})$alkyl, $(C_3-C_8)$cycloalkyl, $(C_1-C_{20})$alkoxy, $(C_2-C_{20})$alkenyl $(C_1-C_{20})$alkanoyl, $(C_1-C_{20})$alkoxycarbonyl, or $(C_2-C_{20})$alkynyl or $R_1$, $R_2$, $R_a$, $R_b$, and $R_c$ is optionally substituted with one or more (e.g. 1, 2, 3, or 4) halo, hydroxy, mercapto, oxo, thioxo, carboxy, $(C_1-C_{20})$alkanoyl, $(C_1-C_{20})$alkoxycarbonyl, aryl, or heteroaryl, and wherein any aryl or heteroaryl is optionally substituted with one or more (1, 2, 3, or 4) halo, hydroxy, mercapto, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl; or a salt thereof.

Suitable compounds that comprise a mercapto group include for example compounds or the formula $R_3SH$ wherein; $R_2$ is $(C_1-C_{20})$alkyl, $(C_3-C_8)$cycloalkyl, $(C_2-C_{20})$alkenyl, $(C_2-C_{20})$alkynyl, aryl, heteroaryl; wherein any $(C_1-C_{20})$alkyl, $(C_3-C_8)$cycloalkyl, $(C_2-C_{20})$alkenyl, or $(C_2-C_{20})$alkynyl or $R_3$ is optionally substituted with one or more (e.g. 1, 2, 3, or 4) halo, hydroxy, mercapto oxo, thioxo, carboxy, $(C_1-C_{20})$alkanoyl, $(C_1-C_{20})$alkoxycarbonyl, aryl, heteroaryl, or $NR_dR_e$; wherein $R_d$ and $R_e$ are each independently hydrogen, $(C_1-C_{20})$alkyl, $(C_3-C_8)$cycloalkyl, $(C_2-C_{20})$alkenyl, $(C_2-C_{20})$alkynyl, $(C_1-C_{20})$alkanoyl, $(C_1-C_{20})$alkoxycarbonyl aryl, or heteroaryl; and wherein any aryl or heteroaryl; and wherein any aryl or heteroaryl is optionally substituted with one or more (1, 2, 3, or 4) halo, mercapto, hydroxy, oxo, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl; or a salt thereof.

Other suitable compounds include for example compounds of the formula $R_4NCS$ wherein: $R_4$ is $(C_1-C_{20})$alkyl, $(C_3-C_8)$cycloalkyl, $(C_2-C_{20})$alkenyl, $(C_2-C_{20})$alkynyl, aryl, or heteroaryl; wherein any $(C_1-C_{20})$alkyl, $(C_3-C_8)$cycloalkyl, $(C_2-C_{20})$alkenyl, or $(C_2-C_{20})$alkenyl or $R_3$ is optionally substituted with one or more (e.g. 1, 2, 3, or 4) halo, hydroxy, mercapto oxo, thioxo, carboxy, $(C_1-C_{20})$alkanoyl, $(C_1-C_{20})$alkoxycarbonyl, aryl, heteroaryl, or $NR_fR_g$; wherein $R_f$ and $R_g$ are each independently hydrogen, $(C_1-C_{20})$alkyl, $(C_3-C_8)$cycloalkyl, $(C_2-C_{20})$alkenyl, $(C_2-C_{20})$alkynyl, $(C_1-C_{20})$alkanoyl, $(C_1-C_{20})$alkoxycarbonyl aryl, or heteroaryl; and wherein any aryl or heteroaryl is optionally substituted with one or more (1, 2, 3, or 4) halo, mercapto, hydroxy, oxo, carboxy, cyano, nitro, trifluoromethyl, trifluoromethoxy $(C_1-C_{20})$alkanoyl, $(C_1-C_{20})$alkanoyloxy, sulfo or $(C_1-C_{20})$alkoxycarbonyl; or a salt thereof.

Other suitable compounds that comprise a carbon-selenium single bond or a carbon sulfur single bond include compounds of formula $R_5$—X—$R_6$ wherein:

X is —S— or —Se—;

$R_5$ is $(C_1-C_{20})$alkyl, $(C_3-C_8)$cycloalkyl, $(C_2-C_{20})$alkenyl, $(C_2-C_{20})$alkynyl, aryl, or heteroaryl, and $R_6$ is hydrogen, $(C_1-C_{20})$alkyl, $(C_3-C_8)$cycloalkyl, $(C_2-C_{20})$alkenyl, $(C_{20}-C_{20})$alkynyl, aryl, or heteroaryl;

or $R_5$ and $R_6$ together with X form a heteroaryl;

wherein any $(C_1-C_{20})$alkyl, $(C_3-C_8)$cycloalkyl, $(C_2-C_{20})$alkenyl, or $(C_2-C_{20})$alkynyl of $R_5$ or $R_6$ is optionally substituted with one or more (e.g., 1, 2, 3, or 4) halo, hydroxy, mercapto oxo, thioxo, carboxy, $(C_1-C_{20})$alkanoyl, $(C_1-C_{20})$alkoxycarbonyl, aryl, heteroaryl, or $NR_kR_m$;

wherein $R_k$ and $R_m$ are each independently hydrogen, $(C_1-C_{20})$alkyl, $(C_3-C_8)$cycloalkyl, $(C_2-C_{20})$alkenyl, $(C_2-C_{20})$alkynyl, $(C_1-C_{20})$alkanoyl, $(C_1-C_{20})$alkoxycarbonyl aryl, or heteroaryl; and wherein any aryl or heteroaryl is optionally substituted with one or more (1, 2, 3, or 4) halo, mercapto, hydroxy, oxo, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl; or salt thereof.

Specific and preferred values listed below for radicals, substituents, and ranges, are for illustration only; they do not exclude other defined values or other values within defined ranges for the radicals and substituents.

Specifically, $(C_1-C_{20})$alkyl can be methyl, ethyl, propyl, isopropyl, butyl, iso-butyl, sec-butyl, pentyl, 3-pentyl, or hexyl; $(C_3-C_8)$cycloalkyl can be cyclopropyl, cyclobutyl, cyclopentyl, or cyclohexyl, $(C_1-C_{20})$alkoxy can be methoxy, ethoxy, propoxy, isopropoxy, butoxy, iso-butoxy, sec-butoxy, pentoxy, 3-pentoxy, or hexyloxy; $(C_2-C_{20})$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl 3-hexenyl, 4-hexenyl, or 5-hexenyl; $(C_2-C_{20})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_{20})$alkanoyl can be acetyl, propanoyl or butanoyl; $(C_1-C_{20})$alkoxycarbonyl can be methoxycarbonyl, ethoxycarbonyl, ethoxycarbonyl, propoxycarbonyl, isopropoxycarbonyl, butoxycarbonyl, pentoxycarbonyl, or hexyloxycarbonyl; $(C_2-C_{20})$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide) thienyl, pyrimidinyl (or its N-oxide), indolyl, isoquinolyl (or its N-oxide) or quinolyl (or its N-oxide).

Specifically, $R_1$ and $R_2$ can each independently be hydrogen, $(C_1-C_{20})$alkyl, $(C_3-C_8)$cycloalkyl, $(C_2-C_{20})$alkenyl, $(C_2-C_{20})$alkynyl, aryl, heteroaryl, or $NR_aR_b$; wherein $R_a$ and $R_b$ are each independently hydrogen, $(C_1-C_{20})$alkyl, $(C_3-C_8)$cycloalkyl, $(C_2-C_{20})$alkenyl, $(C_1-C_{20})$alkanoyl, $(C_1-C_{20})$alkoxycarbonyl, $(C_2-C_{20})$alkynyl, aryl, or heteroaryl; wherein any $(C_1-C_{20})$alkyl, $(C_3-C_8)$cycloalkyl, $(C_1-C_{20})$alkoxy, $(C_2-C_{20})$alkenyl $(C_1-C_{20})$alkanoyl, $(C_1-C_{20})$alkoxycarbonyl, or $(C_2-C_{20})$alkynyl or $R_1$, $R_2$, $R_a$, and $R_b$ is optionally substituted with 1 or 2 halo, hydroxy, mercapto, oxo, thioxo, carboxy, $(C_1-C_{20})$alkanoyl, $(C_1-C_{20})$alkoxycarbonyl, aryl, or heteroaryl; and wherein any aryl or heteroaryl is optionally substituted with one or more halo, hydroxy, mercapto, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl.

Specifically, $R_1$ and $R_2$ can each independently be hydrogen, $(C_1-C_{10})$alkyl, $(C_2-C_{10})$alkenyl, $(C_2-C_{10})$alkynyl, aryl, or $NR_aR_b$.

Specifically, $R_1$ and $R_2$ together with the carbon to which they are attached can form a 5 or 6 membered saturated or unsaturated ring comprising carbon and optionally comprising 1 or 2 heteroatoms selected from oxy (—O—), thio (—S—), or nitrogen (—$NR_c$)—, wherein said ring is optionally substituted with 1, 2, or 3 halo, hydroxy, oxo, thioxo, carboxy, $(C_1-C_{20})$alkyl, $(C_3-C_8)$cycloalkyl, $(C_1-C_{20})$alkoxy, $(C_1-C_{20})$alkanoyl, $(C_1-C_{20})$alkoxycarbonyl, $(C_2-C_{20})$alkenyl, $(C_2-C_{20})$alkynyl, aryl, or heteroaryl; wherein $R_c$ is hydrogen, $(C_1-C_{20})$alkyl, $(C_3-C_8)$cycloalkyl, $(C_2-C_{20})$alkenyl, $(C_1-C_{20})$alkanoyl, $(C_1-C_{20})$alkoxycarbonyl, $(C_2-C_{20})$alkynyl, aryl, heteroaryl; wherein any $(C_1-C_{20})$alkyl, $(C_3-C_{20})$cycloalkyl, $(C_1-C_{20})$alkoxy, $(C_2-C_{20})$alkenyl $(C_1-C_{20})$alkanoyl, $(C_1-C_{20})$alkoxycarbonyl, or $(C_2-C_{20})$alkynyl or $R_1$, $R_2$, and $R_c$ is optionally substituted with one or more halo, hydroxy, mercapto, oxo, thioxo, carboxy, $(C_1-C_{20})$alkanoyl, $(C_1-C_{20})$alkoxycarbonyl, aryl, or heteroaryl; and wherein any aryl or heteroaryl is optionally substituted with one or more halo, hydroxy, mercapto, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl.

Specifically, $R_1$ and $R_2$ can each independently by $NR_aR_b$; wherein $R_a$ and $R_b$ are each independently hydrogen, $(C_1-$ $C_{20}$)alkyl, $(C_3$-$C_8)$cycloalkyl, $(C_2$-$C_{20})$alkenyl, $(C_1$-$C_{20})$alkanoyl, $(C_1$-$C_{20})$alkoxycarbonyl, $(C_2$-$C_{20})$alkynyl, aryl, heteroaryl; wherein any $(C_1$-$C_{20})$alkyl, $(C_3$-$C_8)$cycloalkyl, $(C_2$-$C_{20})$alkenyl $(C_1$-$C_{20})$alkanoyl, $(C_1$-$C_{20})$alkoxycarbonyl, or $(C_2$-$C_{20})$alkynyl is optionally substituted with one or more halo, hydroxy, mercapto, oxo, thioxo, carboxy, aryl, or heteroaryl; and wherein any aryl or heteroaryl is optionally substituted with one or more halo, hydroxy, mercapto, carboxy, cyano, nitro, trifluoromethyl, trifluoromethyl, trifluoromethoxy, $(C_1$-$C_{20})$alkanoyl, $(C_1$-$C_{20})$alkanoyloxy, sulfo or $(C_1$-$C_{20})$alkoxycarbonyl.

Specifically, $R_1$ and $R_2$ can each independently be amino, $(C_1$-$C_{20})$alkyl, $(C_1$-$C_{20})$alkylamino, allylamino, 2-hydroxyethylamino, phenylamino, or 4-thiazoylamino.

Specifically, $R_1$ and $R_2$ can each independently be amino, methyl, allylamino, 2-hydroxyethylamino, phenylamino, or 4-thiazoylamino.

A specific value for $R_3$ is $(C_1$-$C_{20})$alkyl optionally substituted with one or more halo, mercapto oxo, thioxo, carboxy, $(C_1$-$C_{20})$alkanoyl, $(C_1$-$C_{20})$alkoxycarbonyl, aryl, heteroaryl, or $NR_dR_e$.

A specific value for $R_3$ is 2-aminoethyl, 2-amino-2-carboxyethyl, or 2-acylamino-2-carboxyethyl.

A specific value for $R_4$ is aryl, optionally substituted with one or more halo, mercapto, hydroxy, oxo, carboxy, cyano, nitro, trifluoromethyl, trifluoromethoxy, $(C_1$-$C_{20})$alkanoyl, $(C_1$-$C_{20})$alkanoyloxy, sulfo or $(C_1$-$C_{20})$alkoxycarbonyl, Specifically, $R_5$ is $(C_1$-$C_{10})$alkyl, $(C_3$-$C_6)$cycloalkyl, $(C_2$-$C_{10})$alkenyl, $(C_2$-$C_{10})$alkynyl, aryl, or heteroaryl; and $R_6$ is hydrogen, $(C_1$-$C_{10})$alkyl, $(C_3$-$C_6)$cycloalkyl, $(C_2$-$C_{10})$alkenyl, $(C_2$-$C_{10})$alkynyl, aryl, or heteroaryl.

Specifically, $R_5$ and $R_6$ together with X form a heteroaryl.

In one embodiment, the organic compound is not a polypeptide, or protein with one or more mercapto (C—SH) groups.

In one embodiment, the organic compound is not a compound that includes one or more mercapto (C—SH) groups.

Preferred compounds are coenzyme A and DTT.

The compounds described hereinabove are available from commercial sources or can be prepared from commercially available starting materials using procedures that are known in the field of synthetic chemistry. For example, see Jerry March, Advanced Organic Chemistry, 4th ed. Wiley-Interscience. John Wiley and Sons, New York, 1992.

In cases where compounds are sufficiently basic or acidic to form stable salts, use of the compounds as salts in the methods of the invention may be appropriate. Examples of suitable salts include organic acid addition salts, for example, tosylate, methanesulfonate, acetate, citrate, malonate, tartarate, succinate, benzoate, ascorbate, α-ketoglutarate, and α-glycerophosphate salts. Suitable inorganic salts may also be formed, including hydrochloride, sulfate, nitrate, bicarbonate, and carbonate salts.

Salts can be obtained using standard procedures well known in the art, for example by reacting a sufficiently basic compound with a suitable acid. Alkali metal (for example, sodium, potassium or lithium) or alkaline earth metal (for example calcium) salts can also be used.

When used in accord with the methods of the invention, the compounds described herein can be present in a luminescence reaction at any effective concentration. The optimum concentration of a given compound will depend on the luminescent reagent(s) employed, and on the specific conditions under which a given assay is carried out. However, suitable concentrations can be determined using standard techniques that are available in the art.

Specifically, the compound can be present in a luminescence reaction at a concentration of at least about 0.01 µM, or at a concentration of at least about 0.1 µM, e.g., at least about 0.1 mM. More specifically, the compound can be present in the luminescence reaction at a concentration in the range from about 0.1 µM to about 500 mM (inclusive), or in the range from about 0.001 µM, 0.01 µM, or 0.1 µM to about 250 mM (inclusive). Preferably, the compound is present at a concentration in the range from about 0.001 µM, 0.01 µM, 0.1 µM, 1 µM or 10 µM to about 100 mM (inclusive).

Specifically, the assay can be performed in the presence of purified enzymes, cell lystates or whole cells.

Specifically, the assay can be carried out in a solvent comprising at least about 10% water. More specifically, the invention can be carried out in a solvent comprising at least about 25% water, or at least about 40% water.

VII. Kits

The present invention also provides kits for detecting the presence or activity of one or more molecules which are reagents for a reaction, enhance or inhibit a reaction, or for detecting a condition, in a sample such as a sample including intact cells, a cell lysate, e.g., a lysate which is at least partially purified, or a cellular supernatant. In one embodiment, the kit includes a derivative of the invention. For kits of the invention that include two or more of the following, a derivative of luciferin or aminoluciferin, a derivative of a fluorophore, another substrate, enzyme, or reaction mixture, each can be contained in a separate container, some components may be combined in some containers, or they can be contained in a single container. The kit can optionally comprise a buffer solution suitable for use in an assay, and the derivative or enzyme, and the buffer solution can optionally be contained in a single container. Additionally, the derivative and the buffer solution can optionally be contained in a single container. The kits can also optionally include a quenching agent for a nonbioluminescent reaction.

IX. Exemplary Synthesis

A. Experimental Procedures for Luciferin Modifications

Included below are experimental procedures for syntheses of various luciferin derivatives:

I. General procedures for synthesizing esters of luciferins

II. D-cysteine or D-cystine esters

III. Esters of luciferin methyl ether or luciferin-H

IV. Quinolinyl luciferin derivatives

V. Miscellaneous

I. General Procedures for Synthesizing Luciferin Esters

There are two ways of synthesizing esters of D-luciferin and derivatives, including luciferin-H and quinolinyl luciferin: a) by direct cyclization of the corresponding cyano group with D-cysteine or D-cysteine esters, and b) by CsF-promoted esterification with halogenated organic compounds, such as 3-iodomethyl pyridine hydriodide (picolinyl iodide) or 3-iodopropanol.

A. Direct Cyclization

Under this category, two D-cyteine esters are used, one is D-cyteine methyl ester and the other is D-cystine 2-hydroxyethyl ester. The latter requires a reducing agent before cyclization.

i) D-Cyteine Methyl Ester

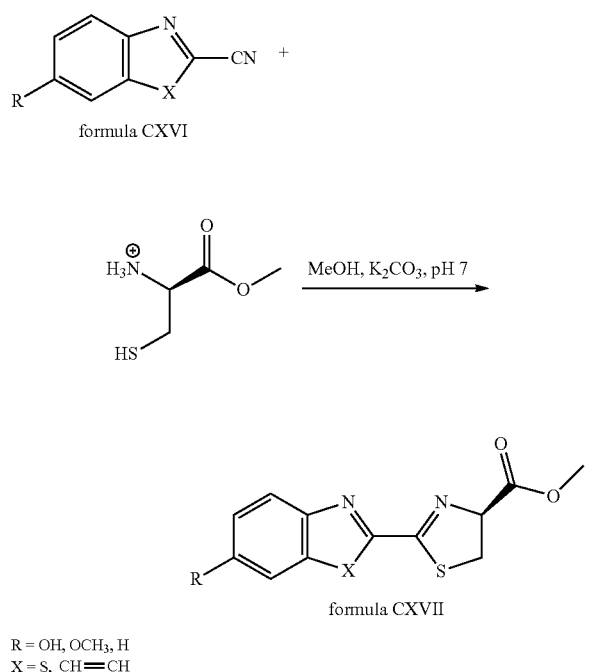

R = OH, OCH₃, H
X = S, CH=CH

A derivative of 2-cyanobenzothiazole or 2-cyanoquinoline (1 equivalent) was dissolved in methanol and was degassed with a gentle stream of nitrogen for 10 minutes. Meanwhile, D-cyteine methyl ester (1.5 equivalents) was dissolved in water and its pH was adjusted to about 7. This solution was also degassed with a gentle stream of nitrogen for 5 minutes. Then, the aqueous solution was added to above organic solution dropwise and the resultant solution was stirred under nitrogen for 30 minutes to a few hours depending on substrates. The reaction was monitored by TLC with methanol in dichloromethane. After the completion of the reaction, the mixture was filtered and was purified by HPLC. Typical HPLC conditions are the following.

Column: Dynamax 60 Å, 1 inch, 250 mm, reversed phase C-18 column

Mobile phase A: water or 100 mM ammonium acetate, pH 7, or 0.1% TFA in water

Mobile phase B: acetonitrile

Flow rate: 20 mL/min

Detection wavelength: 300 nm

Gradient: from 100% A to 100% B, 30 minutes, and keep 100% B for 30 minutes.

The purified compound was then characterized by NMR, MS, UV-Vis, and HPLC.

ii) D-Cystine 2-Hydroxyethyl Ester

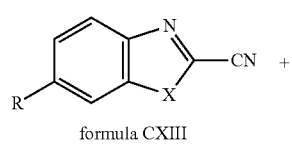

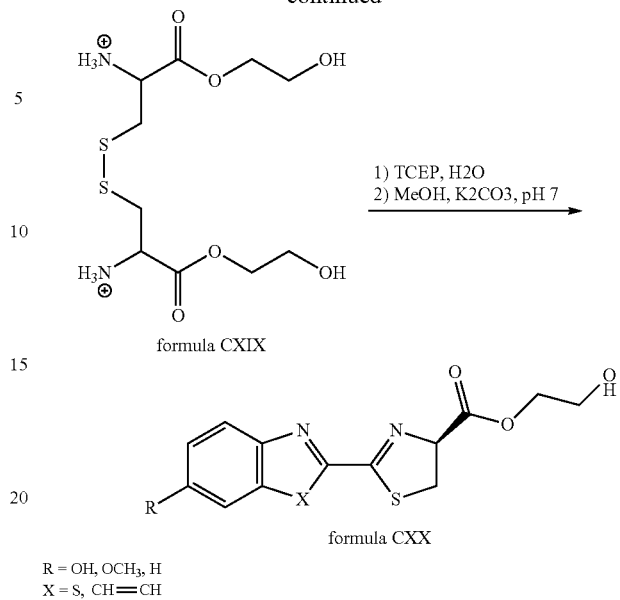

R = OH, OCH₃, H
X = S, CH=CH

The procedure of cyclization with D-cystine 2-hydroxyethyl ester is very similar to D-cyteine methyl ester except 1 equivalent of tris(2-carboxyethyl)phosphine hydroxychloride (TCEP) was added before pH adjustment.

B. CsF-Promoted Esterification

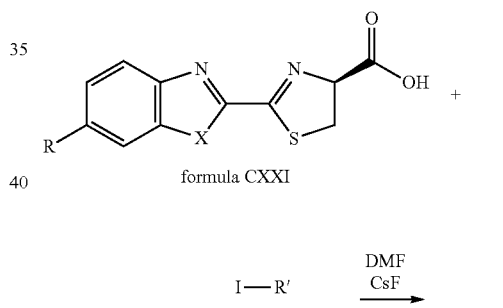

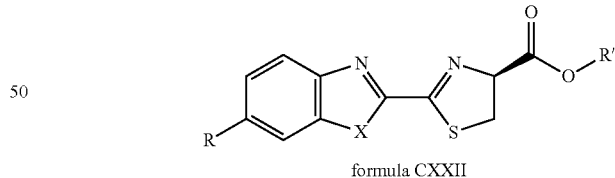

R' = alkyl, aromatic
R = OMe, OH, H
X = S, CH=CH

To a solution luciferin or a derivative (1 equivalent) in DMF was added cesium fluoride (1.5 equivalents), followed by 3-iodomethyl pyridine hydriodide or 3-iodopropanol (1.5 equivalents). After the resultant mixture was stirred at room temperature for a few hours, monitored by TLC with methanol in dichloromethane, the solution was concentrated down and water was added. The mixture was then filtered through a 0.2 μm filter and was subjected to HPLC purification using similar condition described above.

II. D-Cysteine or D-Cystine Esters
1. Synthesis of 2-Hydroxyethyl Ester of D-Cystine

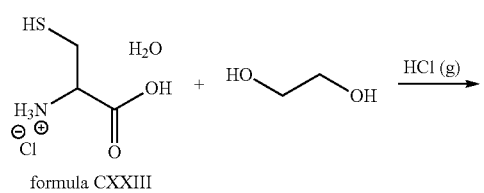

formula CXXIII

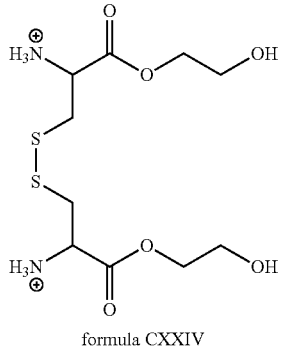

formula CXXIV

To anhydrous ethylene glycol solution (10 mL) was charged D-cysteine hydrochloride monohydrate (1 g). A gentle stream of hydrochloride gas was introduced to bubble the solution for 1 hour. The solution was then let stand over night. Cold isopropyl alcohol (12.5 mL) was added slowly and the resultant mixture was put at −20° C. for 1 hour. The white precipitates were then filtered, washed with cold isopropyl alcohol, and pumped by maintaining the suction of the filtrate cake. White crystals (595 mg) were obtained (yield: 52%).

$^1$H NMR (DMSO-d6): 8.6-88 ppm (broad, 6H), 4.35 ppm (broad singlet, 2H), 4.20 ppm (m, 4H), 3.63 ppm (m, 4H), 3.05 ppm (broad singlet, 4H)

ES$^+$ 330.53 (M.W. 330.44)

2. Synthesis of Methyl Ester of D-Cysteine

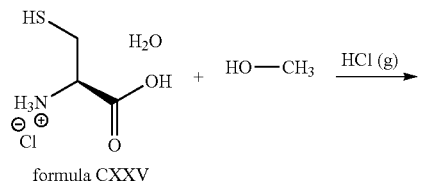

formula CXXV

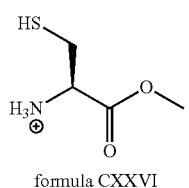

formula CXXVI

To a methanol solution (100 mL) was charged D-cysteine hydrochloride monohydrate (6 g). A gentle stream of hydrochloride gas was introduced to bubble the solution for 105 minutes. The solution was then stirred over night. Then the solvent was then removed under vacuum. The white residue was dissolved in hot methanol (25 mL) and 25 mL of isopropyl alcohol was added. The mixture was put on a rotavap to remove some of the methanol until white precipitates crashed out of the solution. The precipitates were put on ice briefly and then filtered under vacuum, washed with cold isopropyl alcohol, and pumped by maintaining the suction of the filtrate cake.

$^1$H NMR (CD3OD): 4.35 ppm (t, 1H), 3.85 ppm (s, 3), 3.10 ppm (d, 2H)

III. Luciferin Methyl Ether Esters
3. Synthesis of 2-Hydroxyethyl Ester of Luciferin Methyl Ether
a. By 2-hydroxyethyl ester of D-cystine

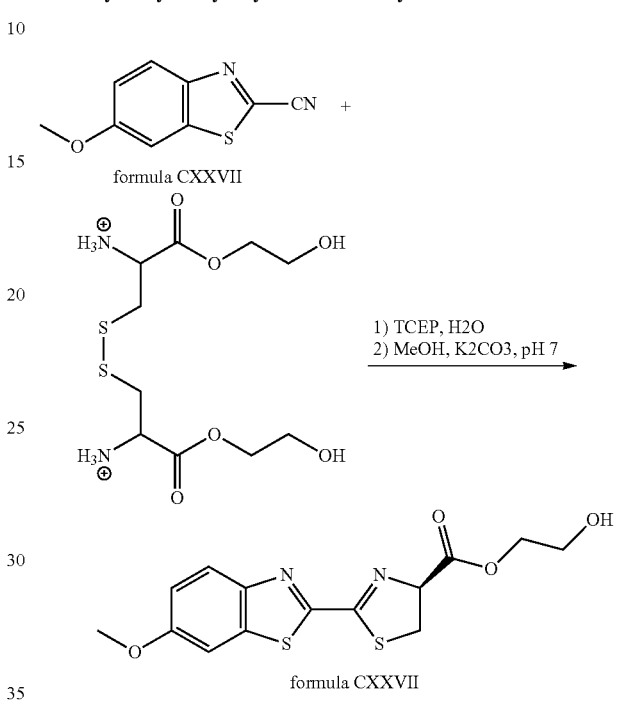

formula CXXVII formula CXXVII 2-cyano-6-methoxybenzothiazole (100 mg, 0.526 mmol) was dissolved in methanol (20 mL) and the resultant solution was degassed with a gentle stream of nitrogen for 10 minutes.

To a solution of 2-hydroxyethyl ester of D-cysteine (87 mg, 0.263 mmol) in water (10 mL) was added tris(2-carboxyethyl)phosphine hydrochloride (TCEP) (77 mg, 0.263 mmol). The pH of this solution was adjusted to about 7 with 1 M potassium carbonate. The resultant solution was added to aforementioned solution dropwise and the mixture was stirred for 30 minutes. The precipitate were filtered out through a 0.2 µm filler and the filtrate was purified by semi-preparative HPLC (see general procedure: Mobile phase A: water). 102 mg of purr compound was obtained (Yield: 52%).

$^1$H NMR (CD3CN): 8.0 ppm (d, 1H), 7.55 ppm (d, 1H), 7.20 ppm (dd, 1H), 5.42 ppm (t, 1H), 4.25 ppm (m, 2H), 3.75 ppm (m, 4H)

MS: ES$^+$ 338.58 (M.W. 338.40)

Extinction coefficient: 16,630 (at 325 nm in acetonitrile)

b. By Ethylene Glycol

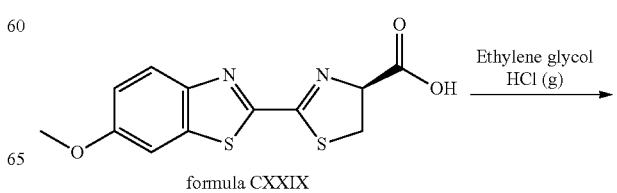

formula CXXIX

-continued

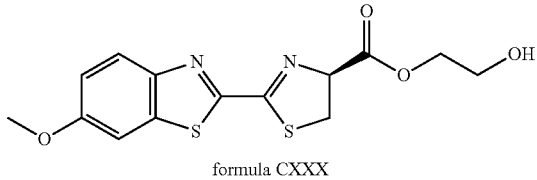

formula CXXX

To a solution of luciferin methyl ether (100 mg, 0.34 mmol) in anhydrous ethylene glycol (4 mL) in a 5 ml. Schlenk flask was introduced a gentle stream of hydrochloride gas. After 5 minutes of bubbling, the flask was sealed and put into an oil bath of 62° C. for 3 hours. The HCl bubbling was repeated for another 5 minutes and put back into the oil bath for another 1 hour. After the solution was cooled to room temperature, water (6 mL) was added and the resultant mixture was filtered and purified with semi-preparative HPLC (see general procedure: Mobile phase A: water).

4. Synthesis of 2-Hydroxy Ethyl Ester of Luciferin-H

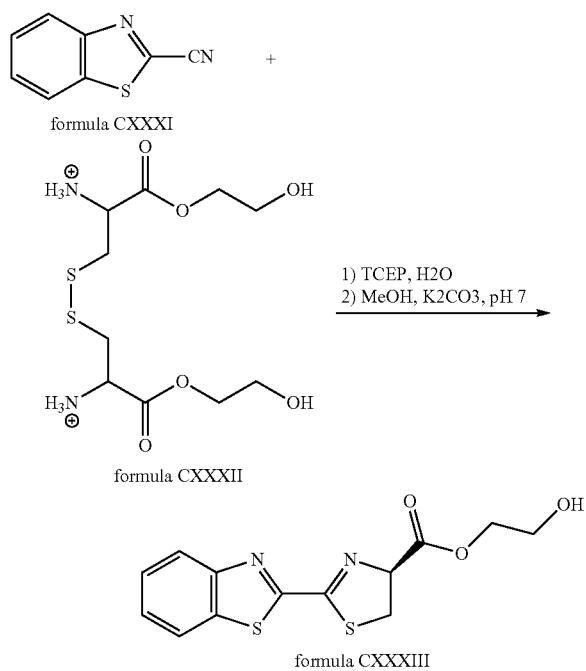

formula CXXXI formula CXXXII

1) TCEP, H2O
2) MeOH, K2CO3, pH 7 formula CXXXIII

This compound was synthesized in a similar way to procedure described in section 3a.

$^1$H NMR (CD3CN): 8.15 ppm (m, 2H), 7.60 ppm (m, 2H), 5.45 ppm (t, 1H), 4.25 ppm (m, 2H), 3.75 ppm (m, 4H), 1.95 ppm (t, 1H)

MS: ES$^+$ 308.58 (M.W. 308.38)

Extinction coefficient 14,050 (at 294 nm in acetonitrile)

5. Synthesis of m-picolinyl Ester of Luciferin Methyl Ether

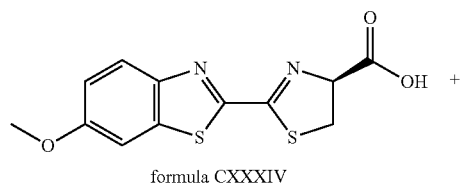

formula CXXXIV

-continued

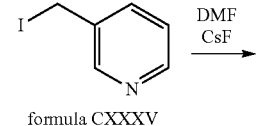

formula CXXXV

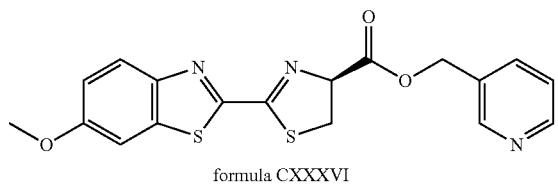

formula CXXXVI

To a solution of luciferin methyl ether (215 mg, 0.73 mmol) in DMF (35 mL) was added cesium fluoride (170 mg, 1.1 mmol), followed by 3-iodomethyl pyridine hydroiodide (380 mg, 1.1 mmol). After the resultant mixture was stirred at room temperature for 3 hours and twenty minutes, the solution was concentrated down to about 10 mL and 6 mL of water was added. The mixture was filtered through a 0.2 μm filter and was subjected to HPLC purification (see general procedure: Mobile phase A: 0.1% TFA in water). 57 mg of pure compound was obtained.

$^1$H NMR (CD$_3$CN): 8.62 ppm (s, 1H), 8.54 ppm (d, 1H), 7.96 ppm (d, 1H), 7.84 ppm (d, 1H), 7.56 ppm (d, 1H), 7.41 ppm (m, 1H), 7.20 ppm (dd, 1H)

MS: ES$^+$ 385.77 (M.W. 385.46)

6. Synthesis of m-Picolinyl Ester of Luciferin

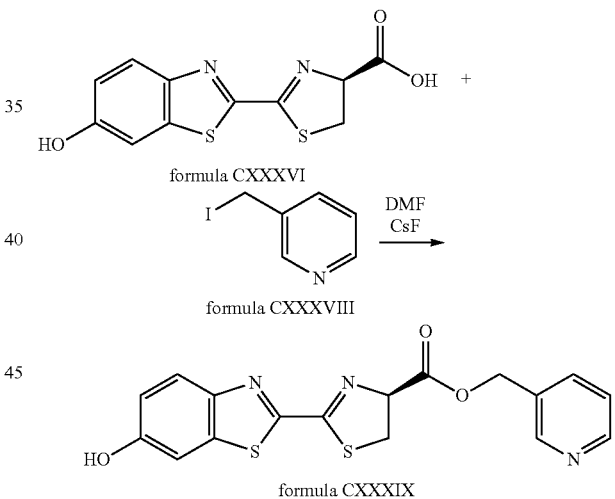

formula CXXXVI formula CXXXVIII formula CXXXIX

To a solution of luciferin mono potassium salt (51 mg, 0.16 mmol) in DMF (10 mL) was added cesium fluoride (24 mg. 0.16 mmol), followed by 3-bromomethyl pyridine hydrobromide (44 mg, 0.17 mmol). After 16 hours of reaction at room temperature, the solvent was stripped away under vacuum. The residue was then dissolved in 10 mL of 60% DMF in water. The resultant solution was filtered through on 0.2 μm filter and was subjected to HPLC purification (see general procedure: Mobile phase A: water). 8.6 mg of pure compound was obtained.

$^1$H NMR (CD3CN-D2O): 8.58 ppm (s, 1H), 8.50 ppm (d, 1H), 7.90 ppm (d, 1H, 7.85 ppm (dd, 1H), 7.42 ppm (dd, 1H), 7.40 ppm (s, 1H), 7.10 ppm (dd, 1H), 5.45 ppm (t, 1H), 5.25 ppm (s, 2H), 3.75 ppm (m, 2H)

MS: ES$^+$: 371.65 (M.W. 371)

UV-Vis: 263 nm and 334 nm

7. Synthesis of m-picolinyl Ester of Luciferin-H

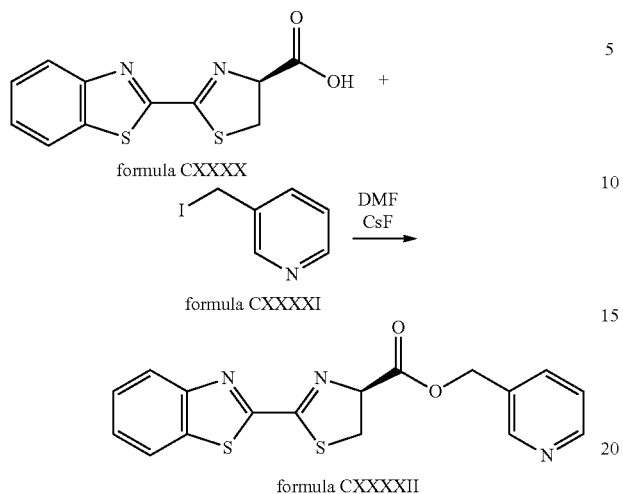

This compound was synthesized and purified in a similar fashion to the synthesis of m-picolinyl ester of luciferin methyl ether using luciferin-H as starting material. 13 mg of pure compound was obtained.

$^1$H NMR (CD3CN-D2O): 8.60 ppm (s, 1H), 8.52 ppm (d, 1H), 8.10 ppm (m, 2H), 7.85 ppm (m, 1H), 7.59 ppm (m, 2H), 7.42 ppm (m, 1H), 5.50 ppm (t, 1H), 5.28 ppm (s, 2H), 3.79 ppm (m, 2H)

MS: ES$^+$ 3.55.54 and 711.36 (dimer) (M.W. 355.43)

8. Synthesis of 3-Hydroxypropyl Ester of Luciferin Methyl Ether

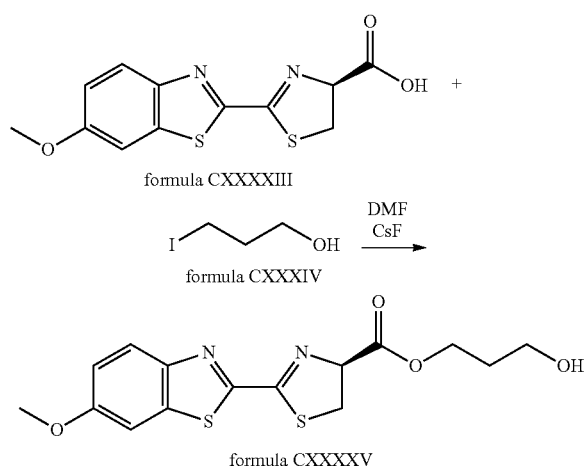

This compound was synthesized in a similar way to m-picolinyl ester of luciferin methyl ether using luciferin methyl ether and 3-iodopropanol as starting materials.

$^1$H NMR (CD3OD): 7.95 ppm (d, 1H), 7.55 ppm (d, 1H) 7.18 ppm (dd, 1H), 5.41 ppm (t, 1H), 4.35 ppm (t, 2H), 3.92 ppm (s, 3H), 3.75 ppm (dd, 2H), 3.65 ppm (t, 2H), 1.92 ppm (m, 2H)

MS: ES$^+$: 353.70 (M.W. 352.43)

UV-Vis: 330 nm and 264 nm.

IV. Quinolinyl Luciferin Derivatives

9. Synthesis of 2-Hydroxy Ester of Quinolinyl Luciferin-H

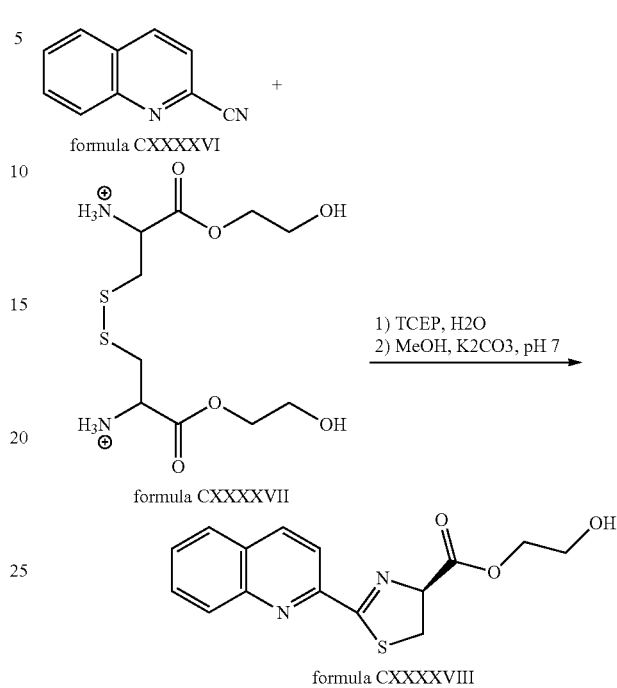

A solution of 2-cyanoquinoline (50 mg, 0.32 mmol) in 1,4-dioxane (5 mL) was degassed for 5 minutes by passing through a gentle stream of nitrogen gas.

Cystine 2-hydroxyethyl ester hydrochloride (53 mg, 0.16 mmol) in water (5 mL) was treated with tris(2-carboxyethyl) phosphine hydrochloride (46 mg, 0.16 mmol). The pH of this solution was adjusted to about 7 with 1 M potassium carbonate. It was then added dropwise to the solution of 2-cyanoquinoline. The resultant solution was stirred at room temperature for 7.5 hours and was purified in a similar way to m-picolinyl ester of luciferin (see general procedure: Mobile phase A:water). 13 mg of pure compound was obtained (yield. 26.7%)

$^1$H NMR (CD3-OD-D2O): 8.40 ppm (d, 1H), 8.15 ppm (d, 1H), 8.10 ppm (d, 1H), 7.95 ppm (d, 1H), 7.82 ppm (m, 1H), 7.68 ppm (m, 1H), 5.53 ppm (t, 1H), 4.25 ppm (m, 2H), 3.75 ppm (m, 2H), 3.65 pppm (m, 2H)

MS: ES$^+$: 302.35, 324.47 (M.W. 302.35)

UV-Vis: 247 nm and 295 nm.

Extinction coefficient: 7,500 (at 288 nm in acetonitrile)

10. Synthesis of Quinolinyl Luciferin-H

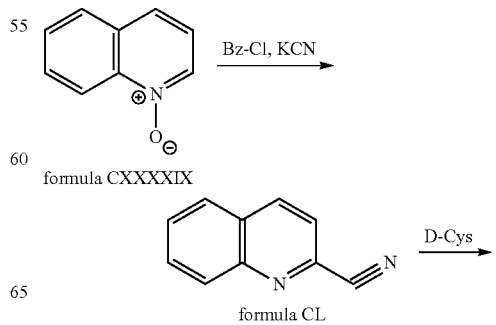

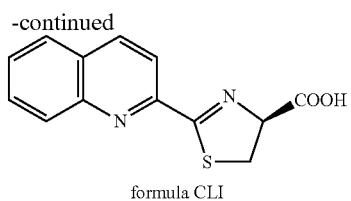

formula CLI a. 2-cyanoquinoline
To a solution of quinoline N-oxide (2 g, 13.8 mmol) was added benzoyl chloride (2.6 mL, 22.0 mmol), followed by water (20 mL). Then, a solution of potassium cyanide (3.6 g, 55.1 mmol) in water (80 mL) was added slowly over a period of 15 minutes with vigorous stirring. Dioxane (15 mL) was added to help the solubility. After the mixture was stirred at RT for 2.5 hours, it was extracted with equal volume of dichloromethane three times. The organic layer was dried over anhydrous sodium sulfate and the solvent was removed under vacuum. The residue was then purified by flash chromatography with 30% of ethyl acetate in hexane, 2.1% of product was obtained (yield: 100%).

NMR (CDCl3): 8.32 ppm (d, 1H), 8.18 ppm (d, 1H), 7.85 ppm (m, 2H), 7.65 ppm (m, 2H)
ES+: 152.44 (M.W. 154.16)

b. Quinolinyl Luciferin-H
2-cyanoquinoline (51 mg, 0.33 mmol) was dissolved in 10 mL of methanol and the resultant solution was degassed with a gentle stream of nitrogen for 10 minutes. Meanwhile D-cyteine hydrochloride monohydrate (90 mg, 0.51 mmol) was dissolved in 5 mL of water and the pH of the resultant solution was adjusted to about 7. It was then degassed with it gentle stream of nitrogen for 5 minutes. The aqueous solution was then added to the organic solution and the resultant mixture was stirred under nitrogen for 4 hours. It was then purified by semipreparative HPLC (see general procedure: Mobile phase A: 0.1% TFA in water).

NMR: characteristic peaks: 5.45 ppm (t, 1H), 3.68 ppm (m, 2H)
ES+: 257.83 (M.W. 256.28)
UV-Vis 295 nm
Extinction coefficient: 28,530 (at 242 nm in methanol)

11. Synthesis of Naphthyl Luciferin Methyl Ether

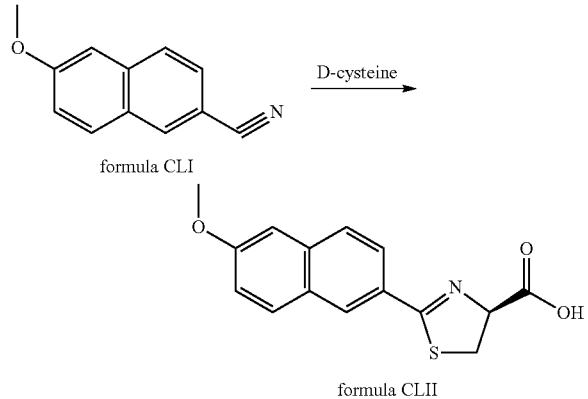

Starting with commercially available 6-methoxy-2-naphthonitrile, this compound was synthesized in one step similar to quinolinyl luciferin-H.

NMR (CD3CN): 8.29 ppm (s, 1H), 8.05 ppm (dd, 1H), 7.94 ppm (d, 1H).

7.86 ppm (d, 1H), 7.36 ppm (d, 1H), 7.25 ppm (dd, 1H), 5.35 ppm (t, 1H),
3.95 ppm (s, 3H), 3.75 ppm (m, 2H)
ES+: 288.23 (M.W. 287.33)
UV-Vis: 253 nm, 279 nm, 315 nm, 339 nm.

12. Synthesis of Methyl Ether of 6'-hydroxyquinolinyl Luciferin Methyl Ether

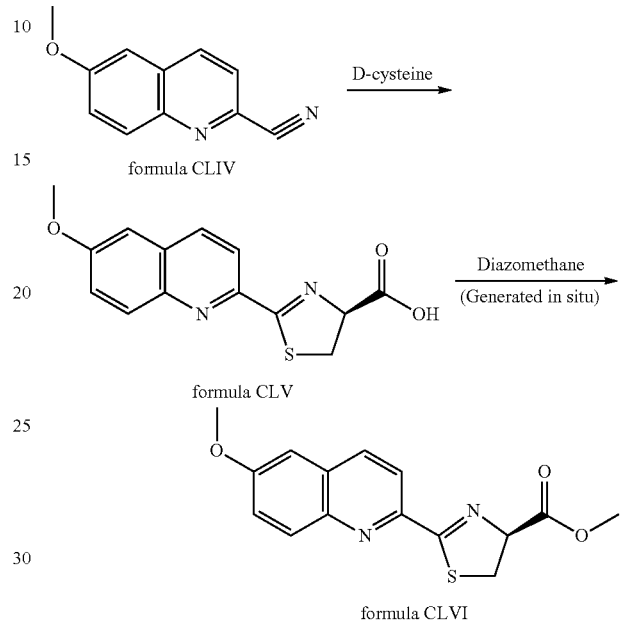

a. 6'-hydroxyquinolinyl luciferin methyl ether
This compound was synthesized in a similar fashion to quinolinyl luciferin-H starting with 2-cyano-6-methoxyquinoline and D-cysteine.

NMR (CD3CN): 8.35 ppm (d, 1H), 8.10 ppm (d, 1H), 8.03 ppm (d, 1H), 7.52 ppm (dd, 1H), 7.38 ppm (d, 1H), 5.45 ppm (t, 1H), 3.97 ppm (s, 3H), 3.75 ppm (m, 2H)
ES+: 289.33 (288.32)
UV-Vis: 343 nm, 329 nm, 261 nm.
Extinction coefficient b. methyl ester of 6'-hydroxyquinolinyl luciferin methyl ether (881-92)
To a mixture of 3 ml of 40% KOH solution and 10 mL of ethyl ether on ice was added N-nitroso-N-methylurea (1 g, 9.7 mmol) in portions over a period of 5 minutes. Once the bubbling died down, the yellow top layer was carefully decanted into an Erlenmyer flask with a few potassium hydroxide pellets. The mixture was let stand on ice for 1 hour.

To a solution of 6-hydroxyquinolinyl luciferin methyl ether (19.5 mg, 0.068 mmol) in 10 mL of anhydrous THF was added dropwise the diazomethane solution made above using a five-polished glass pipet until the yellow color persisted. 5 drops of acetic acid was added to quench the excess diazomethane. The solvent was removed under reduced pressure and the residue was dissolved in 40% water in acetonitrile and was purified by semipreparative HPLC (sec general procedure: Mobile phase A: water).

NMR (CD3CN): 8.25 ppm (d, 1H), 8.14 ppm (d, 1H), 7.96 ppm (d, 1H), 7.45 ppm (dd, 1H) 7.36 ppm (d, 1H), 5.42 ppm (t, 1H), 3.95 ppm (s, 3H) 3.80 ppm (s, 3H), 3.65 ppm (m, 3H)
ES+: 303.49 (M.W. 302.35)
UV-Vis: 249 nm, 265 nm, 326 nm, 341 nm

13. Synthesis of 6-Hydroxyquinolinyl Luciferin (Standard Quinolinyl Luciferin)

This compound was synthesized according to literature procedures.

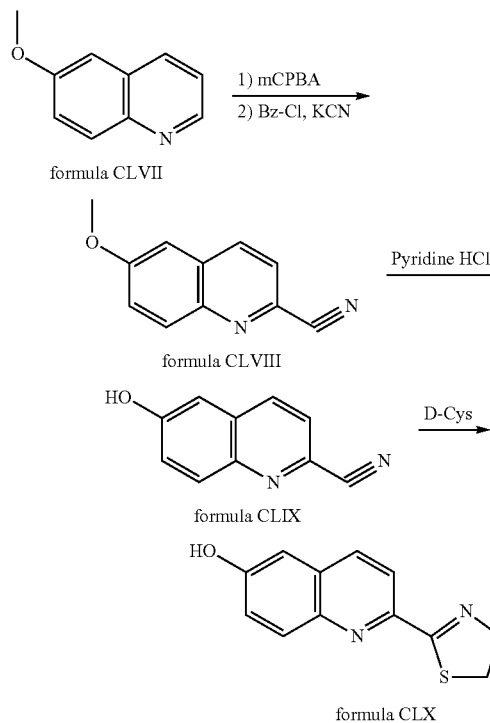

14. Synthesis of 8-Hydroxyquinolinyl Luciferin

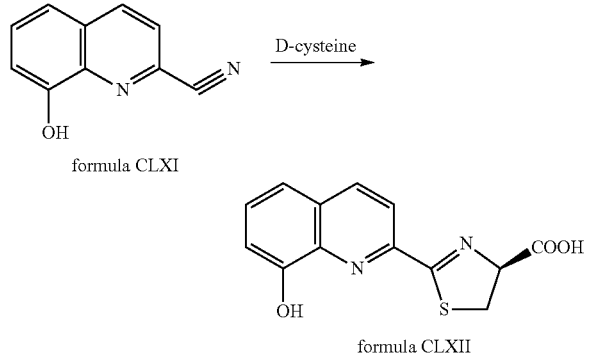

This compound was synthesized in a similar way to quinolinyl luciferin-H with commercially available 2-cyano-8-hydroxyquinoline and D-cysteine as starting materials.

15. Synthesis of 6-Aminoquinolinyl Luciferin

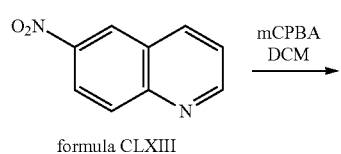

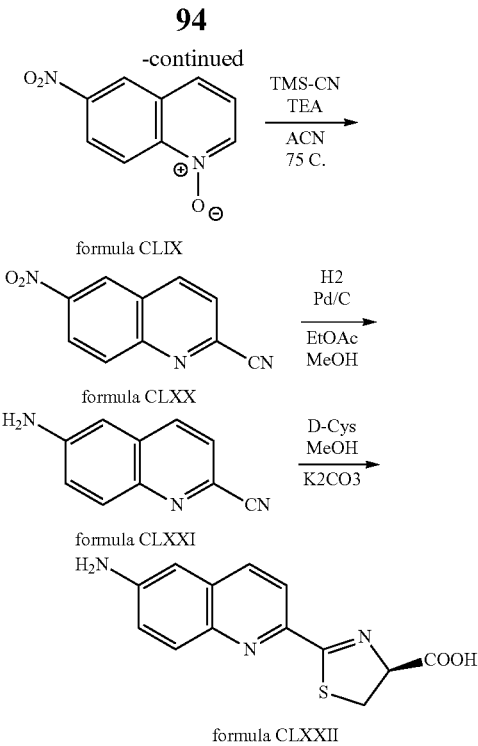

a. 6-amino-2-cyanoquinoline

This compound was synthesized according to a literature procedure (see WO 03/096980 A2).

b. 6-aminoquinolinyl Luciferin 6-amino-2-cyanoquinoline (100 mg, 0.59 mmol) was dissolved in 35 ml of methanol and the resultant solution was degassed with a gentle stream of nitrogen for 10 minutes. Meanwhile, D-cysteine hydrochloride monohydrate (130 mg, 0.74 mmol) was dissolved in 16 mL of water and the resultant solution was degassed with e gentle stream of nitrogen for 5 minutes. The aqueous solution was then added to the organic solution and the resultant mixture was stirred under nitrogen for 4 hours. The volume of the solution was reduced under vacuum and it was then purified by semi-preparative HPLC with and acetonitrile (see general procedure Mobile phase A: 100 mM $NH_4Ac$, pH7).

NMR (CD3CN): 8.25 ppm (d, 1H), 7.95 ppm (m, 2H), 7.46 ppm (dd, 1H),
7.06 ppm (s, 1H), 5.53 ppm (t, 1H), 3.96 ppm (m, 2H)
$ES^+$: 274.67 (M.W. 273.31)
UV-Vis: 265 nm, 330 nm, and 373 nm.
Extinction coefficient: 15, 320 (at 224 nm in MeOH), 13,020 (at 274 nm in MeOH)

16. Synthesis of Quinolinyl Luciferin Benzyloxymethyl Ether

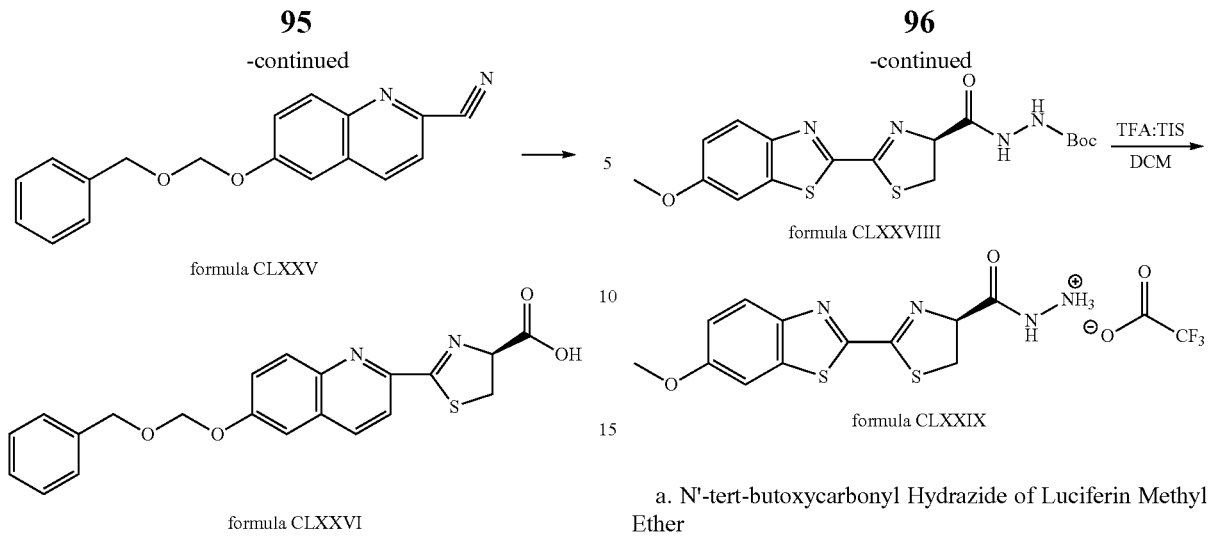

formula CLXXV formula CLXXVI formula CLXXVIIII formula CLXXIX a. 2-cyano-6-benzyloxymethyl Quinoline To a solution of 2-cyano-6-hydroxyquinoline (100 mg) in 10 mL of acetone was added potassium carbonate (122 mg). After stirring at RT for three minutes, the solution was put on ice. Benzyl chloromethyl ether (122 μL) was added through a needle and the resultant solution was stirred on ice for 2 hours. The solvent was then removed under vacuum and the residue was purified by flash chromatography with dichloromethane. 157 mg was obtained.

NMR (CDCl3): 8.18 ppm (d, 1H), 8.12 ppm (d, 1H), 7.65 ppm (d, 1H), 7.56 ppm (dd, 1H), 7.45 ppm (d, 1H), 7.34 ppm (m, 5H), 5.44 ppm (s, 2H), 4.76 ppm (s, 2H)

ES+: 293.89 (M.W. 290.11)

UV-Vis: 250 nm, 325 nm, and 336 nm.

b. Quinolinyl Luciferin Benzyloxymethyl Ether

To a solution of 2-cyano-6-benzyloxymethyl quinoline (75 mg. 0.259 mmol) in 10 ml, of methanol was added D-cysteine hydrochloride monohydrate (55 mg, 0.31 mmol). Triethylamine (44 μL) was added dropwise through a needle. The solution became turbid in about one minute and 3 mL of water was added to make it clear. The resultant solution was stirred at RT for 4 hours. Then, the solution was purified by HPLC (see general procedure: Mobile phase A: 0.1% TFA in water). 37.1 mg of product was obtained.

NMR (CD3CN): 8.28 ppm (d, 1H), 8.17 ppm (d, 1H), 8.03 ppm (d, 1H), 7.55 ppm (m, 4H), 7.33 ppm (m, 5H), 5.49 ppm (s, 3H), 5.44 ppm (t, 1H), 4.78 ppm (s, 3H), 3.63 ppm (m, 2H)

ES+: 396.03 (M.W. 394.14)

UV-Vis: 256 nm, 324 nm and 336 nm

Extinction coefficient: 10,000 (at 323 nm in acetonitrile), 8,770 (at 338 nm in acetonitrile)

V. Miscellaneous

17. Synthesis of Hydrazide of Luciferin Methyl Ether a. N'-tert-butoxycarbonyl Hydrazide of Luciferin Methyl Ether To a suspension solution of luciferin methyl ether (100 mg, 0.34 mmol) in anhydrous THF (5 mL) was added N,N'-diisopropylcarbodiimide (DIC) (130 μL, 0.84 mmol) and a solution of HOBt (110 mg, 0.72 mmol) in anhydrous THF (2 mL) through needles. A solution of tert-butyl carbazate (100 mg, 0.75 mmol) in anhydrous THF (3 mL) was then added. The resultant mixture was stirred in an atmosphere of nitrogen for 29 hours and the solvent was stripped away under vacuum. The residue was purified by flash chromatography with 1% methanol in dichloromethane. 139 mg of product was obtained (100% yield).

$^1$H NMR (CD2Cl2): 8.30 ppm (broad, 1H), 8.00 ppm (d, 1H), 7.40 ppm (d, 1H), 7.17 ppm (dd, 1H), 6.56 ppm (broad, 1H), 5.35 ppm (m, 1H), 3.90 ppm (s, 3H), 3.80 ppm (m, 2H), 1.48 ppm (s, 9H)

b. Hydrazide of Luciferin Methyl Ether

N'-tert-butoxycarbonyl hydrazide of luciferin methyl ether was treated with TFA (10 mL) in the presence of 6 drops of triisopropylsilane (TIS) for 70 minutes. TFA was then removed under vacuum and the residue was dissolved in 10 mL of 1:1:1 mixture of water:acetonitrile:DMF. HPLC purification condition was similar to the procedure for synthesis of m-picolinyl ester of luciferin (see general procedure: Mobile phase A: 0.1% TFA in water) 64 mg of pure compound was obtained $^1$H NMR (CD3OD): 7.98 ppm (d, 1H), 7.56 ppm (d, 1H), 7.19 ppm (dd, 1H), 5.35 ppm (t, 1H), 3.90 ppm (s, 3H), 3.75 ppm (m, 2H)

ES+: 308.36 (M.W. 308.38)

UV-vis: 331 nm, 267 nm

Extinction coefficient: 6,000 (at 329 nm in acetonitrile-water mixture)

18. Synthesis of Hydrazide of Luciferin

This compound was synthesized in a similar way to the hydrazide of luciferin methyl ether.

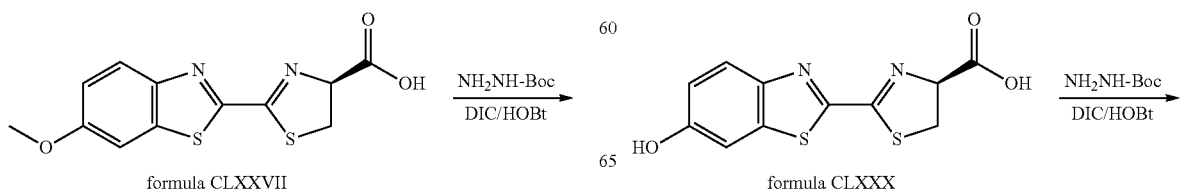

formula CLXXVII formula CLXXX

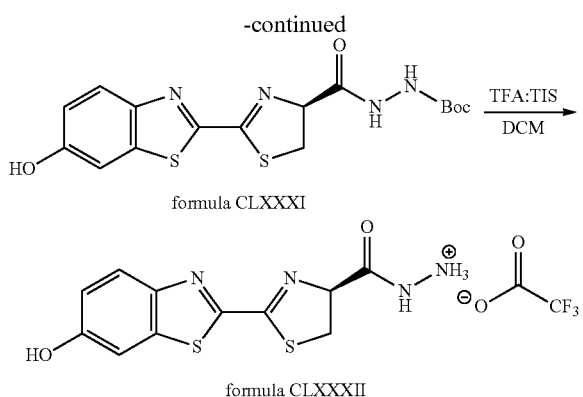

formula CLXXXI formula CLXXXII a. N'-tert-butoxycarbonyl Hydrazide of Luciferin
$^1$H NMR (CDCl3): 7.81 ppm (d, 1H), 7.18 ppm (d, 1H), 6.93 ppm (dd, 1H), 5.20 ppm (m, 1H), 3.63 ppm (m, 2H), 1.33 ppm (s, 9H)
ES$^+$: 396.75 (M.W. 394.35)

b. Hydrazide of Luciferin
$^1$H NMR (DMF-d7), 9.52 ppm (broad, 1H), 8.15 ppm (d, 1H), 7.73 ppm (d, 1H). 7.33 ppm (dd, 1H), 5.47 ppm (t, 1H), 4.63 ppm (broad, 2H), 3.91 ppm (m, 2H)
MS: ES$^+$: 295.53 (M.W. 294.36)
UV-vis: 148 nm and 293 nm
Extinction coefficient: 16,900 (at 327 nm in acetonitrile)

19. Synthesis of Luciferin 3-(4-phenylpiperazin-1-yl)methylbenzyl Ether a. 2-cyano-6-(3-bromomethylbenzyloxy)benzothiazole
To a solution of 2-cyano-6-hydroxybenzothiazole (1.04 g) in 30 mL of acetone was added potassium carbonate 1.63 g), followed by α,α'-dibromo-m-xylene (4.7 g). The resultant solution was stirred at RT for 1 hour and the solvent was removed under reduced pressure. The residue was resuspended in dichloromethane and washed with water. The aqueous phase was extracted with more dichloromethane (2×) and the organic extracts were combined, dried over sodium sulfate, and purified by flash chromatography using dichloromethane. 1.945 g of product was obtained.
$^1$H NMR (CDCl3); 8.15 ppm (d, 1H), 8.44 ppm (d, 1H), 8.40 ppm (m, 4H), 7.20-7.30 ppm (m, 2H), 5.16 ppm (s, 2H), 5.52 ppm (s, 2H)
ES$^+$: 362.60 (Br isotope effect seen) (M.W. 359.24)

b. 2-cyano-6-[3-(4-phenylpiperazin-1-yl)methylbenzyloxy]benzothiazole
To a solution of 2-cyano-6-(3-bromomethylbenzyloxy)benzothiazole (1 g, 2.8 mmol) in 20 mL of dichloromethane was added 1-phenylpiperazine (1.7 mL, 11.2 mmol) dropwise. The resultant solution was stirred at RT for 30 minutes. Then, 20 mL of saturated sodium bicarbonate solution was added. After partition, the aqueous phase was extracted with 20 mL of dichloromethane. The organic extracts were combined, washed with water twice and dried over sodium sulfate. The solvent was removed and the residue was purified by flash chromatography using 1% methanol in dichloromethane, 594 mg of product was obtained.
$^1$H NMR (CDCl3): 8.09 ppm (d, 1H), 7.47 ppm (broad, 1H), 7.43 ppm (d, 1H), 7.37 ppm (m, 2H), 7.34 ppm (d, 1H),

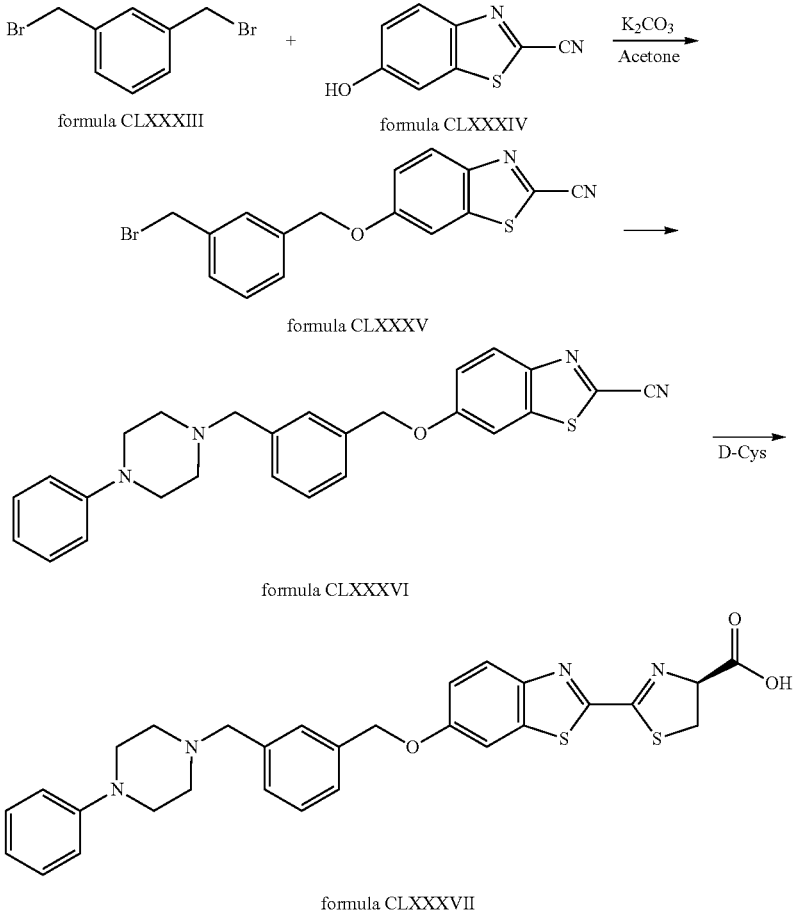

7.30 ppm (m, 1H), 7.26 ppm (d, 1H), 7.24 ppm (m, 1H), 6.92 ppm (d, 2H), 6.86 ppm (m, 1H), 5.18 ppm (s, 2H), 3.20 ppm (m, 4H), 2.63 ppm (m, 4H)

c. Luciferin 3-(4-phenylpiperazin-1-yl)methylbenzyl Ether

This compound was synthesized with 594 mg of 2-cyano-6-[3-(4-phenylpiperazin-1-yl)methylbenzyloxy]benzothiazole and 147 mg of D-cysteine hydrochloride monohydrate according to a procedure similar to 6-aminoquinolinyl luciferin except DMF was used as solvent for 7-cyano-6-[3-(4-phenylpiperazin-1-yl)methylbenzyloxy]benzothiazole due to its poor solubility in methanol. The reaction mixture was purified by HPLC (see general procedure Mobile phase A: 0.1% TFA in water). 282 mg of product was obtained.

$^1$H NMR (CD3CN): 7.95 ppm (d, 1H), 7.40-7.60 ppm (m, 5H), 7.25 ppm (m, 3H), 7.26 ppm (t, 1H), 7.23 ppm (s, 2H), 4.27 ppm (s, 2H), 3.70 ppm (m, 2H), 3.20-3.30 ppm (broad, 8H)

ES$^+$: 546.03 (M.W. 544.69)
UV-vis: 268 nm and 328 nm
Extinction coefficient: 16,380 (at 324 nm in acetonitrile)

20. Synthesis of Luciferin α-trifluoromethylbenzyl Ether

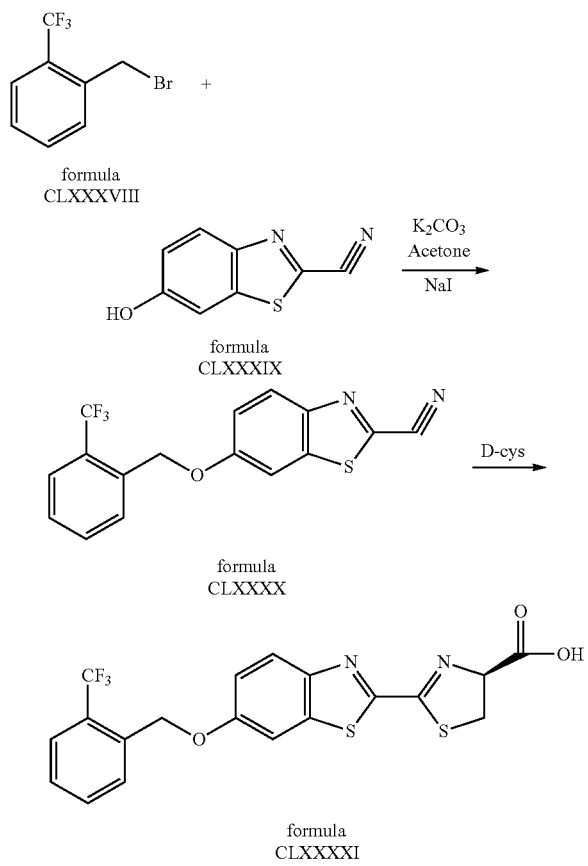

formula CLXXXVIII formula CLXXXIX formula CLXXXX formula CLXXXXI a. 2-cyano-6-(2-trifluoromethylbenzyloxy)benzothiazole To a solution of 2-cyano-6-hydroxybenzothiazole (100 mg, 0.368 mmol) in 10 mL of acetone was added potassium carbonate (157 mg, 1.14 mmol), followed by 2-(trifluoromethyl)benzyl bromide (204 mg, 0.852 mmol). The mixture was then stirred at RT for about 5 hrs. The solvent was removed under reduced pressure and the residue was dissolved in dichloromethane. The resultant solution was then extracted with dichloromethane. The organic phase was dried aver sodium sulfate and purified by flash chromatography using dichloromethane. 148 mg of product was obtained.

$^1$H NMR (CDCl3): 8.12 ppm (d, 1H), 7.75 ppm (d, 2H). 7.60 ppm (t, 1H), 7.48 ppm (t, 1H),7.4 ppm (d, 1H), 7.34 ppm (dd, 1H), 5.28 ppm (s, 2H)

$^{19}$F NMR (CDCl3): 61 ppm
MS: ES$^+$: 335.74 (M.W. 334.32)

b. Luciferin 2-trifluoromethylbenzyl Ether

This compound was synthesized in a similar way to 6-aminoquinolinyl luciferin with 150 mg of 2-cyano-6-(2-trifluoromethylbezyloxy)benzothiazole and 120 mg of D-cysteine hydrochloride monohydrate. The mixture was purified HPLC (see general procedure: Mobile phase A: 0.1% TFA in water). 55 mg of product was obtained.

$^1$H NMR (CD3CN); 8.03 ppm (d, 1H), 7.82 ppm (d, 1H), 7.70 ppm (t, 1H), 7.65 ppm (d, 1H), 7.58 ppm (t, 1H), 7.36 ppm (dd, 1H), 5.40 ppm (t, 1H), 5.39 ppm (s, 2H), 3.75 ppm (d, 2H)

ES$^+$: 440 (M.W. 438.44)
UV-vis: 267 nm and 325 nm
Extinction coefficient: 13,940 at 323 nm 21. Synthesis of Luciferin 2,4,6-trimethylphenyl Ether

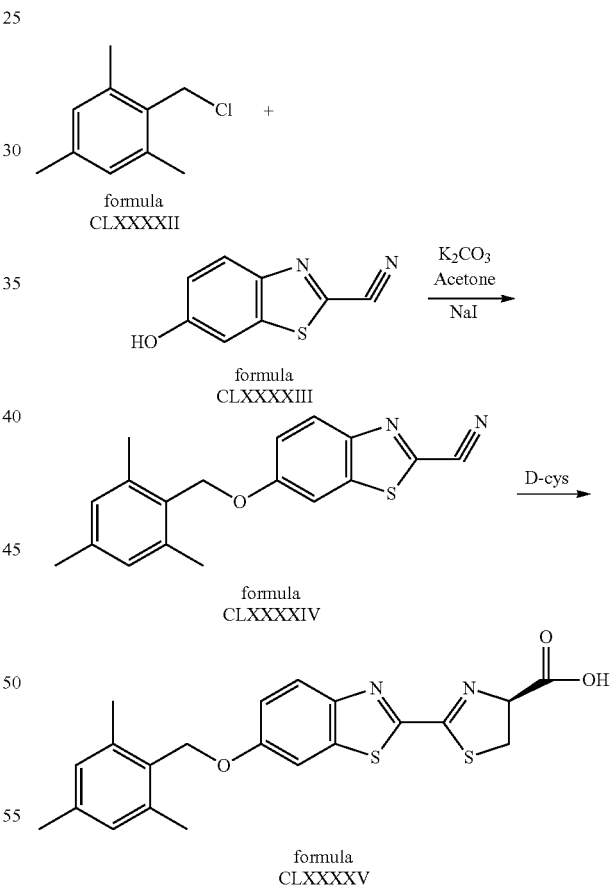

formula CLXXXXII formula CLXXXXIII formula CLXXXXIV formula CLXXXXV a. 2-cyano-6-(2,4,6-trimethylbenzyloxy)benzothiazole This compound was synthesized in a similar way to 2-cyano-6-(2-trifluoromethylbenzyloxy)benzothiazole with α$^2$-chloroisodurene (100 mg, 0.852 mmol). 168 mg product was obtained.

$^1$H NMR (CDCl3): 8.18 ppm (d, 1H), 7.52 ppm (d, 1H), 7.30 ppm (dd, 1H), 6.94 ppm (s, 2H), 5.09 ppm (s, 2H)

ES$^+$: 264.10 (M.W. 263.78)

b. Luciferin 6-(2,4,6-trimethylbenzyl) Ether

This compound was synthesized in a similar way to 2-cyano-6-(2-trifluoromethylbenzyloxy)benzothiazole with 2-cyano-6-(2,4,6-trimethylbenzyloxy)benzothiazole (80 mg. 0.303 mmol). It was then purified by HPLC (see general procedure: Mobile phase A: 0.1% TFA in water). 82 mg of product was obtained.

$^1$H NMR (CD3CN): 7.98 ppm (d, 1H), 7.65 ppm (d, 1H), 7.22 ppm (dd, 1H), 6.92 ppm (s, 2H), 5.40 ppm (t, 1H), 5.12 ppm (s, 2H), 3.75 ppm (d, 2H), 2.32 ppm (s, 6H), 2.28 ppm (s, 3H)

ES$^+$: 414 (M.W. 412.53)

UV-vis 268 nm and 329 nm

Extinction coefficient: 18,240 at 323 nm

22. Synthesis of N-methylephedrine-linker-luciferin (X=O, Y=H) or N-methylephedrine-linker-luciferin (X=NH, Y=Cl)

These compounds were synthesized toward linking an enzyme specific substrate to luciferin through a linker. In this case, the enzyme is a P450 isozyme, but in general, is useful with other enzymes as well.

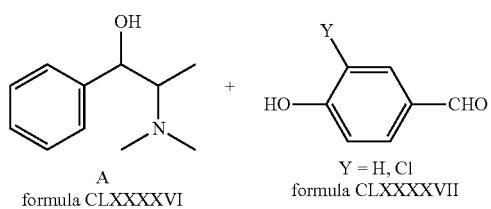

A
formula CLXXXXVI

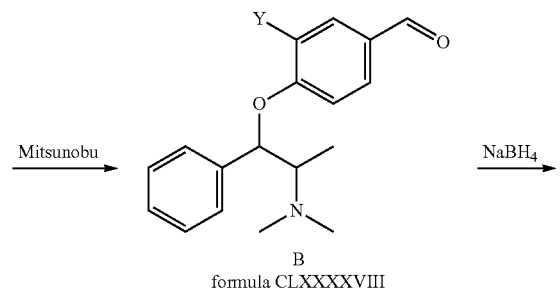

Y = H, Cl
formula CLXXXXVII

B
formula CLXXXXVIII

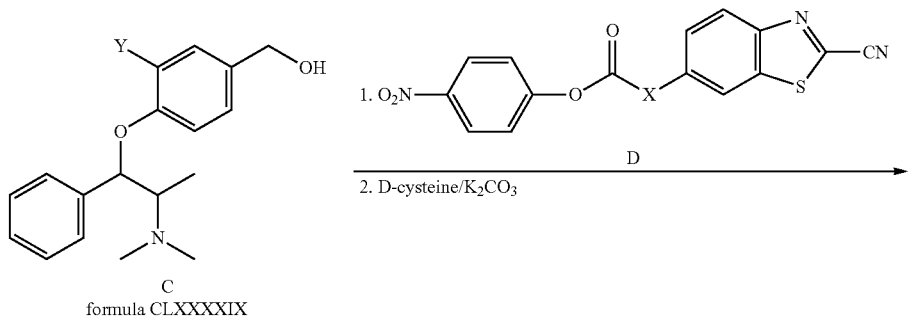

C
formula CLXXXXIX

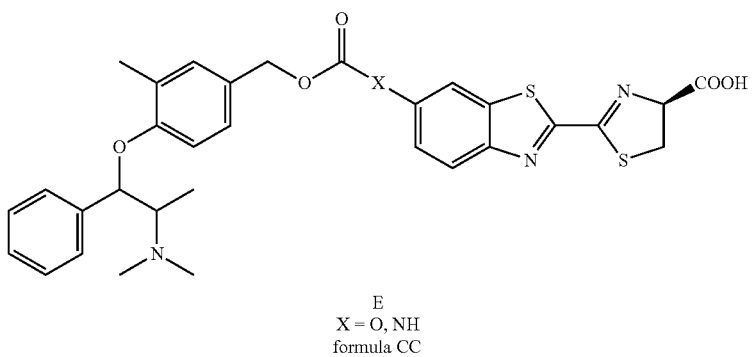

E
X = O, NH
formula CC

Compound B was synthesized under Mitsunobu reaction conditions using diisopropylazodicarboxylate and triphosphine in THF. It was then reduced by NaBH₄ in methanol to produce compound C.

Compound D (X=O for luciferin and X=NH for aminoluciferin) was synthesized separately with corresponding benzothiazole and p-nitrophenyl chloroformate. It was then coupled to compound C under basic condition and a standard D-cysteine cyclization generated the product as shown above.

C. Syntheses for Representative Luciferin Derivatives

Syntheses for luciferin derivatives described in some of the examples above are provided below.

I. Bioluminogenic MAO Substrates

A.

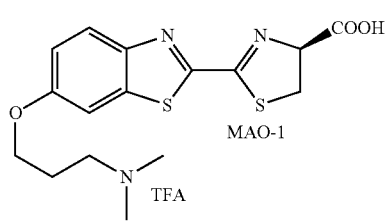

6-(3-Dimethylaminopropoxy)luciferin.

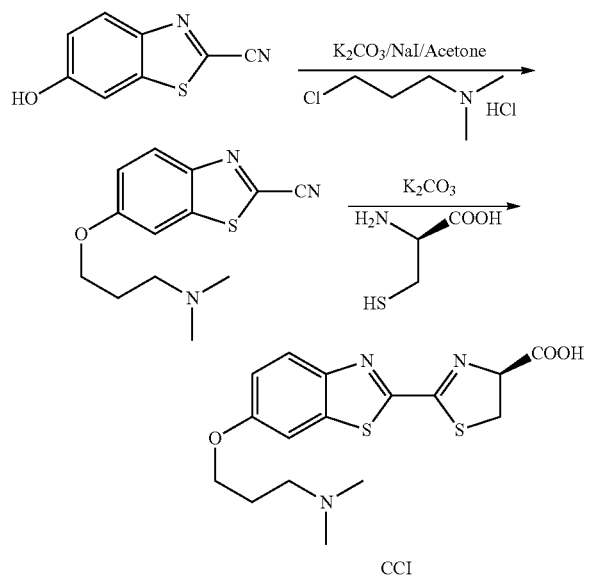

Synthesis of 6-(3-dimethylaminopropoxy)-2-cyanobenzothiozole. The mixture of 6-hydroxy-2-cyanobenzothiozole (0.311 g, 177 mmol), 3-chloropropyldimethylamine hydrochloride (0.36 g, 2.27 mmol), potassium carbonate (0.63 g, 4.57 mmol) and sodium iodide (0.034 g) in acetone (30 ml) was heated to reflux overnight. Upon cooling to room temperature, the insoluble solid was removed by filtration. The compound was purified by flash chromatography using methylene chloride/methanol (96:4) as eluent in a yield of 86% (0.387 g). $^1$H NMR (CD$_2$Cl$_2$): 7.98 (d, J=9.3 Hz, 1H), 7.32 (d, J=2.4 Hz, 1H), 7.16 (dd, J=9.0 Hz, J=2.1 Hz, 1H), 4.04 (t, J=6.4 Hz, 2H, OCH$_2$) 2.36 (t, J=7.2 Hz, 2H, NCH$_2$), 2.13 (s, 6H, CH$_3$), 1.90 (m, 2H, CH$_2$).

Synthesis of MAO-1. To the solution of dimethylamine (0.235 g, 0.90 mmol) and D-cystine (0.158 g, 0.90 mmol) in methanol (5 ml), CH$_2$Cl$_2$ (1 ml) and H$_2$O (1 ml) was added K$_2$CO$_3$ (0.125 g. 0.90 mol). The mixture was stirred at room temperature for 5 min and then neutralized to slightly acidic condition. After removal of organic solvent, the product was purified by HPLC using 0.1% TFA water/acetonitrile as eleuent.

$^1$H NMR (CD$_2$Cl$_2$): 7.90 (d, 1H), 7.23 (s, 1H), 7.04 (d, 1H), 5.37 (t, 1H, CHCOO), 4.10 (t, 2H, OCH$_2$), 3.79 (m, 2H, CH$_2$), 3.32 (t, 2H, CH$_2$N), 2.97 (s, 6H, CH$_3$), 2.30 (m, 2H, CH$_2$). MS (ES): m/e (M+), 365

B.

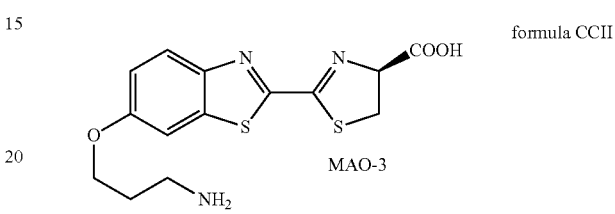

6-Aminopropoxyluciferin, 6-(3-Dimethylaminopropoxy)luciferin

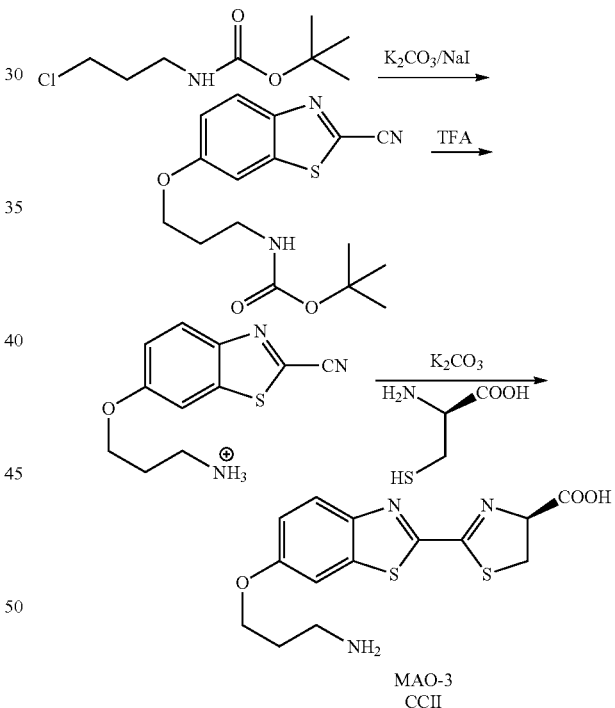

The compound MAO-3 was synthesized by employing the similar method used for the synthesis of MAO-1. Except that amino group was protected by t-BOC and de-protected after alkylation of 6-hydroxyl-2-cyanobenzothiozole. The final compound was precipitated out from the reaction solution and collected by filtration, washed with water and methanol.

$^1$H NMR (d6-DMSO/TFA): 8.04 (d, 1H), 7.75 (s, 1H), 7.19 (d, 1H), 5.40 (t, 1H, CHCOO), 4.08 (t, 2H, OCH$_2$), 3.6-3.8 (m, 2H, CH$_2$), 3.0 (m, 2H, CH$_2$N), 2.05 (m, 2H, CH$_2$). MS (ES): m/e (M+), 337, $\lambda_{max}$ 328 nm, $\varepsilon_{max}$ 15,500 cm$^{-1}$M$^{-1}$ in water.

C.

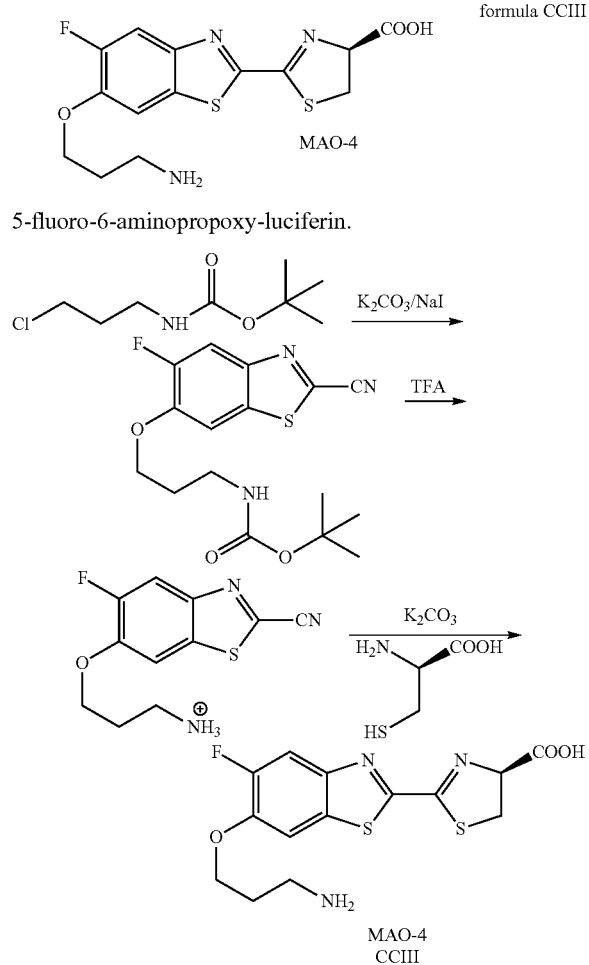

5-fluoro-6-aminopropoxy-luciferin.

The compound MAO-4 was synthesized by employing the similar method used for the synthesis of MAO-3.

$^1$H NMR (d6-DMSO/TFA): 8.07 (d, 1H) 7.97 (d, 1H), 5.41 (t, 1H, CHCOO), 4.24 (t, 2H, OCH$_2$), 3.6-3.8 (m, 2H, CH$_2$), 3.0 (m, 2H, CH$_2$N), 2.08 (m, 2H, CH$_2$). MS (ES): m/e (M+1), 355 $\lambda_{max}$ 326 nm, $\varepsilon_{max}$ 15,600 cm$^{-1}$M$^{-1}$ in water.

D.

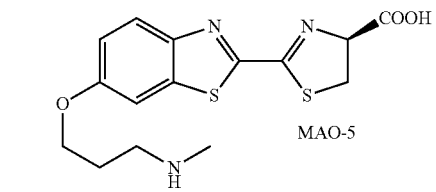

6-methylaminopropoxy-luciferin.

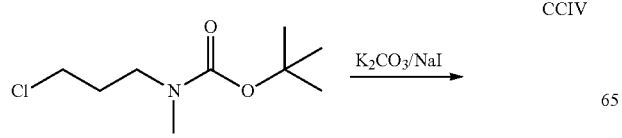

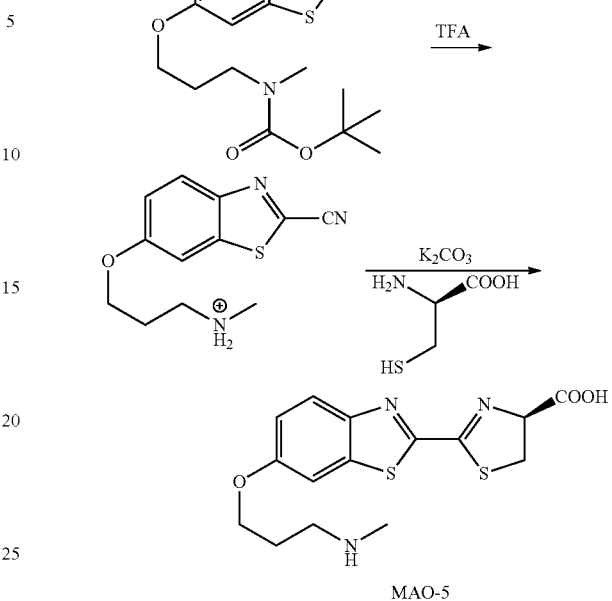

The compound MAO-5 was synthesized by employing the similar method used for the synthesis of MAO-3.

$^1$H NMR (d6-DMSO/TFA): 8.04 (d, 1H), 7.74 (d, 1H), 7.19 (dd, 1H), 5.40 (t, 1H, CHCOO), 4.16 (t, 2H, OCH$_2$), 3.6-3.8 (m, 2H, CH$_2$), 3.07 (m, 2H, CH$_2$N), 2.59 (t, 3H, NCH$_3$), 2.07 (m, 2H, CH$_2$). MS (ES): m/e (M+1), 351 $\lambda_{max}$ 328 nm, $\varepsilon_{max}$ 17,500 cm$^{-1}$M$^{-1}$ in water.

E.

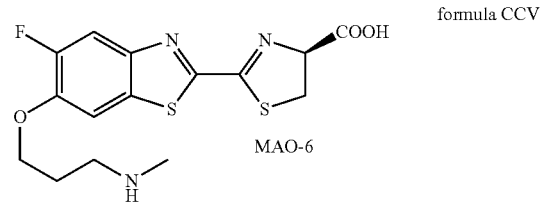

5-fluoro-6-methoylaminopropoxy-luciferin

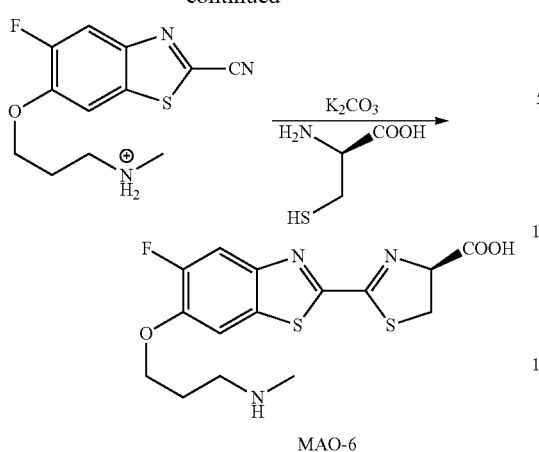

MAO-6

The compound MAO-6 was synthesized by employing the similar method used for the synthesis of MAO-3.

¹H NMR (d6-DMSO/TFA): 8.08 (d, 1H), 7.98 (d, 1H), 5.41 (t, 1H, CHCOO), 4.24 (t, 2H, OCH$_2$), 3.6-3.8 (m, 2H, CH$_2$), 3.08 (m, 2H, CH$_2$N), 2.59 (t, 3H, NCH$_3$), 2.11 (m, 2H, CH$_2$). MS (ES): m/e (M+1), 369

F.

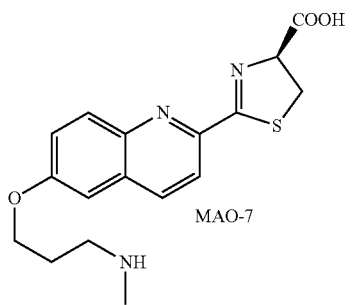

MAO-7

6-(3-methylaminopropoxy)quinolinyl-luciferin.

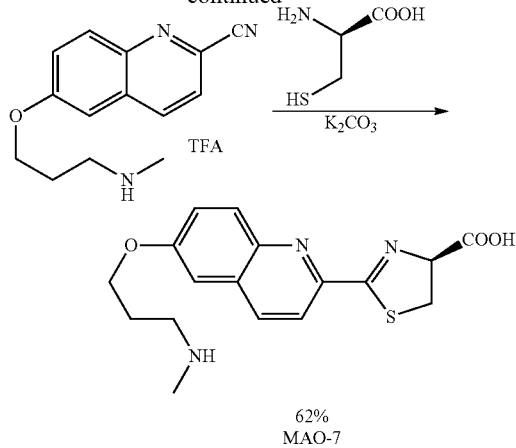

MAO-7

The compound MAO-7 was synthesized by used 6-hydroxyl-2-cyanoquinoline as starting material and by employing the similar method used for the synthesis of MAO-3.

¹H NMR (d6-DMSO/TFA): 8.37 (d, J=8.7 Hz), 8.13 (d, J=9.2 Hz, 1H), 8.02 (d, J=9.0 Hz, 1H), 7.44-7.54 (m-overlap, 2H), 5.45 (dd, J=8.10 Hz, J=8.10 Hz, 1H, CH—COOH), 4.25 (t, J=6.0 Hz, 2H, OCH$_2$), 3.5-3.8 (m, 2H, SCH$_2$), 3.17 (m, 2H, NCH$_2$), 2.63 (m, 3H, CH$_3$), 2.15 (m, 2H, CH$_2$). MS (ES): m/e (M+1), 346 $\lambda_{max}$ (nm)/$\varepsilon_{max}$ (cm$^{-1}$M$^{-1}$): 259/30,600; 326/10,400; 342/10,100 in water.

G.

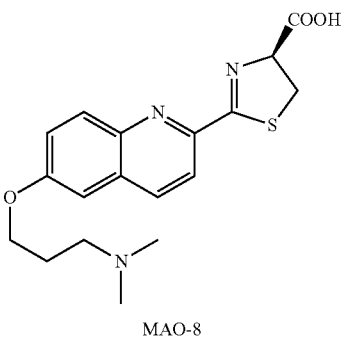

MAO-8

6-(3-dimethylaminopropoxy)quinolinyl-luciferin.

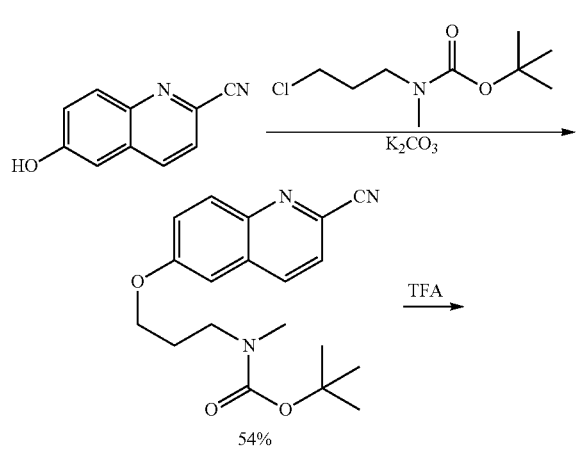

CCVI

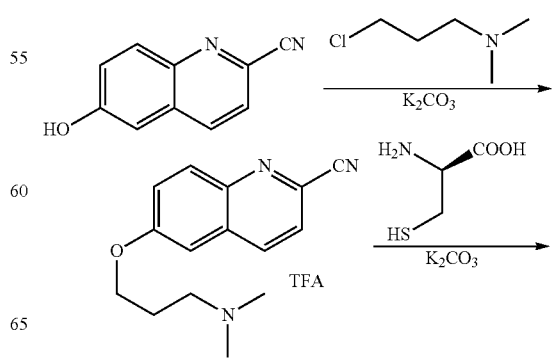

CCVII

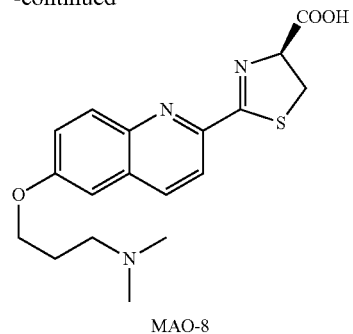

MAO-8

The compound MAO-8 was synthesized by employing the similar method used for the synthesis of MAO-1.

$^1$H NMR (d6-DMSO/TFA): 8.28 (d, J=8.4 Hz), 8.05 (d, J=8.7 Hz, 1H), 7.93 (d, J=10.0 Hz, 1H), 7.94-8.04 (m-overlap, 2H), 5.07 (t, J=9.30 Hz, 1H, CH—COOH), 4.15 (t, j=6.6 Hz, 2H, OCH$_2$), 3.35-3.62 (m, 2H, SCH$_2$), 2.40 (m, 2H, NCH$_2$), 2.16 (s, 6H, CH$_3$), 1.92 (m, 2H, CH$_2$). MS (ES): (M+1) m/e, 359 $\lambda_{max}$ (nm)/$\varepsilon_{max}$ (cm$^{-1}$M$^{-1}$): 258/33,200; 326/10,700; 340/10,700 in water.

H.

formula CCVIII

MAO-9

6-(3-aminopropoxy)quinolinyl-luciferin

MAO-9

The compound MAO-9 was synthesized by employing the similar method used for the synthesis of MAO-3.

$^1$H NMR (d$_6$-DMSO/TFA): 8.35 (d, J=8.7 Hz), 8.10 (d, J=8.4 Hz, 1H), 7.99 (d, J=8.7 Hz, 1H), 7.4-7.5 (m-overlap, 2H), 5.07 (dd, J=8.40 Hz, J=8.4, 1H, CH—COOH), 4.23 (t, J=6.0 Hz, 2H, OCH$_2$), 3.50-3.54 (m, 2H, SCH$_2$), 3.0 (m, 2H, NCH$_2$), 2.08 (m, 2H, CH$_2$). MS (ES): (M+1) m/e, 332 $\lambda_{max}$ (nm)/$\varepsilon_{max}$ (cm$^{-1}$M$^{-1}$): 260/31,600; 327/11,200; 341/11,800 in water.

I.

formula CCIX

MAO-10

6-(3-dimethylamino-3-butoxy)luciferin.

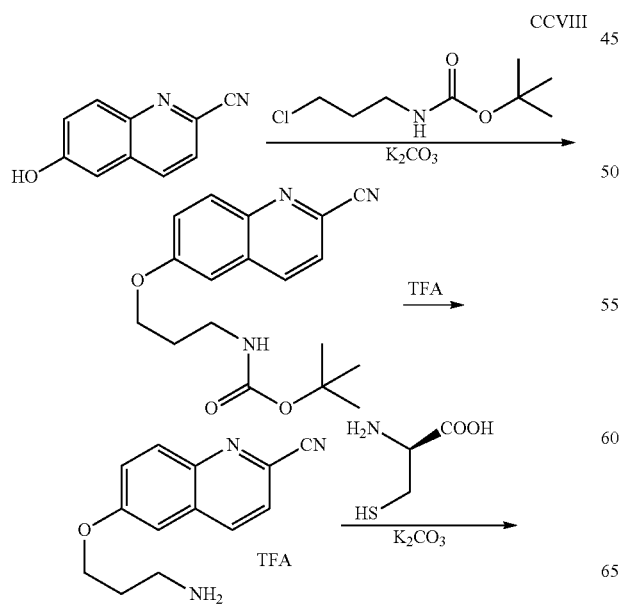

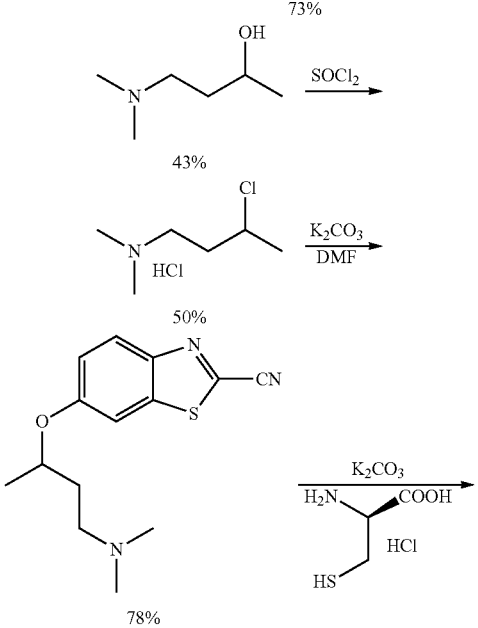

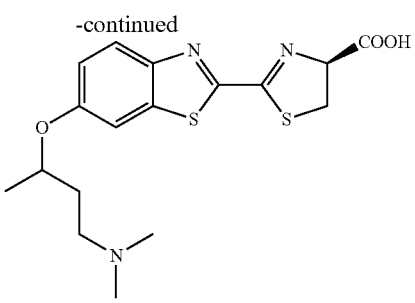

The compound MAO-10 was synthesized by employing the similar method used for the synthesis of MAO-1.

¹H NMR (d6-DMSO); 8.07 (d, 1H), 7.78 (s, 1H), 7.20 (dd, J=9.0 Hz, J=2.1 Hz, 1H), 5.41 (t, 1H, CHCOO), 4.0-4.3 (m, 2H, CH₂), 3.6-3.8 (m, 2H, SCH₂), 2.73 (m, 6H, NCH₃), 1.8-2.4 (m, 2H, CH₂), 1.31 (d, 3H, CH₃). MS(ES): (M+1) m/e, 380 $\lambda_{max}$ 327 nm, $\square_{max}$ 14,700 cm⁻¹M⁻¹ in water.

J.

formula CCX

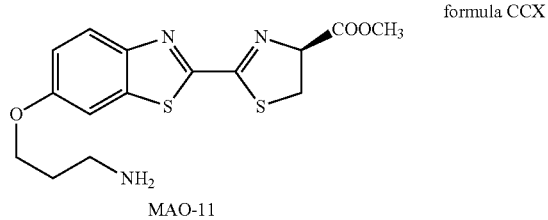

MAO-11

Methyl 6-(3-aminopropoxy) luciferin ester.

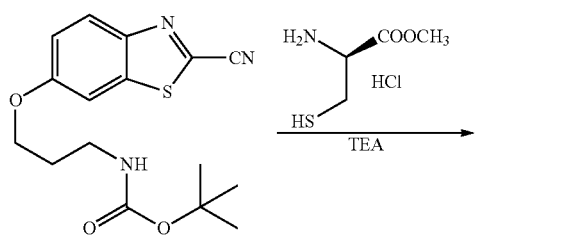

Synthesis of methyl 6-(t-BOC-3-aminopropoxy) luciferin ester. To the solution of 2-cyano-6-(t-BOC-3-amino-propoxy)benzothiazole (0.27 g, 0.82 mmol) and D-cysteine methyl ester (0.20 g, 1.05 mmol) in 10 ml of methanol was added TEA (0.11 g, 0.15 ml). The reaction mixture was stirred for 5 minutes. 20 ml of methylene chloride and 20 ml of water were added. The mixture was extracted three times with methylene chloride and the combined organic layer was dried over magnesium sulfate. The compound was purified by flash chromatography using methylene chloride/ethyl acetate (95:5 to 90:10) as eluent in a yield of 60%. ¹H NMR (CD₂Cl₂): 8.0 (d, J=9.0 Hz, 1H), 7.39 (d, J=2.4 Hz, 1H), 7.16 (dd, J=9.3 Hz, J=2.1 Hz, 1H), 5.35 (t, J=9.3 Hz, 1H, CHCOO), 4.12 (t, 2H, OCH₂), 3.6-3.8 (m, 2H, SCH₂), 3.31 (q, 2H, CH₂N), 2.02 (m, 2H, C₂), 1.42 (s, 9H, CH₃) MS (ES): m/e (M+1), 452.

Synthesis of MAO-11. The solution of TFA (1 ml) and tri-isopropylsilane (3 ul) in 10 ml of methylene chloride was added to methyl 6-(t-BOX-3-aminopropoxy) luciferin ester (0.23 g, 0.488 mmol) at 0° C. The resultant mixture was stirred at 0° C. for 1 hour. 30 ml of ether and 20 ml of methanol were added and the solvent was then removed by evaporation. The residue was purified by flash chromatography using methylene chloride-methanol (95:5) as eluent in a yield of 56%.

¹H NMR (d6-DMSO): 8.06 (d, J=8.7 Hz, 1H), 7.75 (d, J=2.4 Hz, 1H), 7.20 (dd, J=9.0 Hz, J=2.1 Hz, 1H), 5.51 (dd, 1H, CHCOO), 4.08 (t, 2H, OCH₂), 3.6-3.9 (m, SH, OCH₃+CH₂), 2.99 (m, 2H, CH₂N), 2.03 (m, 2H, CH₂). MS (ES): m/e (M+1), 352. $\lambda_{max}$ 331 nm, $\varepsilon_{max}$ 17,100 cm⁻¹M⁻¹ in water.

formula CCXI

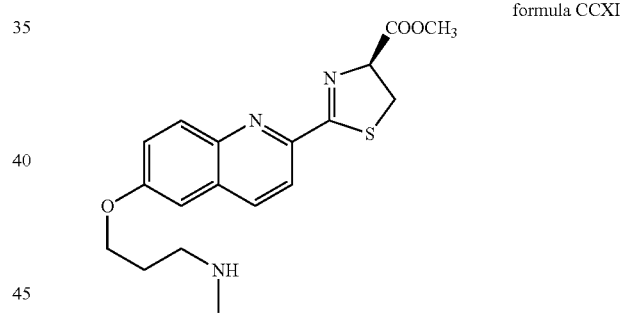

MAO-12

Methyl 6-(3-methylaminopropoxy)quinolinyl-luciferin ester.

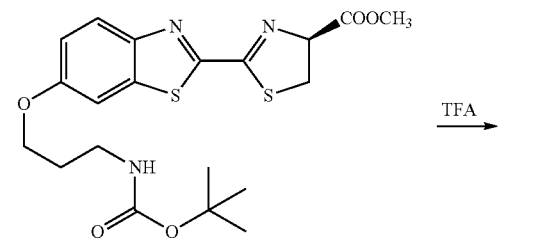

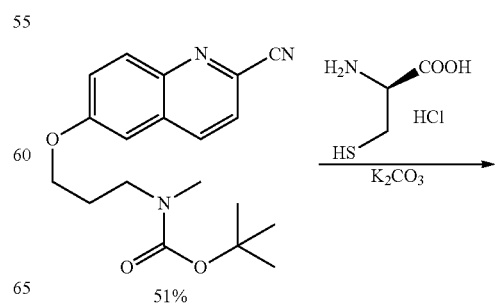

51%

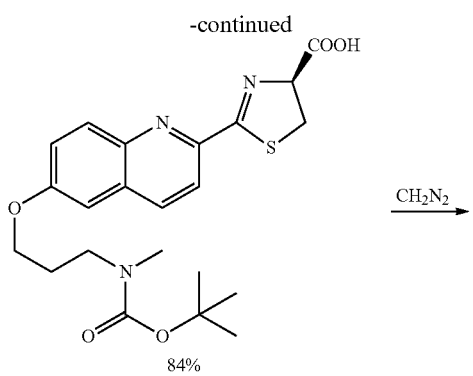

84%

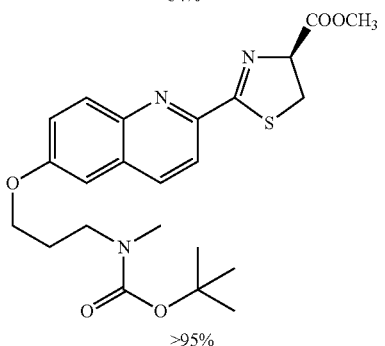

>95%

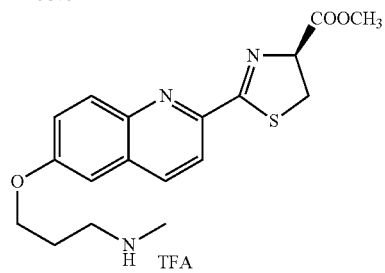

76%
MAO-12

Synthesis of 6-(3-t-BOX-3-methylaminopropoxy)quinolinyl-luciferin. The compound was made by employing the similar method used for the preparation of MAO-3.

$^1$H NMR (d6-DMSO): 8.33 (d, 1H), 8.08 (d, 1H), 7.97 (d, 1H), 7.4-7.5 (m, 2H), 5.51 (dd, 1H, CHCOO), 4.12 (t, 2H, OCH$_2$), 3.6-3.9 (m, SCH$_2$), 3.37 (t, 2H, NCH$_2$), 1.99 (m, 2H, CH$_2$), 1.30 (s, br, 9H, CH$_3$). MS (ES): m/e (M+1) 446

Synthesis of methyl 6-(3-t-BOC-3-methylaminopropoxy)quinolinyl-luciferin ester. To the solution of 6-(3-t-BOC-3-methylaminopropoxy)quinolinyl-luciferin (0.651 g, 1.418 mmol) in 15 ml of THF was added freshly-making diazomethane till the solution became yellow. The resultant mixture was stirred for another 10 mm, acetic acid was added and then 20 ml of water was added. The resultant mixture was extracted three times with methylene chloride and dried over magnesium sulfate. The product was purified by flash chromatography using
methylene chloride/ethyl acetate (100/0 to 90/10) as eluent in a yield of 95%. $^1$H NMR (d6-DMSO): 8.35 (d, 1H), 8.06 (d, 1H, 7.98 (d, 1H), 7.4-7.5 (m, 2H) 5.51 (dd, 1H, CHCOO), 4.06 (t, 2H, OCH$_2$), 3.71 (s, OCH3), 3.6-3.9 (m, SCH$_2$), 3.38 (t, 2H, NCH$_2$), 2.0 (m, 2H, CH$_2$), 1.25 (s, br, 9H, CH$_3$). MS (ES): m/e (M+1), 461

Synthesis of MAO-12. The compound MAO-12 was prepared by deprotection of methyl 6-(3-t-BOC-3-methylaminopropoxy)quinolinyl-luciferin ester by employing the similar method used for the preparation of MAO-11. $^1$H NMR (d6-DMSO): 8.36 (d, J=8.7 Hz), 8.10 (d, J=8.4 Hz, 1H), 7.99 (dd, J=8.1 Hz, Hz, J=2.4 Hz, 1H), 7.45 (dd, J=8.4 Hz, J=2.7 Hz, 1), 7.4s (s, 1H), 5.53 (dd, J=8.40 Hz, J=8.4 Hz, 1H, CH—COOH), 4.23 (t, J=6.0 Hz, 2H, OCH$_2$), 3.74 (s, 3H, CH$_3$), 3.50-3.73 (m, 2H, SCH$_2$), 3.09 (m, 2H, NCH$_2$), 2.60 (s, br, 3H, NCH3), 2.11 (m, 2H, CCH2). MS (ES): m/e (M+1), 361. $\lambda_{max}$ (nm)/$\varepsilon_{max}$ (cm$^{-1}$M$^{-1}$): 259/29,400; 326/9,800; 339/10,000 in water.

II. Fluorogenic MAO Substrates

A.

formula CCXII

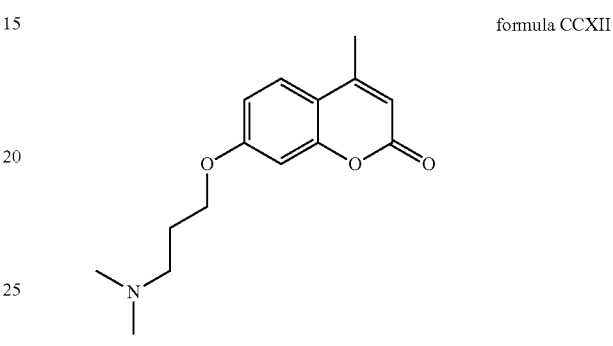

MAO-F1

7-(4-methyl-3-dimethylaminopropoxy)courmarin.

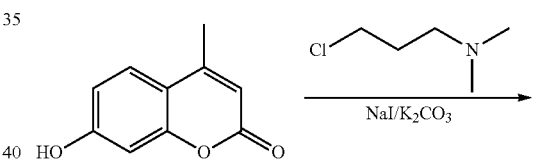

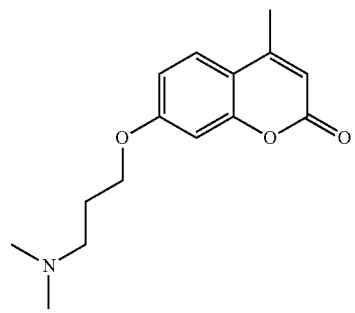

MAO-F1

Compound MAO-F1 was prepared by emptying the similar method used for preparation of MAO-1 precursor by alkylation of 7-(4-methyl-3-propoxy) coumarin with 3-chlorodimethylamino hydrochloride under basic condition. The compound was purified by flash chromatography using methylene chloride/methanol (90:10) as eluent in yield of 21%.

¹H NMR (d6-DMSO): 7.70 (d, 1H), 6.9-7.0 (m, 2H), 6.19 (s, 1H), 4.11 (t, 2H, OCH$_2$), 2.3-2.5 (m, 5H, NCH$_2$+CH$_3$), 2.18 (s, 6H, NCH$_3$), 1.88 (m, 2H, CH$_2$), $\lambda_{max}$ 381 nm, $\varepsilon_{max}$ 16,100 cm$^{-1}$M$^{-1}$ in pH 7.5 buffer.

B.

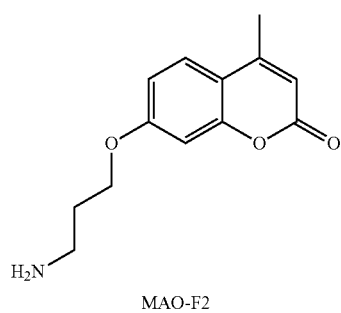

formula CCXIII

MAO-F2

7-(4-methyl-3-aminopropoxy)coumarin.

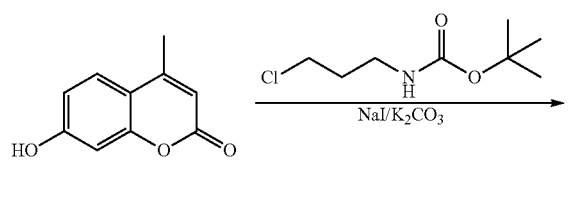

Compound MAO-F2 was employed the similar method used for preparation of MAO-F1 by alkylation of coumarin with t-BOC protected aminopropylchloride, and the deprotection under acidic condition gave the desired product.

¹H NMR (d6-DMSO): 7.68 (d, 1H), 6.9-7.0 (m, 2H), 6-21 (s, 1H), 4.28 (t, 2H, OCH$_2$), 2.95 (m, 2H, NCH$_2$), 2.01 (m, 2H, CH$_2$), $\lambda_{max}$ 384 nm, $\varepsilon_{max}$ 15,500 cm$^{-1}$M$^{-1}$ in pH 7.5 buffer.

C.

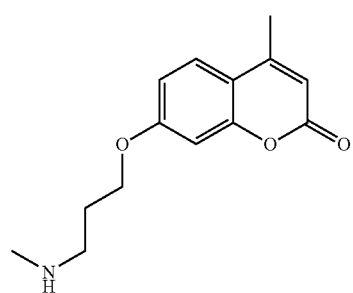

formula CCXIV

MAO-F3

7-(4-methyl-3-N-methylaminopropoxy)coumarin

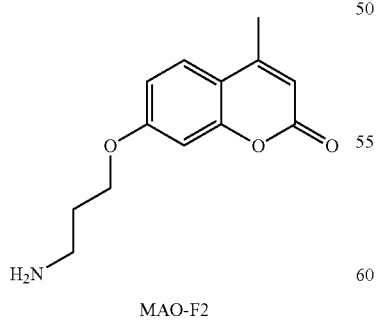

Compound MAO-F3 was prepared by employing the similar method used for the synthesis of MAO-F2.

D.
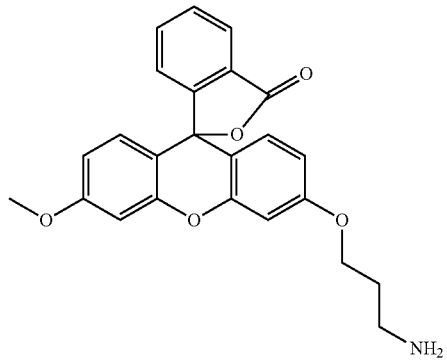
formula CCXV
MAO-F4
1-methoxy-6-aminopropoxyfluorescein lactone.
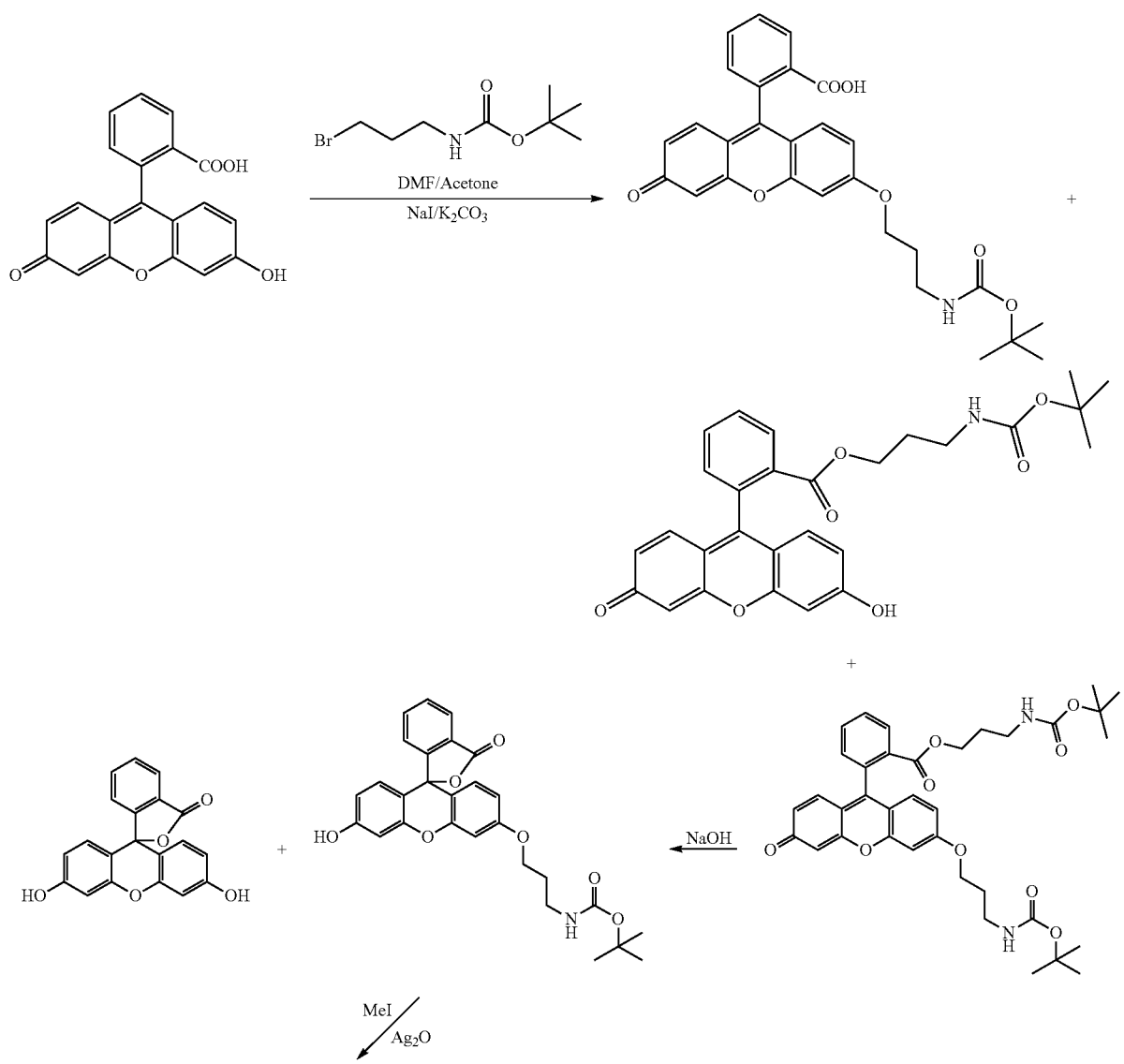

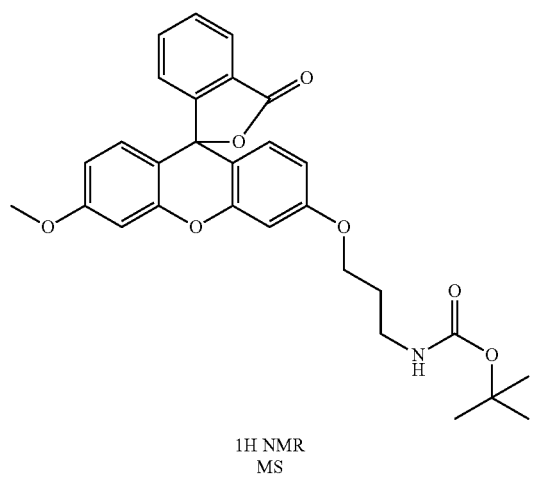

1H NMR
MS

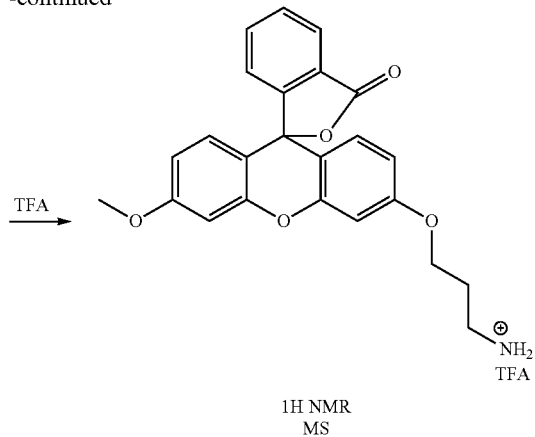

1H NMR
MS

Synthetic of mono-t-BOC-amidopropyl fluorescein. To the solution of fluorescein (1.0 g. 3.0 mmol), t-BOC-amidopropylbromide (0.86 g. 3.61 mmol) and potassium carbonate (0.50 g, 3.62 mmol) in DMF/acetone (1:1) was healed to reflux over night. TLC indicated that three products, mono-ether, mono-ester and diester, were produced which was confirmed by MS. The products were toughly purified by flash chromatography to remove fluorescein. The crude products (0.83 g) obtained were dissolved in 2N sodium hydroxide aqueous solution and heated to reflux for 3 hours. The solution was acidify and extracted three times with ethyl acetate. The combined organic layer was dried over magnesium sulfate. After removal of the solvent, the compound was purified by flash chromatography using heptane/ethyl acetate (7/3 to 1/1) as eluent in a yield of 23%.

$^1$H NMR (CD$_2$Cl$_2$): 7.98 (d, 1H), 7.66 (m, 2H), 7.22 (d, 1H), 6.90 (s, br, 2H), 6.67 (d, 2H), 6.55 (d, 2H), 4.0 (t, 2H, OCH$_2$), 3.05 (q, 2H, NCH$_2$), 1.98 (m, 2H, CH$_2$), 1.38 (s, 9H, CH$_3$). MS (ES): m/e (M+1), 490.

Synthesis of methoxy-t-BOC-amidopropyl fluorescein. To the solution of mono-t-BOC-amidopropyl fluorescein (0.4 g, 0.82 mmol) in THF/benzene (5 ml/15 ml) was added Ag$_2$O (0.56 g. 2.45 mmol) and methyl iodide (0.46 g, 3.26 mmol). The resultant mixture was heated in the dark overnight. Upon cooling to room temperature, the solid was removed by filtration. The solvent of filtrate was removed under reduced pressure and the product was purified by flash chromatography using heptane/ethyl acetate (7/3) as eluent in a yield of 47% $^1$H NMR (CD$_2$Cl$_2$): 7.95 (d, 2H), 7.66 (m, 2H), 7.14 (d, 2H), 6.78 (s, br, 2H), 6.55-6.72 (m, 2H), 4.03 (t, 2H, OCH$_2$), 3.81 (s, 3H, OCH$_3$), 3.25 (q, 2H, NCH$_2$), 1.98 (m, 2H, CH$_2$), 1.40 (s, 9H, CH$_3$). MS (ES), m/e (M+1), 504.

Synthesis of FMAO-4. The compound was made by de-protection of t-BOC as used for the synthesis MAO-11.
$^1$H NMR (CD$_2$Cl$_2$);
MS (ES), m/e (M+1), 404

III. Bioluminogenic FMO Substrates

A.

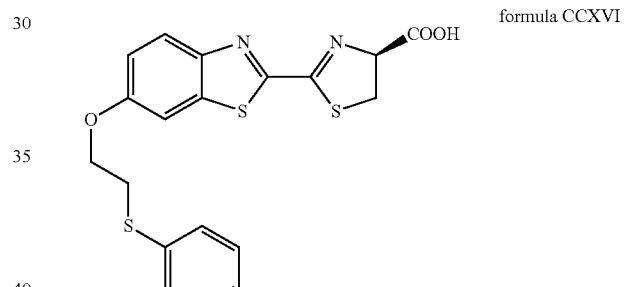

formula CCXVI

FMO-1

6-(2-phenylthiomethoxy)-luciferin

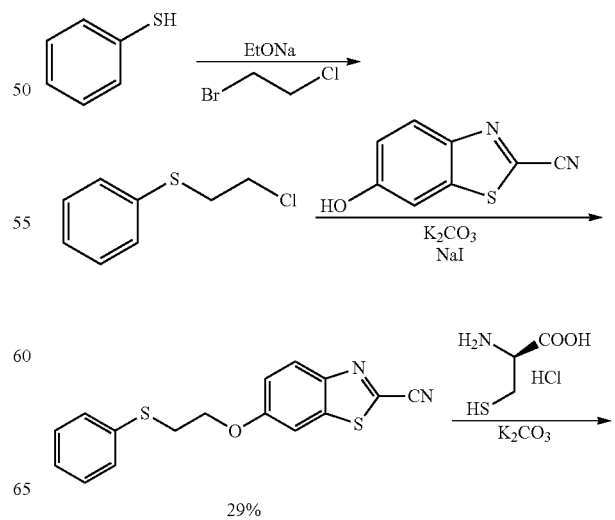

29%

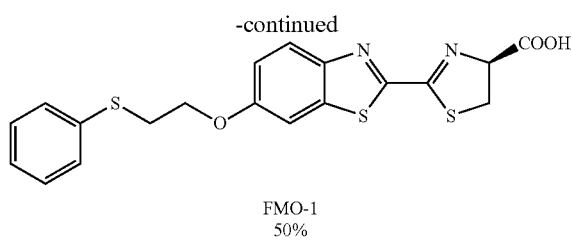

FMO-1
50%

Synthesis of 2-chloroethyl phenyl sulfide. Benzenethiol (15.0 g, 0.136 mol) was added to the solution of sodium ethoxide (0.20 mol) in 200 ml of anhydrous ethanol, and the mixture was stirred at room temperature for 15 minutes and then added to the solution of 1-bromo-2-chloroethane in 100 ml of ethanol. The resultant mixture was stirred at room temperature for 3 hours and poured into 300 ml of water. The mixture was extracted three times with ether and the combined organic layer was dried over magnesium sulfate. After removal of the solvent, the compound was purified by flash chromatography using heptane/ethyl acetate (100 to 97/3) as eluent in a yield of 74%.

$^1$H NMR (CD$_2$Cl$_2$): 7.2-7.5 (m, 5H), 3.64 (t, 2H). 3.23 (t, 2H)

Synthesis of 2-cyano-6-(2-phenylthioethoxy) benzothiozole. The compound was synthesized by employing the similar method for the preparation of MAO-1 precursor and purified by flash chromatography using heptane/ethyl acetate (90:10) as eluent in a yield of 29%.

$^1$H NMR (CD$_2$Cl$_2$): 8.09 (d, 1H), 7.45 (d, 2H), 7.34 (t, 2H), 7.3 (s, 1H), 7.28 (d, 1H), 7.22 (dd, 1H), 4.22 (t, 2H) 3.39 (t, 2H)

Synthesis of FMO-1. The compound was synthesized by employing the similar method for the preparation of MAO-1 and purified by flash chromatography using methylene chloride/methanol (95:5) as eluent in a yield of 50%.

$^1$H NMR (d$_6$-DMSO): 8.0 (d, 1H), 7.71 (s, 1H), 7.40 (d, 2H), 7.32 (t, 2H), 7.20 (t, 1H), 7.12 (d, 1H), 5.39 (t, 1H, CHCOO), 4.24 (t, 2H, OCH$_2$), 3.6-3.8 (m, 2H, CH$_2$), 3.40 (t, 2H, SCH$_2$). MS (ES) m/e (M+1): 417, $\lambda_{max}$ 328 nm, $\varepsilon_{max}$ 19,900 cm$^{-1}$M$^{-1}$ in water

B.

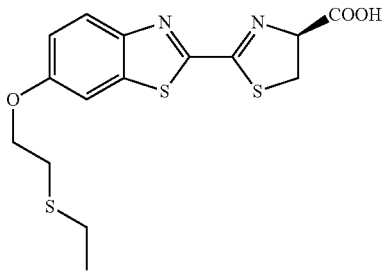

formula CCXVII

FMO-2

6-(2-ethylthioethoxy)-luciferin.

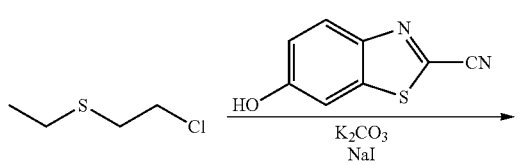

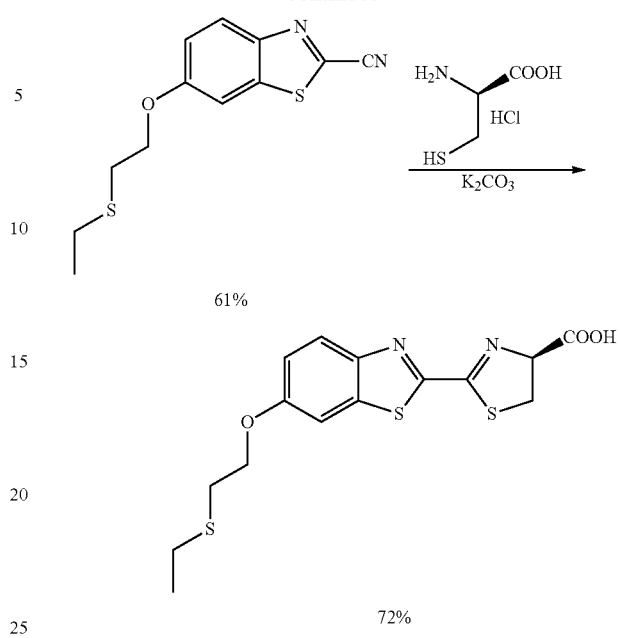

61%

72%

The compound FMO-2 was synthesized by employing the similar method for the preparation of FMO-1.

$^1$H NMR (d$_6$-DMSO): 8.01 (d, 1H), 7.78 (s, 1H), 7.17 (d, 1H), 5.39 (t, 1H, CHCOO), 4.22 (t, 2H, OCH$_2$), 3.6-3.8 (m, 2H, CH$_2$), 2.91 (t, 2H, SCH$_2$), 2.64 (q, 2H, CH2), 1.23 9t, 2H, CH3). MS (ES) m/e (M+1): 370, $\lambda_{max}$ 328 nm, $\varepsilon_{max}$ 17,600 cm$^{-1}$M$^{-1}$ in methanol.

C.

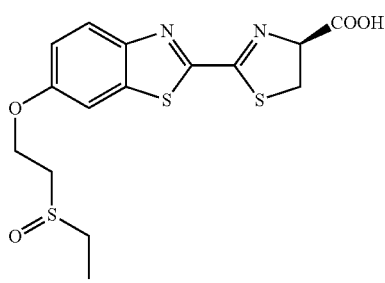

formula CCXVIII

FMO-3

6-(2-ethylsulfoxylethoxy)-luciferin

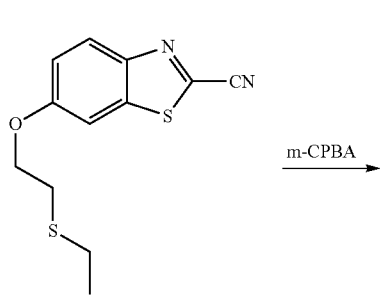

123

-continued

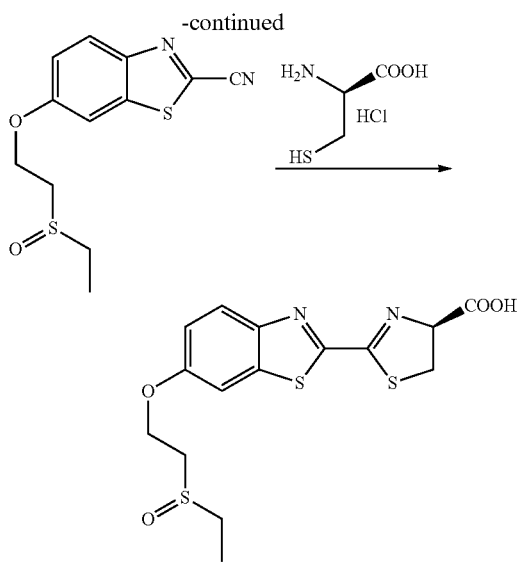

FMO-3

Synthesis of 2-cyano-6-(2-ethylsulfoxylethoxy) benzothiozole. To the solution of 2-cyano-6-(2-ethylthioethoxy) benzobiozole (0.34 g, 1.29 mmol) in 10 ml of methylene chloride was added m-CPBA (0.33 g, 67%, 1.30 mmol). The resultant mixture was stirred for 1 hour. The product was purified by flash chromatography using ethyl acetate/methanol (90/10) as eluent in a yield of 87%.

$^1$H NMR (CD$_2$Cl$_2$): 8.11 (d, 1H), 7.47 (d, 2H), 7.26 (d, 1H), 4.54 (m, 2H, OCH$_2$), 3.0-3.3 (m, 2H, CH$_2$O), 2.88 (m, 2H, CH$_2$CH$_3$), 1.40 (t, 3H, CH$_3$). MS (ES), m/e (M+1), 282

Synthesis of FMO-3. The compound was synthesized by employing the similar method used for the preparation of FMO-1.

$^1$H NMR (d$_6$-DMSO): 8.04 (d, 1H), 7.81 (s, 1H), 7.20 (d, 1H), 5.41 (t, 1H, CHCOO), 4.45 (m, 2H, OCH$_2$), 3.6-3.8 (m, 2H, CH$_2$), 3.0-3.4 (m, 2H, SOCH$_2$), 2.6-3.0 (m, 2H, CH$_2$CH$_3$), 1.23 (t, 2H, CH$_3$). MS (ES) m/e (M+1): 385. $\lambda_{max}$ 328 nm, $\varepsilon_{max}$ 18,000 cm$^-$M$^{-1}$ in methanol.

D.

formula CCXIX

FMO-4

6-(3-methylamino-1-butoxy)luciferin.

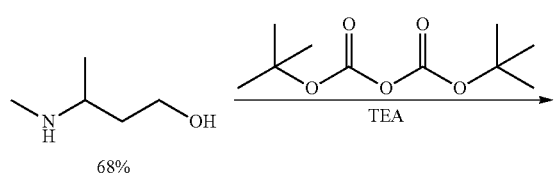

124

-continued

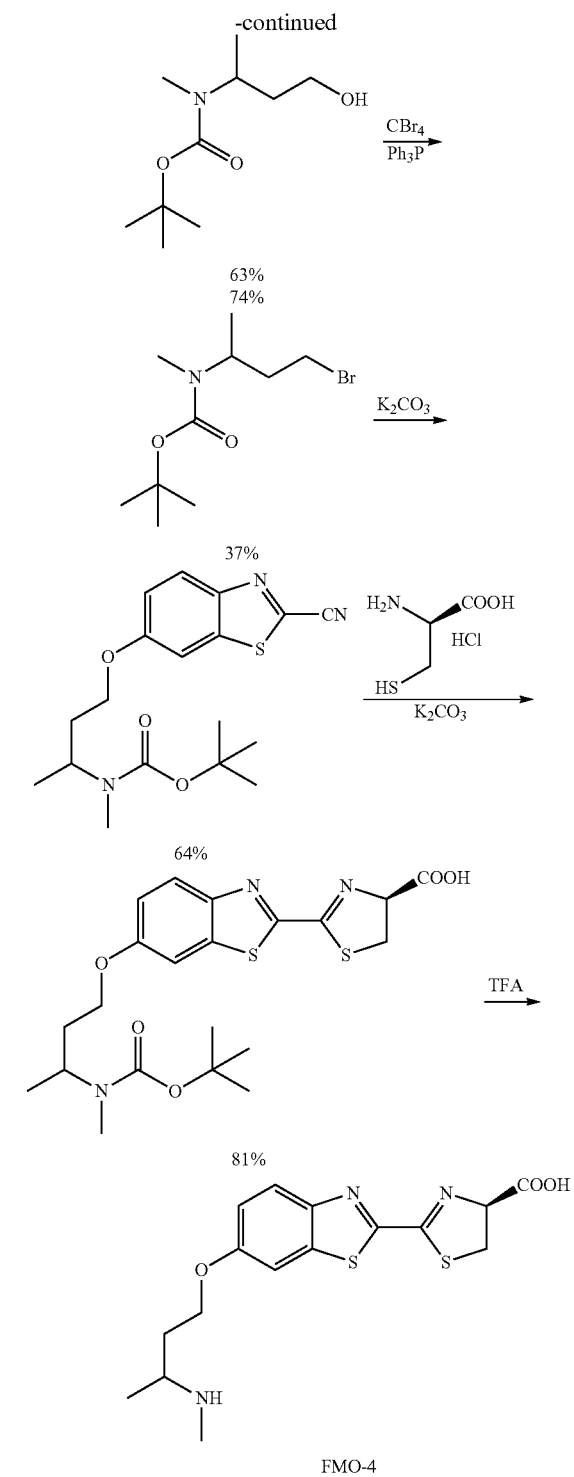

FMO-4

Synthesis of 1-methyl-3-hydroxypropylmethyl-t-BOC-amide. To the solution of t-BOC anhydride (15.8 g, 0.0724 mol) in 150 ml of anhydrous methylene chloride was added the solution of 3-methylamino-1-butanol (6.22 g, 0.0604 mol) and (7.33 g, 0.0724 mol) in 60 ml of methylene chloride at 0° C. The resultant mixture was stirred for 3 hours. 200 ml of methylene chloride was then added. The mixture was washed three times with water and the combined organic layer was dried over magnesium sulfate. After removal of solvent, the product was purified by flash chromatography using heptane/ethyl acetate as eluent (70/30 to 40/60) in a yield of 74%.

$^1$H NMR (CD$_2$Cl$_2$): 3.35 (m, 1H, CH), 2.8-3.5 (m, 2H, OCH$_2$). 2.63 (s, 3H, NCH$_3$). 1.65 (m, 2H, CH$_2$) 1.45 (s, 9H, CH$_3$), 1.18 (d, 3H, CH$_3$). MS (ES) m/e (M+1); 204

Synthesis of 1-methyl-3-bromopropylmethyl-t-BOC-amide. To the solution of 1-methyl 3-hydroxypropylmethyl-t-BOC-amide (9.01 g, 0.0444 mol) and carbon tetrabromide (17.67 g, 0.0533 mol) in 120 ml of anhydrous methylene chloride was added triphenylphosphine (14.0 g. 0.0533 mol) at 0° C. The resultant mixture was stirred overnight. After removal of solvent, the product was purified by flash chromatography using heptane/ethyl acetate as eluent (90/10) in a yield of 37%.

$^1$H NMR (CD$_2$Cl$_2$): 4.32 (m, 1H, CH), 3.34 (t, 2H, BrCH$_2$), 2.69 (s, 3H, NCH$_3$), 1.8-2.2 (m, 2H, CH$_2$), 1.45 (s, 9H, CH$_3$), 1.16 (d, 3H, CH$_3$)

Synthesis of 2-cyano-6-(1-methyl-3-propylmethyl-t-BOC-amide) benzothiozole. The similar procedure was employed by the method for the synthesis of precursor of MAO-1.

Synthesis of 6-(1-methyl-3-propylmethyl-t-BOC-amide) luciferin. The similar procedure was employed by the method for the synthesis of MAO-1.

$^1$H NMR (CD$_2$Cl$_2$): 7.88 (d, 1H), 7.24 (s, 1H), 7.03 (d, 1H), 5.24 (t, 1H, CHCOO), 4.36 (s, br, 1H, CH), 3.91 (t, 2H, OCH$_2$), 3.67 (d, 2H, SCH$_2$), 2.63 (s, 3H, NCH$_3$), 1.7-2.0 (m, 2H, CH$_2$), 1.25 (s, br, 9H, CH$_3$), 1.05 (d, 3H, CH$_3$). MS (ES). m/e (M+2): 467

Synthesis of FMO-4. The compound FMO-4 was made by de-production of t-BOC luciferin with TFA acid as described in the preparation of MAO-11.

$^1$H NMR (do-DMSO): 8.04 (d, 1H), 7.76 (d, 1H), 7.19 (dd, 1H), 5.38 (t, 1H, CHCOO). 4.18 (m, 1H, OCH2), 3.6-3.8 (m, 2H, SCH$_2$), 3.38 (m, 1H, NCH), 2.49 (s, 3H, NCH$_3$), 1.8-2.3 (m, 2H, CH$_2$), 1.24 (d, 3H, CH$_3$). MS (ES), m/e (M+2): 367. $\lambda_{max}$ 326 nm, $\epsilon_{max}$ 16,800 cm$^{-1}$M$^{-1}$ in water.

F.

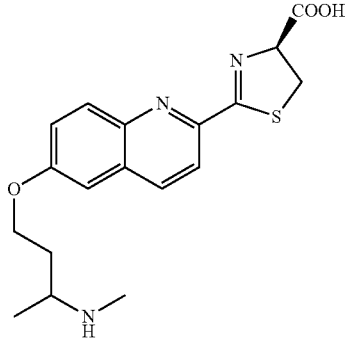

formula CCXX

FMO-5

6-(3-methylamino-1-butoxy)quinolinyl-luciferin.

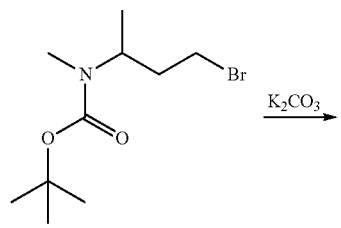

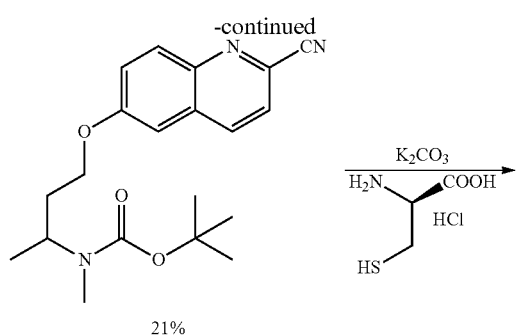

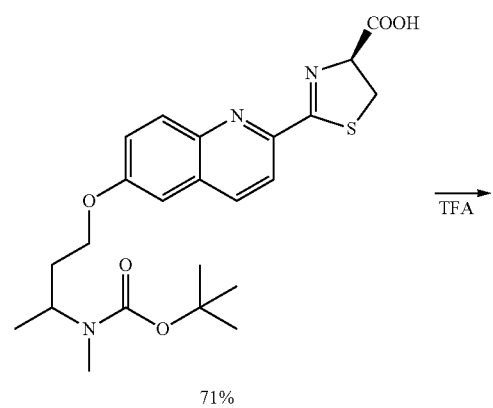

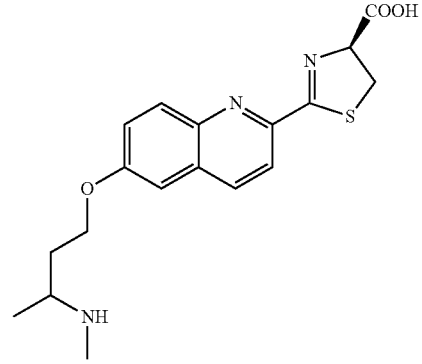

FMO-5

The compound FMO-5 was synthesized by employing the similar method for the preparation of FMO-4.

$^1$H NMR (d6-DMSO): 8.34 (d, 1H), 8.10 (d, 1H), 7.99 (d, 1H), 7.47 (m, overlap, 2H), 5.40 (t, 1H, CHCOO), 4.27 (m, 1H, OCH2), 3.5-3.6 (m, 2H, SCH$_2$), 3.38 (m, 1H, NCH), 2.60 (s, 3H, NCH$_3$), 1.9-2.3 (m, 2H, CH$_2$), 1.28 (d, 3H, CH$_3$). MS(ES), m/e (M+2); 361, $\lambda_{max}$ 327 nm, $\epsilon_{max}$ 9.970 cm$^{-1}$M$^{-1}$ in water.

IV. Bioluminogenic GST/Glutathione Substrates
A.

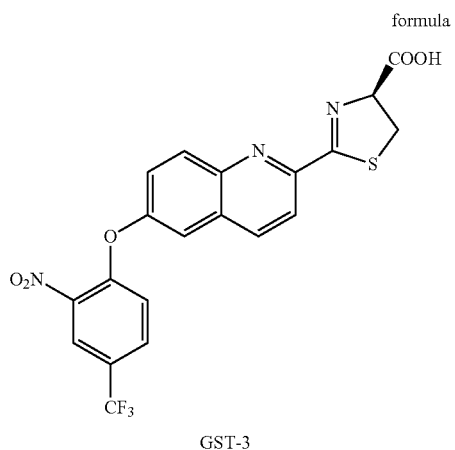

formula CCXXI

GST-3

6-(2-nitro-4-trifluoromethyl-phenoxyl)quinolinyl-luciferin.

30 min. Upon cooling to room temperature, the mixture was poured into 30 ml of cold water and exacted three tunes with methylene chloride. The combined organic layer was washed with water and dried over magnesium sulfate. The product was purified by flash chromatography using heptane/methylene chloride (1:2) as eluent in a yield of 35%. $^1$H NMR (CD$_2$Cl$_2$): 8.36 (d, 1H), 8.25 (dd, 1H), 7.94 (dd, 1H), 7.75 (d, 1H), 7.67 (dd, 1H), 7.43 (d, 1H), 7.31 (d, 1H). MS (ES) m/e (M+2): 361.

Synthesis of GST-3. The compound was synthesized by employing the similar method for the preparation of MAO-1 and was purified by flash chromatograph using methylene chloride/methanol (95:5) as eluent in a yield of 20%.

$^1$H NMR (d$_6$-DMSO): 8.55 (s, 1H), 8.42 (d, 1H), 8.19 (m, 2H), 8.06 (d, 1H), 7.82 (s. 1H), 7.71 (d, 1H), 7.46 (d, 1H), 5.22 (t, 1H, CHCOO), 3.45-3.75 (m, 2H, CH$_2$). MS (ES) m/e (M+1) 464 $\lambda_{max}$ 328 nm, $\varepsilon_{max}$ 9,900 cm$^{-1}$M$^{-1}$ in MeOH.

B.

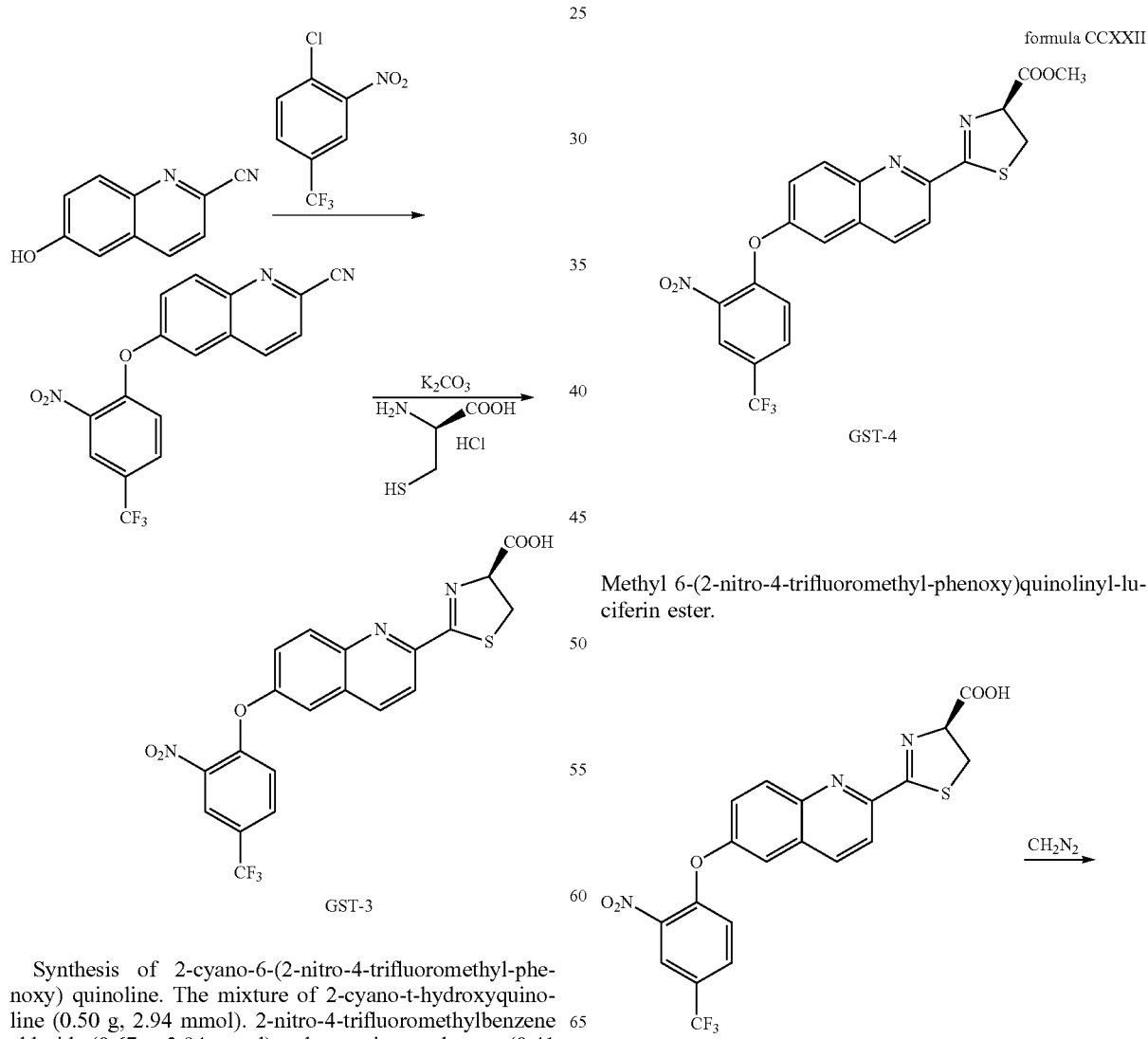

formula CCXXII

GST-4

Methyl 6-(2-nitro-4-trifluoromethyl-phenoxy)quinolinyl-luciferin ester.

GST-3

Synthesis of 2-cyano-6-(2-nitro-4-trifluoromethyl-phenoxy) quinoline. The mixture of 2-cyano-t-hydroxyquinoline (0.50 g, 2.94 mmol). 2-nitro-4-trifluoromethylbenzene chloride (0.67 g, 2.94 mmol) and potassium carbonate (0.41 g, 2.97 mmol) in 30 ml of DMSO was heated to 100° C. for -continued

GST-4

The compound GST-4 was prepared by employing the similar method used for the synthesis of MAO-12 using GST-3 as starting material.

$^1$H NMR (CD$_2$Cl$_2$): 8.23 (s, 1H), 8.0-8.2 (m, 3H), 7.75 (d, 1H)(7.50 (d, 1H), 7.39 (s, 1H), 7.15 (d, 1H), 7.46 (d, 1H), 5.42 (t, 1H, CHCOO), 3.74 (s, 3H, CH$_3$), 3.58 (d, 2H, CH$_2$). MS (ES) m/e (M+1); 478, $\lambda_{max}$ (nm)/$\varepsilon_{max}$ (cm$^{-1}$M$^{-1}$): 322/10,800; 328/8,800 in MeOH.

C.

formula CCXXIII

GST-5

6-(4-nitrophenoxy)quinolinyl-luciferin.

The compound GST-5 was prepared by employing the similar method used for synthesis of GST-3.

$^1$H NMR (d$_6$-DMSO) 8.39 (d, 1H), 8.28 (d, 2H), 8.19 (m, 2H), 7.74 (s, 1H), 7.60 (d, 1H), 7.28 (s, 1H), 5.37 (t, 1H, CHCOO), 3.59 (d, 2H, CH$_2$). MS (ES) m/e (M+2): 397, $\lambda_{max}$ 328 nm, $\varepsilon_{max}$ 17,200 cm$^{-1}$M$^{-1}$ in MeOH.

D.

formula CCXXIV

GST-6

6-(2-nitrophenoxy)quinolinyl-luciferin.

The compound GST-6 was prepared by employing the similar method used for the synthesis of GST-3.

$^1$H NMR (d$_6$-DMSO): 8.39 (d, 1H), 8.13 (m, 3H), 7.78 (t, 1H), 7.63 (d, 1H), 7.56 (s, 1H), 7.48 (t, 1H), 7.38 (d, 1H), 5.37 (t, 1H, CHCOO), 3.59 (m, 2H, CH$_2$), MS (ES) m/e (M+2): 397 $\lambda_{max}$ (nm)/$\varepsilon_{max}$ (cm$^-$M$^{-1}$): 323/10,400; 327/9,500; 337/8,300 in MeOH.

E.

formula CCXXV

GST-7

6-(3-trifluoromethyl-4-nitrophenoxy)quinolinyl-luciferin.

The compound GST-7 was prepared by employing the similar method used for synthesis of GST-3. $^1$H NMR (d$_6$-DMSO): 8.47 (d, 1H), 8.15-8.30 (m, 3H), 7.85 (d, 1H), 7.78 (d, 1H), 7.73 (dd, 1H), 7.55 (d, 1H), 5.45 (t, 1H, CHCOO). 3.5-3.7 (m, 2H, CH$_2$) MS (ES) m/e (M+1): 464. $\lambda_{max}$ 321 nm, $\varepsilon_{max}$ 11,000 cm$^{-1}$M$^{-1}$ in MeOH.

F.

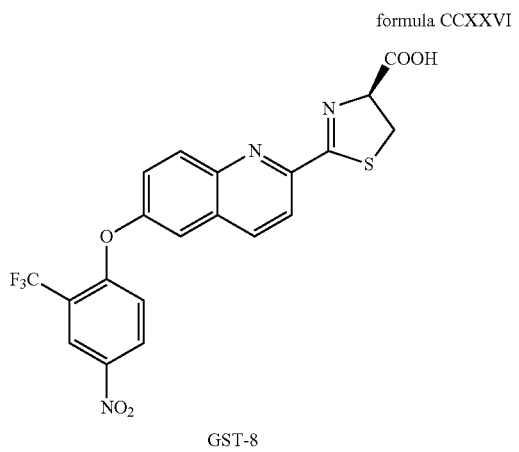 [SMILES: O=C(O)[C@H]1CSC(c2ccc3cc(Oc4ccc([N+](=O)[O-])cc4C(F)(F)F)ccc3n2)=N1]

GST-8

6-(2-trifluoromethyl-4-nitrophenoxy)quinolinyl-luciferin.

The compound GST-8 was prepared by employing the similar method used for synthesis of GST-3.

$^1$H NMR (d$_6$-DMSO): 8.56 (d, 1H), 8.47 (d, 2H), 8.20 (dd, 2H), 7.92 (d, 1H), 7.72 (dd, 1H), 7.33 (d, 1H), 5.44 (t, 1H, CHCOO), 3.5-3.7 (m, 2H, CH$_2$). MS (ES) m/e (M+1): 464. $\lambda_{max}$ 328 nm, $\varepsilon_{max}$ 10,100 cm$^{-1}$M$^{-1}$ in MeOH.

G.

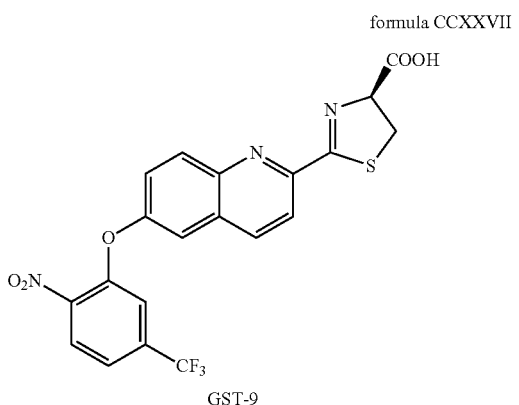 [SMILES: O=C(O)[C@H]1CSC(c2ccc3cc(Oc4cc(C(F)(F)F)ccc4[N+](=O)[O-])ccc3n2)=N1]

GST-9

6-(5-trifluoromethyl-2-nitrophenoxy)quinolinyl-luciferin.

The compound GST-9 was prepared by employing the similar method used for synthesis of GST-3.

$\lambda_{max}$ (nm)/$\varepsilon_{max}$ (cm$^{-1}$M$^{-1}$): 321/10,000; 328/8,300 in MeOH

H.

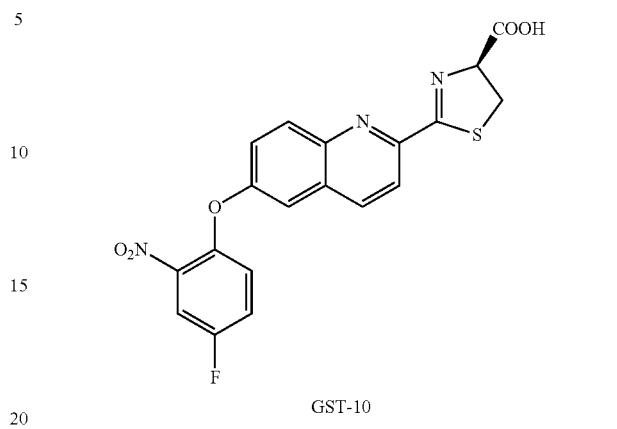

GST-10

6-(4-fluoro-2-nitrophenoxy)quinolinyl-luciferin.

The compound GST-10 was prepared by employing the similar method used for synthesis of GST-3.

$^1$H NMR (d$_6$-DMSO): 8.38 (d, 1H), 8.02-8.2 (m, 3H), 7.6-7.8 (m, 2H), 7.5-7.6 (m, 2H, 1H), 5.34 (t, 1H, CHCOO), 3.5-3.7 (m, 2H, SCH$_2$). MS (ES) m/e (M+2): 415 $\lambda_{max}$ 321 nm, $\varepsilon_{max}$ 10,600 cm$^{-1}$M$^{-1}$ in MeOH.

I.

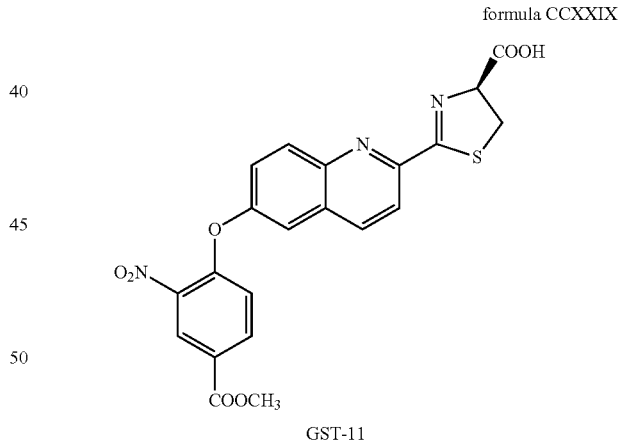

GST-11

6-(2-nitro-4-methylcarboxylphenoxy)quinolinyl-luciferin

The compound GST-11 was prepared by employing the similar method used for synthesis of GST-3.

$^1$H NMR (d$_6$-DMSO): 8.68 (d, 1H), 8.15-8.30 (m, 2H), 8.1-8.2 (m, 2H), 7.64-7.74 (m, 2H), 7.33 (d, 1H), 5.42 (t, 1H, CHCOO), 3.81 (s, 3H, CH$_3$), 3.5-3.7 (m, 2H, CH$_2$). MS(ES) m/e (M+2); 455, $\lambda_{max}$ 321 nm, $\varepsilon_{max}$ 16,200 cm$^{-1}$M$^{-1}$ in MeOH.

J.

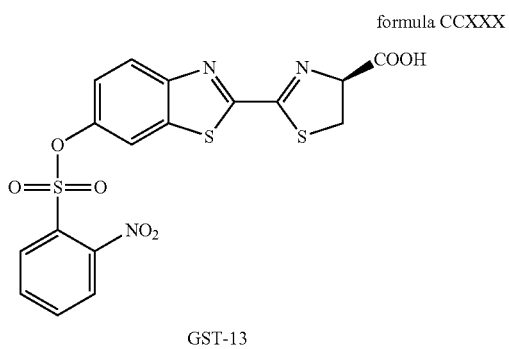 [SMILES: O=C(O)[C@H]1CSC(c2nc3ccc(OS(=O)(=O)c4ccccc4[N+](=O)[O-])cc3s2)=N1]

formula CCXXX

GST-13

6-(2-Nitro-benzenesulfonic acid) luciferin ester.

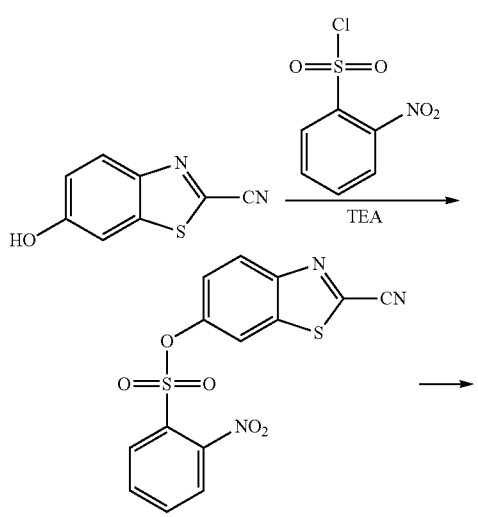

GST-13

Synthesis of 2-cyano-6-(2-nitro-benzenesulfonic acid) benzothiozole. To the solution of 6-hydroxy-2-cyanobenzothiozole (0.50 g, 2.84 mmol) and 2-nitrobenzene-sulfonyl chloride (0.63 g. 2.84 mmol) in 15 ml of anhydrous methylene chloride was added TEA (0.58 g, 5.68 mmol). The resultant mixture was stirred for 3 hours. The product was purified by flash chromatography using heptane/ethyl acetate/methylene chloride (70/30/15) as eluent in a yield of 55%.

Synthesis of GST-13. GST-13 was prepared by employing the similar method for the synthesis of luciferin GST-3.

$^1$H NMR (d$_6$-DMSO); 8.14-3.26 (m, 2H), 8.17 (s, 1H), 8.07 (td, J=7.5 Hz, J=1.3 Hz, 1H), 7.99 (dd, J=8.0 Hz, Hz, J=1.2 Hz, 1H), 7.85 (td, J=7.8 Hz, J=1.2 Hz, 1H), 7.34 (dd, J=9.0 Hz, J=2.4 Hz, 1H), 5.44 (t, J=9.0 Hz, 1H, CH—COOH), 3.6-3.9 (m, 2H, CH$_2$). MS (ES): m/e (M+1), 466. $\lambda_{max}$ 292 nm, $\varepsilon_{max}$ 19,100 cm$^{-1}$M$^{-1}$ in MeOH.

K.

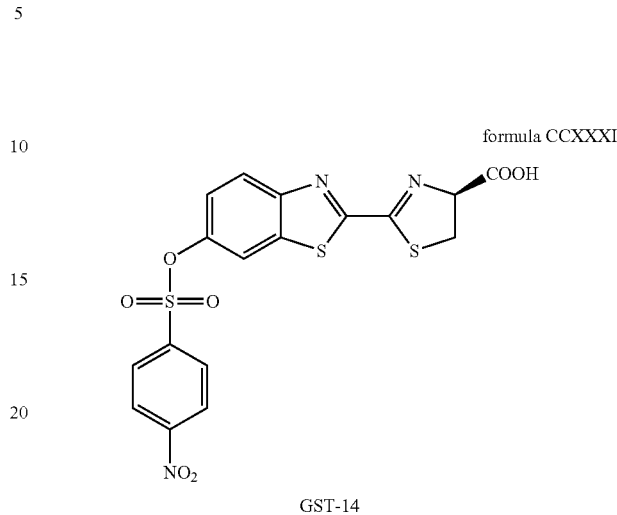

formula CCXXXI

GST-14

6-(4-Nitro-benzenesulfonic acid) luciferin ester.

The compound GST-14 was prepared by employing the similar method used for the synthesis of GST-13.

$^1$H NMR (d$_6$-DMSO): 8.42 (d, 2H), 8.17 (m, 3H), 8.08 (d, 1H), 7.25 (dd, 1H), 5.44 (t, 1H, CH—COOH), 3.6-3.9 (m, 2H, CH$_2$). MS (ES): m/e (M+1), 466. $\lambda_{max}$ 292 nm, $\varepsilon_{max}$ 19,400 cm$^{-1}$M$^{-1}$ in MeOH.

L.

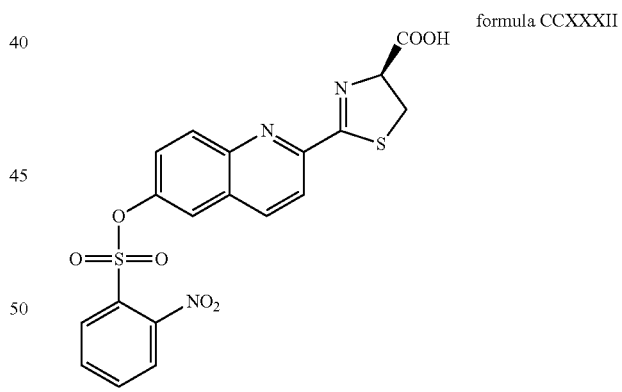

formula CCXXXII

GST-15

6-(2-Nitro-benzenesulfonic acid) quinolinyl-luciferin ester.

The compound GST-15 was prepared by employing the similar method used for the synthesis of GST-13.

$^1$H NMR (d$_6$-DMSO): 8.54 (d, 1H), 7.9-8.3 (m, 6H), 7.85 (t, 1H), 7.57 (dd, 1H), 5.41 (t, 1H, CH—COOH), 3.5-3.7 (m, 2H, CH$_2$). MS (ES): m/e (M+1), 460. $\lambda_{max}$ 285 nm, $\varepsilon_{max}$ 9,010 cm$^{-1}$M$^{-1}$ in MeOH.

M.

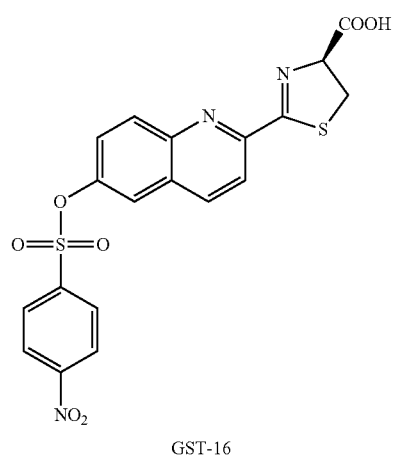

formula CCXXXIII

GST-16

6-(4-Nitro-benzenesulfonic acid) quinolinyl-luciferin ester.

The compound GST-16 was prepared by employing the similar method used for synthesis of GST-13.

$^1$H NMR (d6-DMSO): 8.23 (d, J=8.7 Hz, 1H), 8.43 (d, J=8.7 Hz, 2H), 8.18 (m, 3H), 8.13 (d, J=9.3 Hz, 1H), 7.89 (d, J=2.7 Hz, 1H), 7.51 (dd, J=9.3 Hz, J=3 Hz, 1H), 5.42 (dd, J=8.4 Hz, J=8.4 Hz, CHCOO), 3.5-3.7 (m, 2H, CH2) MS (ES) m/e (M+1): 461. $\lambda_{max}$ 285 nm, $\varepsilon_{max}$ 12,400 cm$^{-1}$M$^{-1}$ in MeOH.

N.

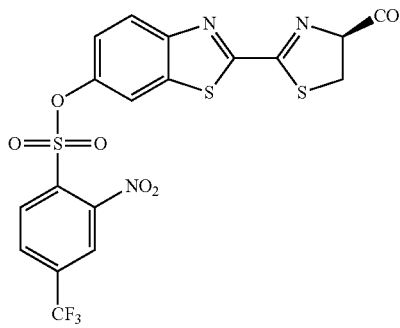

formula CCXXXIV

GST-17

6-(2-Nitro-4-trifluorobenzenesulfonic acid) luciferin ester.

The compound GST-17 was prepared by employing the similar method used for synthesis of GST-13.

$^1$H NMR (d6-DMSO) 8.82 (s, 1H), 8.15-8.30 (m, 4H), 7.43 (d, 1H), 5.43 (t, 1H, CHCOO). 3.6-3.9 (m, 2H, SCH$_2$). MS (ES) m/e (M+1): 534 $\lambda_{max}$ 292 nm, $\varepsilon_{max}$ 18,600 cm$^{-1}$M$^{-1}$ in MeOH.

Figure 44:
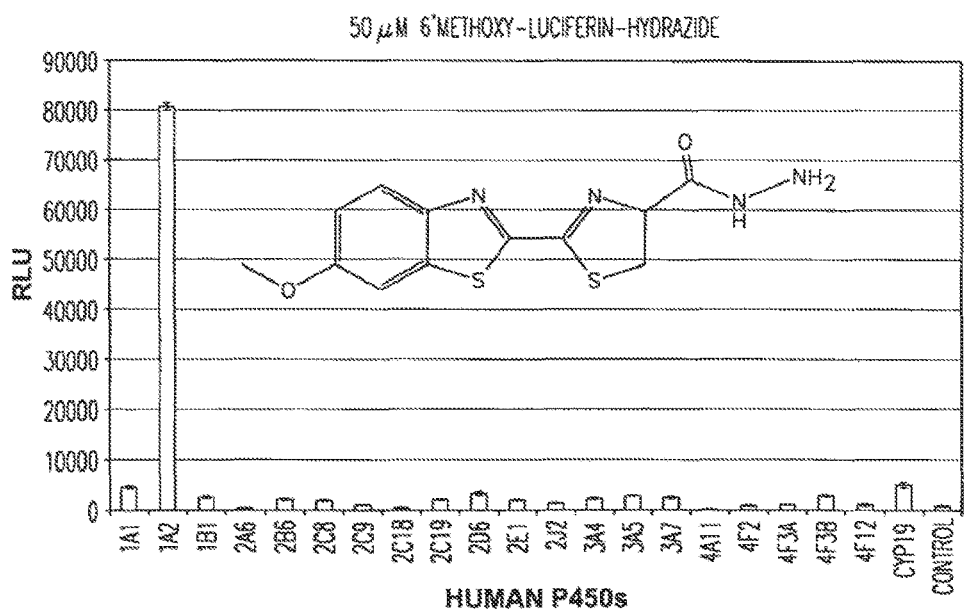
FIG. 44. A graphical representation of RLU for reactions containing one of a panel of P450 enzymes and a luciferin derivative, 6'methoxy-luciferin-hydrazide. Reactions contain 1 pmol of P450 or 5 pmol CYP19.

Other GST substrates are shown in FIG. 44B.

V. Fluorogenic GST/Glutathione Substrates

A.

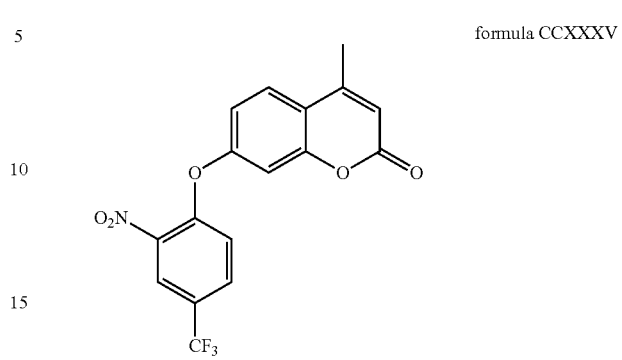

formula CCXXXV 7-(5-trifluoromethyl-2-nitrophenoxy)-4-methyl-coumarin.

The compound was prepared by employing the similar method used for synthesis of the precursor of GST-3.

$^1$H NMR (CD$_2$Cl$_2$): 8.37 (s, 1H), 7.88 (d, 2H), 7.70 (m, 2H), 7.28 (d, 1H), 7.05 (d, 1H), 7.00 (s, 1H), 6.25 (s, 1H), 2.43 (s, 3H, CH$_3$). MS (ES) m/e (M+2): 367. $\lambda_{max}$ 320 nm, $\varepsilon_{max}$ 12,700 cm$^{-1}$M$^{-1}$ in MeOH.

B.

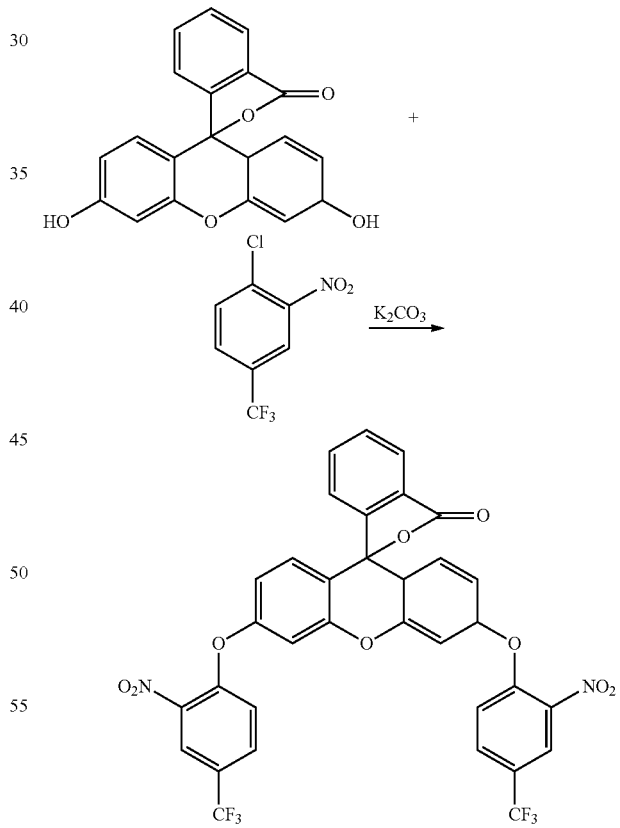

formula CCXXXVI

Synthesis of bis(-(5-trifluoromethyl-2-nitrophenoxy)-fluorescein lactone. The mixture of fluorescein (2.0 g, 60 mmol), 2-nitro-4-trifluoromethylbenzene chloride (3.0 g, 13.3 mmol) and potassium carbonate (2.0 g, 14.5 mmol) in 50 ml of DMSO was heated to 100° C. for 1 hour min. Upon cooling to room temperature, the mixture was poured into 30 ml of cold water and exacted three times with methylene chloride. The combined organic layer was washed with water and dried over magnesium sulfate. The product was purified by flash chromatography using heptane/methylene chloride/ethyl acetate (7/3/0 to 7/3/) as eluent in a yield of 88%

$^1$H NMR (CD$_2$Cl$_2$): 8.28 (s, br, 2H), 8.05 (d, 1H), 7.84 (d, 2H), 7/56-7.82 (m, 2H), 7.26 (d, 2H), 7.03 (d, 2H), 6.92 (d, 2H), 6.84 (dd, 2H).

VI. Bioluminogenic Alkaline Phosphatase Substrates

A.

formula CCXXXVII

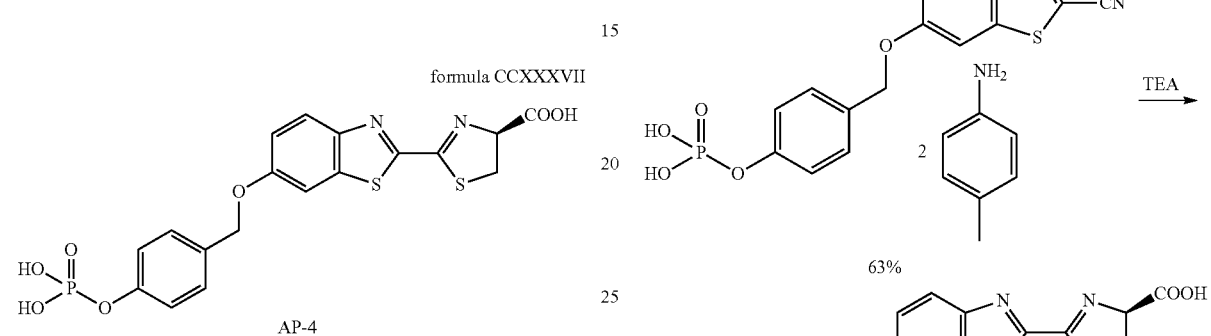

AP-4

6-(4-phosphoric acid benzylether) luciferin.

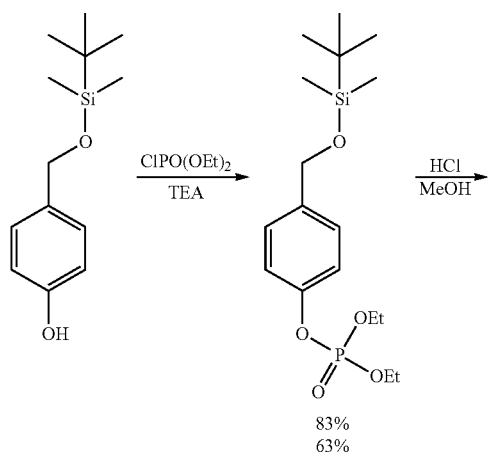

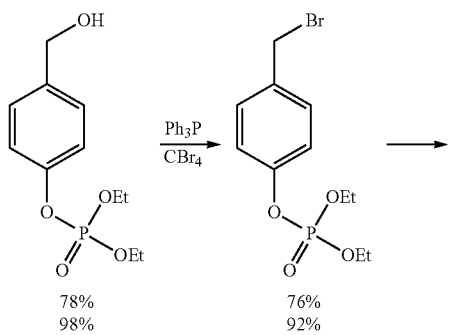

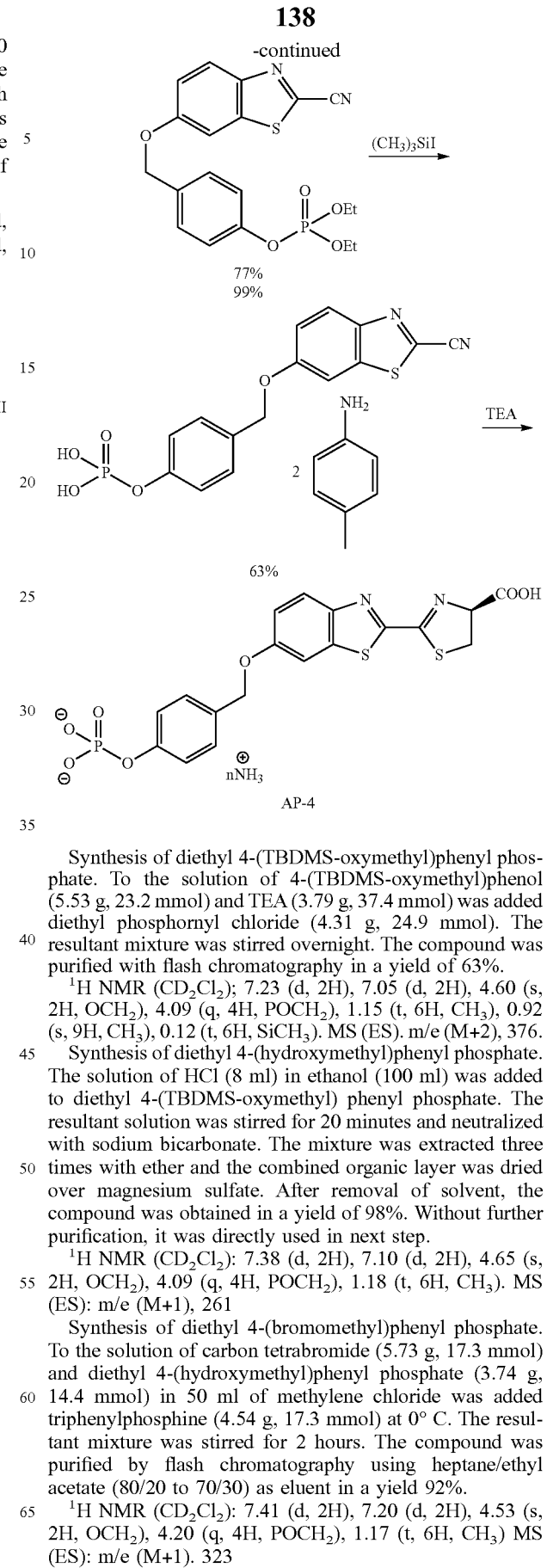

Synthesis of diethyl 4-(TBDMS-oxymethyl)phenyl phosphate. To the solution of 4-(TBDMS-oxymethyl)phenol (5.53 g, 23.2 mmol) and TEA (3.79 g, 37.4 mmol) was added diethyl phosphornyl chloride (4.31 g, 24.9 mmol). The resultant mixture was stirred overnight. The compound was purified with flash chromatography in a yield of 63%.

$^1$H NMR (CD$_2$Cl$_2$); 7.23 (d, 2H), 7.05 (d, 2H), 4.60 (s, 2H, OCH$_2$), 4.09 (q, 4H, POCH$_2$), 1.15 (t, 6H, CH$_3$), 0.92 (s, 9H, CH$_3$), 0.12 (t, 6H, SiCH$_3$). MS (ES). m/e (M+2), 376.

Synthesis of diethyl 4-(hydroxymethyl)phenyl phosphate. The solution of HCl (8 ml) in ethanol (100 ml) was added to diethyl 4-(TBDMS-oxymethyl) phenyl phosphate. The resultant solution was stirred for 20 minutes and neutralized with sodium bicarbonate. The mixture was extracted three times with ether and the combined organic layer was dried over magnesium sulfate. After removal of solvent, the compound was obtained in a yield of 98%. Without further purification, it was directly used in next step.

$^1$H NMR (CD$_2$Cl$_2$): 7.38 (d, 2H), 7.10 (d, 2H), 4.65 (s, 2H, OCH$_2$), 4.09 (q, 4H, POCH$_2$), 1.18 (t, 6H, CH$_3$). MS (ES): m/e (M+1), 261

Synthesis of diethyl 4-(bromomethyl)phenyl phosphate. To the solution of carbon tetrabromide (5.73 g, 17.3 mmol) and diethyl 4-(hydroxymethyl)phenyl phosphate (3.74 g, 14.4 mmol) in 50 ml of methylene chloride was added triphenylphosphine (4.54 g, 17.3 mmol) at 0° C. The resultant mixture was stirred for 2 hours. The compound was purified by flash chromatography using heptane/ethyl acetate (80/20 to 70/30) as eluent in a yield 92%.

$^1$H NMR (CD$_2$Cl$_2$): 7.41 (d, 2H), 7.20 (d, 2H), 4.53 (s, 2H, OCH$_2$), 4.20 (q, 4H, POCH$_2$), 1.17 (t, 6H, CH$_3$) MS (ES): m/e (M+1). 323

Synthesis of phosphoric acid 4-(2-cyano-benzothiazol-6-yloxymethyl)-phenyl diethyl ester. The compound was synthesized by employing the similar method for the synthesis of precursor MAO-1.

$^1$H NMR (CD$_2$Cl$_2$): 8.12 (d, 1H), 7.49 (s, 1H), 7.46 (d, 2H), 7.33 (d, 1H), 7.26 (d, 2H), 5.11 (s, 2H, OCH$_2$), 4.20 (m, 4H, POCH$_2$), 1.34 (t, 6H, CH$_3$). MS (ES) m/e (M+1), 420

Synthesis of 4-(2-cyano-benzothiazol-6-yloxymethyl)-phenyl phosphoric acid. To the solution of phosphoric acid 4-(2-cyano-denzothiazol-6-yloxymethyl)-phenyl diethyl ester in 15 ml of methylene chloride was added iodotrimethylsilane (0.46 g, 2.31 mmol). The resultant mixture was stirred for 40 minutes and then added to the solution of p-toluidine (1.50 g, 14.0 mmol) in 20 ml. After the solvent was partially removed, the light yellow precipitate was collected by filtration and washed with ethanol and ether to give a yield of 63%.

$^1$H NMR (d6-DMSO): 8.18 (d, 1H), 8.0 (s, 1H), 7.43 (d, 2H), 7.38 (d, 1H), 7.19 (d, 2H). 6.82 (d, 3.75H), 6.45 (d, 3.75H), 5.19 (s, 2H, OCH$_2$), 2.16 (s, ~6H, CH3). (Containing about 3.3 molar equivalent toluidine). MS (ES): m/e (M+2), 362

Synthesis of AP-4. The compound was synthesized by employing the similar method used for the preparation of MAO-1 and purified by HPLC using 5 mM ammonium acetate buffer/acetonitrile as eluent.

$^1$H NMR (D$_2$O): 7.82 (d, 1H), 7.56 (s, 1H), 7.39 (d, 2H), 7.15 (d, 1H), 7.10 (d, 2H), 5.11 (t, 1H, CH—COOH), 5.06 (s, 2H, OCH$_2$), 3.45-3.80 (m, 2H, CH$_2$). MS (ES): m/e (M+2), 468, $\lambda_{max}$ 329 nm, $\varepsilon_{max}$ 19,000 cm$^{-1}$M$^{-1}$ in water.

B.

formula CCXXXVIII

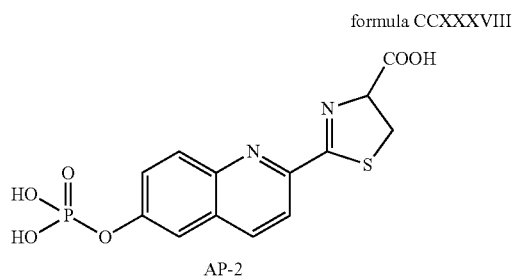

AP-2

6-Phosphoric acid-quinolinyl-luciferin

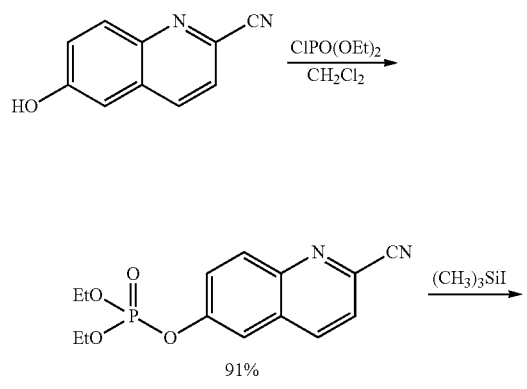

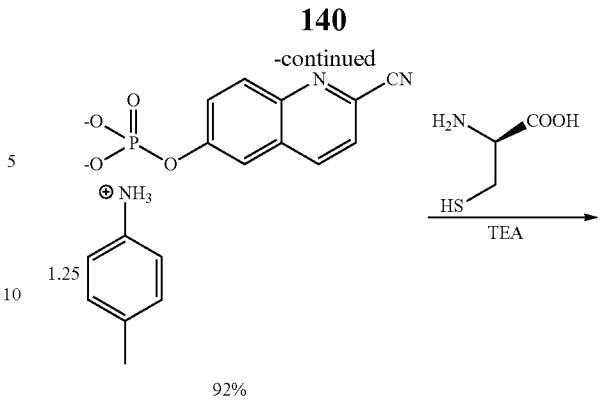

92%

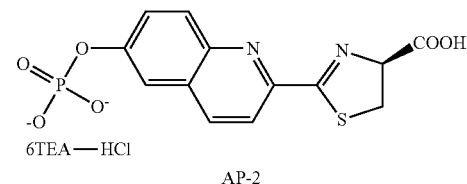

AP-2

Synthesis of diethyl (2-cyano-quinolin-6-yl) phosphate. To the mixture of 2-cyano-6-hydroxyquinoline (0.50 g, 2.94 mmol) and diethyl phosphorochloride (0.67 g, 3.53 mmol) in 15 ml of anhydrous methylene chloride was added triethylamine (0.59 g, 5.88 mmol). The resultant mixture was stirred for 5 hours at room temperature. After removal of the solvent, the product was purified by flash chromatography using heptane/ethyl acetate as eluent in a yield of 91%.

$^1$H NMR (CD$_2$Cl$_2$): 8.35 (d, 1H), 8.18 (d, 1H), 7.80 (s, 1H), 7.6-7.8 (m, 2H), 4.26 (m, 4H, CH$_2$), 1.18 (t, 6H, CH$_3$). MS (ES) m/e (M−2); 306

Synthesis of (2-cyano-quinolin-6-yl) phosphoric acid. To the solution of diethyl (2-cyano-quinolin-6-yl) phosphate (0.58 g, 1.86 mmol) in 10 ml of methylene chloride was added iodotrimethylsilane (0.82 g, 4.1 mmol). The resultant mixture was stirred for 40 minutes and then added to the solution of p-toluidine (1.50 g, 14.0 mmol) in 20 ml. After the solvent was partially removed, the white yellow precipitate was collected by filtration and washed with ethanol and ether to give a yield of 92%.

$^1$H NMR (d6-DMSO), 8.54 (d, 1H), 8.07 (d, 1H), 7.95 (d, 1H), 7.47 (d, 1H), 7.82 (s, br, 1H), 7.71 (dd, 1H), 6.85 (d, 2.5H), 6.55 (d, 2.5H), 2.13 (s, 3.85H, CH3). (Containing 1.25 molar equivalent toludine as counter-ions). MS (ES) m/e (M−2): 248

Synthesis of of AP-2. The compound was synthesized by employing the similar method for the preparation of AP-4.

$^1$H NMR (d6-DMSO): 8.29 (d, J=8.7 Hz, 1H), 8.05 (d, J=8.4 Hz, 1H), 7.95 (d, J=9.0 Hz, 1H), 7.71 (d, J=2.4 Hz, 1H), 7.64 (dd, J=8.7 Hz, J=2.4 Hz, 1H), 5.89 (dd, 8.4 Hz, J=8.4 Hz, 1H, CHCOO), 3.4-3.65 (m, 2H, CH$_2$). (Containing −8 molar equivalent TEA/HCl as counter-ions). MS (ES) m/e (M+): 352

C.

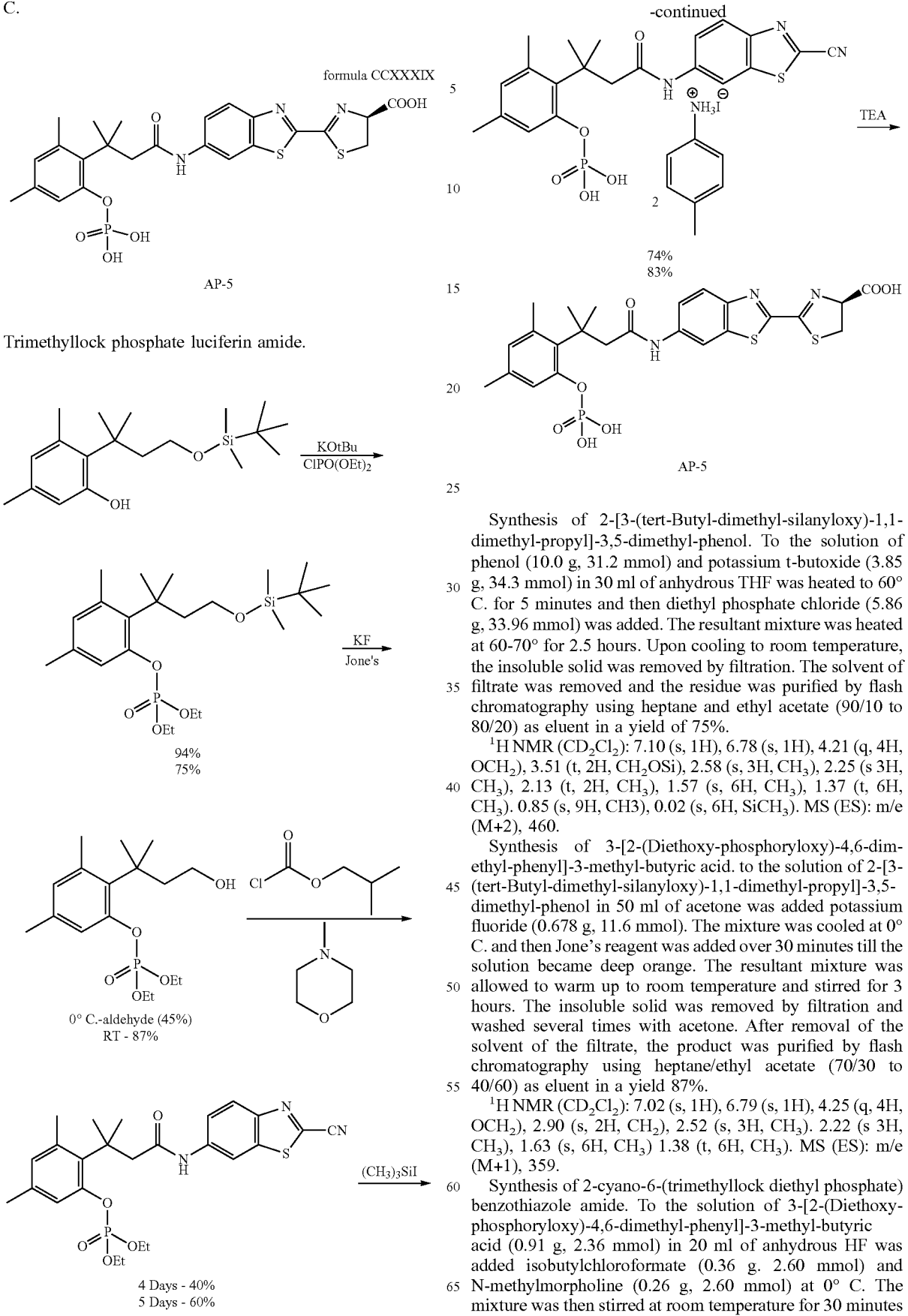

Trimethyllock phosphate luciferin amide.

Synthesis of 2-[3-(tert-Butyl-dimethyl-silanyloxy)-1,1-dimethyl-propyl]-3,5-dimethyl-phenol. To the solution of phenol (10.0 g, 31.2 mmol) and potassium t-butoxide (3.85 g, 34.3 mmol) in 30 ml of anhydrous THF was heated to 60° C. for 5 minutes and then diethyl phosphate chloride (5.86 g, 33.96 mmol) was added. The resultant mixture was heated at 60-70° for 2.5 hours. Upon cooling to room temperature, the insoluble solid was removed by filtration. The solvent of filtrate was removed and the residue was purified by flash chromatography using heptane and ethyl acetate (90/10 to 80/20) as eluent in a yield of 75%.

$^1$H NMR (CD$_2$Cl$_2$): 7.10 (s, 1H), 6.78 (s, 1H), 4.21 (q, 4H, OCH$_2$), 3.51 (t, 2H, CH$_2$OSi), 2.58 (s, 3H, CH$_3$), 2.25 (s 3H, CH$_3$), 2.13 (t, 2H, CH$_3$), 1.57 (s, 6H, CH$_3$), 1.37 (t, 6H, CH$_3$). 0.85 (s, 9H, CH3), 0.02 (s, 6H, SiCH$_3$). MS (ES): m/e (M+2), 460.

Synthesis of 3-[2-(Diethoxy-phosphoryloxy)-4,6-dimethyl-phenyl]-3-methyl-butyric acid. to the solution of 2-[3-(tert-Butyl-dimethyl-silanyloxy)-1,1-dimethyl-propyl]-3,5-dimethyl-phenol in 50 ml of acetone was added potassium fluoride (0.678 g, 11.6 mmol). The mixture was cooled at 0° C. and then Jone's reagent was added over 30 minutes till the solution became deep orange. The resultant mixture was allowed to warm up to room temperature and stirred for 3 hours. The insoluble solid was removed by filtration and washed several times with acetone. After removal of the solvent of the filtrate, the product was purified by flash chromatography using heptane/ethyl acetate (70/30 to 40/60) as eluent in a yield 87%.

$^1$H NMR (CD$_2$Cl$_2$): 7.02 (s, 1H), 6.79 (s, 1H), 4.25 (q, 4H, OCH$_2$), 2.90 (s, 2H, CH$_2$), 2.52 (s, 3H, CH$_3$). 2.22 (s 3H, CH$_3$), 1.63 (s, 6H, CH$_3$) 1.38 (t, 6H, CH$_3$). MS (ES): m/e (M+1), 359.

Synthesis of 2-cyano-6-(trimethyllock diethyl phosphate) benzothiazole amide. To the solution of 3-[2-(Diethoxy-phosphoryloxy)-4,6-dimethyl-phenyl]-3-methyl-butyric acid (0.91 g, 2.36 mmol) in 20 ml of anhydrous HF was added isobutylchloroformate (0.36 g. 2.60 mmol) and N-methylmorpholine (0.26 g, 2.60 mmol) at 0° C. The mixture was then stirred at room temperature for 30 minutes (the reaction should be checked by TLC to ensure acid is completely converted into anhydride) 6-Aminobenzothiazole (0.275 g, 1.57 mmol) and N-methylmorpholine (0.53 g, 5.20 mmol) were added and the mixture was stirred for 5 days at room temperature. After removal of the solvent, the compound was purified by flash chromatography using heptane/ethyl acetate (80/20 to 70/30) as eluent in a yield of 60%.

$^{1}$H NMR (CD$_2$-Cl$_2$): 9.58 (s, 1H, NH), 8.55 (d, 1H), 7.98 (d, 1H), 7.38 (dd, 1H), 7.0 (s, 1H), 6.69 (s, 1H), 4.36 (q, 4H, OCH2), 2.80 (s, 2H, CH$_2$), 2.42 (s, 3H, CH$_3$), 2.20 (s, 3H, CH$_3$), 1.78 (s, 6H, CH$_3$), 1.48 (t, 6H, CH$_3$). MS (ES): m/e (M+1), 516

Synthesis of 2-cyano-6-(trimethyllockphosphoric acid) benzothiazole amide. Diethyl phosphate timethyllock amide was de-ethylated by employing the similar method used for the synthesis of AP-4 precursor.

$^{1}$H NMR (d6-DMSO) 8.62 (d, 1H), 8.03 (d, 1H), 7.50 (dd, 1H), 7.11 (s, 1H), 6.98 (d, 4.5H), 6.75 (d, 4.5H), 6.48 (s, 1H), 2.86 (s, 2H, CH$_2$). 2.38 (s, 3H, CH$_3$). 2.19 (s, ~6.75H, CH3), 2.07 (s 3H, CH$_3$), 1.65 (s, 6H, CH$_3$). (Containing 2.25 equivalent molar toluididne an counter-ions) MS (ES): m/e (M−1), 459.

Synthesis of AP-5. The compound AP-5 was prepared by ring cyclization used for the synthesis of AP-4 and purified by HPLC using 5 mM ammonium acetate buffer/acetonitrile as solvent.

$^{1}$H NMR (D$_2$O): 7.80 (s, 1H), 7.77 (d, 1H), 7.21 (s, 1H), 7.06 (d, 1H), 6.53 (s, 1H), 5.12 (t, 1H, CH—COOH), 3.5-3.8 (m, 2H, CH$_2$), 2.85 (s, 2H, CH$_3$), 2.28 (s, 3H, CH$_3$), 2.07 (s 3H, CH$_3$), 1.60 (s, 6H, CH$_3$). MS (ES): m/e (M+1), 564 $\lambda_{max}$ 322 nm, $\varepsilon_{max}$ 16,700 cm$^{-1}$M$^{-1}$ in water.

VII. Miscellaneous

A.

formula CCXXXX

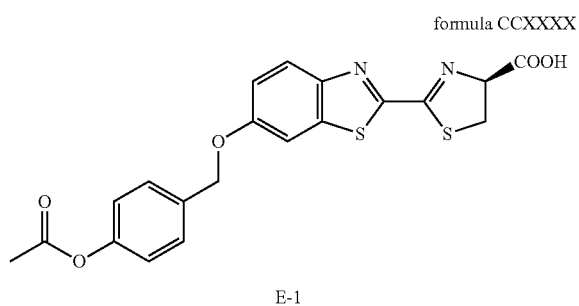 [SMILES: CC(=O)Oc1ccc(COc2ccc3nc(C4=N[C@@H](C(=O)O)CS4)sc3c2)cc1]

E-1

6-(4-phosphoric acid benzylether) luciferin.

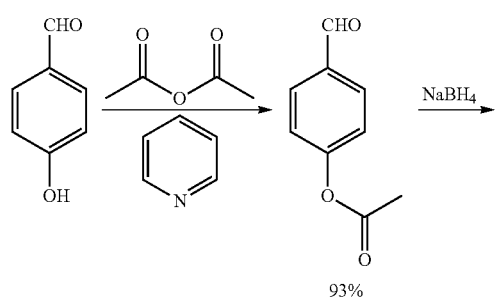

93%

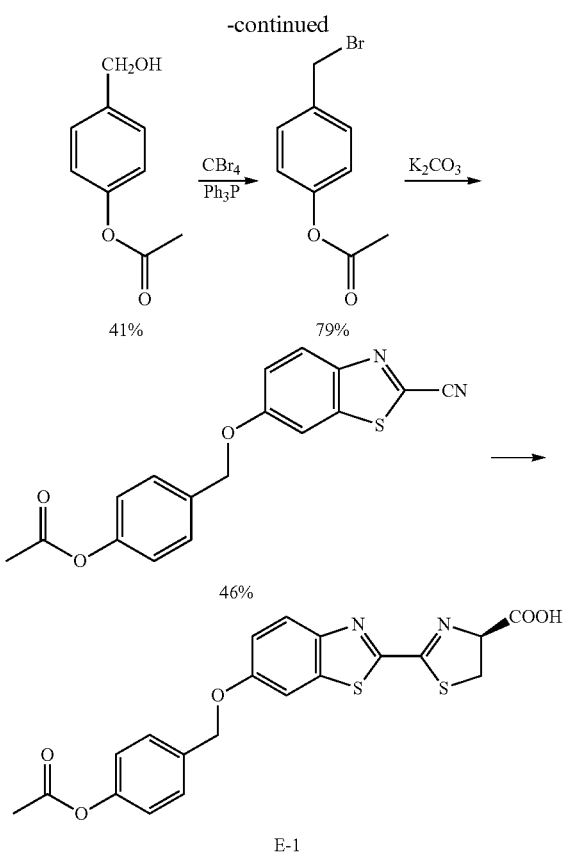

Synthesis of 4-formylphenol acetate. To the solution of 4-hydroxybenzaldehyde (10.0 g, 81.9 mmol) in 150 ml of pyridine was added acetic anhydride (60 ml). The resultant mixture was stirred at room temperature for 2 hours. After removal of the solvent, the compound was purified by flash chromatography using heptane/methylene chloride/ethyl acetate (20/20/10) as eluent in a yield of 93%.

$^{1}$H NMR (CD$_2$Cl$_2$): 10.0 (s, 1H, CHO), 7.86 (d, 2H), 7.30 (d, 2H), 2.32 (s, 3H, CH$_3$)

Synthesis of 4-hydroxymethylphenol acetate. To the solution of 4-formylphenol acetate (6.0 g, 36.4 mmol) in 60 ml of methanol was added sodium boronhydride (1.50 g, 39.6 mmol) at 0° C. The resultant mixture was stirred for 1 hour, neutralized with acetic acid and then poured into water. The mixture was extracted three times with ether and the combined organic layer was dried over magnesium sulfate. After removal of solvent, the compound was purified by flash chromatography using heptane/ethyl acetate (80/20-70/30) as eluent in a yield of 41%.

$^{1}$H NMR (CD$_2$Cl$_2$): 7.4 (d, 2H), 7.08 (d, 2H), 4.67 (s, 2H, CH$_2$), 2.30 (s, 3H, CH$_3$)

Synthesis of 4-bromomethylphenol acetate. To the solution of 4-hydroxymethylphenol acetate (2.50 g, 15.0 mmol) and carbon tetrabromide (5.97 g, 18.0 mmol) in 40 ml of methylene chloride was added triphenylphosphine (4.73 g, 180 mmol) under nitrogen. The resultant mixture was stirred for 3 hours. The product was purified by flash chromatography using heptane/ethyl acetate (90/10-80/20) as eluent in a yield of 79%.

$^{1}$H NMR (CD$_2$Cl$_2$): 7.45 (d, 2H), 7.07 (d, 2H), 4.53 (9, 2H, CH$_2$). 2.29 (s, 3H, CH$_3$)

Synthesis of 4-(2-cyano-benzothiazol-6-yloxymethyl)-phenol acetate. The compound was synthesized by employing the similar method for the synthesis of precursor MAO-1.

145

¹H NMR (CD₂Cl₂): 8.14 (d, 1H), 7.49 (m, 3H), 7.26 (d, 1H), 7.14 (d, 1H), 5.18 (s, 2H, OCH₂). 2.30 (s, 3H, CH₃).

Synthesis of E-1. The compound was synthesized by employing the similar method for the preparation of GST-13.

¹H NMR (d6-DMSO): 8.05 (d, J=9.0 Hz, 1H), 7.86 (d, J=2.4 Hz, 1H), 7.51 (d, J=8.7 Hz, 2H), 7.26 (dd, J=9.0 Hz, J=2.7 Hz, 1H), 7.15 (d, J=8.7 Hz, 2H), 5.41 (dd, J=8.40 Hz, J=8.1 Hz, 1H, CH—COOH), 5.20 (s, 2H, OCH₂), 3.6-3.80 (m, 2H, CH₂), 2.26 (s, 3H, CH₃). MS (ES): m/e (M+1), 429. λ$_{max}$ 325 nm, ε$_{max}$ 19,100 cm⁻¹M⁻¹ in MeOH

B formula CCXXXXI

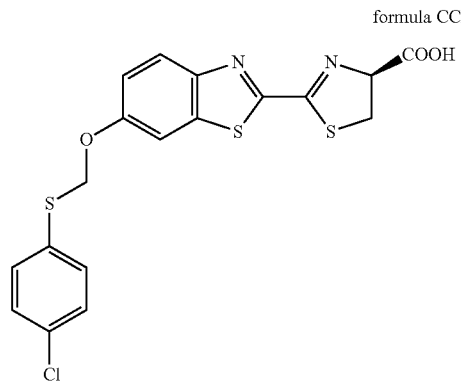

6-(4-Chloro-phenylthiomethoxy) luciferin.

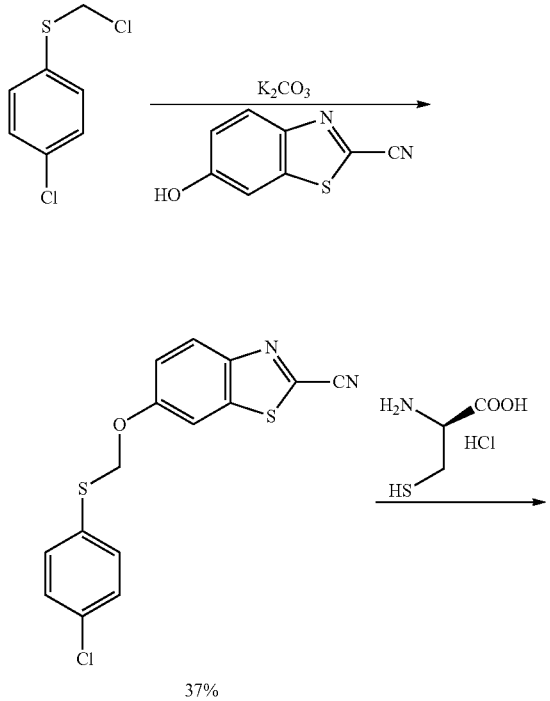

37%

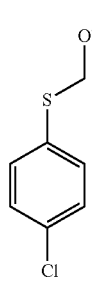

65%

Synthesis of 2-cyano-6-(4-chloro-phenylthiomethoxy)-benzothiazole. The mixture of 6-hydroxy-2-cyanobenzothiazole (0.45 g, 2.59 mmol), 1-chloro-4-chloromethylthiobenzene (0.50 g, 2.59 mmol), potassium carbonate (0.36 g. 2.61 mmol) and sodium iodide (0.01 g) in acetone (30 ml) was heated to reflux 30 minutes. Upon cooling to room temperature, the insoluble solid was removed by filtration. The solvent of filtrate was removed under reduced pressure, the residue was dissolved minimum amount of acetone with heating. The solution was cooled at 0° C. and yellow crystals were formed immediately. The solid was collected by filtration to give a yield of 37%.

¹H NMR (CD₂Cl₂): 8.14 (d, 1H), 7.47 (d, 1H), 7.45 (d, 2H), 7.34 (d, 2H, 7.32 (dd, 1H), 5.57 (z, 1H, CH₂).

Synthesis of 6-(4-chloro-phenylthiomethoxy) luciferin. The compound was made by employing the similar method for the synthesis of MAO-1 and was purified by flash chromatography.

¹H NMR (d6-DMSO): 8.16 (d, 1H), 7.87 (d, 1H), 7.47 (d, 2H), 7.20 (d, 2H), 7.23 (dd, 1H), 5.79 (z, 1H, OCH₂). 5.22 (t, 1H, CH), 3.68 (d, 2H, CH₂). MS (ES): m/e (M+), 436. λ$_{max}$ 324 nm, ε$_{max}$ 16,300 cm⁻¹M⁻¹ in water.

C.

formula CCXXXXII

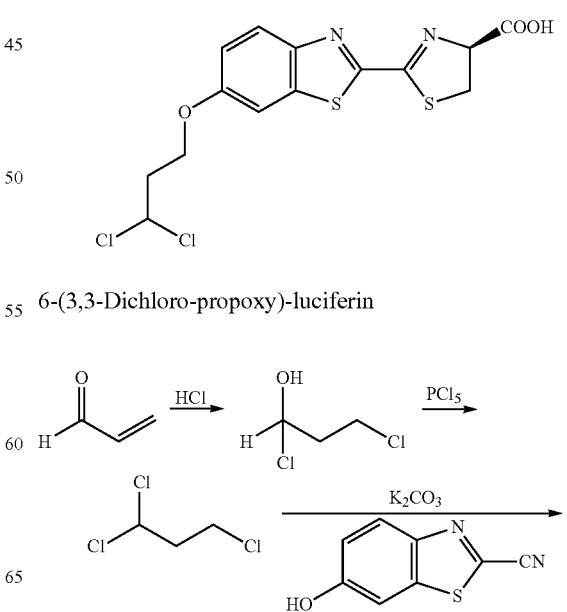

6-(3,3-Dichloro-propoxy)-luciferin

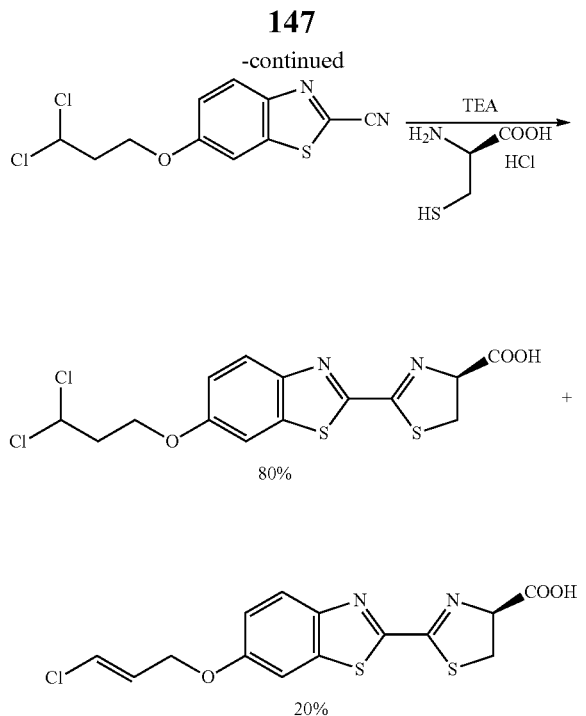

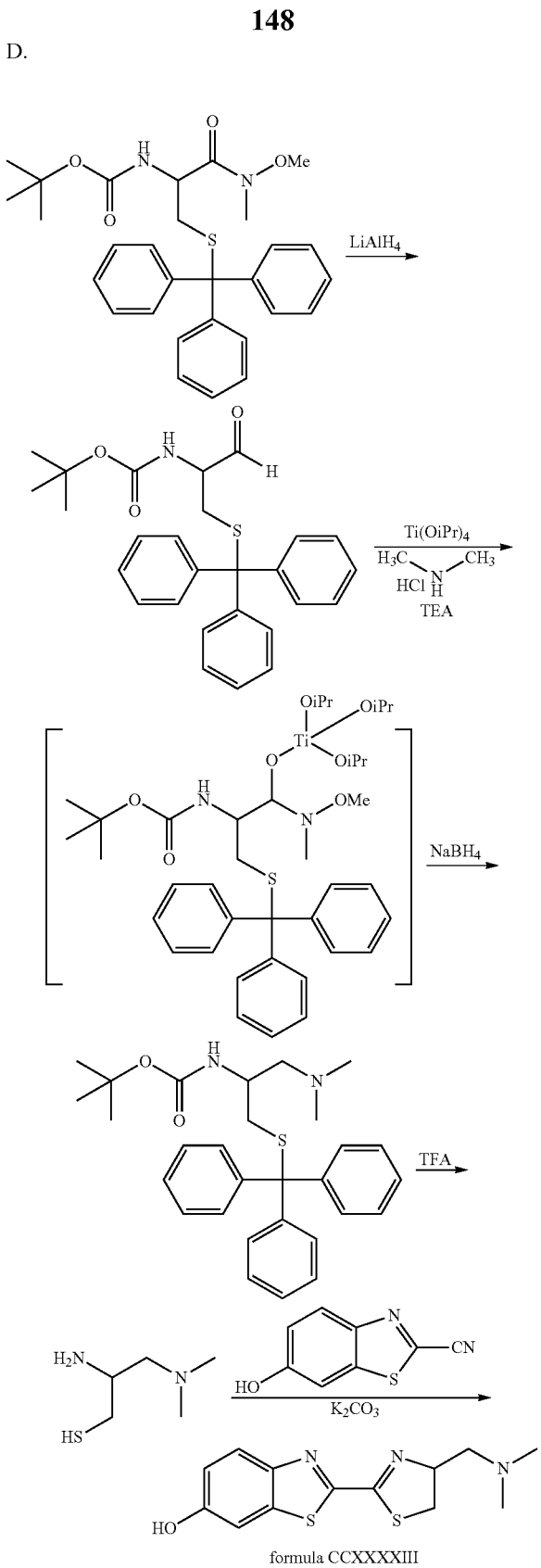

formula CCXXXXIII

Synthesis of 1,3-dichloropropanol. HCl gas was bubbled through acrolein (5.0 g, 89.2 mmol) at 0° C. for 3 hours. To the reaction mixture was added methylene chloride (200 ml), and the resultant solution was washed with water three times and dried over magnesium sulfate. After removal solvent, the product was used directly in next step without further purification.

$^1$H NMR (CD$_2$Cl$_2$): 5.17 (t, 1H), 3.68 (t, 2H, OCH$_2$), 2.13 (q, 2H, CH$_2$).

Synthesis of 1,1,3-trichloropropane. To the mixture of PCl$_6$ (23.50 g, 0.113 mol) in 100 ml of petroleum ether (40-60° C.) was added 1,3-dichloropanol (14.5 g, 0.113 mol) dropwise. The solvent was evaporated at 40-60° C., the temperature was increased to 120° C., and the fraction (70-90° C.) was collected under reduced pressure (70-80 mmHg). The distilled liquid was then poured into ice-water and stirred, for 4 hours and extracted with petroleum ether (40-60° C.). The combined organic layer was dried over magnesium sulfate. Repeat the above procedures until pH of the distilled liquid in aqueous solution is neutral. The final distillation gave a yield of 3.64 g of product (22%).

$^1$H NMR (CD$_2$Cl$_2$): 6.03 (t, 1H), 3.74 (t, 2H, ClCH$_2$), 2.64 (q, 2H, CH$_2$).

Synthesis of 2-cyano-6-(3,3-Dichloro-propoxy)-benzothiazole. The compound was made by employing the similar procedure used for the synthesis of MAO-1 precursor.

$^1$H NMR (CD$_2$Cl$_2$): 8.12 (d, 1H), 7.45 (d, 1H), 7.23 (dd, 1H), 6.51 (t, 1H, CHCl$_2$), 4.24 (t, 2H, OCH$_2$), 2.75 (q, 2H, SCH$_2$).

Synthesis of 6-(3,3-Dichloro-propoxy)-luciferin. The compound was made by employing the similar procedure used for the synthesis of GST-3.

$^1$H NMR (d6-DMSO): 8.02 (d, 1H), 7.80 (d, 1H), 7.19 (dd, 1H), 6.46 (t, 1H, CHCl$_2$), 5.35 (t, 1H, CHCOO), 4.24 (t, 2H, OCH$_2$), 3.6-3.8 (m, 2H, SCH$_2$), 2.69 (q, 2H, CH$_2$).

Synthesis of (1-formyl-2-tritylthioethyl)carbamic acid tert-butyl ester. To the solution of t-BOC-trityl-Weinreb amide (1.67 g, 3.30 mmol) in 30 of anhydrous ether was added LiAlH$_4$ (0.25 g, 6.59 mmol) in three portions at −50° C. The temperature was allowed to warm up to −35° C. and the resultant mixture was stirred at −35° C. for 2 hours. The reaction was quenched by adding 15 ml of ice-water slowly. The mixture was extracted three times with ether and the combined organic layer was dried over magnesium sulfate. After removal of the solvent, the product was purified by flash chromatography using heptane/ethylacetate (8/2 to 7/3) as eluent in a yield of 87%.

$^1$H NMR (CD$_2$Cl$_2$): 9.21 (s, 1H, CHO), 7.2-7.7 (m, 15H, Ar—H), 5.10 (s, br, 1H, NHCO), 3.83 (m, 1H, CH), 2.4-2.8 (m, 2H, CH$_2$), 1.22 (s, 9H, CH$_3$).

Synthesis of (1-dimethylaminomethyl-2-trithioethyl)-carbamic acid tert-butyl ester. To the solution of triethylamine (0.11 g, 1.12 mmol) in absolute ethanol (5 ml) were added dimethyl amine hydrochloride (0.0912 g. 1.12 mmol), titanium (IV) isopropoxide (0.317 g, 1.12 mmol) and (1-formyl-2'tritylthioethyl)carbamic acid tert-butyl ester (0.25 g, 0.56 mmol). The reaction mixture was stirred for 10 hours at room temperature. NaBH$_4$ (0.045 g, 1.12 mmol) was added to the mixture, the resultant mixture was stirred for another 4 hours, and the reaction was quenched by adding 10 ml of water the mixture. The mixture was extracted with ether three times and the combined organic layer was dried over magnesium sulfate. After removal of the solvent, the product was purified by flash chromatography using methylene chloride/methanol as eluent (95/5) in a yield of 41%.

$^1$H NMR (CD$_2$Cl$_2$): 7.2-7.7 (m, 15H, Ar—H), 4.65 (s, br, 1H, NHCO), 3.62 (m, 1H, CH), 2.42 (t, 2H, NCH$_2$), 2.20 (m, 2H, SCH$_2$), 2.17 (s, 6H, NCH$_3$), 1.41 (s, 9H, CH$_3$). MS(ES): m/e (M+1), 477

Synthesis of dimethylaminoluciferin. To (1-dimethyl-amino-methyl-2-trithioethyl)-carbamic acid tert-butyl ester (0.18 g, 3.78 mmol) was added the solution of TFA (50%) and triisopropylsilane (0.077 g). The resultant solution was stirred for 30 minutes and 20 ml of ether was added. The solvent was removed under reduced pressure, the residue was triturated with ether and the yellow solid was collected by filtration. Without further purification, the solid was carried on next step.

The above solid and 2-cyano-6-hydroxybenzothiozole (0.067 g, 0.38 mmol) were dissolved in methanol (2.5 ml), CH$_2$Cl$_2$ (0.5 ml) and H$_2$O (1 ml). To the solution was added K$_2$CO$_3$ (0.052 g, 0.38 mmol). The mixture was stirred at room temperature for 1 hour and then neutralized to slightly acidic condition. After removal of organic solvent, the product was purified by HPLC using 0.1% TFA water/acetonitrile as eleuent.

$^1$H NMR (CD$_3$OD); 7.51 (d, 1H), 7.36 (d, 1H), 7.25 (dd, 1H), 6.46 (t, 1H, CHCl$_2$), 5.12 (m, 1H, CH), 3.75-3.22 (m, 2H, SCH$_2$), 3.50 (m, 2H, NCH$_2$), 3.04 (s, 6H, CH$_3$). MS (ES): m/e (M+), 293.

E.

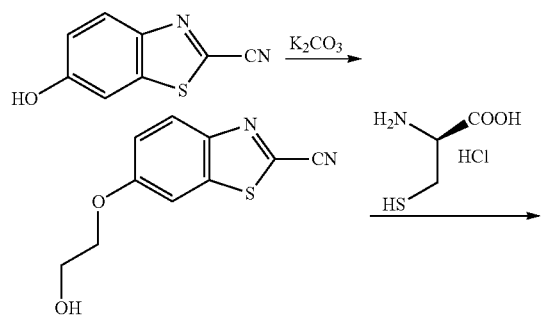

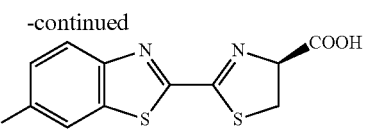

formula CCXXXXIV

Synthesis 6'-(2-hydroxyethoxyl) luciferin. The compound was synthesized by employing the similar method used for the synthesis of GST-3.

$^1$H NMR (d6-DMSO): 8.0 (d, 1H), 7.72 (d, 1H), 7.17 (dd, 1H), 5.18 (t, 1H, CH), 4.08 (t, 2H, OCH$_2$), 3.74 (t, 2H, HOCH$_2$), 3.64 (m, 2H, SCH$_2$). MS (ES): m/e (M+1), 325. $\lambda_{max}$ 328 nm, $\varepsilon_{max}$ 16,500 cm$^{-1}$M$^{-1}$ in water.

F. 6'-(2,3,4,5,6-pentafluorobenzyloxy)-luciferin.

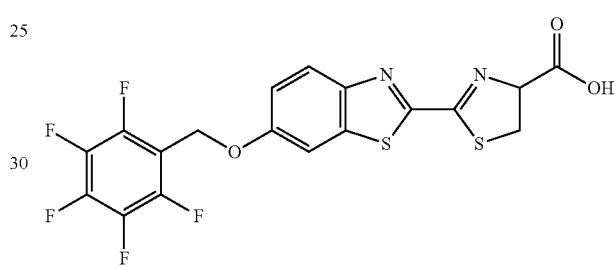

formula CCXXXXV

6'(2,3,4,5,6-pentafluorobenzyloxy)-luceiferin was synthesized in a similar way as luciferin benzyl ether (LucBE) by using pentafluorobenzyl bromide instead of benzy bromide as a starting material. 6'(2,3,4,5,6-pentafluorobenzyloxy)-luciferin (compound of formula I', III', VII', or VIII') was tested in CYP assays.

G. 6'-(2,3,4,6-tetrafluoro-5-((4-phenylpiperizin-1-yl)methyl)benzyloxy)-luciferin (LucPPXE4F).

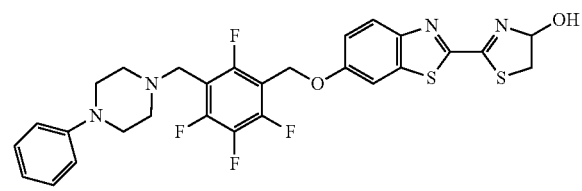

formula CCXXXXVI

This synthesis is same as the synthesis for 6'-(3-((4-phenylpiperizin-1-yl)benzyloxy)-luciferin (LucPPXE) by using α,α'-dibromo-m-tetrafluoroxylene, which was synthesized from tetrafluoroisophthalic acid in two steps. The first step was reduction of tetrafluoroisophthalic acid with borarte in THF to produce α,α'-dihydroxy-m-tetrafluoroxylene. The second step was to convert the α,α'-dihydroxy-m-tetrafluoroxylene into α,α'-dibromo-m-tetrafluoroxylene. The major side product is monobrominated compound. 6'-(2,3,4,6-tetrafluoro-5-((4-phenylpiperizin-1-yl)methyl)benzyloxy) luciferin (compound of formula IX') was tested in CYP assays.

a. α,α'-dihydroxy-m-tetrafluoroxylene

To a solution of tetrafluoroisophthalic acid (2 g, 8.4 mmol) in 50 mL of anhydrous tetrahydrofuran was added 1 M borane-tetrahydrofuran complex in tetrahydrofuran (34 mL, 33.6 mmol). The mixture was remixed under nitrogen atmosphere for 4 hours. The solution was cooled down to room temperature, 200 mL of water was added and the resultant mixture was extracted with ethyl ether (2×174 mL). The extracts were combined and washed with saturated sodium bicarbonate (2×200 mL) and water (1×200 mL). The organic phase was dried over anhydrous sodium sulfate and the solvent was removed under reduced pressure. The residue was pumped over night without further purification (1.3 g, 73.7% yield).

b. α,α'-dibromo-m-tetrafluoroxylene

To a mixture of lithium bromide (350 mg, 4 mmol) in 5 mL of anhydrous acetonitrile was added trimethylsilyl chloride (650 µL, 5 mmol). To this solution was the added α,α'-dihydroxy-m-tetrafluoroxylene (210 mg, 1 mmol) in 10 mL of anhydrous acetonitrile. The resultant mixture was then refluxed under nitrogen atmosphere for 6 hours. The mixture was then taken up by 40 mL of ethyl ether, washed successively with water (2×40 mL), 1M sodium bicarbonate (1×40 mL), and brine (1×40 mL). The organic phase was then dried over sodium sulfate and the solvent was removed under reduced pressure and the residue was then purified by flash chromatography with 70% heptane in ethyl acetate (85 mg, 25% yield).

B. Synthetic Schemes for Derivatives for Redox or Dealkylase Bioluminescent Assays The appropriately substituted ortho-aminohalopyridine is converted to the 2-thiohydroxylpyridothiazole followed by alkylation with methyl iodide to yield a 2-methylthiopyridothiazole. The thioether functionality is oxidized to the sulfone. The pyridine amine is either oxidized to the N-oxide or methylated depending on the desired product. The sulfone is displaced with cyanide to yield the corresponding 2-cyanopyridothiazole. Cysteine (D, L, DL with or without the carboxylic acid esterified) is condensed with the cyanopyridothiazole. Any remaining protecting groups are removed by standard means known in the art to yield the appropriate methylated or oxidized aza-luciferins.

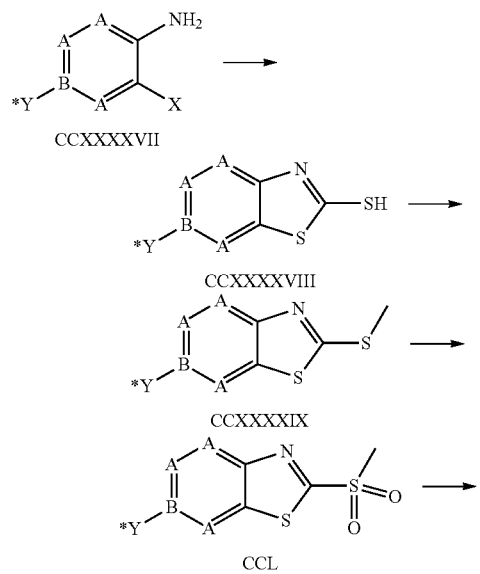

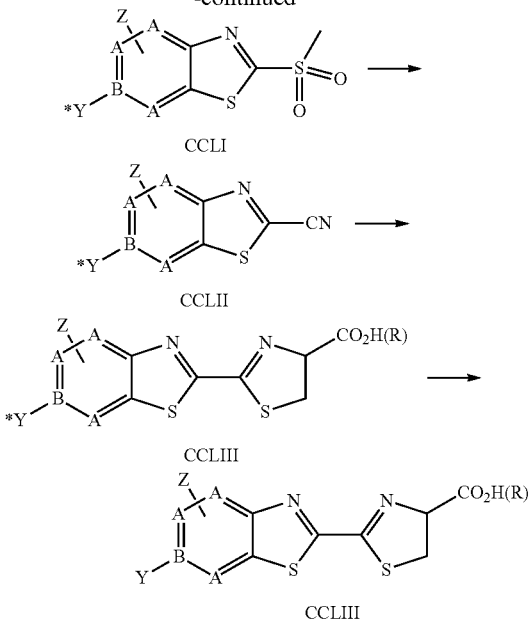

A = N or CH; B = N, C; if B is C then *Y = a protected O or N; Z = Me or O; Y = OH or NH2

Examples of starting orthoaminohalopyridines

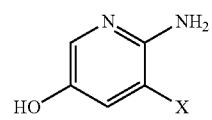

Starting material 1

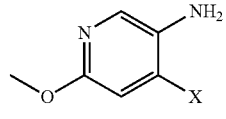

Starting material 2

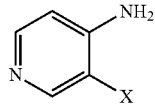

Starting material 3

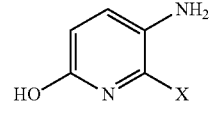

Starting material 4

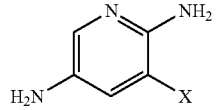

Starting material 5

Starting material 6

References for synthesis of either example starting materials

Starting materials 1, 3 and 4 are commercially available. Starting material 2 is described in Mazeas. *Heterocycles*, 50: 1065 (1999)), starting material 5 in Kuramochi (U.S. published application 20050004103); and starting material 6 in Kolesnikov (U.S. published application 20040225036).

The N3-oxide of luciferin is synthesized by oxidation of 6-hydroxy-2-methylbenzthiazole or 6-amino-2-methylbenzthiazole to yield the oxidized methylbenzthiazole. The methyl is converted to a nitrite using procedures similar to those known in the art (Takahashi et al., *Chem & Pharm. Bull.*, 18: 1176 (1970); Sasson et al., *Org. Lett.*, 7:2177 (2005))). The nitrile is condensed with cysteine (D,L,DL, with or without the carboxylic acid esterified).

The N1-oxide of quinolinyl luciferin is synthesized by oxidation of 2-methyl-6-hydroxyquinoline or to yield the oxidized methylquinolinol. The methyl is converted to a nitrile using procedures similar to those known in the art (Takahashi et al., *Chem & Pharm. Bull.*, 18:1176 (1970); Sasson et al., *Org. Lett.*, 7:2177 (2005)) The nitrile is condensed with cysteine (D,L,DL, with or without the carboxylic acid esterified).

The invention will be described by the following non-limiting examples.

Example 1

Measurement of Glutathione S Transferase Activity or Glutathione with Luciferin Derivatives A. Assay at pH 6.6

A luciferin derivative, GST #3, was prepared as a substrate for GST. The derivative was tested in a two step format. For the first step, the derivative was added to a mixture with one of three GSTs with or without glutathione. At different times after the reaction was initiated, a portion was removed and mixed with a luciferase reaction mixture. Reactions in which light production increased over time indicate that GST#3 is a substrate for the GST in that reaction.

Materials and Methods

Equine GST Solution: 25 mg of equine GST (Part G 6511, Sigma Chemical Company, St. Louis, Mo.) was dissolved in 5 ml of 10 mM BisTris buffer, pH 6.6. Porcine GST Solution: 10 mg of porcine GST (Sigma Chemical Company G 6636) was dissolved in 2 ml of 10 mM BisTris, pH 6.6. *S. japonica* GST: 1 vial with 3 mg GST (Part C5663, Sigma Chemical Company) was dissolved in 500 µl of 10 mM BisTris, pH 6.6. Glutathione (reduced) (Part G 4251, Sigma Chemical Company) was dissolved in water to create a 100 mM solution. GST #3 was dissolved in acetonitrile to produce a 12 mM solution.

A bottle of Luciferin Detection Reagent (V859B, Promega Corp., Madison. Wis.) was dissolved with a bottle of P450-Glo Buffer (V865B, Promega Corp.), thawed and allowed to come to room temperature. A 10 ml sample of the resulting solution was mixed with 8 ml of water to create a luciferin detection solution.

The reactions (Table 1) was assembled by first adding the water and 1 M BisTris solutions in individual 0.5 ml microfuge tubes, then adding the other components except for the GST #3 solution. Finally, the GST #3 (FIG. 12) solution was added to the reactions, the resulting solution was mixed, and the time of addition noted. At 0.1, 5, 10, and 15 minutes post mixing, a 10 µl sample was mixed with 90 µl of the luciferin detection solution and the light produced by the solution was immediately read using a Turner TP 20/20 Luminometer (Promega Corp.).

TABLE 1

| Component | Reaction | | | | | | | |
|---|---|---|---|---|---|---|---|---|
| | 1 | 2 | 3 | 4 | 5 | 6 | 7 | 8 |
| GST substrate | 5 µl | 5 µl | 5 µl | 5 µl | 5 µl | 5 µl | 5 µl | 5 µl |
| 1M BisTris pH 6.6 | 5 µl | 5 µl | 5 µl | 5 µl | 5 µl | 5 µl | 5 µl | 5 µl |
| 100 mM Glutathione (red) | | 2 µl | | 2 µl | | 2 µl | | 2 µl |
| Redissolved S.j. GST | | | 5 µl | 5 µl | | | | |
| Redissolved porcine GST | | | | | 5 µl | 5 µl | | |
| Redissolved equine GST | | | | | | | 5 µl | 5 µl |
| Water | 90 µl | 88 µl | 85 µl | 83 µl | 85 µl | 83 µl | 85 µl | 83 µl |

Results

Reactions were assembled with a luciferin derivative, a glutathione S transferase (GST) from one of three sources, in the presence and absence of glutathione. Samples from those reactions were then added to a luciferase reaction mixture. The light production from the mixture of the reactions with the luciferin detection reagent was measured using a Turner TD 20/20 Luminometer. The light values measured for the reactions are shown in Table 2.

TABLE 2

| Time (minutes) | 1 | 2 | 3 | 4 | 5 | 6 | 7 | 8 |
|---|---|---|---|---|---|---|---|---|
| 0.1 | 33.26 | 35.72 | 32.67 | 32.57 | 46.95 | 71.1 | 30.42 | 252.2 |
| 5 | 38.2 | 36.07 | 32.42 | 40.79 | 51.85 | 269.1 | 32.98 | 3662 |
| 10 | 32.17 | 40.85 | 38.65 | 48.64 | 51.15 | 463.2 | 38.75 | 7629 |
| 15 | 35.53 | 46.43 | 33.82 | 61.54 | 48.41 | 619.3 | 38.39 | 9324 |

The light values obtained from reactions without glutathione even in the presence of GST (reactions 1, 2, 3, 5 and 7) did not increase greatly over time. However, the light values measured in reactions containing both glutathione and GST in addition to GST #3 increased substantially over time. That result indicated that the action of the transferase in combination with glutathione results in production of a product that allows increased light production from the luciferase based reaction relative to the starting solution, and that the luciferin derivative permitted detection of the GST.

B. Assay at Slightly Basic pH

Common assays for GST are performed at a pH value around pH 6.5 even though the enzyme does not display maximal activity at this pH. The selection of such a suboptimal pH is the result of the need to prevent the rapid, non-enzymatic attack of glutathione itself on the substrate, which leads to a very high background value for control reactions run to measure this rate. To determine whether a luciferin derivative that is a GST substrate was useful in reactions at lower pHs, the luciferin derivative, one of the GSTs and a reagent (glutathione) from Example 1A were tested over pHs from 6.5 to 8.5.

Materials and Methods

Buffer stock solutions (1 M) of BisTris at pH 6.5, HEPES, pH 7.0, 7.5 and 8.0 and Tricine pH 8.5 were prepared by dissolving solid reagent obtained from Sigma Chemical Corporation and adjusting the pH to the desired value. These new buffer stocks were used with stock reagents in Example 1A to produce the solutions shown in Table 3.

TABLE 3

| Reaction | Buffer | GST #3 | Water | 100 mM Glutathione |
|---|---|---|---|---|
| 1 | 5 μl of 1M BisTris pH 6.5 | 2 μl | 93 μl | 0 |
| 2 | 5 μl of 1M BisTris pH 6.5 | 2 μl | 88 μl | 5 μl |
| 3 | 5 μl of 1M HEPES, pH 7.0 | 2 μl | 93 μl | 0 |
| 4 | 5 μl of 1M HEPES, pH 7.0 | 2 μl | 88 μl | 5 μl |
| 5 | 5 μl of 1M HEPES, pH 7.5 | 2 μl | 93 μl | 0 |
| 6 | 5 μl of 1M HEPES, pH 7.5 | 2 μl | 88 μl | 5 μl |
| 7 | 5 μl of 1M HEPES, pH 8.0 | 2 μl | 93 μl | 0 |
| 8 | 5 μl of 1M HEPES, pH 8.0 | 2 μl | 88 μl | 5 μl |
| 9 | 5 μl of 1M Tricine, pH 8.5 | 2 μl | 93 μl | 0 |
| 10 | 5 μl of 1M Tricine, pH 8.5 | 2 μl | 88 μl | 5 μl |

The GST #3 addition was performed last and the solutions were mixed immediately after addition of GST #3. After mixing, 10 μl samples were removed immediately and at 20 and 40 minutes post mixing, and the samples were added to 90 μl of luciferin detection solution assembled as described in Example 1A. After mixing, the light produced by the solution was measured using a Turner TD 20/20 luminometer.

Results

Reactions were assembled at various pH values and the rate of transformation of GST #3 was measured in the presence and absence of glutathione. Reactions were then assembled containing *S. japonica* GST with and without glutathione. The light values were recorded (Table 4).

TABLE 4

| | Light Output | | |
|---|---|---|---|
| Reaction | time of mixing | 20 minutes post mixing | 40 minutes post mixing |
| 1 | 1.01 | 0.976 | 1.099 |
| 2 | 1.13 | 1.287 | 1.761 |
| 3 | 1.198 | 1.368 | 1.202 |
| 4 | 1.156 | 1.178 | 2.2 |
| 5 | 1.19 | 1.214 | 1.194 |
| 6 | 1.171 | 2.788 | 5.173 |
| 7 | 1.167 | 1.172 | 1.236 |
| 8 | 1.198 | 6.662 | 13.38 |
| 9 | 1.182 | 1.199 | 1.246 |
| 10 | 1.342 | 25.24 | 47.01 |

The light signal from the incubations containing glutathione (reactions 2, 4, 6, 8, and 10) increased overtime while those from the incubations without glutathione did not change greatly. In fact, the rate of signal increase was greater as the pH of the solution was varied from pH 6.5 to 8.5. This rise in light value could be used as a way to measure glutathione in a solution, particularly if the solution is incubated with an appropriate luciferin derivative at an elevated pH. As shown in Example 1, this particular GST did not produce a very strong light signal when used at a relatively high enzyme concentration. However, by running the GST reaction at an elevated pH, a lower amount of this enzyme was shown to generate a stronger signal.

The signal produced from reactions containing GST were compared with those measured in the absence of GST to determine if the net signal seen with enzyme becomes very small versus that produced by the enzyme. In addition, the stock of 100 mM glutathione (GSH) was diluted 1:10 with water to produce a 10 mM GSH stock and this solution was added at various levels to determine if a lower non-enzymatic light signal could be produced while maintaining the same net light increase upon enzyme addition.

The stock of *S. japonica* GST used in Example 1A was diluted to 1 mg/ml with 10 mM BisTris pH 6.5. The solutions which were assembled are shown in Table 5.

TABLE 5

| Rx | GST #3 | Buffer | Amt buffer | Enzyme | GSH (10 mM) | Water |
|---|---|---|---|---|---|---|
| 1 | 5 μl | 1M HEPES, pH 7.5 | 5 μl | 0 | 50 μl | 40 μl |
| 2 | 5 μl | 1M HEPES, pH 7.5 | 5 μl | 10 μl | 50 μl | 30 μl |
| 3 | 5 μl | 1M HEPES, pH 7.5 | 5 μl | 0 | 30 μl | 60 μl |
| 4 | 5 μl | 1M HEPES, pH 7.5 | 5 μl | 10 μl | 30 μl | 50 μl |
| 5 | 5 μl | 1M HEPES, pH 7.5 | 5 μl | 0 | 10 μl | 80 μl |
| 6 | 5 μl | 1M HEPES, pH 7.5 | 5 μl | 10 μl | 10 μl | 70 μl |
| 7 | 5 μl | 1M HEPES, pH 8.0 | 5 μl | 0 | 50 μl | 40 μl |
| 8 | 5 μl | 1M HEPES, pH 8.0 | 5 μl | 10 μl | 50 μl | 30 μl |
| 9 | 5 μl | 1M HEPES, pH 8.0 | 5 μl | 0 | 30 μl | 60 μl |
| 10 | 5 μl | 1M HEPES, pH 8.0 | 5 μl | 10 μl | 30 μl | 50 μl |
| 11 | 5 μl | 1M HEPES, pH 8.0 | 5 μl | 0 | 10 μl | 80 μl |
| 12 | 5 μl | 1M HEPES, pH 8.0 | 5 μl | 10 μl | 10 μl | 70 μl |
| 13 | 5 μl | 1M Tricine, pH 8.5 | 5 μl | 0 | 50 μl | 40 μl |
| 14 | 5 μl | 1M Tricine, pH 8.5 | 5 μl | 10 μl | 50 μl | 30 μl |
| 15 | 5 μl | 1M Tricine, pH 8.5 | 5 μl | 0 | 30 μl | 60 μl |
| 16 | 5 μl | 1M Tricine, pH 8.5 | 5 μl | 10 μl | 30 μl | 50 μl |
| 17 | 5 μl | 1M Tricine, pH 8.5 | 5 μl | 0 | 10 μl | 80 μl |
| 18 | 5 μl | 1M Tricine, pH 8.5 | 5 μl | 10 μl | 10 μl | 70 μl |

The reactions were initiated by addition of GST #3 and mixing. At 45 minutes post mixing, 10 μl samples were removed and added to 90 μl of the luciferin detection reagent and the light read using a Turner TD 20/20 Luminometer. These readings are shown in Table 6.

TABLE 6

| Reaction | Light Reading |
|---|---|
| 1 | 26.3 |
| 2 | 61.58 |
| 3 | 19.21 |
| 4 | 55.18 |
| 5 | 10.73 |
| 6 | 52.23 |
| 7 | 65.98 |
| 8 | 152.3 |
| 9 | 48.41 |
| 10 | 135.6 |
| 11 | 22.52 |
| 12 | 97.47 |
| 13 | 295.2 |
| 14 | 532.4 |
| 15 | 199.4 |
| 16 | 416.7 |
| 17 | 97.89 |
| 18 | 267.3 |

The data in Table 6 can be rearranged to allow easy calculation of the signal change with and without enzyme at the pH levels and glutathione levels used (see Table 7).

TABLE 7

| Reaction pH | | Reaction with enzyme | Reaction w/o enzyme | Net light difference |
|---|---|---|---|---|
| 7.5 | 5 mM GSH | 26.3 | 61.58 | 35.28 |
| | 3 mM GSH | 19.21 | 55.18 | 35.97 |
| | 1 mM GSH | 10.73 | 52.23 | 41.5 |
| 8.0 | 5 mM GSH | 65.98 | 152.3 | 86.32 |
| | 3 mM GSH | 48.41 | 135.6 | 87.19 |
| | 1 mM GSH | 22.52 | 97.47 | 74.95 |
| 8.5 | 5 mM GSH | 295.2 | 532.4 | 237.2 |
| | 3 mM GSH | 199.4 | 416.7 | 217.3 |
| | 1 mM GSH | 97.89 | 267.3 | 169.41 |

These results confirm that GST #3 can be used to measure glutathione by measuring the light produced in reactions not containing GST. In addition, they indicate that stronger net light signals can be seen in reactions at pH values above pH 7.5. Finally, the results indicate that lowering the glutathione level from 5 mM to a lower level resulted in a lower light signal and that the net signal produced by S. japonica GST did not change greatly when the glutathione level was reduced from 5 mM to 3 mM.

C. Detection and Measurement of Glutathione

In Example 1B, it was shown that a luciferin derivative can be transformed to a species that produces a more intense light signal when the added solution contains glutathione. Moreover, in reactions that did not contain enzyme, the results indicated that a non-enzymatic transformation was possible. To detect much lower levels of glutathione, the ability of GST to catalyze this conversion was utilized in the presence of much lower levels of glutathione.

Materials and Methods

Master mix: 200 mM HEPES buffet, pH 7.5 also containing 0.4 mg/ml blot qualified BSA (Promega Corp. W3841), and 200 µg/ml equine GST (diluted from a 5 mg/ml solution of equine GST, Sigma Chemical Corp. enzyme) Substrate (GST #3): 200 µM GST #3 in water. DTT: A stock of 20 mM DTT was made by dissolving solid DTT (Promega Corp. V3151) in water. This stock was used to create a 4 mM DTT stock by dilution with water. 2 Mercaptoethanol: A 20 mM solution of 2 mercaptoethanol was made by diluting neat 2 mercaptoethanol (M6250, Sigma Chemical Corp.) in water. This stock was used to create a 4 mM 2-mercaptoethanol stock by dilution with water. A 100 mM glutathione stock (reduced) was diluted to produce solutions at 400, 320, 240, 200, 160, 80, and 20 µM glutathione by dilution into distilled water.

Cell Extract Samples: A solution of diluted rabbit reticulocyte lysate was prepared by diluting a rabbit reticulocyte lysate (Promega Corp.) with water at a ratio of 2 µl lysate per 25 µl of solution A solution of diluted wheat germ lysate was made by diluting wheat germ extract (Promega Corp.) with water at a ratio of 2 µl extract per 25 µl of solution.

Luciferin Detection Reagent (see Example 1A).

The reactions were performed room temperature in a microliter plate. The reactions were initiated by the addition of the Master Mix solution. The following materials were added to the wells to the microliter plate.

Columns 1-3: 25 µl of substrate solution and 25 µl of water were added to all wells in columns 1-3 rows A-H. In addition, 25 µl of glutathione solution at 400, 320, 240, 260 80 and 20 mM, was added to rows A-G, respectively. An additional 25 µl of water was added to columns 1-3 row H.

Columns 4-6; 25 µl of substrate solution and 25 µl water were added to columns 4-6 rows A, C, E and G. Additions of 25 µl substrate and 25 µl of 200 µM glutathione were added to columns 4-6 rows B, D, F and H. Then, 25 µl of 4 mM DTT was added to columns 4-6 rows A and B; 25 µl of 20 mM DTT was added to columns 4-6 rows C and D; 25 µl of 4 mM 2 mercaptoethanol was added to columns 4-6; rows E and F, and 25 µl of 20 mM 2 mercaptoethanol was added to columns 4-6 rows G and H.

Columns 7-9. These reactions were assembled as for columns 1-3 with the exception that the 25 µl of water was replaced with 25 µl of diluted wheat germ extract.

Columns 10-13. These reactions were assembled as for columns 1-3 with the exception that the 25 µl of water was replaced with 25 µl of diluted rabbit reticulocyte lysate.

After all these solutions were assembled, the reactions were started by addition of 25 µl of master mix to the solutions using a multichannel pipette and mixing the solution by pipetting up and down 3 times. Immediately after mixing, 10 µl of the solutions were removed with a multichannel pipette and added to 90 µl of Luciferin Detection Reagent in a Microliter Luminometer Plate. After addition of samples from all wells of the original microliter plate, the luminometer plate was sealed with a clear plate sealer, allowed to sit at room temperature for 15 minutes and then the light produced was read on a Veritas luminometer.

Additional 10 µl samples were taken from the original microliter plate, diluted into Luciferin Detection Reagent and read as above at 14.8, 33.7, 44.75, 59.6 and 140 minutes post addition of master mix.

Result

Reactions with GST #3, with or without GST, and with or without a source of glutathione were prepared, and at various times after initiation of the reactions, a portion was added to a luciferase reaction mixture. The light readings from the triplicate reactions were averaged and are shown in the tables below.

TABLE 8

Light Signals Measured in Reactions Without Added Lysate or Reductants

| | Glutathione Concentration (µM) Added | | | | | | | |
|---|---|---|---|---|---|---|---|---|
| Time (minutes) | 0 | 5 | 10 | 20 | 40 | 60 | 80 | 100 |
| 0 | 1234 | 1592 | 2269 | 2821 | 5110 | 5248 | 8038 | 6604 |
| 14.8 | 2689 | 43107 | 73802 | 125110 | 218325 | 273665 | 324305 | 337276 |
| 33.7 | 4362 | 90387 | 154525 | 277975 | 444877 | 552806 | 693907 | 773268 |
| 44.75 | 5378 | 107668 | 195083 | 361281 | 567948 | 741797 | 888763 | 935822 |
| 58.6 | 6015 | 142988 | 264698 | 694628 | 702468 | 956594 | 992455 | 1197938 |
| 140 | 11744 | 280230 | 498136 | 830155 | 1268954 | 1796833 | 2129202 | 2480280 |

The data in Table 8 demonstrate that even a solution of 5 µM glutathione can produce a light signal far above that seen in the absence of any glutathione and that the signal increases over time and over glutathione concentration at least over the ranges of values tested.

TABLE 9

Light Signals Measured in Reactions With Wheat Germ Extract

| Time (minutes) | Glutathione Concentration Added (µM) | | | | | | | |
|---|---|---|---|---|---|---|---|---|
| | 0 | 5 | 10 | 20 | 40 | 60 | 80 | 100 |
| 0 | 1851 | 1964 | 2390 | 2512 | 4371 | 3611 | 5335 | 4235 |
| 14.8 | 49004 | 71860 | 90718 | 115137 | 136851 | 182746 | 203690 | 218906 |
| 33.7 | 99432 | 152066 | 189073 | 279159 | 330741 | 435730 | 504985 | 519121 |
| 44.75 | 138755 | 195962 | 237008 | 333459 | 480389 | 540647 | 627461 | 558359 |
| 58.6 | 179435 | 244615 | 289289 | 618643 | 569417 | 586894 | 715805 | 835949 |
| 140 | 362693 | 465865 | 511594 | 816161 | 1053306 | 1316857 | 1265144 | 1809120 |

The light values measured in the reactions containing wheat germ extract (Table 9) without added glutathione increased much more rapidly than is seen for reactions that did not contain added glutathione or wheat germ extract (compare the 0 µM glutathione addition columns in the tables above). However, the presence of the extract also produced a lower net light signal in reactions given a glutathione spike above about 10 mM (see Table 10).

TABLE 10

Net Light Signal in Reactions With or Without Wheat Germ Extract

| Time (minutes) | Glutathione Concentration Added (µM) | | | | | | | |
|---|---|---|---|---|---|---|---|---|
| | 0 | 5 | 10 | 20 | 40 | 60 | 80 | 100 |
| 0 | 617 | 372 | 120 | −309 | −739 | −1637 | −2703 | −2369 |
| 14.8 | 46316 | 28753 | 16916 | −9973 | −81473 | −90918 | −120614 | −118371 |
| 33.7 | 95071 | 61679 | 34548 | 1185 | −114136 | −117076 | −188922 | −254147 |
| 44.75 | 133377 | 88294 | 41926 | −27822 | −87559 | −201150 | −261302 | −377463 |
| 58.6 | 173420 | 101627 | 24591 | −75985 | −133051 | −369700 | −276650 | −361989 |
| 140 | 350949 | 185634 | 13458 | −13994 | −215648 | −479975 | −864057 | −671160 |

Thus, the wheat germ extract most likely contains a significant level of glutathione and also may contain an interfering substance that reduced the level of signal generated at high glutathione concentrations. However, one technique that is used to estimate the level of starting compound in a sample which may have both a significant level of analyte yet also have an interfering substance is to determine if the signal increases in a relatively linear manner with added analyte and to then determine the amount of added analyte needed to produce a signal in the sample that is twice the signal generated in the sample without added analyte. In this case, the signal increase was relatively linear with added analyte to the sample and thus the value of glutathione in the diluted extract can be estimated to produce a glutathione concentration in the reaction of between 10 and 20 µM glutathione. Since this increase was seen from a 2 µl sample of starting extract, the estimated concentration in the actual sample was between 500 µM and 1 mM glutathione.

The light readings in reactions containing rabbit reticulocyte lysate but without added glutathione increased much more rapidly over reactions without added glutathione or lysate (compare readings over time in Table 8, no glutathione added column to the no glutathione added column in Table 11).

TABLE 11

Light Signals Measured in Reactions Including Rabbit Reticulocyte Lysate

| Time [min] | Glutathione Concentration Added (µM) | | | | | | | |
|---|---|---|---|---|---|---|---|---|
| | 0 | 5 | 10 | 20 | 40 | 60 | 80 | 100 |
| 0 | 2084 | 1816 | 1890 | 2168 | 2876 | 2754 | 3937 | 2822 |
| 14.8 | 83403 | 87258 | 90540 | 104181 | 130163 | 144804 | 152024 | 164924 |
| 33.7 | 171939 | 176106 | 188794 | 229026 | 269989 | 312938 | 348543 | 378781 |
| 44.75 | 229277 | 232897 | 237699 | 290097 | 345094 | 386012 | 448978 | 453140 |
| 58.6 | 292086 | 306830 | 308048 | 445066 | 442405 | 504909 | 553766 | 587558 |
| 140 | 572193 | 572518 | 610619 | 705215 | 819448 | 981057 | 1097061 | 1184652 |

However, with the rabbit reticulocyte lysate, a much smaller net signal increase was seen when glutathione was spiked into the lysates and the signal did not double until 100 µM glutathione was added in the spike (Table 11). The signal increases produced by spiking glutathione into the reactions was again approximately linear with glutathione added and thus again allowed the glutathione concentration present from the sample to be estimated. However, in this case, the estimated final concentration of glutathione generated by dilution of the lysate itself is 100 µm. Since this increase was seen from a 2 µl sample of the starting extract, the estimated concentration in the original lysate is approximated to be between 2.5 and 5 mM glutathione.

The averaged results from the reactions performed with DTP or 2-mercaptoethanol with or without spiked glutathione are presented in Table 12.

TABLE 12

Average Signals in Reactions with Added DTT or 2-mercaptoethanol (ME)

| Reductant | 50 µM glutathione | Time (minutes) | | | | | |
|---|---|---|---|---|---|---|---|
| | | 0 | 14.8 | 33.7 | 44.75 | 58.6 | 140 |
| none | none | 1234 | 2689 | 4362 | 5378 | 6015 | 11744 |
| 1 mM DTT | − | 1672 | 61526 | 145772 | 153924 | 220284 | 565135 |
| 1 mM DTT | + | 7220 | 305825 | 731311 | 857849 | 1069468 | 1944007 |
| 5 mM DTT | − | 2332 | 67536 | 155069 | 197547 | 241226 | 526501 |
| 5 mM DTT | + | 7408 | 266152 | 636054 | 791397 | 960823 | 1648897 |
| 1 mM 2-ME | − | 1123 | 24736 | 62528 | 90732 | S.L.* | 260865 |
| 1 mM 2-ME | + | 5209 | 259259 | 542606 | 626141 | S.L. | 1763802 |
| 5 mM 2-ME | − | 1442 | 34787 | 88417 | 118636 | 160571 | 339791 |
| 5 mM 2-ME | + | 5708 | 252675 | 606326 | 850061 | 1060698 | 2073466 |
| none | +** | 5179 | 245995 | 498842 | 654873 | 829531 | 1532893 |

*samples lost,
**estimated from results of 40 and 60 µM glutathione reactions presented in Table 11.

The reactions with reducing agent but without added glutathione show a light signal well above that seen without these reducing agents. However, when the net signal is calculated from these results, the net signals in the presence of these reductants was very near that seen in their absence (Table 13).

The reaction scheme was relatively insensitive to the presence of other reducing agents in the sample and it can be used in at least two complex cell lysates, wheat germ extract and rabbit reticulocyte lysate.

TABLE 13

Net signal in Reactions With and Without Reductant

| Reductant | Time (minutes) | | | | | |
|---|---|---|---|---|---|---|
| | 0 | 14.8 | 33.7 | 44.75 | 58.6 | 140 |
| None | 3945 | 243306 | 494480 | 649495 | 823516 | 1521149 |
| 1 mM DTT | 5548 | 244299 | 585540 | 703926 | 849184 | 1378872 |
| 5 mM DTT | 5077 | 198616 | 480985 | 593850 | 719597 | 1122396 |
| 1 mM 2-ME | 4086 | 234523 | 480078 | 535409 | N.A. | 1502937 |
| 5 mM 2-ME | 4266 | 217888 | 517909 | 731426 | 900127 | 1733675 |

D. Use of Luciferin Esters for Measurement of Glutathione and GST

To determine whether different GSTs had a preference for certain luciferin derivatives, a bioluminogenic assay was conducted with various GSTs (or a control with glutathione alone) and acetyl luciferin.

Materials and Methods

Enzyme and glutathione stock solutions are described in Example 1A.

Acetyl luciferin was dissolved in 9 mM in acetonitrile.

P450 Glo Reagent was made by dissolving a bottle of Luciferin Detection Reagent (V859B, Promega Corp.) with a bottle of P450-Glo Buffer (V865B, Promega Corp.)

Thirty-six 90 µl reaction solutions were created that were designed to contain the following materials when diluted to 100 µl: reactions 1-3, 50 mM HEPES pH 7.5, 20 µM acetyl luciferin; reactions 4-18, 50 mM HEPES pH 7.5, 20 µM acetyl luciferin, 2 mM glutathione, reactions 19-21, 50 mM HEPES, pH 7.5, 2 µM acetyl luciferin, and; reactions 22-36, 50 mM HEPES, pH 7.5, 2 µM acetyl luciferin, 2 mM glutathione. After assembly, the enzyme stock solutions were diluted 1:10 into 10 mM HEPES, pH 7.5 and the following additions were made to the reactions.

GST A11 (Sigma) is an enzyme found in a few body tissues, including kidney, intestine, lung and liver. GST M1-1 (Sigma) is a type b allelic variant, which corresponds to GST psi purified from human liver.

| Reaction | Reaction Type | Addition |
|---|---|---|
| 1-3 and 19-21 | Buffer control | 10 µl water |
| 4-6 and 22-24 | Glutathione alone | 10 µl water |
| 7-9 and 25-27 | S. japonica GST | 10 µl 1:10 S. japonica GST |
| 10-12 and 28-30 | Equine GST | 10 µl 1:10 Equine GST |
| 13-15 and 31-33 | GST A1-1 | 10 µl 1:10 GST A1-1 |
| 16-18 and 34-36 | GST M1-1 | 10 µl 1:10 GST M1-1 |

The reactions were allowed to proceed for 30 minutes at room temperature and then 100 µl of P450 Glo reagent was added to each reaction and the light produced by the subsequent solution was measured on a Veritas luminometer. The readings recorded are shown in Table 14.

TABLE 14

| | Raw Data | | Glutathione Signal | Net Enzyme Signal | |
|---|---|---|---|---|---|
| Reaction | 20 mM AL* | 2 mM AL | | Net 20 mM | Net 20 mM |
| Buffer Alone | 183,852 | 20,649 | | | |
| Glutathione Alone | 330,916 | 35,206 | 147,064 | 14,557 | |
| S. japonica GST | 1,233,119 | 126,288 | | 902,203 | 91,082 |
| Equine GST | 361,356 | 39,036 | | 30,440 | 3,830 |
| GST A1-1 | 365,770 | 42,725 | | 34,854 | 7,519 |
| GST M1-1 | 419,400 | 42,867 | | 88,484 | 7,661 |

*Acetyl Luciferin

Results

The results above demonstrate that a substantial non-enzymatic signal can be generated by incubation of acetyl luciferin with glutathione Thus, such incubations can be used to detect and measure the presence of glutathione in a sample.

In addition, the results indicated that a much stronger net signal was generated by *S. japonica* GST with acetyl luciferin relative to the other GST enzymes. This is in contrast to the results seen with GST #3, where *S. japonica* GST did not generate nearly as strong of a net signal than is seen with the other enzymes (Example 1). Thus, modification of the chemical groups attached to luciferin can change the relative preference of the resulting substrate for various GST enzymes.

In this example, an ester of luciferin (acetylluciferin) was demonstrated to be utilized by various GST enzymes but with more reactivity towards the enzyme from *S. japonica* than for mammalian GST enzymes, the reverse of the preference seen with GST #3. Acetyl luciferin was also shown to be able to read in solutions with 2 mM glutathione.

Summary

Figure 12A:
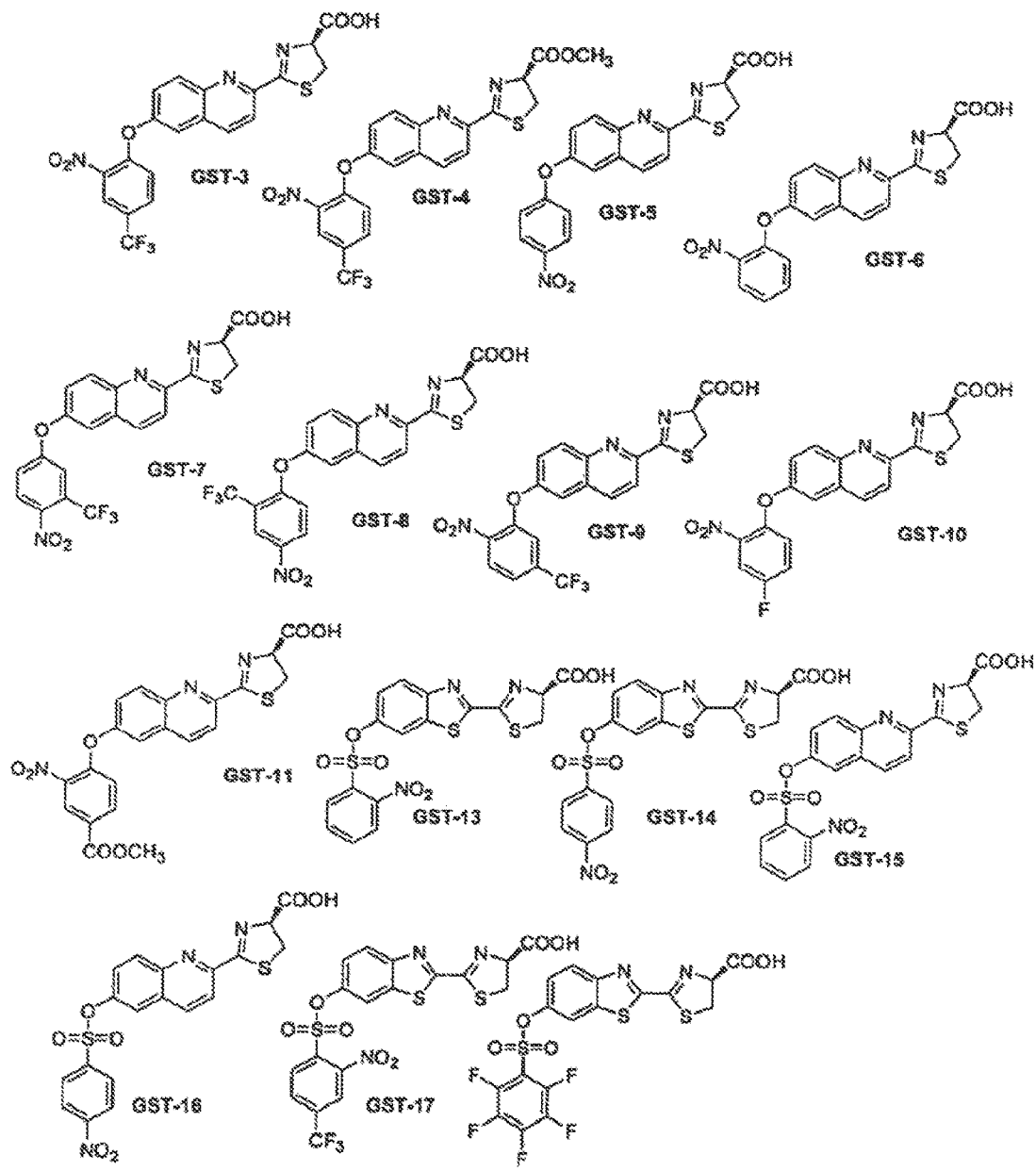
FIGS. 12A-B. Luciferin derivatives useful to detect glutathione S transferase (GST).
Figure 12B:
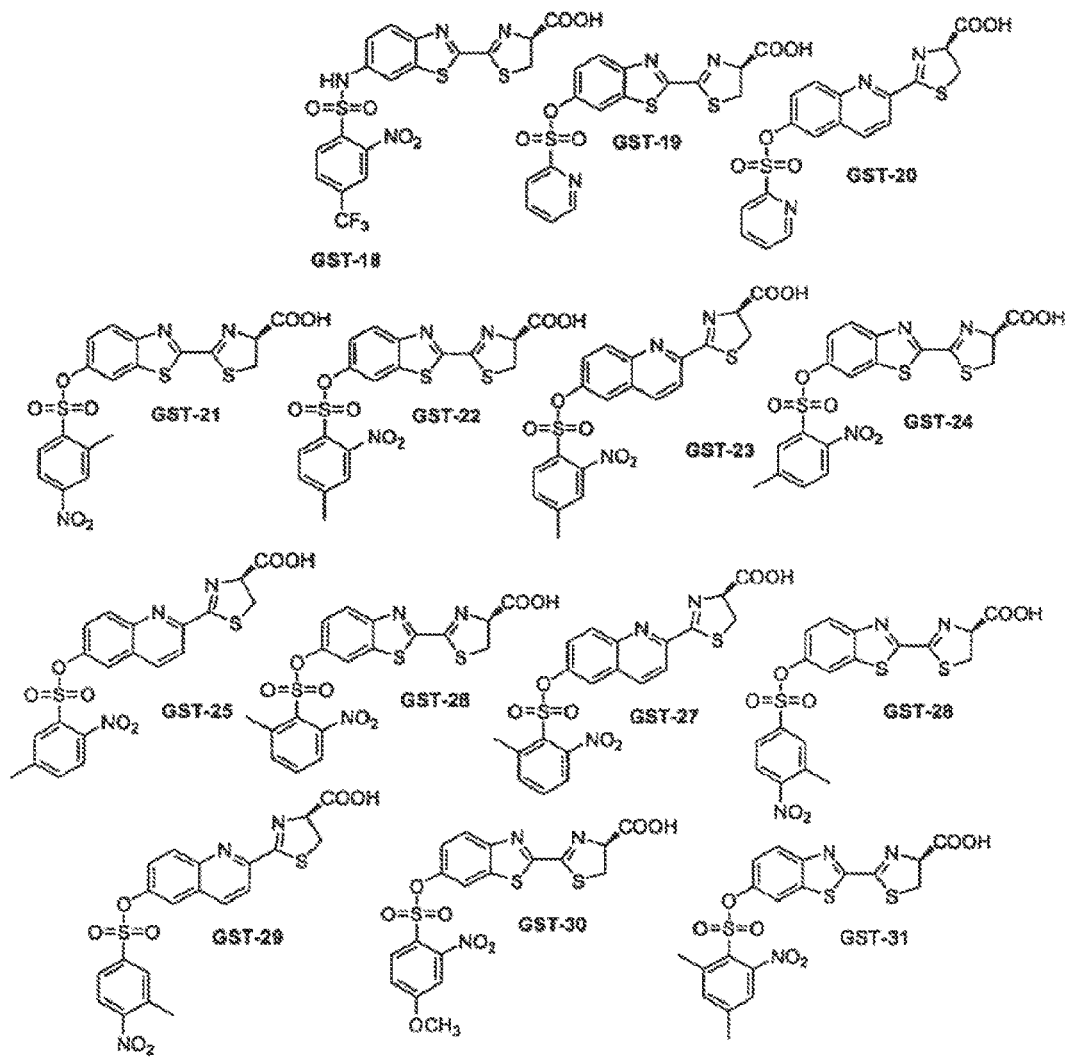
Figure 13A:
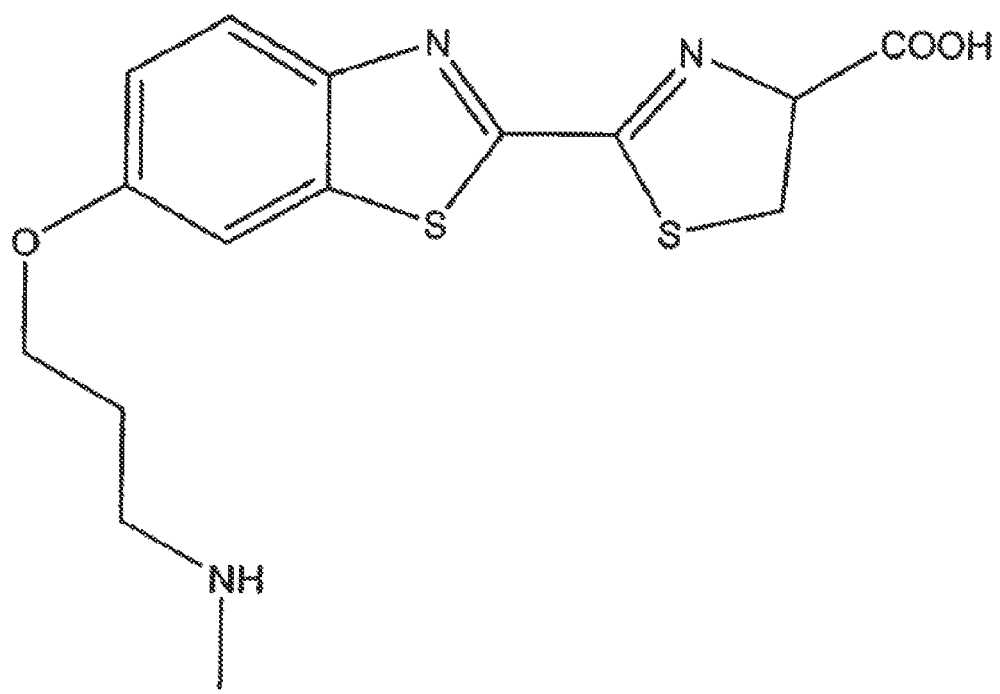
FIGS. 13A-D. A graphical representation of derivatives of luciferin derivatives for MAO assays. The derivative in FIG. 13B was not utilized by MAO.
Figure 13B:
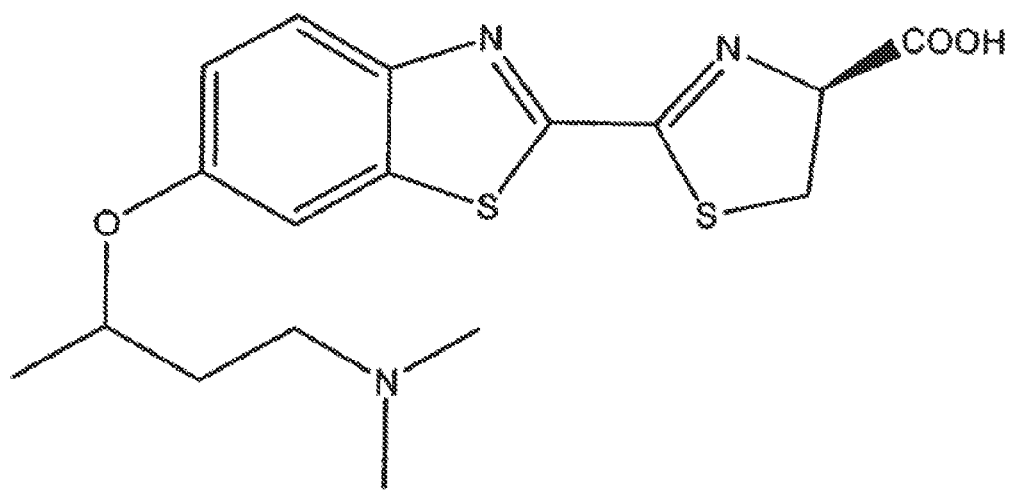
Figure 13C:
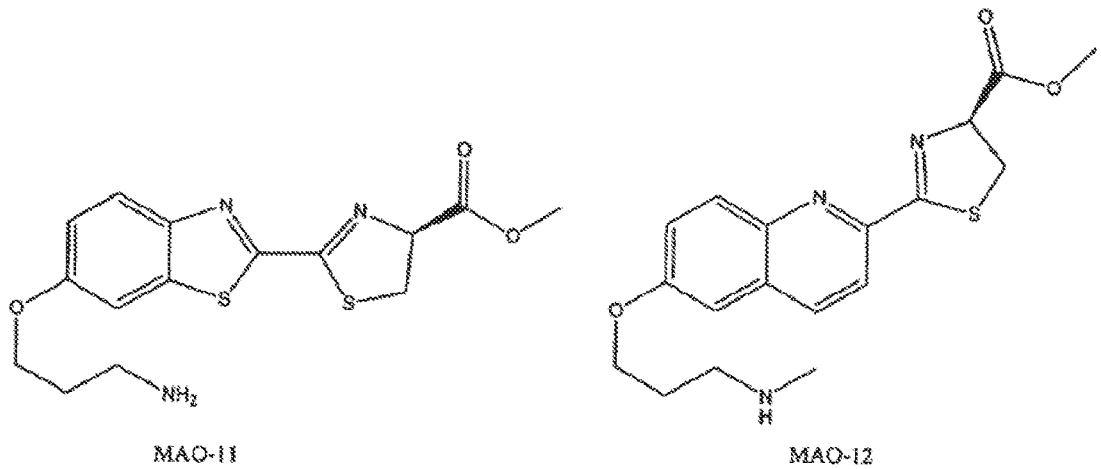
Figure 13D:
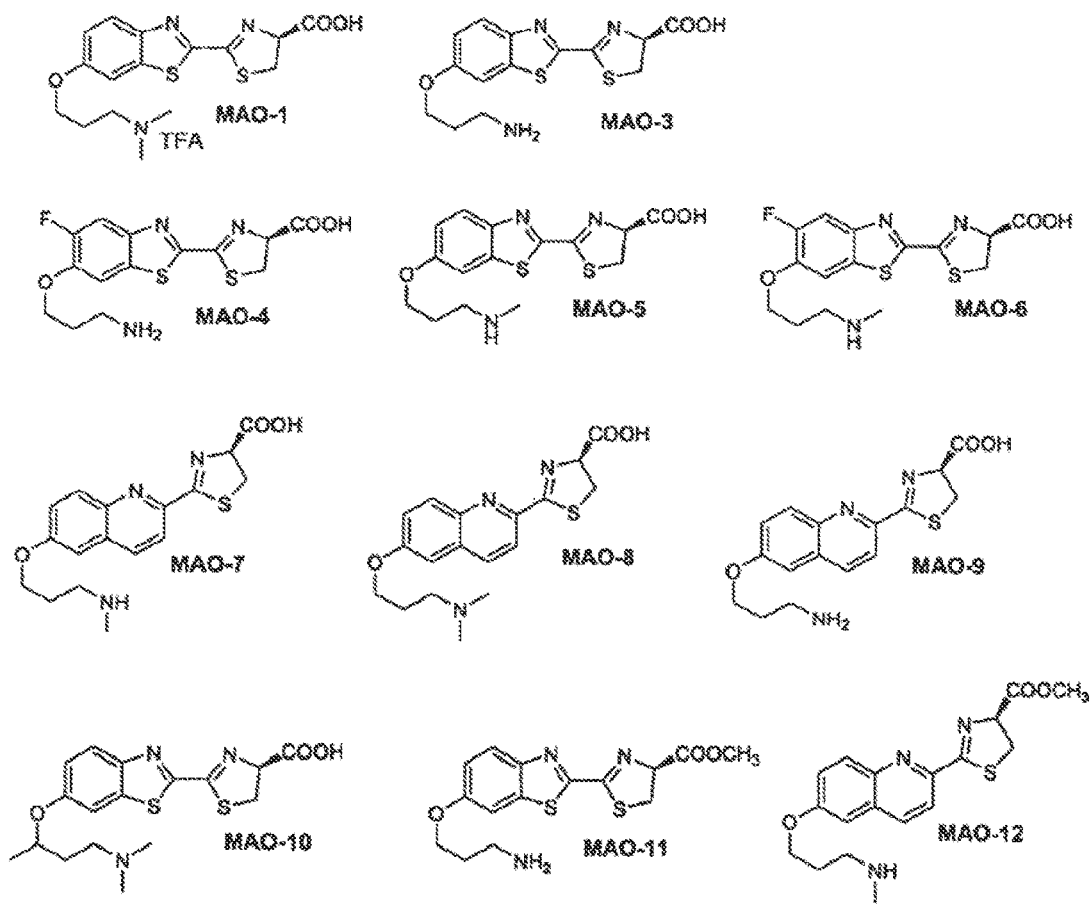

In a manner similar to that used in Example 1A, other luciferin derivatives were shown to be substrates with various preferences for GSTs (see FIG. 12). Thus, luciferins modified in various ways can be transformed by GST in the presence of glutathione to a form that can be utilized more effectively by luciferase, as demonstrated by an increasing light signal. Moreover, glutathione concentrations can be measured at high concentration through the direct attack of this agent onto the luciferin derivative or at much reduced concentration through a reaction catalyzed by GST. Further, GST enzymes show differential preferences for luciferin derivative, dependent upon the particular modifications present on the luciferin derivative.

In particular, GST #3 and a sample suspected of having a GST may be assayed at pHs from 6.5 to at least 8.0. The ester of GST #3 was a better substrate for GST M1-1 in a light generating reaction than GST A1-1, while GST#3 was a better substrate for equine GST in a light generating reaction than GST M1-1 and GST A1-1.

For some derivatives, a detergent may be added to the reaction mixture to enhance the solubility of the derivative. For example, a detergent such as Triton X-114, e.g., about 0.01 to about 20%, including about 0.1 to about 0.5% Triton X-114, was added to reaction mixtures having GST-22.

Example 2

A. Detection of Equine Alcohol Dehydrogenase

A luciferin derivative, luciferol, was employed as a substrate for alcohol dehydrogenase (ADH). The derivative was tested in a two step format. For the first step, the derivative was added to a mixture with one of four ADHs. At different times after the reaction was initiated, a portion was removed and mixed with a luciferase reaction mixture. Reactions in which light production increased over time indicate that luciferol is a substrate for the ADH in that reaction.

Materials and Methods

A solution of 500 mM Bis Tris, pH 6.5 was created by dissolving the solid and adjusting the pH to pH 6.5. A 50 mM solution was then made from this stock by dilution with water.

Al DH solution: 25 units of aldehyde dehydrogenase (Sigma Chemical Co. A-6338) was dissolved in 1 ml of 50 mM Bis Tris, pH 6.5.

Eq ADH solution: 20 units of equine alcohol dehydrogenase (Sigma Chem Co. A 9589) was devolved in 1 ml of 50 mM Bis Tris pH 6.5.

Y ADH solution: 7500 units of yeast alcohol dehydrogenase (Sigma Chem Co. A 7011) was dissolved in 1 ml of 50 mM Bis Tris pH 6.5.

NAD+ solution: 66 mg of NAD+ (Sigma Chem. Co. N 1511-250) was dissolved in 2 ml of Bis Tris, pH 6.5 and 8 ml of water.

Luciferol solution: approximately 4 mg of luciferol was dissolved in 1 ml of dimethylformamide (Aldrich 27,054-7).

Luciferase detection solution: A bottle of P450 Glo Buffer (Promega Corp. V865B) was used to dissolve a cake of Luciferin Detection Reagent (Promega Corp. V859B) then 10 ml of the resulting solution was diluted with 8 ml of water to create the defection solution used in this example.

The reaction solutions shown in Table 15 were assembled.

Table 15

TABLE 15

| Reaction | 500 mM BisTris, pH 6.5 | NAD+ Sol'n | Water | Eq ADH | Y ADH | Al DH |
|---|---|---|---|---|---|---|
| Rx 1 | 20 µl | 20 µl | 155 µl | 0 µl | 0 µl | 0 µl |
| Rx 2 | 20 µl | 20 µl | 145 µl | 5 µl | 0 µl | 5 µl |
| Rx 3 | 20 µl | 20 µl | 145 µl | 0 µl | 5 µl | 5 µl |
| Rx 4 | 20 µl | 20 µl | 150 µl | 5 µl | 0 µl | 0 µl |
| Rx 5 | 20 µl | 20 µl | 150 µl | 0 µl | 5 µl | 0 µl |
| Rx 6 | 20 µl | 20 µl | 150 µl | 0 µl | 0 µl | 5 µl |

A 5 µl sample of the luciferol DMF solution was added to each of the reactions above and a timer was started upon the addition of the first luciferol/DMF solution to reaction 1. All reactions were kept at room temperature.

As each reaction reached 10 minutes post luciferol addition, a 10 µl sample of each reaction was added to 90 µl of luciferin detection solution in a luminometer tube. After incubating 5 minutes at room temperature, the light produced by these samples was measured using a Turner TD 20 luminometer. Additional samples were taken and mixed with luciferin detection reagent and read as above as each reaction reached 20 and 40 minutes post luciferol addition.

TABLE 16

| Time | Rx 1 | Rx 2 | Rx 3 | Rx 4 | Rx 5 | Rx 6 |
|---|---|---|---|---|---|---|
| 10 minutes | 8.452 | 9.857 | 7.481 | 11.40 | 7.396 | 7.640 |
| 20 minutes | 10.04 | 13.91 | 8.292 | 15.26 | 8.670 | 7.640 |
| 40 minutes | 8.406 | 16.80 | 8.465 | 19.16 | 8.194 | 8.475 |

Results

Comparison of light values generated from samples of the reaction without enzyme (reaction 1) to that with equine ADH with Al DH reaction 2) or alone (reaction 4) demonstrated that a solution of equine alcohol dehydrogenase and NAD+ can convert luciferol into a form that is more effectively used for light production (Table 16). However, samples from solutions of yeast alcohol dehydrogenase (with NAD+) alone (reaction 5) or with Al DH (reaction 3) or Al DH alone (reaction 6) showed no significant light production above that seen for reactions not given enzyme (reaction 1).

The results are somewhat surprising as: 1) alcohol dehydrogenase usually produces an aldehyde product and such a product is not thought to be an effective luciferase substrate, and 2) a second alcohol dehydrogenase, from yeast, was not able to convert sufficient luciferol to be effectively measured even in the presence of aldehyde dehydrogenase, an enzyme that is capable of transforming aldehydes to the corresponding acids.

B. Conversion of Luciferol by Alcohol Dehydrogenase

To determine whether enzyme concentration or temperature alter the kinetics of a reaction between different ADHs and a luciferin derivative, reactions similar to those in Example 2A were conducted, and light production over a longer period of time measured.

Materials and Methods

Buffer; $KPO_4$ Buffer: A 500 mM solution of $KPO_4$, pH 7.4 was produced by dissolving $KH_2PO_4$ in water and adjusting the pH with KOH.

NAD+; Solid NAD+, 66 mg (Sigma Chem Co. N1511-250) was dissolved in 10 ml of 50 mM $KPO_4$, pH 7.4.

The equine ADH, yeast ADH and aldehyde dehydrogenase and luciferol solutions were those described in Example 5.

Luciferin detection reagent: A bottle of P450 Glo Buffer (Promega Corp. V865B) was used to dissolve a cake of Luciferin Detection Reagent (Promega Corp. V859B) then 5 ml of the resulting solution was diluted with 3 ml of water to create the detection solution used in this example.

Table 17 summarizes the assembled reactions.

TABLE 17

| Reaction | NAD+ sol'n | $KPO_4$ Buffer | Water | Enzyme |
|---|---|---|---|---|
| Rx 1 and 11 | 20 µl | 18 µl | 157 µl | None |
| Rx 2 and 12 | 20 µl | 18 µl | 147 µl | 10 µl equine ADH |
| Rx 3 and 13 | 20 µl | 18 µl | 137 µl | 20 µl equine ADH |
| Rx 4 and 14 | 20 µl | 18 µl | 127 µl | 30 µl equine ADH |
| Rx 5 and 15 | 20 µl | 18 µl | 117 µl | 40 µl equine ADH |
| Rx 6 | 20 µl | 18 µl | 112 µl | 40 µl equine ADH |
| Rx 7 | 20 µl | 18 µl | 152 µl | 5 µl yeast ADH |
| Rx 8 | 20 µl | 18 µl | 147 µl | 10 µl yeast ADH |
| Rx 9 | 20 µl | 18 µl | 137 µl | 20 µl yeast ADH |
| Rx 10 | 20 µl | 18 µl | 132 µl | 20 µl yeast ADH |

To initiate the conversions, 5 µl of luciferol solution was added to reactions 1-5, 6-9, and 11-15, and 10 µl of luciferol was added to reactions 5 and 10 and the tubes mixed after that addition. Immediately after luciferol addition to reaction 1, a timer was started and the time of luciferol addition to the other tubes noted. After mixing, reaction 11-15 were placed at 37° C.

As each tube reached 30 minutes post luciferol addition, 5 µl samples of the reaction were removed, added to 95 µl of luciferin detection reagent and the tube mixed. After incubating 10 minutes at room temperature, the light produced by these samples was read using a Turner TD 20 luminometer (Table 18). Samples were also taken at 60, 95, 190 and 280 minutes post luciferol addition and mixed with luciferin detection reagent and read (Table 18).

TABLE 18

| Reaction | 30 minutes | 60 minutes | 95 minutes | 190 minutes | 280 minutes |
|---|---|---|---|---|---|
| Rx 1 | 6.077 | 6.091 | 5.849 | 4.364 | 7.694 |
| Rx 2 | 13.86 | 21.41 | 29.38 | 50.88 | 74.52 |
| Rx 3 | 28.21 | 49.00 | 69.94 | 123.5 | 166.5 |
| Rx 4 | 35.79 | 62.64 | 94.04 | 163.9 | 245.9 |
| Rx 5 | 42.30 | 80.23 | 120.5 | 199.8 | 297.6 |
| Rx 6 | 44.49 | 83.19 | 123.8 | 210.2 | 298.1 |
| Rx 7 | 6.184 | 6.052 | 5.980 | 6.640 | 7.988 |
| Rx 8 | 6.126 | 5.468 | 5.552 | 6.198 | 6.903 |
| Rx 9 | 5.406 | 5.608 | 6.301 | 5.825 | 6.734 |
| Rx 10 | 9.672 | 9.531 | 10.00 | 10.36 | 11.71 |
| Rx 11 | 5.814 | 6.078 | 6.302 | 6.889 | 8.399 |
| Rx 12 | 71.30 | 119.4 | 151.5 | 224.0 | 286.5 |

TABLE 18-continued

| Reaction | 30 minutes | 60 minutes | 95 minutes | 190 minutes | 280 minutes |
|---|---|---|---|---|---|
| Rx 13 | 127.0 | 213.3 | 293.1 | 461.0 | 619.7 |
| Rx 14 | 161.7 | 292.1 | 433.1 | 682.2 | 844.5 |
| Rx 15 | 192.7 | 365.4 | 525.7 | 842.8 | 1138 |

Results

Solutions of equine alcohol dehydrogenase and NAD+ converted luciferol to a form more effectively used by luciferase for light production. The strength of the light signal produced was dependent upon the length of time used in the conversion reaction (comparing light signals from reaction 5 at 30, 60, 95, 190 and 280 minutes and the amount of equine ADH added and comparing signals of reactions 1-5 over time). In addition, a much faster rate of signal rise was seen when the reactions were incubated at 37° C. versus room temperature (compare paired reactions such as reaction 5 and reaction 15). Finally, doubling the luciferol concentration in the reactions with equine ADH did not increase the signal strength greatly (reaction 5 versus 6), and no major light signal change was seen with yeast alcohol dehydrogenase. Thus, the rate of conversion of luciferol by alcohol dehydrogenase was shown to be dependent upon the amount of the enzyme present in the reaction solution and the temperature of the reaction.

C. Effect of Inhibitor on the Conversion of Luciferol by Equine Alcohol Dehydrogenase As discussed herein, bioluminogenic reactions with luciferin derivatives can be employed to detect agents that modulate a nonluciferase-mediated reaction or a luciferase-mediated reaction. A known inhibitor of equine ADH was tested in a bioluminogenic reaction having the luciferin derivative luciferol.

Materials and Methods

A solution of equine alcohol dehydrogenase (Sigma Chemical Corp., A 9589) 15 mg was dissolved in 750 µl of water.

Pyrazol Solution: 3.4 mg of pyrazol (Sigma Chemical Corp P 5660-5) was dissolved in 50 ml of water.

Trichloroethanol solution: A 0.48 ml sample of trichloroethanol (Aldrich T5480-5) was dissolved in water.

The other solutions used are described in Examples 5-6.

Duplicate reactions were assembled (see Table 19)

TABLE 19

| Reaction | NAD+ | $KPO_4$ Buffer | Water | Equine ADH | Other |
|---|---|---|---|---|---|
| Control | 10 µl | 9 µl | 59.5 µl | 20 µl | None |
| +Pyrazol | 10 µl | 9 µl | 49.5 µl | 20 µl | 10 µl pyrazol |
| +Trichloro-ethanol | 10 µl | 9 µl | 49.5 µl | 20 µl | 10 µl trichloro-ethanol |

Results

Reactions were initiated by addition of 1.5 µl of luciferol solution. Upon addition of the luciferol solution, the reactions were mixed and placed at 37° C. After 30 minutes, a 5 µl sample was removed from each reaction, mixed with 95 µl of luciferin detection reagent and the light produced by these solutions was measured using a Turner TD 20 luminometer after allowing the solutions to sit 10 minutes at room temperature. The following light readings were recorded (Table 20).

TABLE 20

| Reaction | Relative Light Units |
| --- | --- |
| Control #1 | 1023 |
| Control #2 | 1087 |
| +Pyrazol #1 | 516.4 |
| +Pyrazol #2 | 490.7 |
| +trichloroethanol #1 | 524.8 |
| +trichloroethanol #2 | 342.1 |

Thus, the conversion of luciferol by solutions of equine alcohol dehydrogenase and NAD+ was slowed by known inhibitors of equine alcohol dehydrogenase. This reduction in the rate of conversion can be used to identify agents effecting this enzyme.

Example 3

MAO and FMO Assays with Derivatives of the Invention

A. Luciferin Derivatives for MAO Assays

A series of luciferin derivatives was prepared as substrates for monoamine oxidases (MAO), and those substrates tested in two step assays with different types of MAO (MAO A and MAO B). Additional assays were conducted with test compounds to determine whether the compound inhibited the MAO mediated reaction. Also, as described hereinbelow, fluorogenic MAO substrates were prepared and tested in a one step assay. The bioluminogenic and fluorogenic MAO substrates may be oxidized by monoamine oxidase (MAO) A and/or B, e.g., to produce minimum and/or aldehyde intermediates that may undergo a secondary β-elimination to liberate 7-hydroxyluciferins or a derivative thereof, or hydroxy fluorescent products including umbelliferone, fluoroscein, and their derivatives. The formation of these products is measured by light output from bioluminescence, where the product of the reaction between MAO and a luciferin derivative is oxidized by luciferase(s), or from fluorescence. Bioluminogenic and/or fluorogenic monoamine oxidase substrates and their relevant compositions provide a highly sensitive and convenient tool for detecting monoamine oxidase activities. Thus, these derivatives are very useful for high throughput screening for monoamine oxidase substrates and inhibitors thereof.

Materials and Methods

In the reactions described in this example, a luciferin derivative was incubated with MAO (Step 1). This may generate a species that may undergo spontaneous beta-elimination to form luciferin.

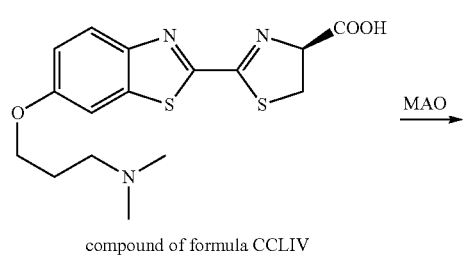

compound of formula CCLIV

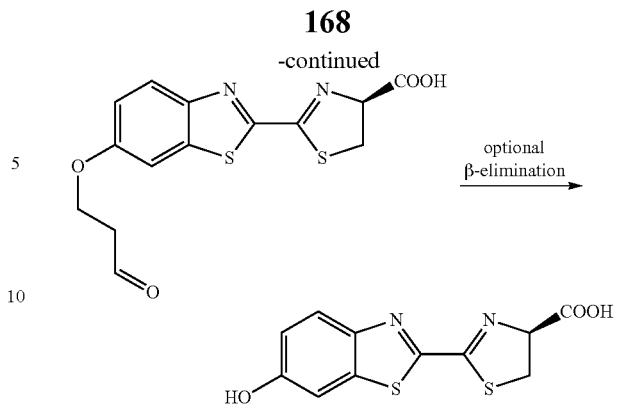

Alternatively, the product or the reaction between the derivative and MAO yields a product that is not D-luciferin but is a substrate of luciferase. A reconstituted luciferin detection reagent was then added (Step 2), and the light production from the mixture was measured with either a Dynex or Veritas plate luminometer.

For instance, to prepare a compound of formula CCLIV, a solution of dimethylamine (0.235 g. 0.00090 mol) and D-cysteine (0.158 g. 0.00090 mol) in methanol (5 ml), $CH_2Cl_2$ (1 ml) and $H_2O$ (1 ml) was added $K_2CO_3$ (0125 g, 0.00090 mol). The mixture was stirred at room temperature for 5 minutes and then neutralized to a slightly acidic condition. After removal of organic solvent, the product was purified by HPLC using 0.1% TFA water/acetonitrile as eleuent. The compound was confirmed by 1H NMR/MS. The yield was 0.23 g. The compound was characterized by 1H NMR and Mass spectra. Related compounds include compound of formula CCLV:

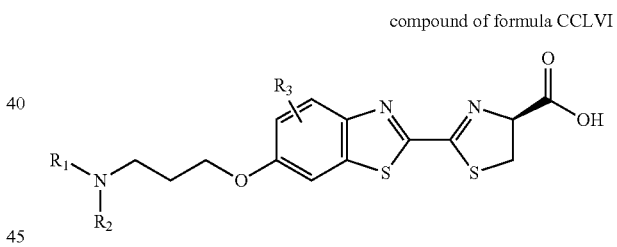

compound of formula CCLVI

The reconstituted luciferin detection reagent for Step 2 was generated by thawing a bottle of P450-Glo Buffer (V865A, Promega Corp. Madison Wis.), allowing it to come to room temperature, and then adding it to a bottle of Luciferin Detection Reagent (V859A, Promega Corp., Madison Wis. with 100 µl of 20% dodecyltrimethylammonium bromide (DTAB) (D-8638, Sigma Chemical Company). The DTAB was added to inactivate MAO.

Results

MAOB and MAO-3

In this example, substrate MAO-3 (FIG. 13; stock=8.19 mM in DMSO) was serially diluted in DMSO, and 5 µl aliquots of each substrate dilution were placed in separate wells of a white, opaque 96-well plate. To initiate Step 1, 45 µl of enzyme and buffer were added to each well. This 45 µl contained 10 µl 1 M Tricine pH 8.3, 5 µl 200 mM $MgSO_4$, 29 µl $H_2O$, and 1 µl of 5 mg/ml microsomes containing human recombinant monoamine oxidase B (MAO B) expressed in baculovirus infected insect cells (M-7441, Sigma Chemical Company). Step 1 was incubated at room temperature for one hour. Step 2 was initiated by adding 50

μl of the reconstituted luciferin detection reagent to each well. After 20 minutes, the luminescent signal from the 100 μl reaction was read on a Veritas plate luminometer. To measure the activity of luciferase towards the luciferin derivative, the luminescent signal was also read from control wells in which MAO B was substituted with $H_2O$ in Step 1. The relative light units (RLUs) measured are shown in Table 21.

TABLE 21

| [MAO-3] (μM) | no MAO | MAO B | net RLUs |
|---|---|---|---|
| 819.00 | 28342 | 54262 | 25920 |
| 409.50 | 13966 | 37602 | 23636 |
| 204.75 | 7294 | 29701 | 22407 |
| 102.38 | 3535 | 24242 | 20707 |
| 51.19 | 1757 | 20078 | 18321 |
| 25.59 | 1070 | 14104 | 13034 |
| 12.80 | 522 | 9317 | 8795 |
| 6.40 | 284 | 5493 | 5209 |
| 3.20 | 215 | 2973 | 2758 |
| 1.60 | 138 | 1617 | 1479 |
| 0.80 | 112 | 962 | 850 |

A fit of this data in TableCurve Windows v1.0 (Jandel Scientific AISN Software) yielded a $K_m$ value of 24±1 μM and a signal-to-background ratio at the $K_m$ value of about 13.
MAO A and MAO-7

In this example, microsomes (5 mg/ml) containing human recombinant monoamine oxidase A (MAO A) expressed in baculovirus infected insect cells (M-7316, Sigma Chemical Company) were diluted 10-fold in 100 mM Tricine pH 8.3, and 10 μl aliquots of the diluted microsomes were placed in separate wells of a white, opaque 96-well plate. Substrate MAO-7 (FIG. 13, stock=23.2 mM in DMSO) was serially diluted in DMSO. To initiate Step 1, 40 μl of substrate and buffer were added to each well. This 40 μl contained 10 μl 1 M Tricine pH 8.3, 5 μl 200 mM $MgSO_4$, 15 μl $H_2O$, and 10 μl of each substrate dilution. Step 1 was incubated at room temperature for one hour. Step 2 was initiated by adding 50 μl of the reconstituted luciferin detection reagent to each well. After 20 minutes, the luminescent signal from the 100 μl reaction was read on a Dynex plate luminometer. To measure the activity of luciferase towards the luciferin derivative, the luminescent signal was also read from control wells in which MAO A was substituted with $H_2O$ in Step 1.

The relative light units (RLUs) measured are shown in Table 22.

TABLE 22

| [MAO-7] (μM) | no MAO | MAO A | net RLUs |
|---|---|---|---|
| 4640 | 11.504 | 650.305 | 638.801 |
| 2320 | 6.0332 | 542.257 | 536.2238 |
| 1160 | 3.2977 | 390.469 | 387.1713 |
| 580 | 1.6627 | 224.458 | 222.7953 |
| 290 | 0.8456 | 124.435 | 123.5894 |
| 145 | 0.4563 | 64.975 | 64.5187 |
| 72.5 | 0.2556 | 32.52 | 32.2644 |
| 36.3 | 0.1312 | 16.821 | 16.6898 |
| 18.1 | 0.1033 | 8.5338 | 8.4305 |

A fit of this data in TableCurve Windows v1.0 (Jandel Scientific, AlSN Software) yielded a $K_m$ value of 1560±130 μM and a signal-to-background ratio at the $K_m$ value of about 95.
MAO A and MAO-3, MAO A and MAO-7, MAO B and MAO-3, MAO B and MAO-7

In this example, microsomes (5 mg/ml) containing human recombinant monoamine oxidise A (MAO A) expressed in baculovirus infected insect cells (M-7316, Sigma Chemical Company) were diluted 10-fold in 200 nM Tricine pH 8.3, and 10 μl aliquots of the diluted microsomes were placed in separate wells of a white, opaque 96-well plate. Substrates MAO-3 (stock=9.2 mM in 0.2% $H_2SO_4$/DMSO) and MAO-7 (stock=26 mM in 0.2% $H_2SO_4$/DMSO) were serially diluted in 0.2% $H_2SO_4$/DMSO. To initiate Step 1, 40 μl of substrate and buffer were added to each well. This 40 μl contained 10 μl 1 M Tricine pH 8.3, 5 μl 200 mM $MgSO_4$, 5 μl 10% Tergitol NP-9, 10 μl $H_2O$, and 10 μl of each substrate dilution. Step 1 was incubated at room temperature for one hour. Step 2 was initiated by adding 50 μl of the reconstituted luciferin detection reagent to each well. After 20 minutes, the luminescent signal from the 100 μl reaction was read on a Dynex plate luminometer. To measure the activity of luciferase towards the luciferin derivative, the luminescent signal was also read from control wells in which MAO A or MAO B was substituted with $H_2O$ in Step 1.

The relative light units (RLUs) measured are shown in Tables 23-24.

TABLE 23

| [MAO-3] (μM) | no MAO | MAO A | MAO B | net A | net B |
|---|---|---|---|---|---|
| 1840 | 34.224 | 155.693 | 362.398 | 121.469 | 328.174 |
| 920 | 19.128 | 108.18 | 231.563 | 89.052 | 212.435 |
| 460 | 10.157 | 65.297 | 143.784 | 55.14 | 133.627 |
| 230 | 4.8948 | 33.833 | 77.778 | 28.9382 | 72.8832 |
| 115 | 2.4175 | 17.977 | 40.089 | 15.5595 | 37.6715 |
| 57.5 | 1.2856 | 9.4777 | 20.741 | 8.1921 | 19.4554 |
| 28.8 | 0.5877 | 4.5843 | 10.46 | 3.9966 | 9.8723 |
| 14.4 | 0.3338 | 2.1812 | 5.5996 | 1.8474 | 5.2658 |
| 7.2 | 0.1692 | 1.2114 | 2.7601 | 1.0422 | 2.5909 |
| 3.6 | 0.1074 | 0.6851 | 1.6472 | 0.5777 | 1.5398 |

TABLE 24

| [MAO-7] (μM) | no MAO | MAO A | MAO B | net A | net B |
|---|---|---|---|---|---|
| 5200 | 10.65 | 553.51 | 52.972 | 542.86 | 42.322 |
| 2600 | 6.7022 | 490.271 | 43.713 | 483.5688 | 37.0108 |
| 1300 | 3.8297 | 342.71 | 39.242 | 338.8803 | 35.4123 |
| 650 | 2.1547 | 196.223 | 26.367 | 194.0683 | 24.2123 |
| 325 | 1.189 | 97.309 | 16.235 | 96.12 | 15.046 |
| 162.5 | 0.5589 | 50.033 | 9.1463 | 49.4741 | 8.5874 |
| 81.3 | 0.3343 | 22.845 | 5.0852 | 22.5107 | 4.7509 |
| 40.6 | 0.1641 | 11.762 | 2.7455 | 11.5979 | 2.5814 |
| 20.3 | 0.0942 | 6.1583 | 1.4467 | 6.0641 | 1.3525 |
| 10.2 | 0.0754 | 2.8488 | 0.7627 | 2.7734 | 0.6873 |

A fit of this data in TableCurve Windows v1.0 (Jandel Scientific, AlSN Software) yielded the $RLU_{max}$, and $K_m$ values shown in Table 25. As indicated by the ratio $RLU_{max}/K_m$, MAO-3 is a more specific substrate for MAO B and MAO-7 is a more specific substrate for MAO A.

TABLE 25

| | $RLU_{max}$ | $K_m$ (mM) | $RLU_{max}/K_m$ (mM$^{-1}$) |
|---|---|---|---|
| MAO A & MAO-3 | 210 | 1.32 | 159 |
| MAO B & MAO-3 | 660 | 1.88 | 351 |

TABLE 25-continued

|  | $RLU_{max}$ | $K_m$ (mM) | $RLU_{max}/K_m$ (mM$^{-1}$) |
|---|---|---|---|
| MAO A & MAO-7 | 750 | 1.7 | 441 |
| MAO B & MAO-7 | 48 | 0.65 | 74 |

MAO A and MAO-11, and MAO B and MAO-11

In this example, MAO-11 (FIG. 13), the methyl ester derivative of MAO-3, was synthesized in an effort to increase enzyme specificity by decreasing the charge of the substrate and lowering the $K_m$ values of the MAO enzymes. Microsomes (5 mg/ml) containing human recombinant monoamine oxidase A (MAO A) or B (MAO B) expressed in baculovirus infected insect cells (M-7316 and M-7441, respectively. Sigma Chemical Company) were diluted 5-fold in 100 mM HEPES pH 7.4, and 5 µl aliquots of the diluted microsomes were placed in separate wells of a white, opaque 96-well plate. Substrate MaO-11 (stock=16.4 mM in DMSO) was serially diluted in DMSO. To initiate Step 1, 45 µl of substrate and buffer was added to each well. This 45 µl contained 10 µl 500 mM HEPES pH 7.4, 5 µl 200 mM MgSO$_4$, 28 µl H$_2$O, and 2 µl of each substrate dilution. Step 1 was incubated at room temperature for one hour. Step 2 was initiated by adding 50 µl of the reconstituted luciferin detection reagent to each well; 0.5 µl of 3.57 units/µl porcine liver esterase (E-2884, Sigma Chemical Company) was also added to each well to remove the ester prior to reaction with luciferase. After 10 minutes, the luminescent signal from the 100 µl reaction was read on a Veritas plate luminometer. To measure the activity of luciferase towards the luciferin derivative, the luminescent signal was also read from control wells in which MAO A or MAO B was substituted with H$_2$O in Step 1.

The relative light units (RLUs) measured are shown in Table 26.

TABLE 26

| [MAO-11] (µM) | no MAO | MAO A | MAO B | net A | net B |
|---|---|---|---|---|---|
| 656 | 117465 | 8633713 | 551608 | 8516248 | 434143 |
| 328 | 62791 | 8924217 | 515953 | 8861426 | 453162 |
| 164 | 33056 | 8079844 | 509311 | 8046788 | 476255 |
| 82 | 17316 | 6575618 | 466321 | 6558302 | 449005 |
| 41 | 10457 | 4799614 | 467175 | 4789157 | 456718 |
| 20.5 | 6653 | 2856723 | 454410 | 2850070 | 447757 |
| 10.25 | 3671 | 1136043 | 348002 | 1132372 | 344331 |
| 5.13 | 2084 | 475853 | 251284 | 473769 | 249200 |

TABLE 26-continued

| [MAO-11] (µM) | no MAO | MAO A | MAO B | net A | net B |
|---|---|---|---|---|---|
| 2.56 | 1271 | 211752 | 183244 | 210481 | 181973 |
| 1.28 | 823 | 94496 | 114581 | 93673 | 113758 |
| 0.64 | 647 | 44547 | 67136 | 43900 | 66489 |
| 0.32 | 441 | 19973 | 31996 | 19532 | 31555 |

A fit of this data in TableCurve Windows v1.0 (Jandel Scientific, AISN Software) yielded $K_m$ values of 47±6 µM and 4.4±0.4 µM and signal-to-background ratios at the $K_m$ values of about 450 and about 130 for MAO A and MAO B, respectively. This represents 33-fold and 5.5-fold decreases in the $K_m$ values for MAO A and MAO B, respectively, and demonstrates the advantage of using esterified substrates in Step 1 and including esterase in Step 2.

Measurement of IC$_{50}$ Values

In this example, test compounds were serially dilated in H$_2$O and 12.5 µl aliquots of each dilution were placed in separate wells of a while, opaque 96-well plate. Substrate MAO-11 was diluted (stock=16.4 mM) in 200 mM HEPES, 10% glycerol, pH 7.4 (+20% dimethyl sulfoxide for MAO B), and 12.5 µl aliquots of 160 µM or 16 µM MAO-11 were added to each well for reactions with MAO A or MAO B, respectively. Microsomes (5 mg/ml) containing human recombinant monoamine oxidase A (MAO A) or B (MAO B) expressed in baculovirus infected insect cells (M-7316 and M-7441, respectively. Sigma Chemical Company) were diluted 25-fold in 100 mM HEPES, 5% glycerol, pH 7.4 (+10% dimethyl sulfoxide for MAO B), and to initiate Step 1, 25 µl aliquots of the diluted microsomes were added to each well. Step 1 was incubated at room temperature for one hour. Step 2 was initiated by adding 50 µl of a modified, reconstituted luciferin detection reagent to each well. In this modified reagent, a bottle of Luciferin Detection Reagent (V859A, Promega Corp., Madison Wis.) was dissolved in 200 mM PIPES, pH 6.7, 6.8 mM MgSO$_4$, 2% Tergitol NP-9, 0.2% dodecyltrimethylammonium bromide (DTAB) (D-8638, Sigma Chemical Company). 0.2% Mazu DF-204, 18 µM 2-(4-aminophenyl)-6-methylbenzthiazole (APMBT), and 20 U/ml porcine liver esterase (E-2884, Sigma Chemical Company). After 30 minutes, the luminescent signal from the 100 µl reaction was read on a Dynex plate luminometer. To measure the activity of luciferase towards the luciferin derivative, the luminescent signal was also read from control wells in which MAO A or MAO B was substituted with 100 mM HEPES, 5% glycerol, pH 7.4 (+10% dimethyl sulfoxide for MAO B) in Step 1.

The relative light units (RLUs) measured are shown in Tables 27-29.

TABLE 27

|  | MAO A | | MAO B | | percent activity | |
|---|---|---|---|---|---|---|
| [CLOR] (mM) | enzyme | no enzyme | enzyme | no enzyme | MAO A | MAO B |
| 250.0000 | 20.839 | 25.21 | 96.566 | 4.2724 | −0.009 | 11.286 |
| 83.3333 | 20.754 | 19.884 | 231.028 | 4.0911 | −0.010 | 27.679 |
| 27.7778 | 22.496 | 19.544 | 460.408 | 3.992 | 0.018 | 55.645 |
| 9.2593 | 27.131 | 20.336 | 748.578 | 4.016 | 0.091 | 90.778 |
| 3.0864 | 35.455 | 20.883 | 799.833 | 3.8485 | 0.224 | 97.027 |
| 1.0288 | 66.13 | 21.173 | 824.099 | 4.052 | 0.714 | 99.985 |
| 0.3429 | 125.226 | 21.205 | 835.201 | 4.2169 | 1.657 | 101.339 |
| 0.1143 | 359.688 | 20.964 | 848.71 | 3.8082 | 5.399 | 102.986 |
| 0.0381 | 4403.78 | 20.538 | 855.032 | 3.8881 | 69.939 | 103.756 |
| 0.0127 | 5556.07 | 20.811 | 827.772 | 3.8107 | 88.329 | 100.433 |
| 0.0042 | 5848.05 | 21.288 | 828.424 | 3.9595 | 92.988 | 100.512 |
| 0.0014 | 6287.39 | 24.955 | 824.222 | 4.028 | 100.000 | 100.000 |

TABLE 28

| [DEP] (mM) | MAO A enzyme | MAO A no enzyme | MAO B enzyme | MAO B no enzyme | percent activity MAO A | percent activity MAO B |
|---|---|---|---|---|---|---|
| 125.00000 | 389.273 | 25.21 | 7.0808 | 4.2724 | 5.667 | 0.379 |
| 41.66667 | 1421.31 | 19.884 | 12.698 | 4.0911 | 21.565 | 1.071 |
| 13.88889 | 2941.09 | 19.544 | 25.154 | 3.992 | 44.977 | 2.603 |
| 4.62963 | 4928.34 | 20.336 | 55.661 | 4.016 | 75.590 | 6.357 |
| 1.54321 | 6019.12 | 20.883 | 129.138 | 3.8485 | 92.393 | 15.399 |
| 0.51440 | 6375.81 | 21.173 | 290.883 | 4.052 | 97.888 | 35.303 |
| 0.17147 | 6702.08 | 21.205 | 521.983 | 4.2169 | 102.914 | 63.742 |
| 0.05716 | 6549.63 | 20.964 | 704.981 | 3.8082 | 100.565 | 86.261 |
| 0.01905 | 6607.84 | 20.538 | 789.888 | 3.8881 | 101.462 | 96.709 |
| 0.00635 | 6810.54 | 20.811 | 825.09 | 3.8107 | 104.584 | 101.041 |
| 0.00212 | 6494.65 | 21.288 | 805.968 | 3.9595 | 99.718 | 98.688 |
| 0.00071 | 6512.94 | 24.955 | 816.628 | 4.028 | 100.000 | 100.000 |

TABLE 29

| [PEA] (mM) | MAO A enzyme | MAO A no enzyme | MAO B enzyme | MAO B no enzyme | percent activity MAO A | percent activity MAO B |
|---|---|---|---|---|---|---|
| 13650.000 | 84.655 | 25.21 | 7.5654 | 4.2724 | 0.986 | 0.417 |
| 4550.000 | 282.629 | 19.884 | 11.202 | 4.0911 | 4.072 | 0.842 |
| 1516.667 | 789.167 | 19.544 | 24.813 | 3.992 | 11.969 | 2.434 |
| 505.556 | 2001.33 | 20.336 | 57.877 | 4.016 | 30.866 | 6.301 |
| 168.519 | 3890.4 | 20.883 | 130.845 | 3.8485 | 60.315 | 14.833 |
| 56.173 | 5520.26 | 21.173 | 322.368 | 4.052 | 85.723 | 37.230 |
| 18.724 | 6127.62 | 21.205 | 623.72 | 4.2169 | 95.192 | 72.470 |
| 6.241 | 6374.2 | 20.964 | 757.033 | 3.8082 | 99.036 | 88.060 |
| 2.080 | 6623.63 | 20.538 | 827.386 | 3.8881 | 102.924 | 96.287 |
| 0.693 | 6497.46 | 20.811 | 822.64 | 3.8107 | 100.957 | 95.732 |
| 0.231 | 6497.21 | 21.288 | 855.314 | 3.9595 | 100.953 | 99.553 |
| 0.077 | 6436.06 | 24.955 | 859.135 | 4.028 | 100.000 | 100.000 |

A fit of this data in TableCurve Windows v1.0 (Jandel Scientific, AISN Software) yielded $IC_{50}$ values that match published values (see Table 30).

TABLE 30

| compound | $IC_{50}$ (µM) MAO A | $IC_{50}$ (µM) MAO B | published values (µM) MAO A | published values (µM) MAO B |
|---|---|---|---|---|
| clorgyline (CLOR) | 0.024 ± 0.007 | 24 ± 5 | 0.025 | 79 |
| deprenyl (DEP) | 7.1 ± 0.8 | 0.151 ± 0.008 | 5 | 0.13 |
| phenethyl-amine (PEA) | 134 ± 9 | 20 ± 2 | 78-280 | 2-150 |

B. Assays with a Fluorogenic Derivative

In the following example, reactions were assembled in which a substrate exhibiting low fluorescence was incubated with MAO. This may generate a species that may undergo spontaneous P-elimination to form a product exhibiting high fluorescence. The fluorescent signal was then measured (excitation/emission=355/460 nm) on a Fluoroskan Ascent plate fluorometer.

Microsomes containing human recombinant monoamine oxidase A (MAO A) or B (MAO B) expressed in baculovirus infected insect cells (M-7316 and M-7441, respectively, Sigma Chemical Company) were diluted 10-fold in 200 mM Tricine pH 8.3, and 10 µl aliquots of the diluted microsomes were placed in separate wells of a black 96-well plate. Substrate MAO-F3 (FIG. 11; stock=69.1 mM in DMSO) was serially diluted in DMSO. To initiate the reaction, 90 µl of substrate and buffer was added to each well. This 90 µl contained 35 µl 200 mM Tricine pH 8.3, 35 µl 200 mM Tricine pH 8.7 (or water), 10 µl 200 mM $MgSO_4$, and 10 µl of each substrate dilution. The 100 µl reaction was incubated at room temperature for one hour and the fluorescent signal was read on a Fluoroskan Ascent plate fluorometer. To measure the fluorescence of the derivative, the fluorescent signal was also read from control wells in which MAO A or MAO B was substituted with $H_2O$.

The relative fluorescent signals measured are shown in Table 31.

TABLE 31

| [MAO-F3] (µM) | no MAO | MAO A | MAO B | net A | net B |
|---|---|---|---|---|---|
| 863.75 | 6461 | 21154 | 17322 | 14393 | 10561 |
| 431.88 | 5097 | 19530 | 16590 | 14433 | 11493 |
| 215.94 | 3375 | 16721 | 14149 | 13346 | 10774 |
| 107.97 | 2037 | 13930 | 11704 | 11893 | 9667 |
| 53.98 | 1210 | 11555 | 9885 | 10345 | 8675 |
| 26.99 | 633 | 8461 | 7468 | 7828 | 6835 |
| 13.50 | 348 | 6078 | 5239 | 5730 | 4891 |
| 6.75 | 197 | 4129 | 3683 | 3932 | 3486 |
| 3.37 | 118 | 2604 | 2198 | 2486 | 2080 |
| 1.69 | 78 | 1486 | 1353 | 1408 | 1275 |
| 0.84 | 57 | 815 | 689 | 758 | 632 |
| 0.42 | 48 | 431 | 375 | 383 | 327 |
| 0.21 | 48 | 240 | 202 | 192 | 154 |

A fit of this data in TableCurve Windows v1.0 (Jandel Scientific, AISN Software) yielded $K_m$ values of 21±1 µM and 16±1 µM and signal-to-background ratios at the $K_m$ values of about 15 and about 13 for MAO A and MAO B, respectively.

Conclusion

Thus, luciferin and fluorophore derivatives allow MAO (see FIGS. 11 and 13) to be measured through conversion of the derivative. Conversion of the derivative may not directly generate native luciferin or a fluorogenic molecule, but may yield an intermediate that converts to luciferin or the fluorogenic molecule, or produces an intermediate that is a substrate for luciferase. Such compounds are useful to measure MAO, or inhibitors or substrates for MAO. One luciferin derivative tested (fluoroluciferin) gave a non-pH dependent light signal.

In particular, luciferin derivatives such as MAO #1, 3 and the like were transformed by monoamine oxidases A and B to a product that may be utilized by luciferases much more effectively than the derivative, allowing these enzymes to be measured easily and effectively. Some of these compounds, such as MAO #1, #3, #4 (FIG. 13), were designed such that the monoamine oxidase reaction would generate a product that would be able to spontaneously cleave off the luciferin nucleus in an elimination reaction. The data suggested that this elimination reaction, if it takes place, surprisingly takes place very rapidly. Such a reaction thus allows for the measurement of the MAO enzymes without the need for a second incubation step for the elimination reaction to go to completion. Additional derivatives were generated that were designed to increase the rate of the elimination reaction by inclusion of a fluoride atom on the luciferin nucleus. Such an enhancement may be generally useful in other elimination reactions. Moreover, the product of those reactions may be utilized as a luciferase substrate.

C. Luciferin Derivatives for FMO Assay

In the following examples, reactions were assembled in which a luciferin derivative was incubated with FMO (Step 1). This may generate a species that may undergo spontaneous beta-elimination to form luciferin. A reconstituted luciferin detection reagent (see previous examples) was then added (Step 2), and the light production from the mixture was measured with either a Dynex or Veritas plate luminometer.

FMO 1 and FMO 3 and Substrate FMO-2

In this example, 1 µl aliquots of microsomes containing human recombinant flavin-containing monooxygenase 1 (FMO 1) or 3 (FMO 3) expressed in baculovirus infected insect cells (F-4928 and F-5053, respectively, Sigma Chemical Company) were placed in separate wells of a white, opaque 96-well plate. To initiate Step 1, 49 µl of substrate and buffer was added to each well. This 49 µl contained 5 µl 200 mM CHES pH 9.5, 2.5 µl Solution A, 0.5 µl Solution B, 39 µl $H_2O$, and 2 µl of 3.75 mM substrate FMO-2. Solution A and Solution B are components of the NADPH Regeneration System (V9510, Promega Corp., Madison Wis.). Solution A contains 26 mM $NADP^+$, 66 mM glucose-6-phoshate, and 66 mM $MgCl_2$. Solution B contains 40 units/ml glucose-6-phosphate dehydrogenase in 5 mM citrate pH 5.5. Step 1 was incubated at room temperature for four hours. Step 2 was initiated by adding 50 µl of the reconstituted luciferin detection reagent to each well. After 30 minutes, the luminescent signal from the 100 µl reaction was read on a Dynex plate luminometer. To measure the activity of luciferase towards the luciferin derivative, the luminescent signal was also read from control wells in which FMO 1 or FMO 3 was substituted with microsomes from wild type baculovirus infected insect cells (M-7566, Sigma Chemical Company) in Step 1.

The relative light units (RLUs) measured are shown in Table 32.

TABLE 32

| sample | control | | FMO 1 | | FMO 3 | |
|---|---|---|---|---|---|---|
| RLUs | 8.7102 | 8.5489 | 11.778 | 12.006 | 12.194 | 10.425 |

FMO 3 and Substrate MAO-7

In this example, 5 µl aliquots of microsomes containing human recombinant flavin-containing monooxygenase 3 (FMO 3) expressed in baculovirus infected insect cells (F-5053, Sigma Chemical Company) were placed in separate wells of a white, opaque 96-well plate. Substrate MAO-7 (FIG. 13, stock=17.2 mM in DMSO) wax serially diluted in DMSO.

To initiate Step 1, 45 µl of substrate and buffer was added to each well. This 45 µl contained 10 µl 200 mM CHES pH 9.5, 2.5 µl Solution A, 0.5 µl Solution B, 30 µl $H_2O$, and 2 µl of each substrate dilution. Solution A and Solution B are components of the NADPH Regeneration System (V9510, Promega Corp., Madison Wis.). Solution A contains 26 mM $NADP^+$, 66 mM glucose-6-phosphate, and 66 mM $MgCl_2$. Solution B contains 40 units/ml glucose-6-phosphate dehydrogenase in 5 mM citrate pH 5.5. Step 1 was incubated at room temperature for one hour. Step 2 was initiated by adding 50 µl of the reconstituted luciferin detection reagent to each well.

After 30 minutes, the luminescent signal from the 100 µl reaction was read on a Veritas plate luminometer. To measure the activity of luciferin towards the luciferin derivative, the luminescent signal was also read from control wells in which FMO 3 was substituted with microsomes from wild type baculovirus infected insect cells (M-7566, Sigma Chemical Company) in Step 1. The relative light units (RLUs) measured are shown in Table 33.

TABLE 33

| [MAO-7] (µM) | control | FMO 3 | net FMO 3 |
|---|---|---|---|
| 688 | 7213 | 42707 | 35494 |
| 516 | 6137 | 40329 | 34192 |
| 344 | 4486 | 34036 | 29550 |
| 258 | 3592 | 28987 | 25395 |
| 172 | 2571 | 22463 | 19892 |
| 129 | 2004 | 19332 | 17328 |
| 86 | 1585 | 13646 | 12061 |
| 43 | 1043 | 8220 | 7177 |

Figure 14:
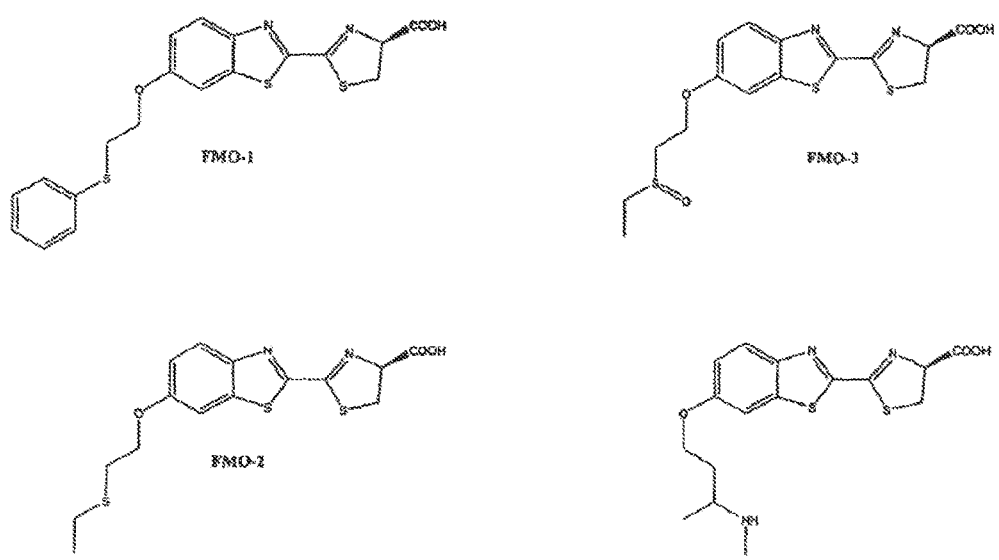
FIG. 14. Derivatives of luciferin useful as flavin monooxygenase (FMO) substrates.
Figure 15:
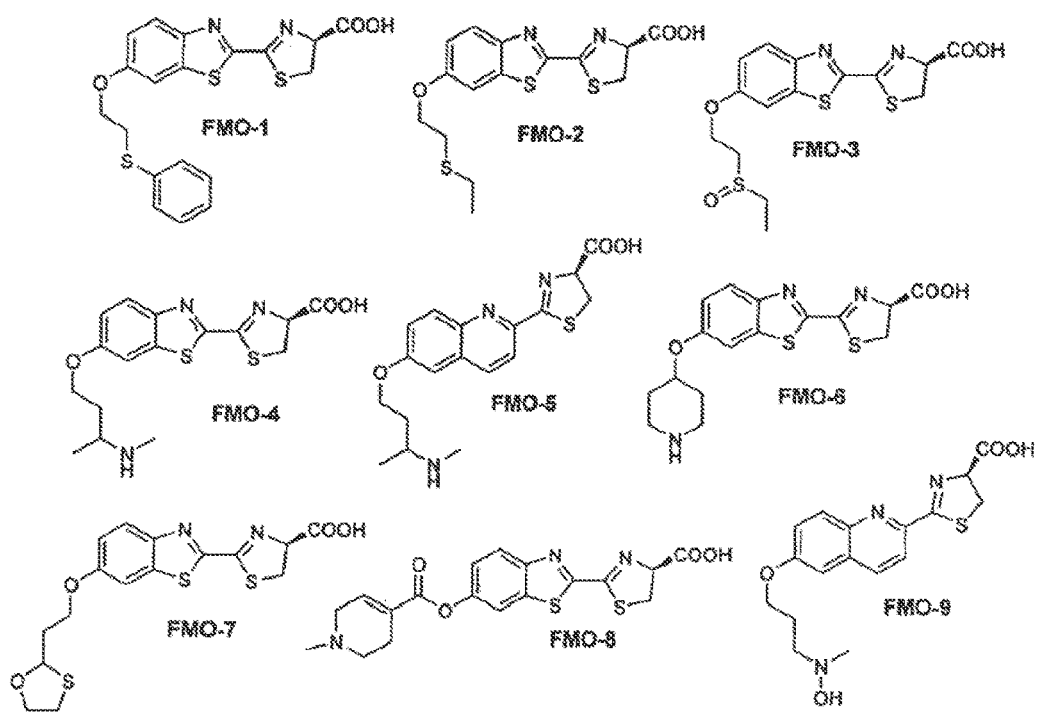
FIG. 15. Exemplary FMO substrates.

A fit of this data in TableCurve Windows v1.0 (Jandel Scientific, AISN Software) yielded a $K_m$ value of 200±20 µM and a signal-to-background ratio at the $K_m$ value of about 8.5. FIGS. 14-15 provide exemplary FMO substrates.

Example 4

Luciferin Derivatives as Substrates of Alkaline Phosphatase

In this example, AP4, a luciferin derivative, was reacted with various amounts of calf intestinal alkaline phosphatase in the presence of luciferase and ATP and light production recorded as a way of measuring alkaline phosphatase activity.

Materials and Methods

Luciferin derivative AP4, was dissolved in 50 mM Tris Cl pH 7.5 to produce a 4.3 mM solution of the compound.

Alkaline Phosphatase (Promega Corp. M1821) was diluted in 50 mM Tris Cl, pH 9.3, 1 mM $MgCl_2$, 0.1 mM $ZnCl_2$ to a concentration of 1 fmol/µl to 0.01 zeptomole/µl.

A reaction solution was assembled containing 1 µM AP4 (FIG. 69); 100 µg/ml of the thermostable luciferase, 2 mM ATP; 10 mM $MgCl_2$; 100 µM $ZnCl_2$ in 50 mM Tris Cl, pH 8.5. This solution was allowed to incubate for 1 hour at room temperature to reduce background light production.

Quadruplicate wells in a luminometer plate (Nunc Maxisorb plate) were given 10 µl of the diluted alkaline phosphatase stocks and 100 µl of reaction solution. The plate was incubated at room temperature for 30 minutes, then the light produced by the solutions was measured using a Veritas Luminometer.

Results

The following average light readings were calculated from the raw data (Table 34).

TABLE 34

| # AP molecules | Reaction 1 | Reaction 2 | Reaction 3 | Reaction 4 | Avg Reading | Net Reading |
|---|---|---|---|---|---|---|
| 0 | 2620 | 2735 | 2612 | 2531 | 2624.5 | 0 |
| 6 | 2706 | 2807 | 2631 | [lost] | 2714.67 | 89 |
| 60 | 2920 | 2795 | 2728 | 2647 | 2772.5 | 148 |
| 600 | 3118 | 3051 | 3345 | 2805 | 3079.8 | 455 |
| 6,000 | 3189 | 3144 | 3002 | 3405 | 3185 | 560 |
| 60,000 | 5956 | 5641 | 5416 | 5728 | 5685.3 | 3060 |
| 600,000 | 30042 | 31132 | 29781 | 31679 | 30658.5 | 28034 |
| 6,000,000 | 281115 | 254693 | 265592 | 296642 | 274510.5 | 271886 |
| 60,000,000 | 2639163 | 2283882 | 2320675 | 2334267 | 2394497 | 2391872 |

Figure 16:
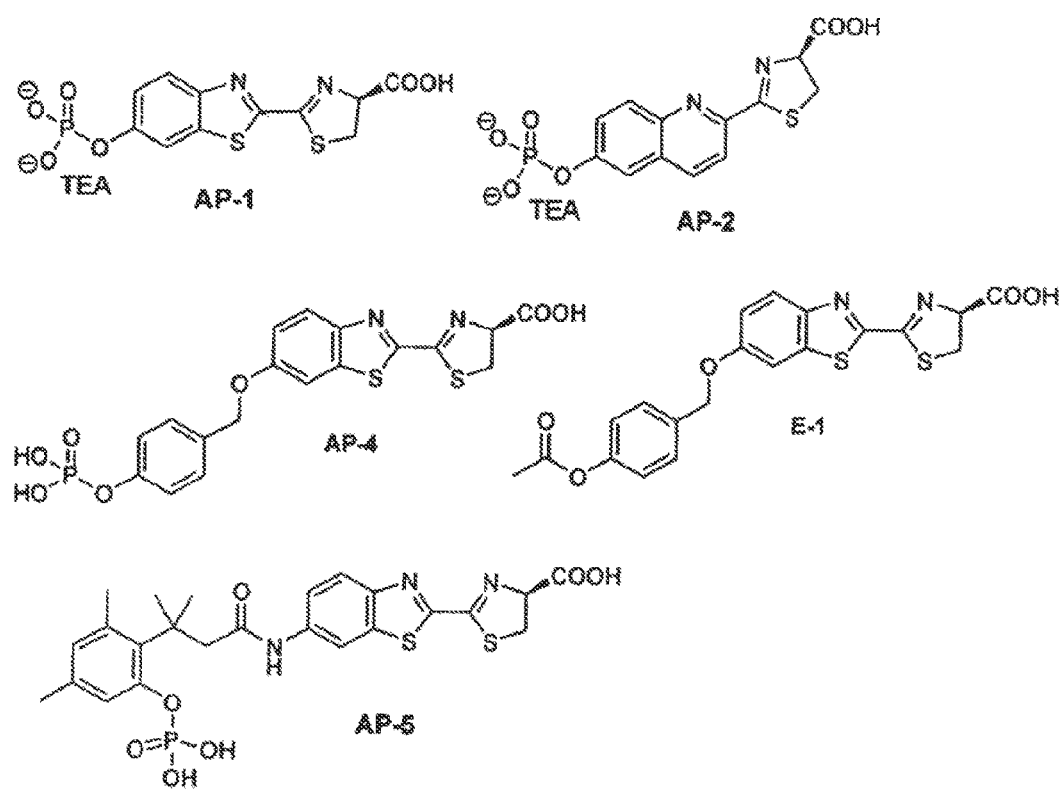
FIG. 16. Exemplary AP substrates.

Since the signal seen increased incrementally with increasing numbers of alkaline phosphate molecules, the signal was due to the action of alkaline phosphate. Exemplary AP substrates are shown in FIG. 16.

Example 5

A. Screening a Human Cytochrome P450 with Luciferin Derivatives

A number of luciferin derivatives useful to detect P450 enzymes in a two step format were prepared: A, B and C ring modifications on (4S)-4,5-dihydro-2-(6-hydroxybenzothiazolyl)-4-thiazolecarboxylic acid (D-luciferin), and A ring modifications on (4S)-4,5-dihydro-2-(6-aminobenzothiazolyl)-4-thiazolecarboxylic acid (aminoluciferin). In particular, these derivatives were prepared in an effort to identify luminogenic substrates for P450 enzymes that were not substantially active with previously prepared luminogenic substrates (U.S. published application 20040171099) or that showed stronger activity with certain enzymes. In addition, it was also of interest to identify substrates with improved selectivity for single P450 enzymes. As described below, in addition to new P450 substrates, luciferin esters were identified that are luminogenic substrates, for carboxylesterases. Luciferin derivatives were tested as substrates for each of a panel of cytochrome P450 enzymes. Derivatives useful as P450 substrates may be employed in assays to detect inhibitors for particular P450 enzymes (see FIGS. 17-18).

A two-step luminescent approach was used to measure P450 activity (Cali, *Cell Notes:* 7:2 (2003); Cali et al., *Cell Notes*, 13:8 (2005a); and Cali, *Biolouminescent P450 assays that use D-luciferin derivatives as substrates for CYP1A1, 1A2, 1B1, 2C8, 2C9, 2J2, 3A4, 3A7, 4A11, 4F3B, 4F12 and 19*, Proc. 14*th* Int. conf. Cytochromes P450, Medimond Int. Proc. (2005b)). Briefly, a P450 enzyme reacts with a luciferin derivative to leave D-luciferin as a reaction product. The D-luciferin is then detected in a luciferase reaction mixture, where luminescence in the reaction is directly proportional to the amount of D-luciferin generated. A sample that contains active P450 enzyme is compared to a control that is devoid of P450 activity. A P450-containing sample that gives a luminescent signal in significant excess over the control is scored as native without suggesting a reaction mechanism.

Materials and Methods

P450s are Supersomes™ purchased from Discovery Labware (BD/Gentest). These are membrane fractions from an insect cell expression system where the P450 has been co-expressed with P450 reductase. CYP2A6, 2B6, 2C8, 2C9, 2C19, 2E1, 2I2, 3A4, 3A7, 4F2, 4F3A, 4F3B and 4F12 also contain cytochrome b5. HLM is human liver microsomes.

In samples labeled "control", P450 Supersomes™ or HLM was replaced with a membrane preparation without P450 expression from the insect cell expression system used for the Supersomes™.

A 2× concentrated P450 reaction mixture for each P450 was prepared with an appropriate buffer and substrate:

1× buffers:
100 mM $KPO_4$, pH 7.4: cYP1A1, 1A2, 1B1, 2D6, 2E1, 3A5, 3A7, 2J2, 4F12, 19, HLM and insect cell control
50 mM $KPO_4$, pH 7.4: CYP2B6, 2C8, 2C19, 4F2, 4F3A, 4F3B.
25 mM $KPO_4$, pH 7.4: CYP2C9
200 mM $KPO_4$, pH 7.4: CYP3A4 (the $KPO_4$ is withheld from the CYP3A4 mix but added with the NADPH regeneration solution in a subsequent step).
100 mM TrisHCl, pH 7.5: CYP2A6, 2C18, 4A11.
1×substrate concentration: 50 µM.

Each Supersome™ reaction mixture contained 1 pmole P450/50 µL reaction (except CYP19 that was used at 5 pmoles/50 µL reaction where indicated). The HLM reactions contained 20 mg HLM/50 µL reaction, except where indicated otherwise. Control insect cell membranes were at 50 µg/50 µL.

A 2×NADPH regeneration solution was prepared as follows for all reactions except CYP3A4: 2.6 mM NADP+, 6.6 mM glucose-6-phosphate, 6.6 mM $MgCl_2$ and 0.8 U/ml glucose-6-phosphate dehydrogenase. A 1×NADPH regeneration solution was prepared for use with CYP3A4: 2.6 mM NADP+, 6.6 mM glucose-6-phosphate, 6.6 mM $MgCl_2$, 0.8 U/ml glucose-6-phosphate dehydrogenase and 400 mM $KPO_4$.

25 µl of each 2× P450 reaction mixture was added to 3 wells of a white opaque 96 well plate. Reactions were initiated by adding 25 µl of the 2×NADPH regeneration solution. The plate was placed in a 37° C. $H_2O$ bath for 30 minutes. The reactions were stopped and luminescence initiated by adding 50 µl of a P450-Glo™ luciferin detection reagent (LDR) (Promega Corp.). 20 units/ml of porcine or rabbit esterase (PE) was added to LDR in cases where the P450 luminogenic substrate was a carboxyl ester (see individual experiments for an indication of when esterase was included). The plate was moved to room temperature and after 20 minutes, luminescence was read as relative light units (RLU) on a plate reading luminometer (Polarstar Optima by BMG Labtech or Veritas™ by Turner Biosystems).

Results

Figure 17:
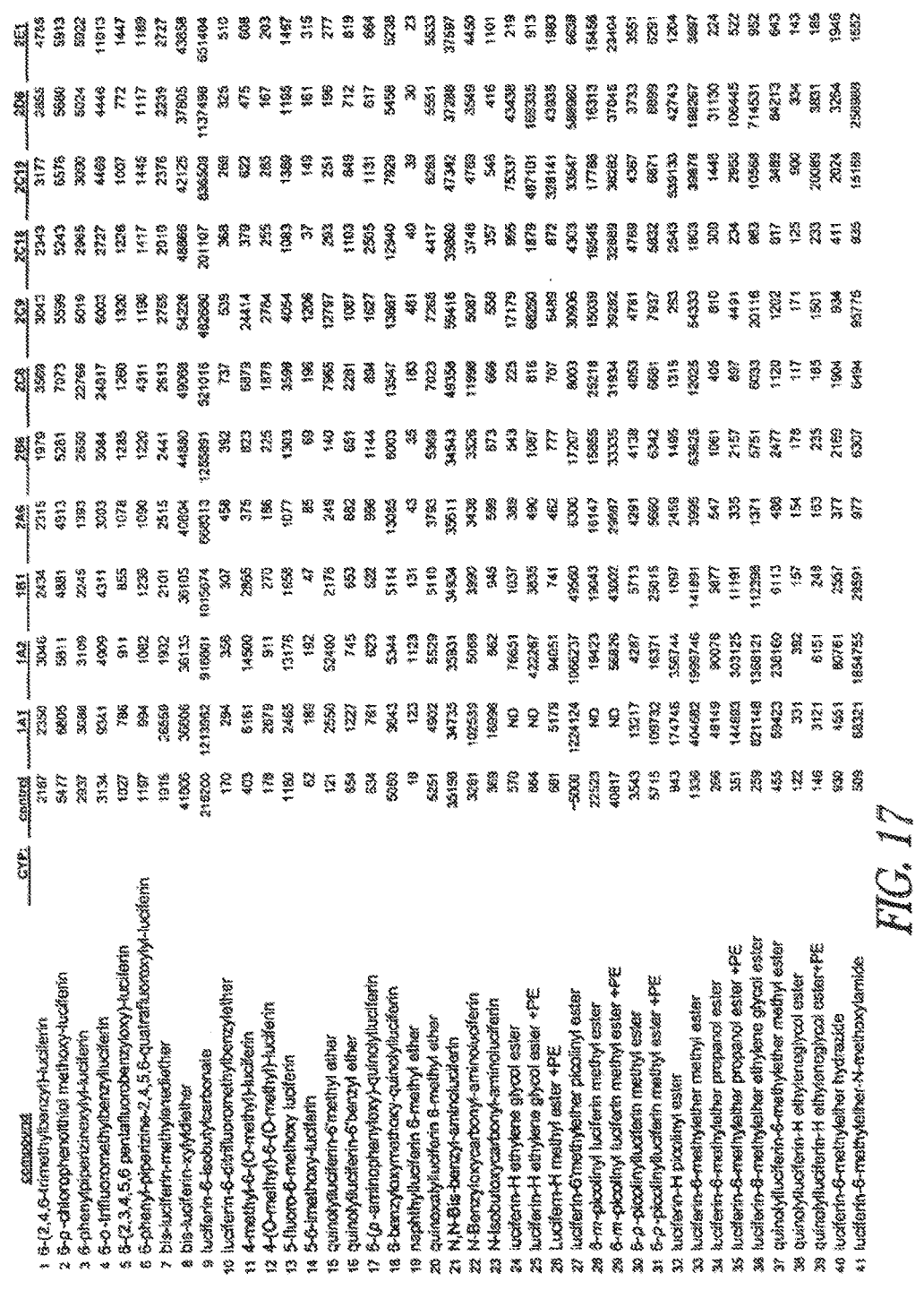
Figure 18:
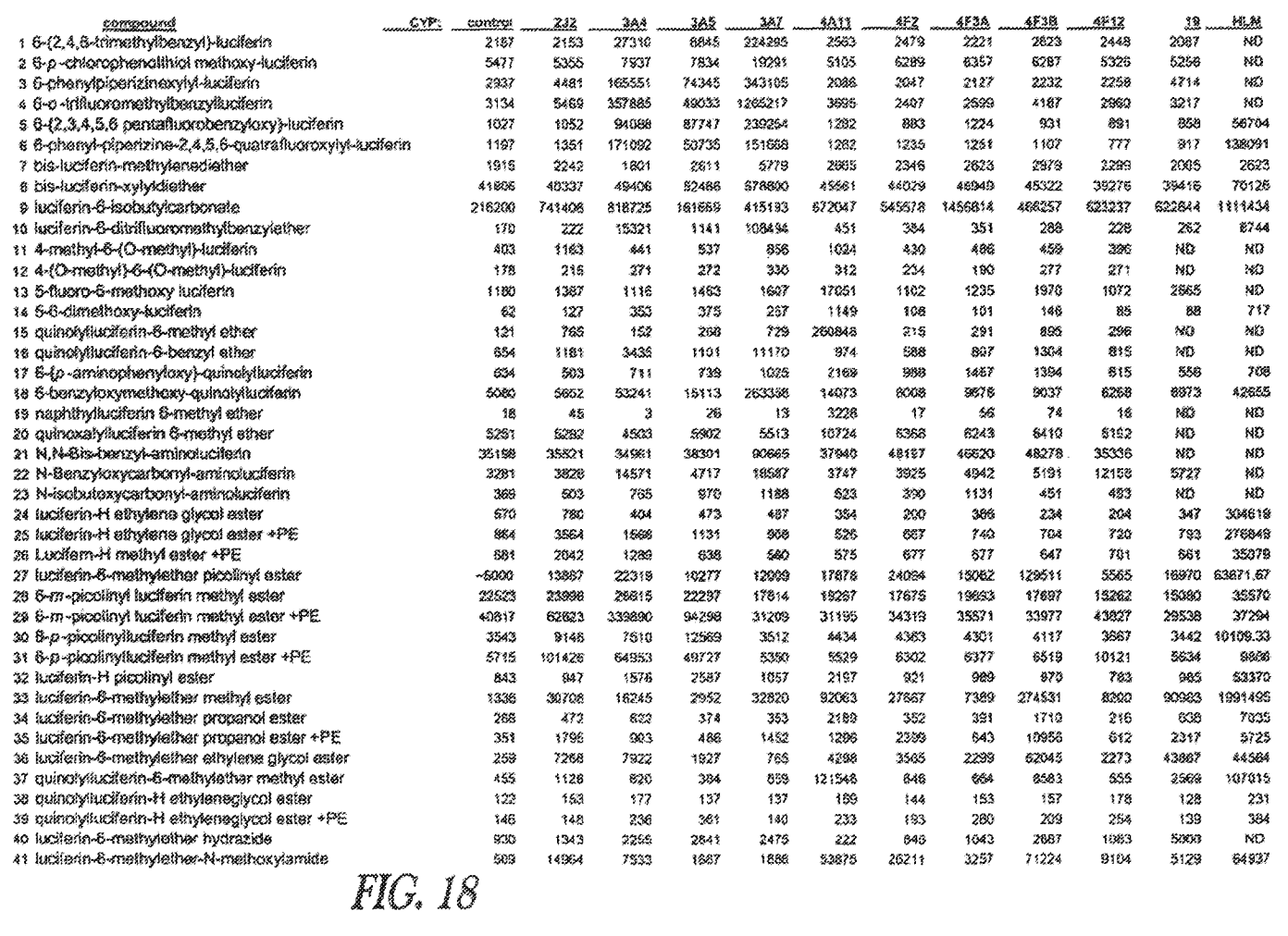

FIGS. 17-18 show data for a panel of recombinant human P450s, HLMs and a control insect cell membrane preparation devoid of P450 activity with 41 different luciferin derivatives. P450s that converted a derivative to a luminogenic product are identified as those that gave signals that were greater than the control samples. P450 activity against a derivative is also indicated by signals from HLM reactions that were greater than control. Lines 11-14 of FIGS. 17-18 show data for 4 different luciferin derivatives with two A ring modifications. The derivative in line 11 is modified at positions 4 and 6 and is a preferred substrate for isozymes 1A1, 1A2, 2C8 and 2C9. The derivative shown in line 12 is also modified at positions 4 and 6, and is a preferred substrate for isozymes 1A1, 1A2, 2C8 and 2C9. The derivative in line 13 is modified at positions 5 and 6, and is a preferred substrate for isozymes 1A2 and 4A11, and to a lesser degree, a substrate of 2C8 and 2C9. The derivative in line 14 is modified at positions 5 and 6, and is a preferred substrate for isozymes 2C9 and 4A11.

Lines 1-10 of FIGS. 17-18 give RLU for a panel of cytochrome P450 enzymes with 10 different single A ring modified luciferin derivatives. All ten derivatives were substrates for P450s, but had different enzyme selectivity profiles The compounds in lines 7 and 8 are bisluciferins.

Lines 15-20 of FIGS. 17-18 give RLU for a panel of P450 enzymes with luciferin derivative, with a A ring modification and a B ring modification. Quinolylluciferin 6-methyl ether a preferred substrate for 1A2 and 4A11, while quinolylluciferin 6-benzyl ether was a preferred substrate tor 3A7, and to a lesser degree a substrate for 3A4 and 2C8. Naphthylluciferin 6-methyl ether and quinoxalylluciferin 6-methyl ether are a substrate for 4A11.

Lines 21-23 of FIGS. 17-18 show data for aminoluciferin derivatives. Two of the derivatives were a preferred substrate for 1A1, while the other derivative was a substrate for 3A7, and to a lesser degree a substrate for 2C8 and 2C9, although background RLUs for that derivative were high.

Lines 24-36 of FIGS. 17-18 show data for derivatives with a C ring and a A ring modification. Derivatives with C and A ring modifications showed substantial signals above controls with certain P450 enzymes (e.g. CYP1A1, CYP1A2, CYP2C19, CYP2D6) It was also demonstrated with some of these derivatives (luciferin H ethyleneglycol ester, 6-m-picolinyl luciferin methyl ester, 6-p-picolinyl luciferin methyl ester, and luciferin 6-methylether propanol ester) that the addition of esterase (+PE) causes substantially more light to be produced than without PE. This indicates that P450s react at the site of the A-ring modification and that the carboxyl esters (C-ring modifications) are cleaved by carboxyl esterase activity (PE). With the addition of a C-ring modification to an A ring derivative it was possible to alter the P450 enzyme selectivity profile. For example, the compounds in lines 33-36, all C-ring derivatives of luciferin 6 methyl ether (an A ring derivative) showed substantial activity with CYP2D6, whereas luciferin 6-methyl ether has an extremely low activity with CYP2D6.

The addition of a picolinyl to the A or C ring of D-luciferin yielded substrates with different specificities for P450 isozymes and RLUs (lines 27 and 28-32 in FIGS. 17-18).

The RLU for some reactions where RLU is less than robust may be enhanced by the addition of esterase (lines 24-25, 28-29, 30-31, 34-35, and 38-39 in FIG. 17-18).

Data for other derivatives and P450 enzymes are also shown in FIGS. 20-26, 28-37A, and 38-50.

Showing activity for P450s for which no adequate luminogenic substrate currently exists were 5,6-dimethoxyluciferin, 6(p-aminophenyloxy)-quinolylluciferin and luciferin-6-isobutylcarbonate (lines 14, 17 and 9 in FIGS. 17-18). CYP2A6, CYP2E1 and CYP2C18 are enzymes that reacted with these compounds but not with previously available luminogenic compound v 5,6-dimethoxyluciferin and 6(p-aminophenyloxy)-quinolylluciferin did not produce large luminescent signals with any P450, indicating that the enzymes that react with these substrates do so at a slow rate. Luciferin 6-isobutylcarbonate was non-selective in that it gave large luminescent signals with several P450s. This compound also gave a large background signal (minus P450 control samples) suggesting that it is chemically unstable in a way that gives rise to free D-luciferin.

Figure 47:
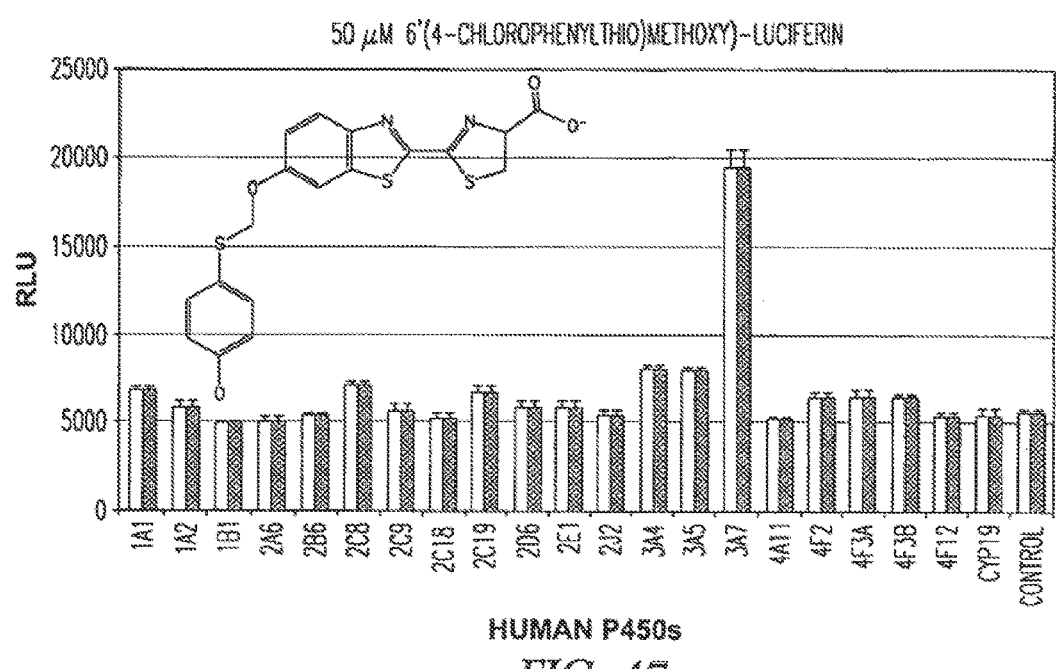
FIG. 47. A graphical representation of RLU for reactions containing one of a panel of P450 enzymes and a luciferin derivative, 6'(4-chlorophenylthio)methoxyluciferin. Reactions contained 1 pmol of P450 or 5 pmol CYP19.
Figure 48:
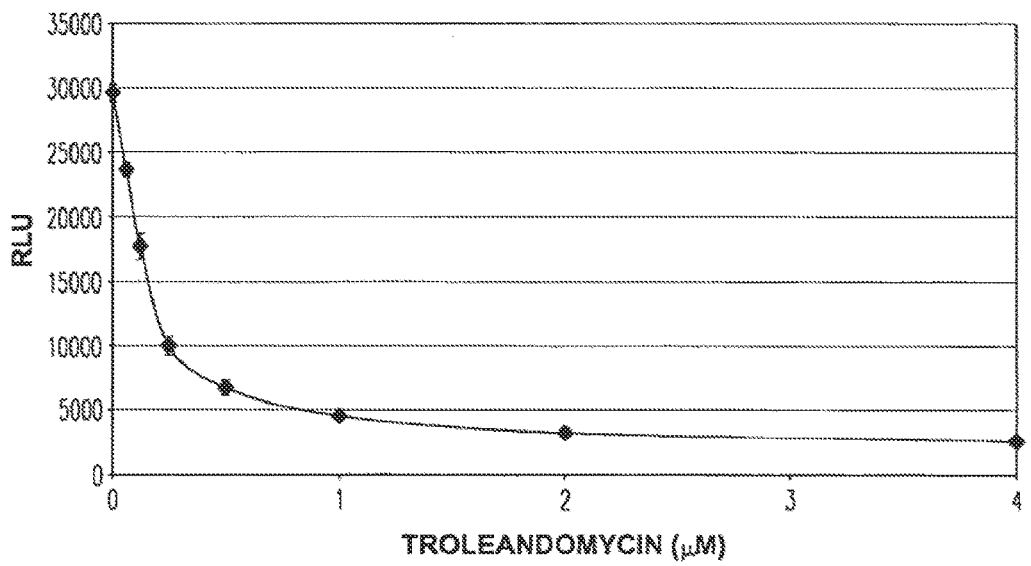
FIG. 48. Inhibition of CYP3A4 activity by troleanomycin in a reaction with luciferin-$F_5$BE (6'-(2,3,4,5,6pentafluorobenzyloxy)-luciferin).
Figure 49:
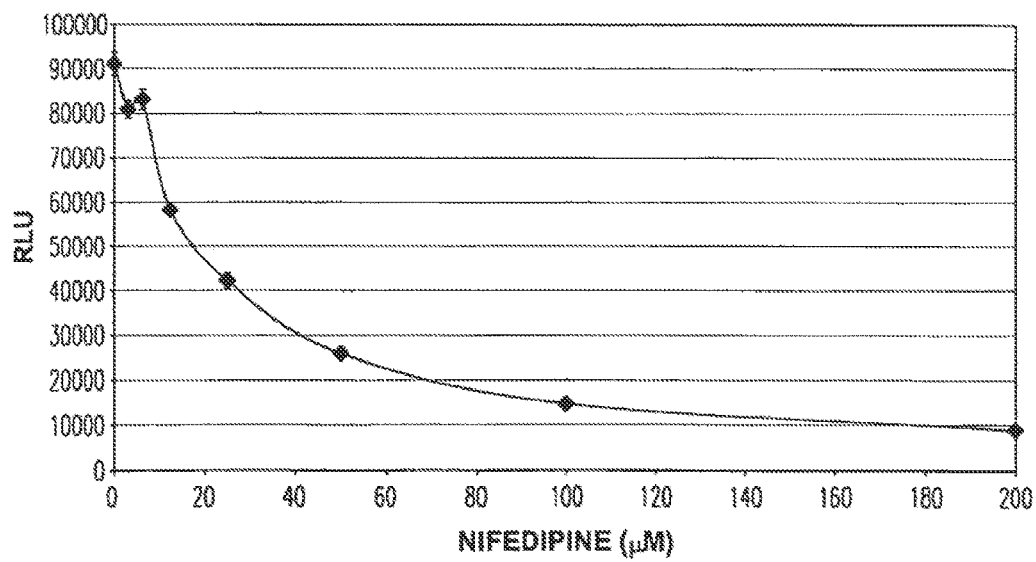
FIG. 49. Inhibition of CYP3A4 activity by nifedipine in a reaction with luciferin-PPX4FE (6'-(2,3,4,6-tetrafluoro-5-((4-phenylpiperazin-1-yl)methyl)benzyloxy)-luciferin).

Some compounds showed good selectivity for a single P450 enzyme over other P450 enzymes. Bis-luciferin-methylenediether and bis-luciferin-xylyldiether were selective for CYP1A1 or CYP3A7, respectively. The selectivity of the latter compound for CYP3A7 indicates that it would be a highly selective probe substrate for CYP3A7, 6'-chlorophenylthiol-methoxy-luciferin (line 2 in FIGS. 17-18) also showed selectivity for CYP3A7 (FIG. 47). CYP3A7 selective substrates may be particularly useful in fetal and neonatal liver samples where CYP3A7 is the dominant P450 and in pediatric samples where CYP3A7 is gradually replaced over time by CYP3A4 (Stevens et al., *J. Pharm. Exp. Ther.*, 307: 573 (2003)). With these substrates CYP3A7 activity could be selectively measured against a background of CYP3A4 and other P450 activities. The selectivity of bis-luciferin-methylenediether for CYP1A1 would be particularly useful for differentiating CYP1A1 activity from other P450s, especially CYP1A2 and CYP1B1, which react with many of the same substrates as CYP1A1 and are also co-expressed with CYP1A1 in certain tissues (Shimade et al., *Drug Metab. Dispos.*, 29:617 (1997)). Additional compounds were synthesized that showed improved selectivity for a single P450. Notably, N-benzyloxycarbonyl aminoluciferin and N-isobutoxycarbonyl aminoluciferin showed strong selectivity for CYP1A1 (lines 22-23 in FIGS. 17-18).

Figure 45:
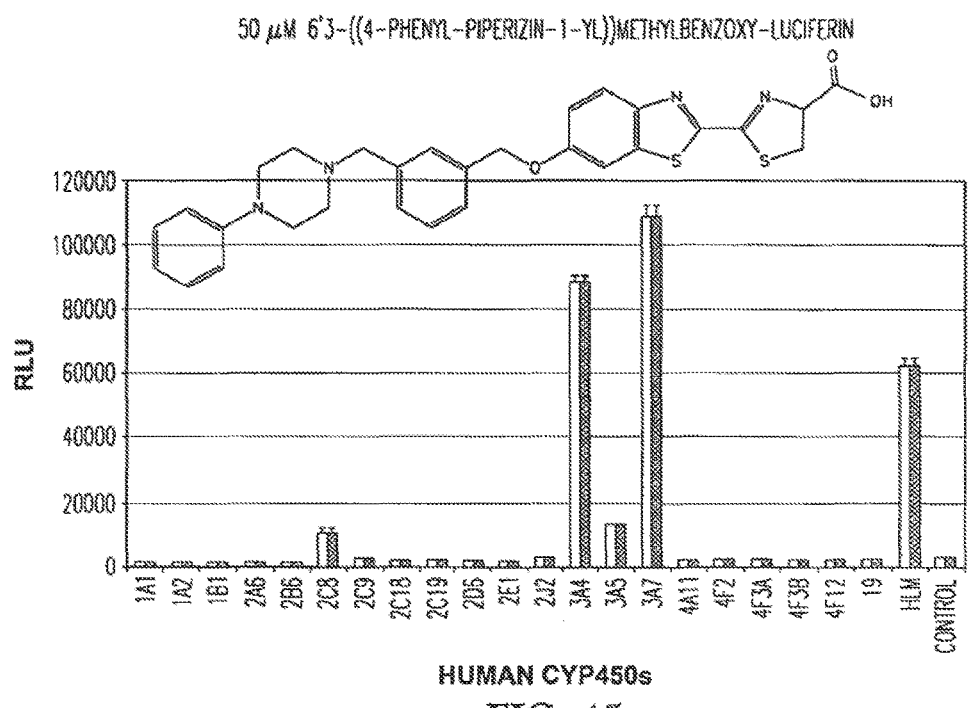
FIG. 45. A graphical representation of RLU for reactions containing one of a panel of P450 enzymes and a luciferin derivative, 6'-(3-((4-phenylpiperizin-1-yl))methyl)benzyloxy)-luciferin. Reactions contained 1 pmol P450 or 20 µg HLM.
Figure 46:
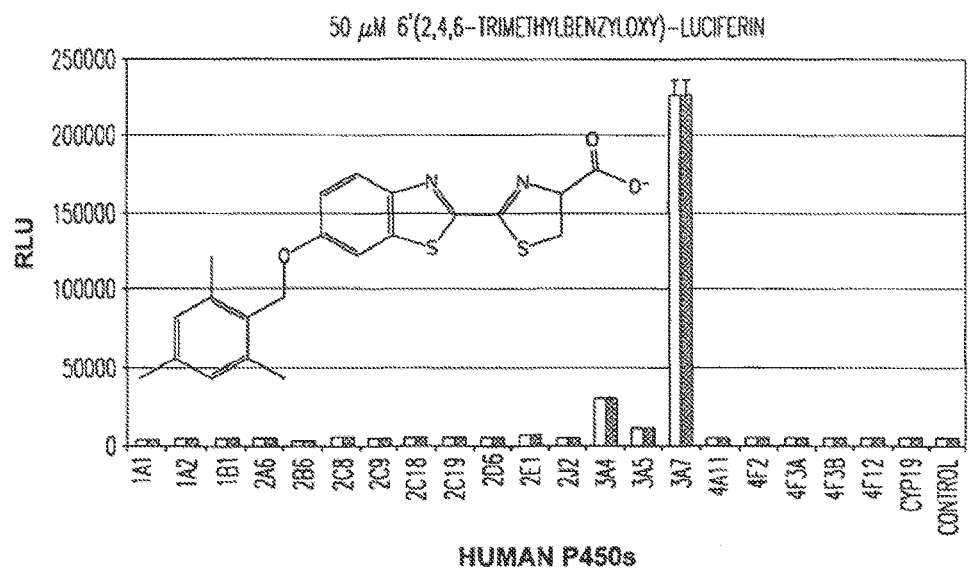
FIG. 46. A graphical representation of RLU for reactions containing one of a panel of P450 enzymes and a luciferin derivative, 6'-(2,4,6-trimethylbenzyloxy)-luciferin. 1 pmol of P450 or 5 pmol CYP19.

The non-carboxylic acid luciferins, luciferin-6-methylether hydrazide and luciferin-6-methylether-methoxylamide showed good selectivity for CYP1A2 over the other P450s tested (lines 40 and 41 in FIGS. 17-18). 6(2,5-ditrifluoromethylbenzyloxy)-luciferin, 6'-(o-trifluoromethylbenzyloxy)-luciferin, 6'(2,3,4,5,6 pentafluoro-benzyloxy)-luciferin, 6'-(2,3,4,6-tetrafluoro-5-((4-phenylpiperizin-1-yl)methyl)benzyloxy)-luciferin, 6-(3-((4-phenyl-piperizin-1-yl)methyl)benzyloxy)-luciferin, 6'(2,4,6-trimethylbenzyloxy)-luciferin and 6benzyloxymethoxy-quinolylluciferin were selective for three members of the CYP3A subfamily, CYP3A4, CYP3A5 and CYP3A7 (FIGS. 45-46). This was an improvement in selectivity for CYP3A over benzyloxy luciferin, which was previously shown to react also with CYP4F12 (Cali, 2005b).

The human CYP3A4 enzyme is the most prominent drug-metabolizing P450. To determine whether certain luminogenic substrates for CYP3A4 had improved properties over the previously identified 3A4 substrates, luciferin 6-benzyl ether and luciferin 6'3-picolinyl ether, some luciferin derivatives were synthesized and tested for improved selectivity, reduced background luminescence and increased turnover rate, which leads to brighter signals. The benzyl and picolinyl ethers cross reacted significantly with human 3A7 and the benzyl ether also cross reacted with human CYP4F12. The benzyl ether also showed a high background luminescence that could be from an inefficient light generating reaction with luciferase that occurs even in the absence of debenzylation by P450.

To improve substrates to assay for CYP3A4, e.g., substrates with increased stability, reduced background and/or useful in cell-based assays, luciferin derivatives, some with halogens were prepared (lines 5 and 6 in FIGS. 17-18). For instance, modifications to benzyl on luciferin-6-benzylether, e.g., including adding halogen, alkyl, OH or $NH_2$ to one or more ring atoms, may lead in lower background luminescence. Thus, the following compounds may have increased specificity and/or reduced background awl may be useful in cell-based assays.

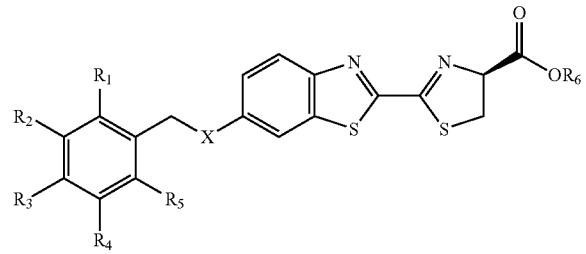

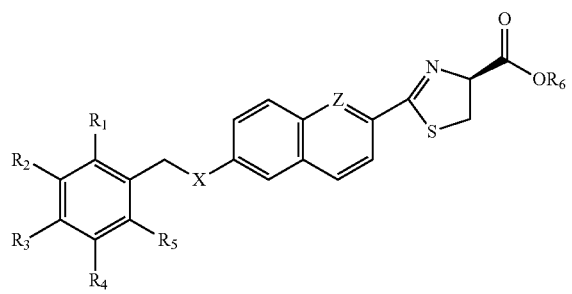

X=O or NH
R1-R5 are independently H, F or

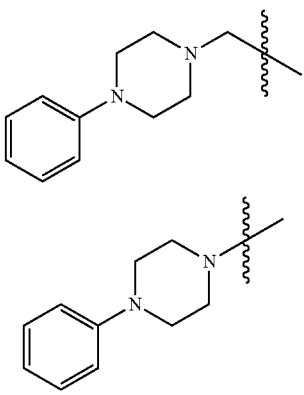

R6 is H, lower alkyl, hydroxyalkyl, or short PEG
For instance, the following were synthesized:

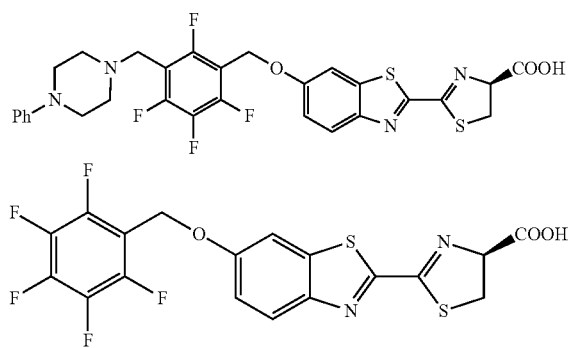

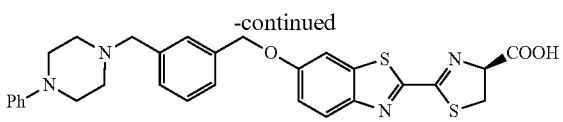

Results

6'(3-((4-phenylpiperizin-1-yl))methyl)benzyloxy) luciferin (6-phenylpiperazinexylyl-luciferin, line 3 in FIGS. 17-18) did not cross react with 4F12, and its reaction with 3A4 was insensitive to DMSO at commonly used concentration. The background luminoscence for 6-phenyl piperazinexylyl-luciferin was lower than luciferin-6-benzylether (about 2200 versus about 5000 RLU on a BMG luminometer), and signals for 6-phenyl piperazinexylyl-luciferin were similar to luciferin-6-benzylether. Moreover, 6-phenyl piperazinexylyl-luciferin was competitive at 2 of the 5 substrate binding sites on CYP3A4 compared to luciferin-6-benzylether, which was only competitive at 1 site. Initial results indicated that 6-phenyl piperazinexylyl-luciferin can be employed in cell-based assays.

6(2,3,4,5,6-pentafluorobenzyl)-luciferin had lower background luminescence than luciferin-6-benzylether and 6-phenyl piperazinexylyl-luciferin (about 900 RLU on a BMG luminometer). The fluorines may stabilize the compound so that there is less non-enzymatic degradation or reduce the preference of luciferase for the compound compared to luciferin-6-benzylether. Thus, 6-phenyl piperazinexylyl-luciferin may be further stabilized by adding fluorines to the proximal benzyl group, resulting in a compound with even lower background luminescence.

6(2,4,6 trimethylbenzyl)-luciferin, 6-phenylpiperizinexylyl-luciferin, 6-o-trifluoromethylbenzyl luciferin, 6(2,3,4,5,6 pentafluorbenzyloxy)-luciferin and 6-phenylpiperizine-2,3,5,6-quatrafluoroxylyl-luciferin showed substantial activity with CYP3A4 and did not show substantial cross reactivity with CYP4F12 (lines 1-3 and 5-6 of FIGS. 17-18). Some of these compounds showed reduced background luminescence and stronger signals with human CYP3A4. Lower background luminescence from the compounds provides for improved CYP3A assay sensitiviiy.

Luciferin-6-trifluoromethylbenzylether showed enhanced selectivity for CYP3A5 (line 10 in FIGS. 17-18). 4-methyl-6-(O-methyl)-luciferin and 4-(O-methyl)-6-(O-methyl)-luciferin (lines 11-12 in FIGS. 17-18) showed enhanced selectivity for 1A2, 2C8 and 2C9 in that CYP4A11 did not react with these compounds in contrast to a previously described compound, luciferin-6-methylether and quinolyl luciferin-6-methyl ether (line 15 in FIGS. 17-18) showed enhanced selectivity for CYP4A11 compared luciferin-6-methylether.

B. Screening Inhibitors of CYP3A4, CYP2D6 and CYP2C19 with Luciferase Derivative Materials and Methods CYP3A4, CYP2D6 and 2C19 Supersomes™ were purchased from Discovery Labware (BD/Gentest). "Insect cell control" is a membrane preparation without P450 expression from the expression system used for the Supersomes™.

A 4× concentrated P450 reaction mature for each P450 was prepared with an appropriate buffer and substrate.

4× CYP2D6 reaction mix: 400 mM KPO$_4$ (pH 7.4), 140 µM luciferin-6-methylether ethylene glycol ester (line 36 in FIGS. 17-18), 10 pmoles CYP2D6 Supersomes™/ml.

4×CYP2C19 reactions mix: 200 mM KPO$_4$ (pH 7.4), 100 µM luciferin-H ethylene glycol ester (lines 24 and 25 in FIGS. 17-18), 10 pmoles CYP2C19 Supersomes™/ml.

4× CYP3A4 reaction mix: 200 µM (6(2,3,4,5,6-pentafluorbenzyloxy)-luciferin or 6-phenylpiperizinexylyl-luciferin (lines 3 and 5 in FIGS. 17-18), 40 pmoles CYP3A4 Supersomes™/ml.

4× control reaction mix for CYP2D6: 400 mM $KPO_4$ (pH 7.4), 140 µM luciferin-6-methylether ethylene glycol ester, 100 µg/ml mg Supersome™ insect cell control membranes.

4× control reaction mix for CYP2C19: 200 mM $KPO_4$ (pH 7.4), 100 µM luciferin-H ethylene glycol ester, 100 µg/ml Supersome™ insect cell control membranes.

4× control reaction mix for CYP3A4 reaction mix: 200 µM 6(2,3,4,5,6-pentafluorbenzyloxy)-luciferin or 6-phenylpiperizinexylyl-luciferin (lines 3 and 5 in FIGS. 17-18), 400 µg/ml Supersomes™ insect cell control membranes. Luciferin-6-methylether ethylene glycol ester and luciferin-H ethylene glycol ester were diluted from 10 mM stock solutions dissolved in acetonitrile, the CYP3A4 substrates, from 50 mM stock solutions dissolved in DMSO.

2× NADPH regeneration solutions were prepared as described above. Test inhibitors were prepared at a 4× concentration. They were diluted in $H_2O$ from stock solution as shown in Table 34. A dilution series of each 4× inhibitor was prepared in $H_2O$ plus an amount of the vehicle from the stock equivalent to what was earned into the most concentrated 4× solution. 0 inhibitor is the stock solution vehicle diluted in $H_2O$. 12.5 µl of each dilution of 4× inhibitor was added to 3 wells of a white opaque 90 well for the P450 reactions and 3 wells for the control reactions. 12.5 µl of each 4× P450 reaction mixture or control reaction mixture was added to the appropriate wells with the 4× inhibitors or 0 inhibitor vehicle controls. Plates were placed in a 37° C. $H_2O$ bath for 10 minutes. Reactions were then initiated by adding 25 µl of the 2× NADPH regeneration solution. Plates were incubated in the 37° C. $H_2O$ bath for 30 minutes The reactions were stopped and luminescence initiated by adding 50 µl of P450-Glo™ luciferin detection reagent (Promega Corporation) with 20 units/ml of porcine esterase added per reaction. Plates were moved to room temperature and after a 20 minute wait luminescence was read as RLU on a plate reading luminometer (Polarstar Optima by BMG Labtech or Veritas™ by Turner Biosystems). Luminescence of the control reactions were subtracted from P450 reactions and curve fits (sigmoidal dose response with variable slope) and $IC_{50}$ calculations were performed using the program Graph-Pad PRISM™. Each inhibitor caused a hyperbolic, dose dependent inhibition with a characteristic $IC_{50}$ (Tables 35-30). This data provides examples of how two luciferin derivatives each having a left ring modification and a C ring modification can be used in reactions with two different P450 enzymes to test for P450 inhibition.

TABLE 35

| CYP inhibitor | mM stock solution | carrier | 4× (dilution into water), mM | 1× carrier conc |
|---|---|---|---|---|
| terfedadine | 10 | DMSO | 0.1 | 0.25% DMSO |
| quinidine | 20 | $H_2O$ | 4 | |
| bufuralol | 20 | $H_2O$ | 4 | |
| verapamil | 20 | $H_2O$ | 4 | |
| clotrimazole | 10 | DMSO | 4 | 10% DMSO |
| nifedipine | 50 | DMSO | 4 | 2% DMSO |
| nicardipine | 150 | DMSO | 4 | 0.67% DMSO |
| Troleandomycin | 10 | Acetonitrile | 0.4 | 1% acetonitile |
| bupropion | 150 | DMSO | 4 | 0.67% DMSO |

TABLE 35-continued

| CYP inhibitor | mM stock solution | carrier | 4× (dilution into water), mM | 1× carrier conc |
|---|---|---|---|---|
| haloperidol | 50 | DMSO | 0.1 | 0.05% DMSO |
| quinine | 125 | $H_2O$ | 4 | |
| debrisoquine | 100 | $H_2O$ | 4 | |
| pindolol | 100 | DMSO | 4 | 1% DMSO |
| disopyramide | 100 | $H_2O$ | 4 | 1.6% acetonitrile |
| (s)-(+)-mephenytoin | 50 | Acetonitrile | 3.2 | |
| Fluvoxamine | 5 | $H_2O$ | 0.004 | |
| isoniazid | 50 | $H_2O$ | 1.6 | |

TABLE 36

| Inhibitor | CYP2C19 $IC_{50}$ (µM) | CYP2D6 $IC_{50}$ (µM) | CYP3A4 6(2,3,4,5,6-pentafluor-benzyloxy)-luciferin $IC_{50}$ (µM) | CYP3A4 6-phenyl-piperizinexylyl-luciferin $IC_{50}$ (µM) |
|---|---|---|---|---|
| terfedadine | — | 3.6 | — | — |
| quinidine | — | 0.01 | — | — |
| bufuralol | — | 37 | — | — |
| verapamil | — | 67 | — | — |
| clotrimazole | — | 22.6 | — | — |
| nifedipine | — | 131 | — | 19.8 |
| nicardipine | — | 8 | — | — |
| troleandomycin | — | — | 0.14 | — |
| bupropion | — | 33 | — | — |
| haloperidol | — | 18 | — | — |
| quinine | — | 11 | — | — |
| desbrisoquine | — | 77 | — | — |
| pindolol | — | 76 | — | — |
| disopyramide | — | 220 | — | — |
| (s)-(+)-mephenytoin | 69 | — | — | — |
| Fluvoxamine | 0.25 | — | — | — |
| isoniazid | 76 | — | — | — |

C. Luciferin Derivatives for P450 Assays

A number of luciferin derivatives useful to detect P450 enzymes in a two step format were prepared: 6' ether modifications on (4S)-4,5-dihydro-2-(6-hydroxybenzothiazolyl)-4-thiazolecarboxylic acid (D-luciferin), 6' modifications on (4S)-4,5-dihydro-2-(6-aminobenzothiazolyl)-4-thiazolecarboxylic acid (aminoluciferin), 6' modifications on quinolyl luciferin and carboxyl esters of D-luciferin, and 6' modified D-luciferins and 6' modified quinolyl luciferins. In particular, these derivatives were prepared in an effort to identify luminogenic substrates for P450 enzymes that were not substantially active with previously prepared luminogenic substrates (U.S. published application 20040171099) or that showed stronger activity with certain enzymes. In addition, it was also of interest to identify substrates with improved selectivity for single P450 enzymes. As described below, in addition to new P450 substrates, luciferin esters were identified that are luminogenic substrates for carboxylesterases.

Human P450 enzymes CYP2D6 and CYP2C19 oxidize numerous therapeutic drugs currently in use (Rendic, *Drug Metab. Rev.* 34: 83-448 (2002)). Drug development efforts therefore include screens of new chemical entities against CYP2D6 and CYP2C19 for modulatory effects of the compounds on the P450 activities. Thus, there is a need for robust assays for these enzymes.

Materials and Methods

Figure 20:
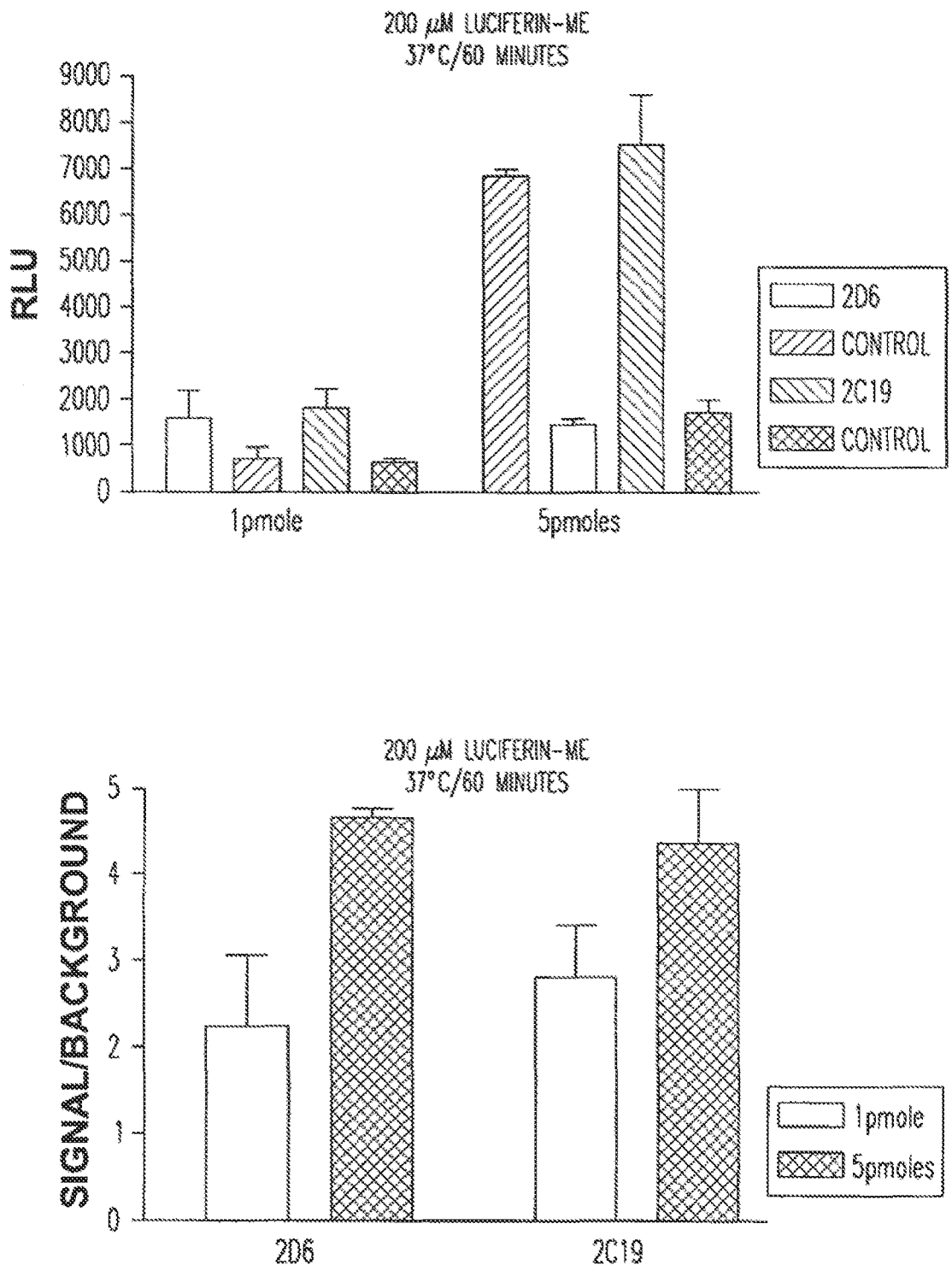
FIG. 20. A graphical representation of CYP2D6 and CYP2C19 activity against luciferin-ME.
Figure 21:
FIG. 21. A graphical representation of P430 activities with luciferin-ME methyl ester.
Figure 22:
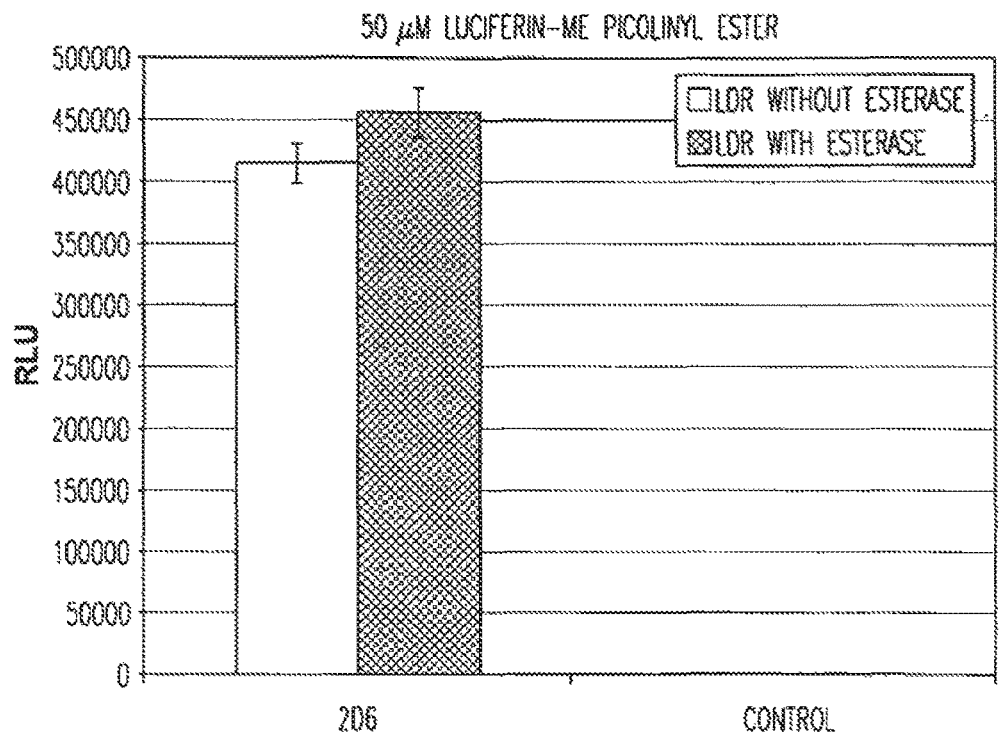
FIG. 22. A graphical representation of CYP2U6 activity with luciferin-ME picolinyl ester with and without esterase. Reactions contained 1 pmol CYP2D6.
Figure 23:
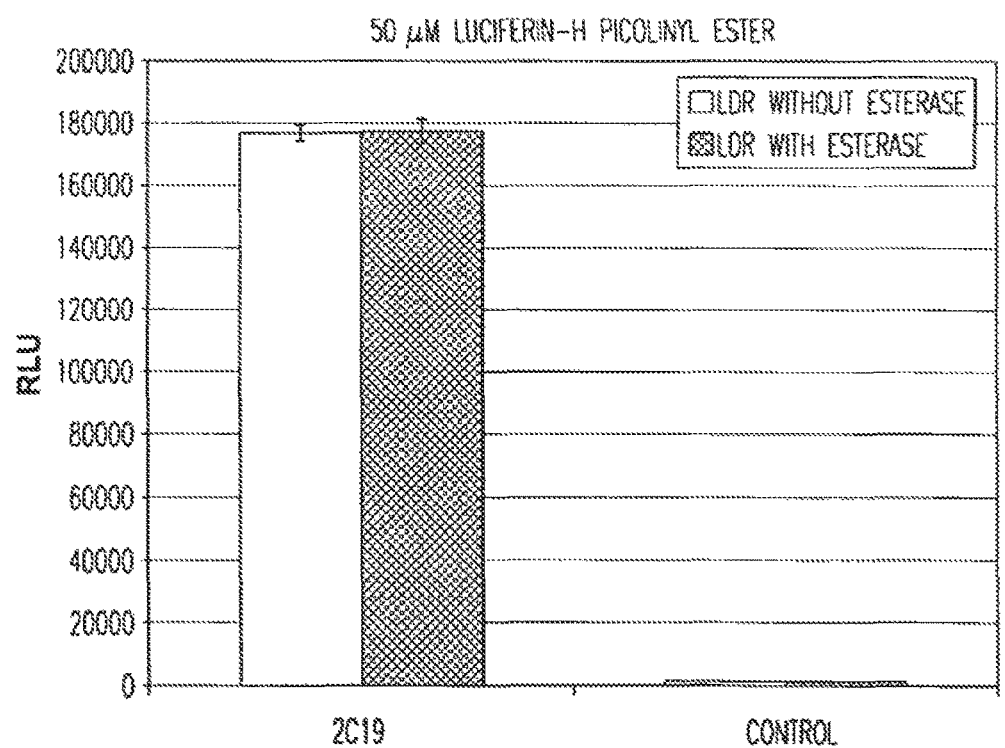
FIG. 23. A graphical representation of CYP2C19 activity with luciferin-H-picolinylester with and without esterase. Reactions contained 1 pmol CYP2C19.
Figure 24:
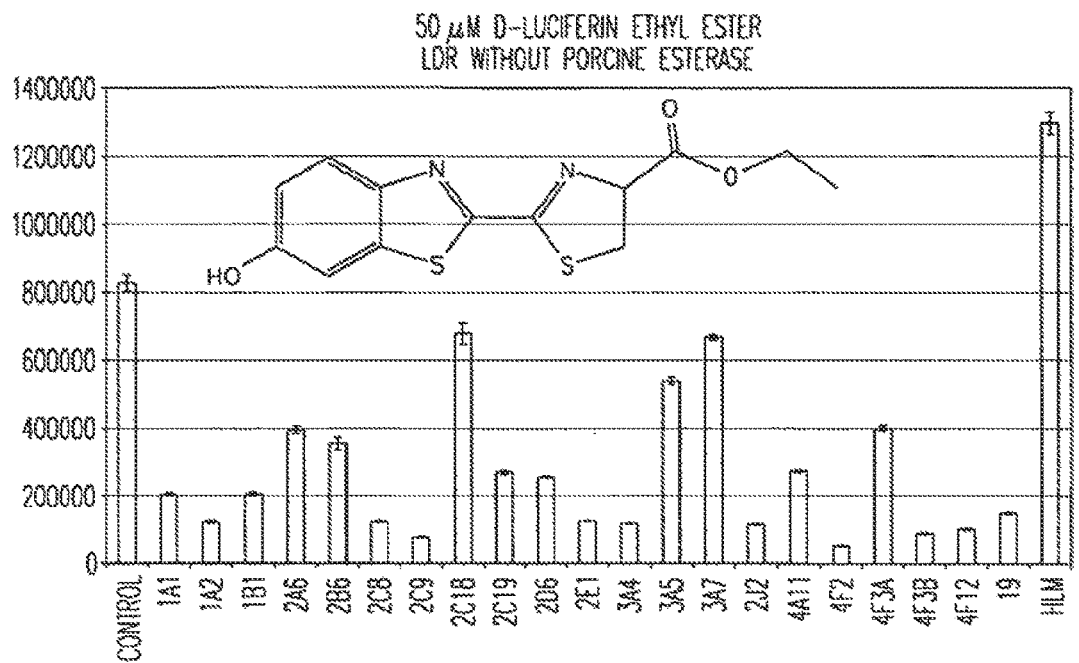
FIG. 24. A graphical representation of RLU for reactions containing one of a panel of P450 enzymes and a luciferin derivative. D-luciferin ethyl ester with a C ring modification. Reactions contained 1 pmol P450.
Figure 25:
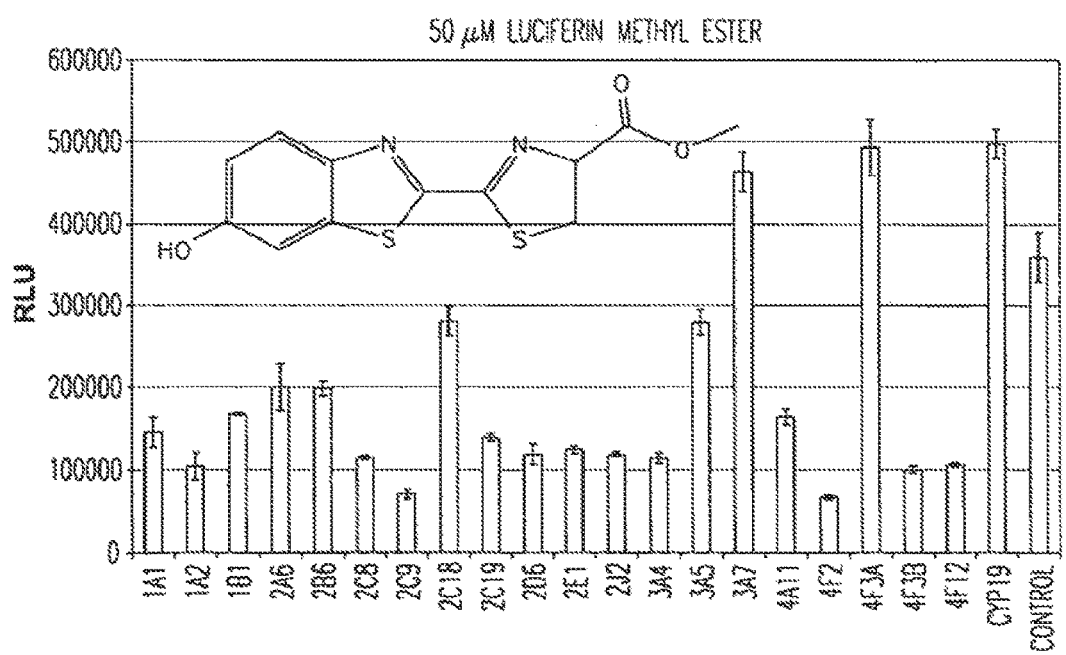
FIG. 25. A graphical representation of RLU for reactions containing one of a panel of P450 enzymes and a luciferin derivative, luciferin methyl ester with a C ring modification. Reactions contained 1 pmol P450 or 5 pmol CYP19.
Figure 26:
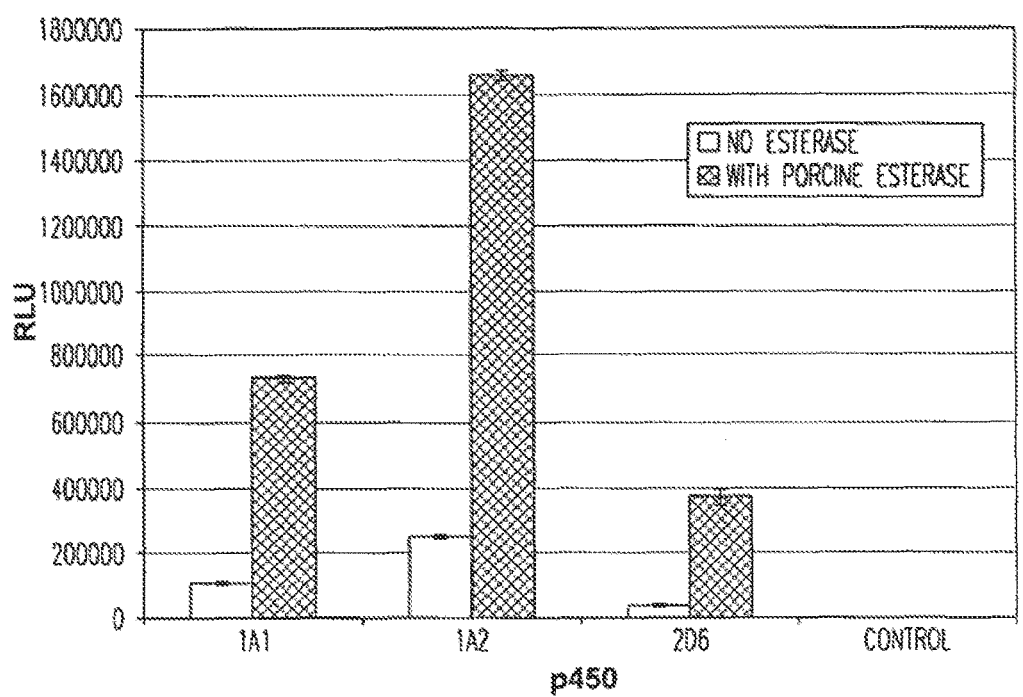
FIG. 26. Graphical representation of RLU for reactions containing one of three P450 enzymes and luciferin-ME-ethylene glycol ester, with or without esterase.
Figure 27A:
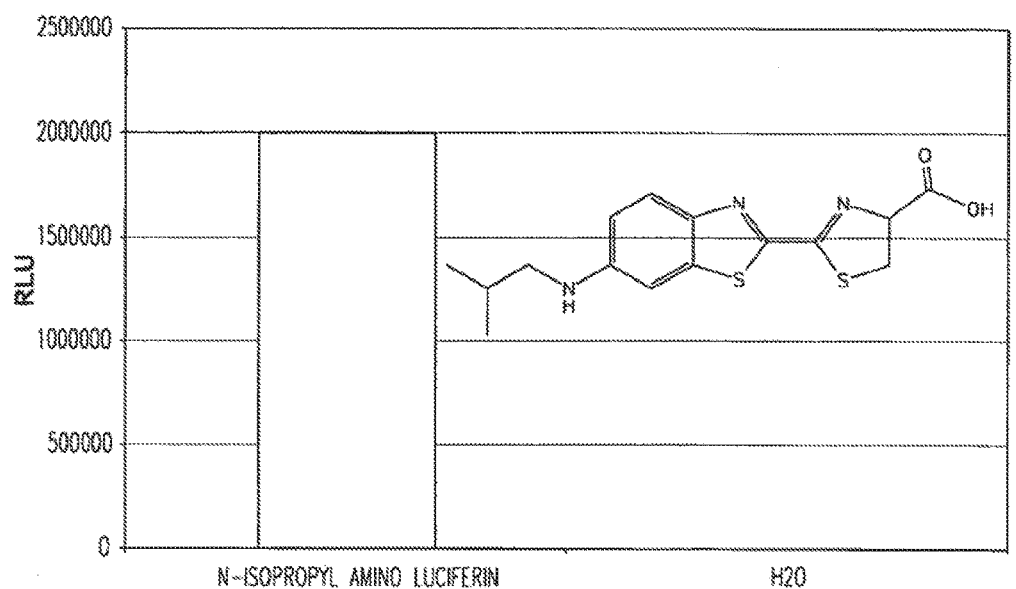
FIG. 27A. A graphical representation of RLU for an aminoluciferin derivative (N-isopropylaminoluciferin) (50 µM) in a luciferase reaction.
Figure 27B:
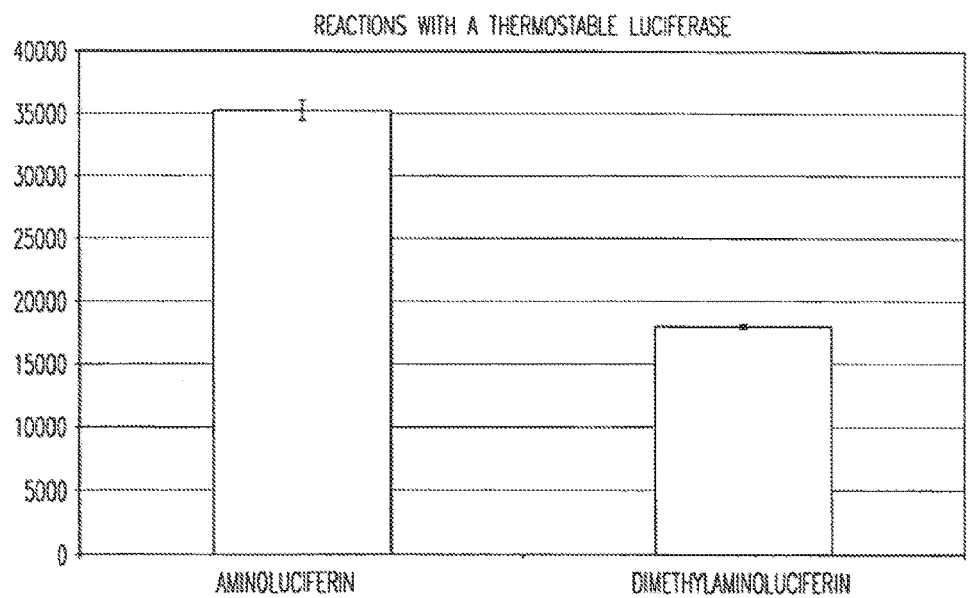
FIG. 27B. A graphical representation of RLU for an aminoluciferin derivative (dimethyl aminoluciferin; 100 µM) and aminoluciferin (100 µM) in a luciferase reaction.
Figure 28:
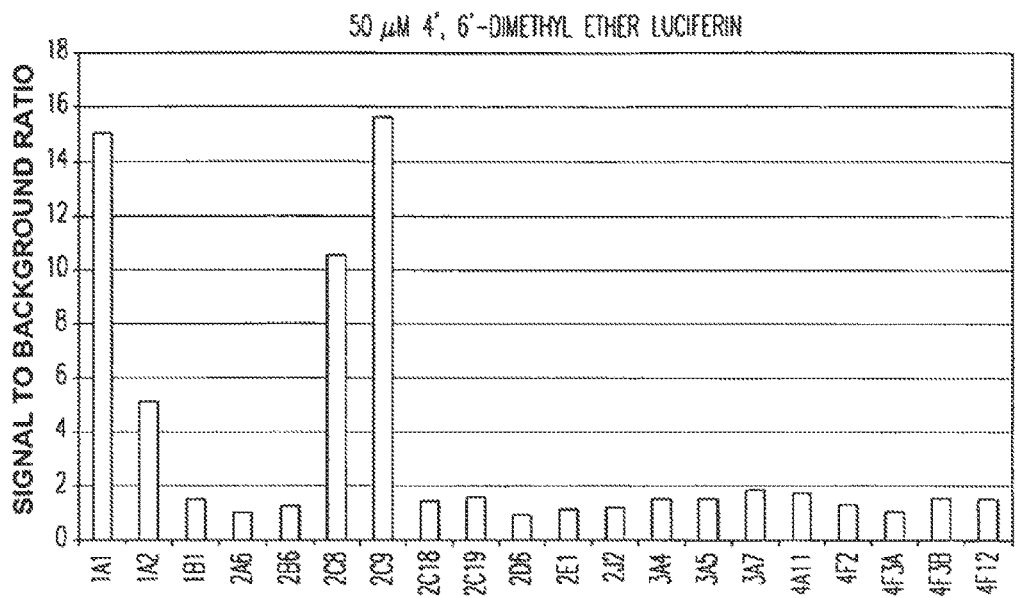
FIG. 28. A graphical representation of signal to background ratio for a reaction between 4',6' dimethyl ether luciferin and each of a panel of P450 enzymes. Reactions contained 1 pmol P450.
Figure 29:
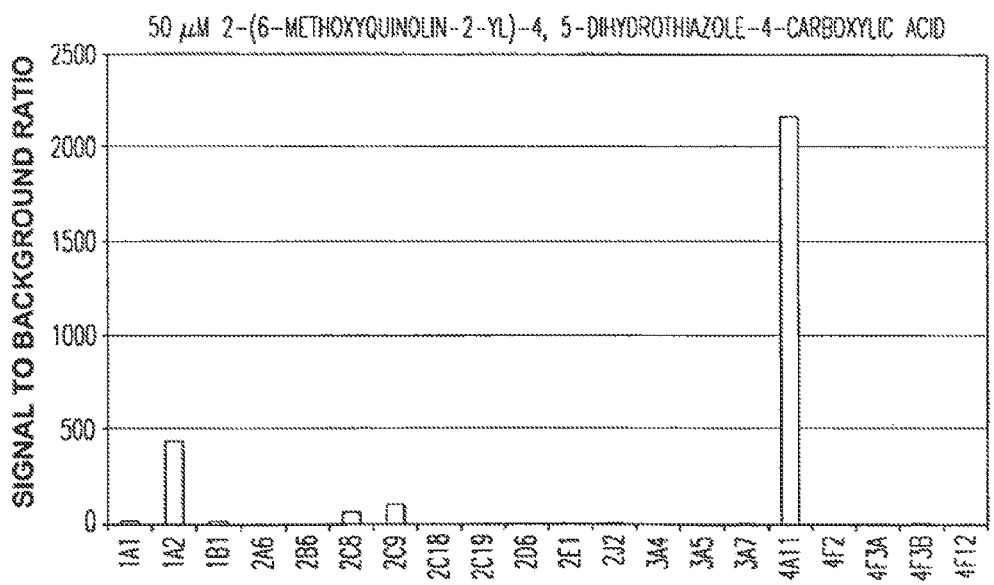
FIG. 29. A graphical representation of signal background ratio for a reaction between a luciferin derivative, (2-(6-methoxyquinolin-2-yl)-4,5-dihydrothiazole-4-carboxylate) and each of a panel of P450 enzymes. Reactions contained 1 pmol P450.
Figures 30, 31:
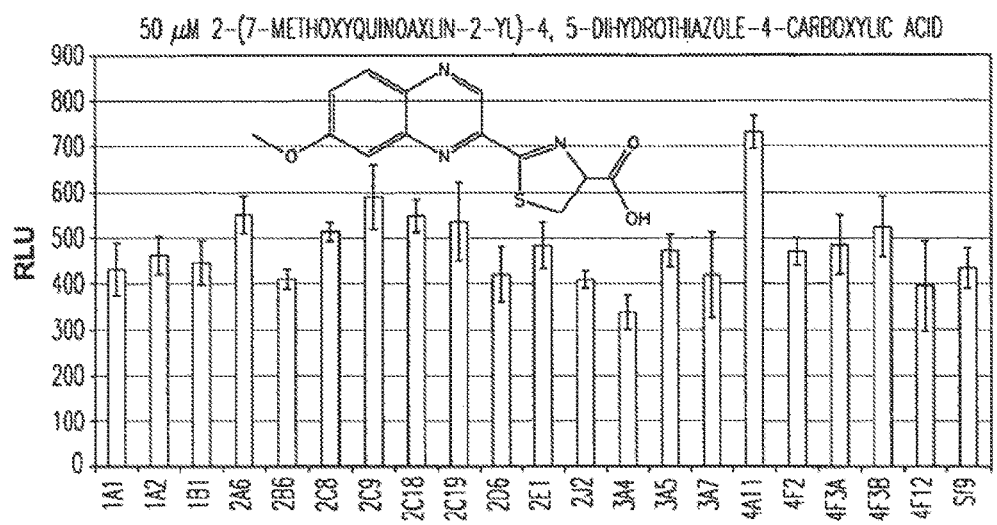
FIG. 30. A graphical representation of RLU for reactions containing one of a panel of P450 enzymes and a luciferin derivative, 2-(7-methoxy-quinoxalin-2-yl)-4,5-dihydrothiazole-4-carboxylic acid. Reactions contained 1 pmol P450.
FIG. 31. A graphical representation of RLU for reactions containing one of s panel of P450 enzymes and a luciferin derivative, (N-((3-chloro-4-(2-(dimethylamino)-1-phenylpropoxy)benzyloxy)carbonyl)-6'-aminoluciferin). Reactions contained 1 pmol P450 or 5 pmol CYP19.
Figure 32:
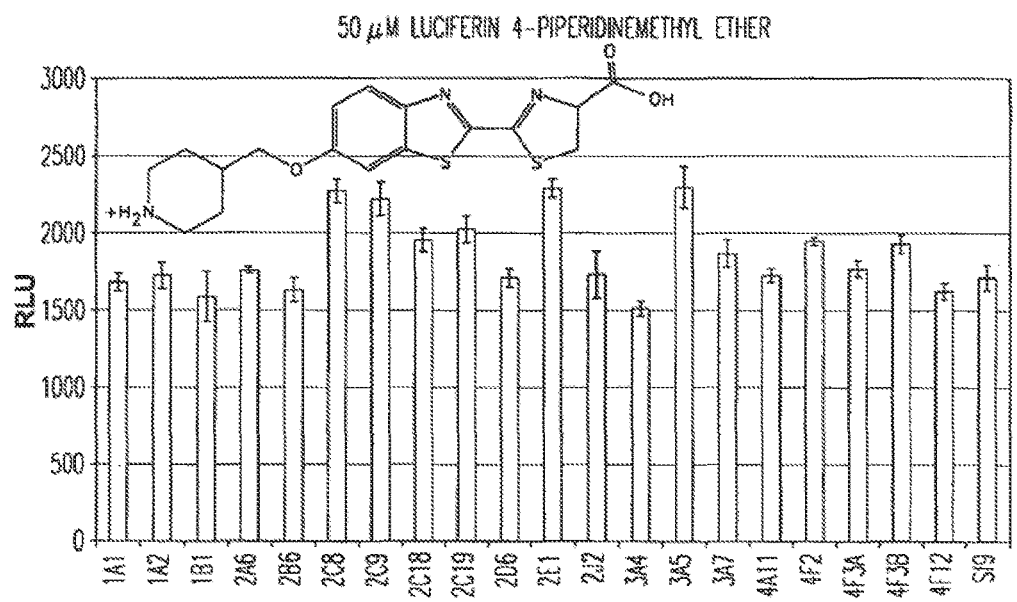
FIG. 32. A graphical representation of RLU for reactions containing one of a panel of P450 enzymes and a luciferin derivative, luciferin 4-piperidinemethyl ether. Reactions contained 1 pmol P450.
Figure 33:
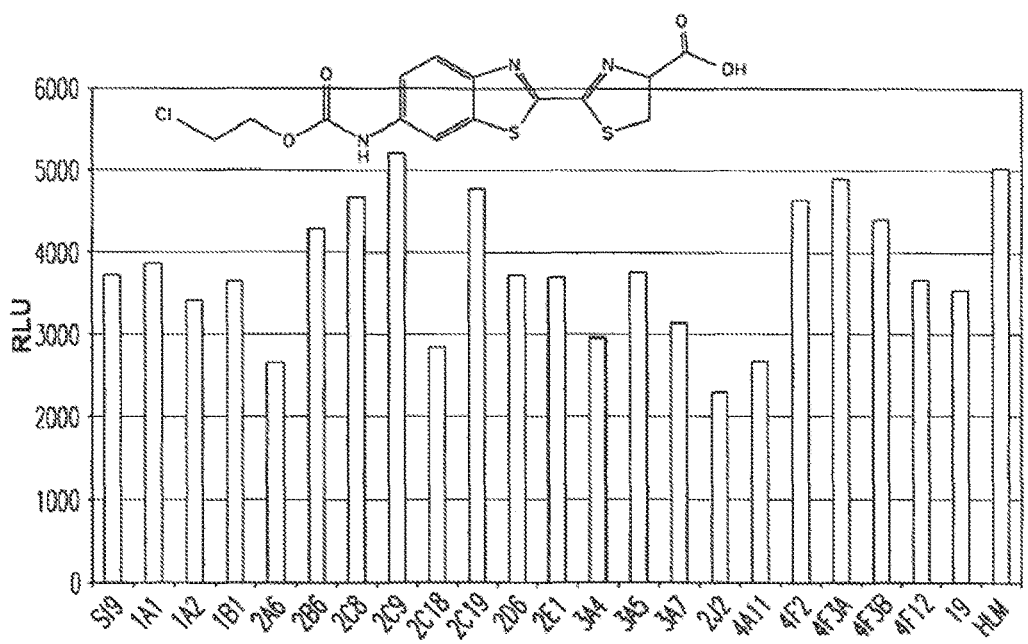
FIG. 33. A graphical representation of RLU for reactions containing one of a panel of P450 enzymes and a luciferin derivative, N-(2-chloroethoxycarbonyl)-aminoluciferin. Reactions contained 1 pmol P450.
Figure 34:
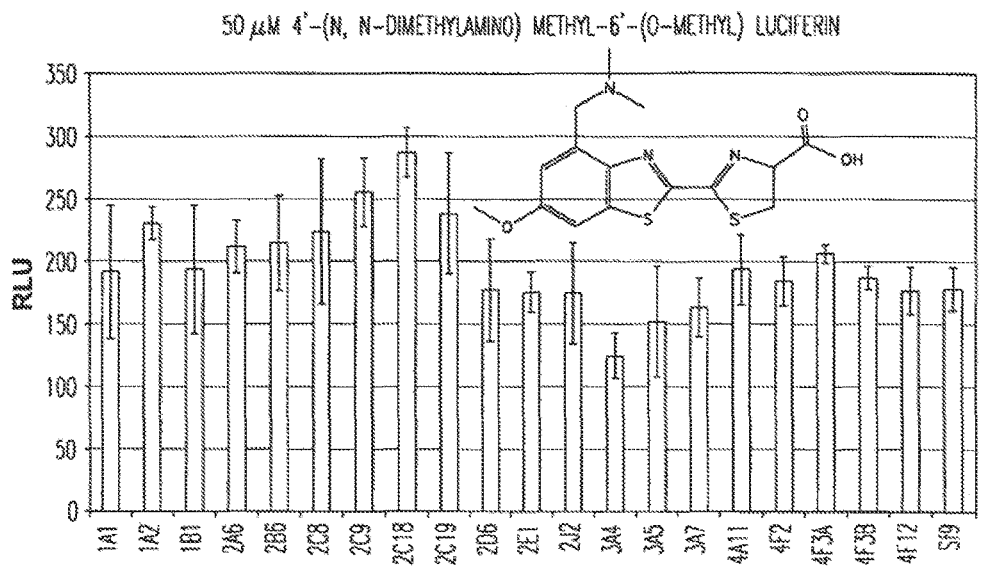
FIG. 34. A graphical representation of RLU for reactions containing one of a panel of P450 enzymes and a luciferin derivative, 4'-(N,N-dimethylamino)methyl-6-(O-methyl) luciferin. Reactions contained 1 pmol P450.
Figure 35:
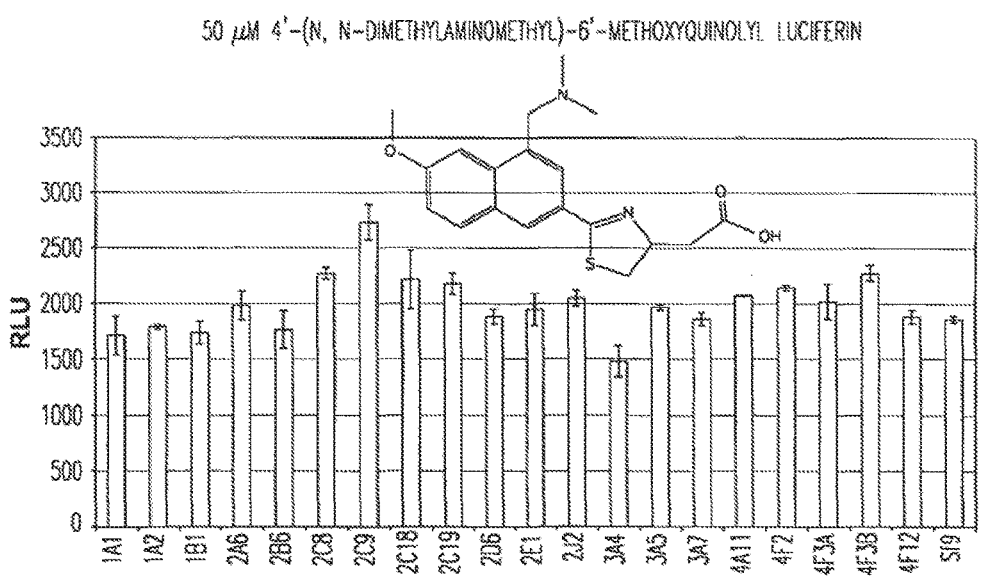
FIG. 35. A graphical representation of RLU for reactions containing one of a panel of P450 enzymes and a luciferin derivative, 4-(N,N-dimethylaminomethyl)-6-methoxyquinolyl luciferin. Reactions contained 1 pmol P450.
Figure 36:
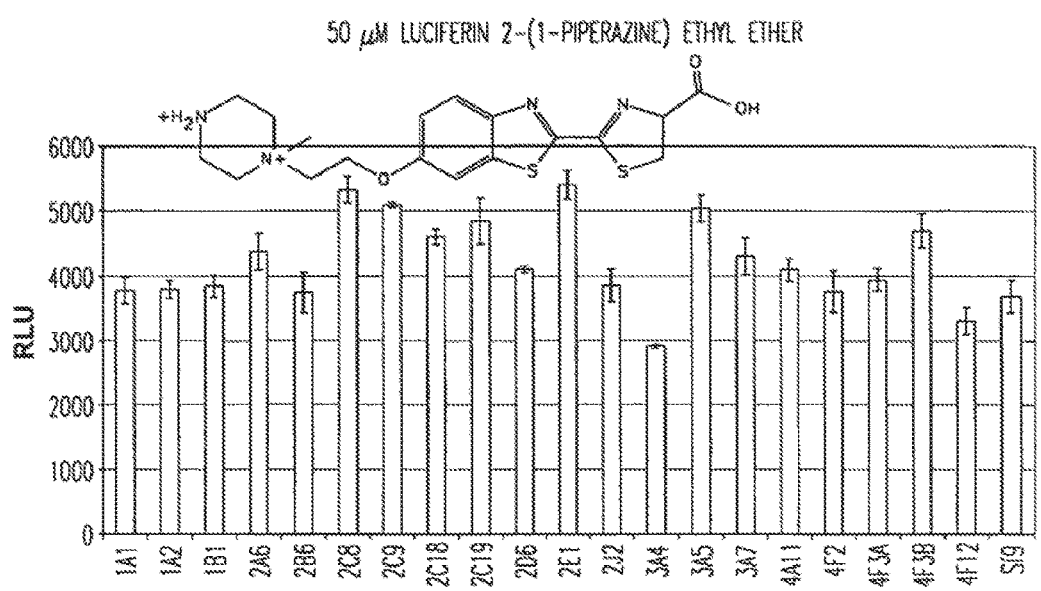
FIG. 36. A graphical representation of RLU for reactions containing one of a panel of P450 enzymes and a luciferin derivative, luciferin 2-(1-piperazine)ethyl ether. Reactions contained 1 pmol P450.
Figure 37A:
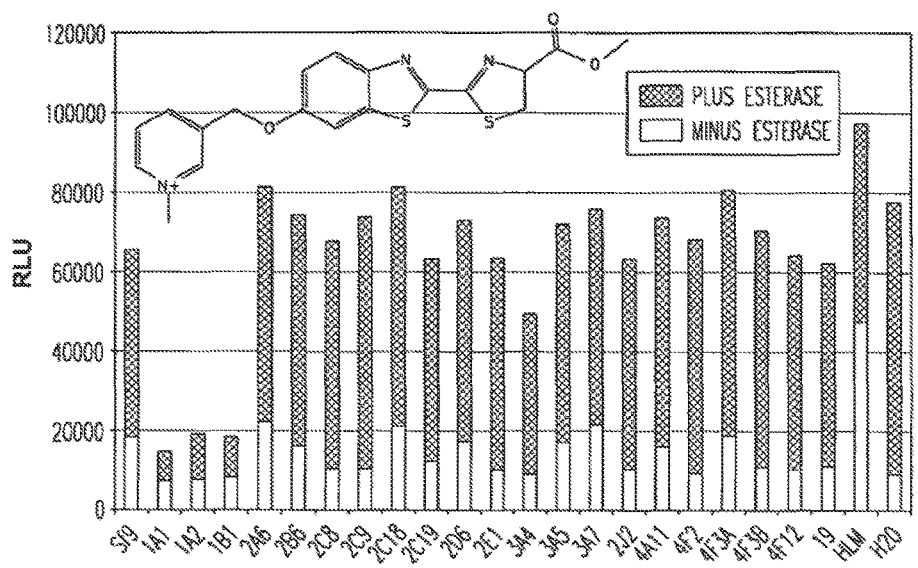
FIG. 37A. A graphical representation of RLU for reactions containing one of a panel of P450 enzymes and a luciferin derivative, meta-N-methyl picolinyl luciferin methyl ester. Reactions contained 1 pmol P450. A 30 minute incubation at 37° C. was followed by a 20 minute incubation at room temperature with or without esterase in luciferin detection reagent.
Figure 37B:
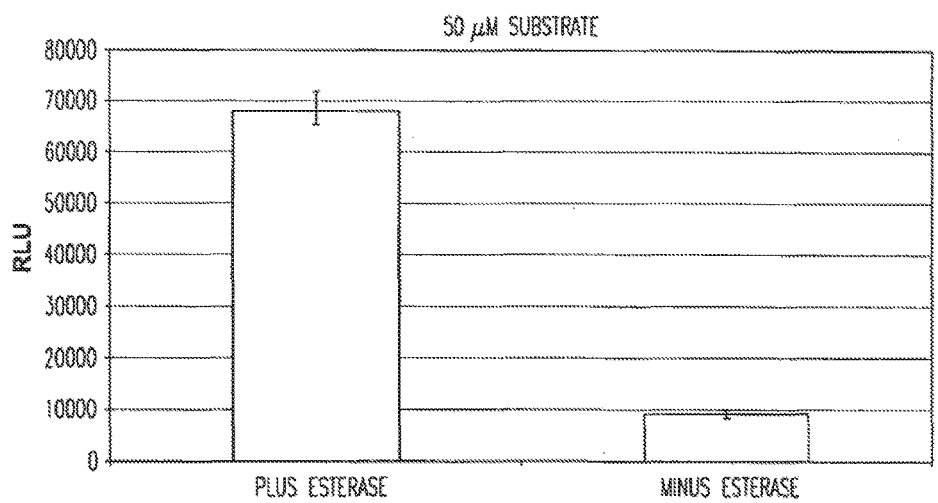
FIG. 37B. A graphical representation of RLU for reactions containing a luciferin derivative, meta-N-methyl picolinyl luciferin methyl ester, with or without esterase. 20 minute incubation at room temperature.
Figure 38:
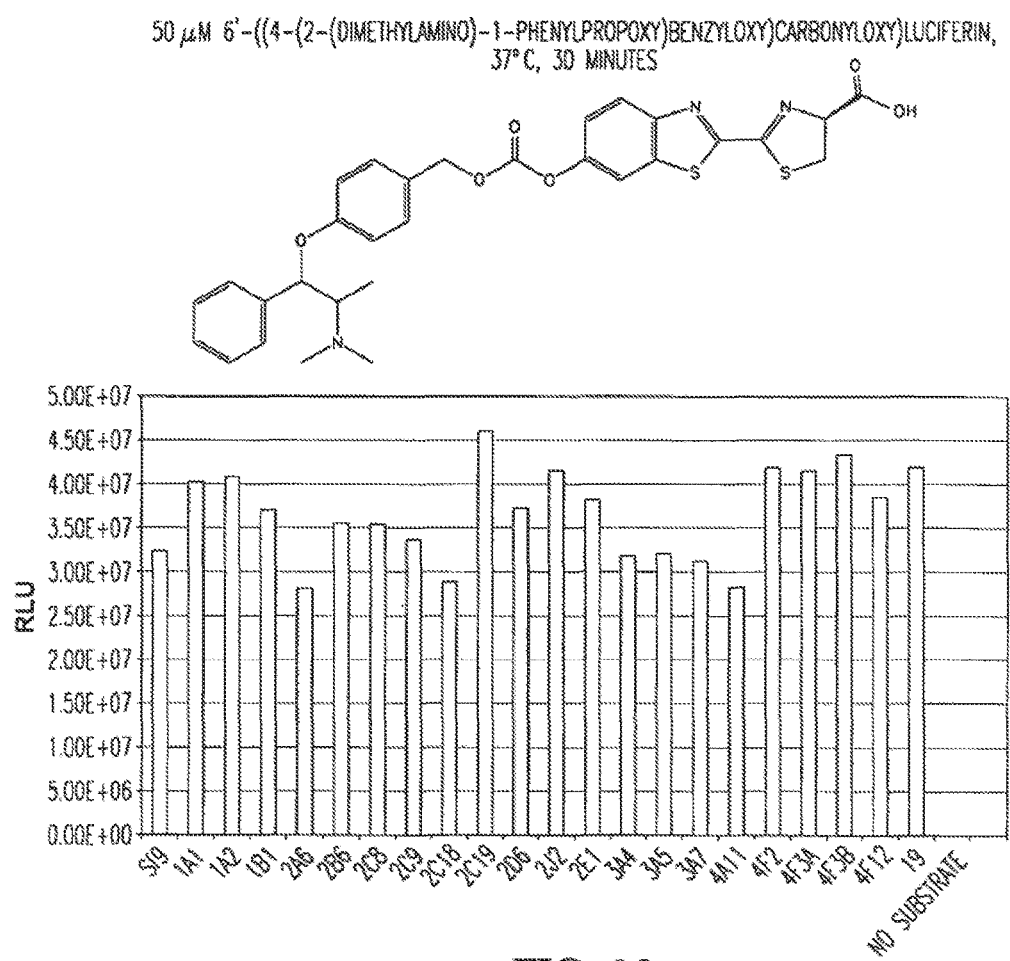
FIG. 38. A graphical representation of RLU for reactions containing one of a panel of P450 enzymes and a luciferin derivative, methamphetamine-luciferin Reactions contained 1 pmol P450.
Figure 39:
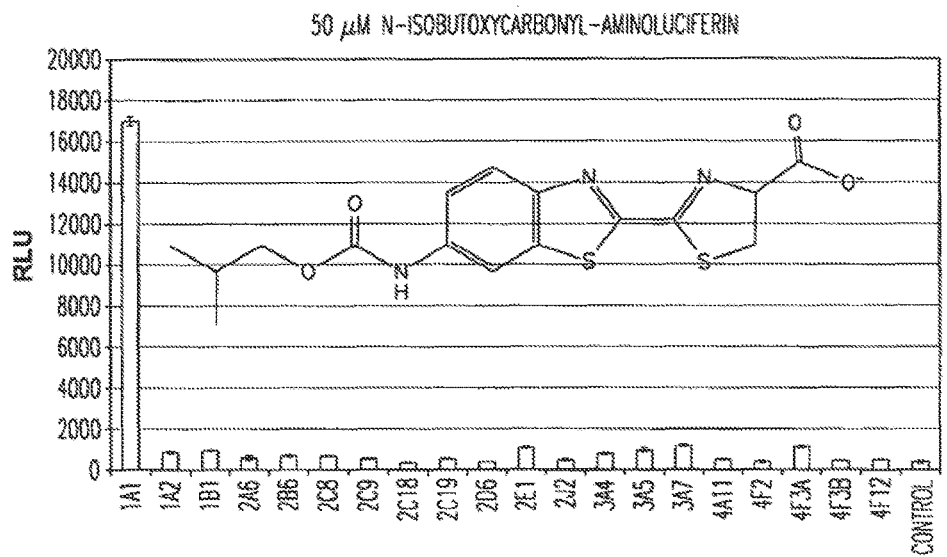
FIG. 39. A graphical representation of RLU for reactions containing one of a panel of P450 enzymes and a luciferin derivative. N-isobutoxycarbonyl-aminoluciferin. Reactions contained 1 pmol P450.
Figure 40:
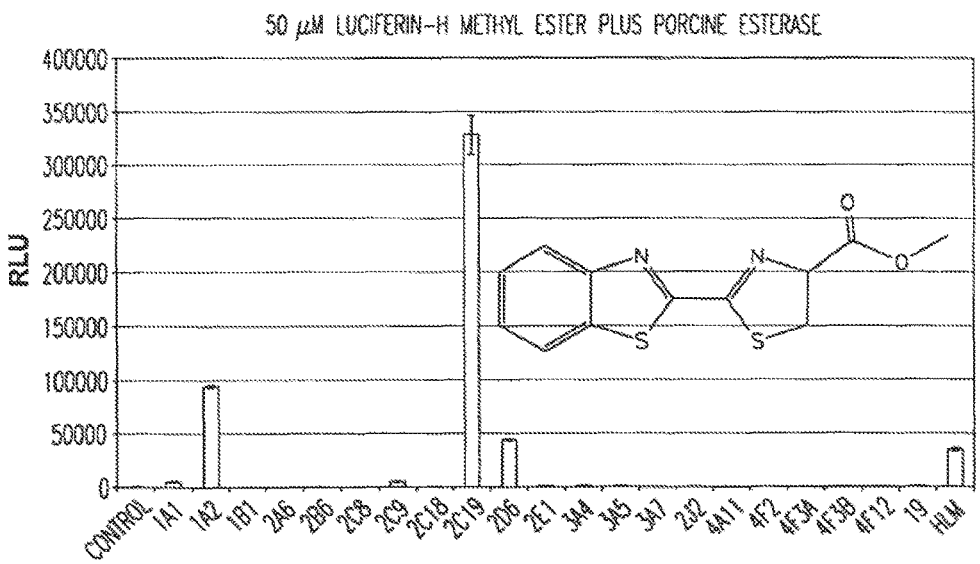
FIG. 40. A graphical representation of RLU for reactions containing one of a panel of P450 enzymes and a luciferin derivative, luciferin-H-methyl ester and esterase. Reactions contained 1 pmol P450.
Figures 41, 42:
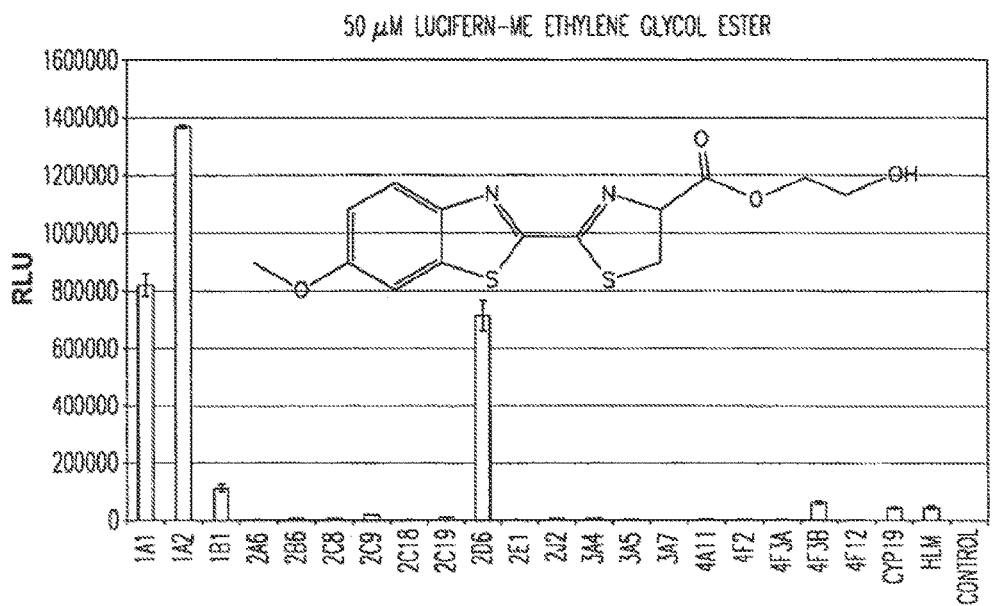
FIG. 41. A graphical representation of RLU for reactions containing one of a panel of P450 enzymes and a luciferin derivative, luciferin-ME ethylene glycolester. Reactions contained 1 pmol P450, 5 pmol CYP19, or 40 µg HLM.
FIG. 42. A graphical representation of RLU for reactions containing one of a panel of P450 enzymes and a luciferin derivative, methoxyquinolyl luciferin methyl ester. Reactions contained 1 pmol P450.
Figure 43:
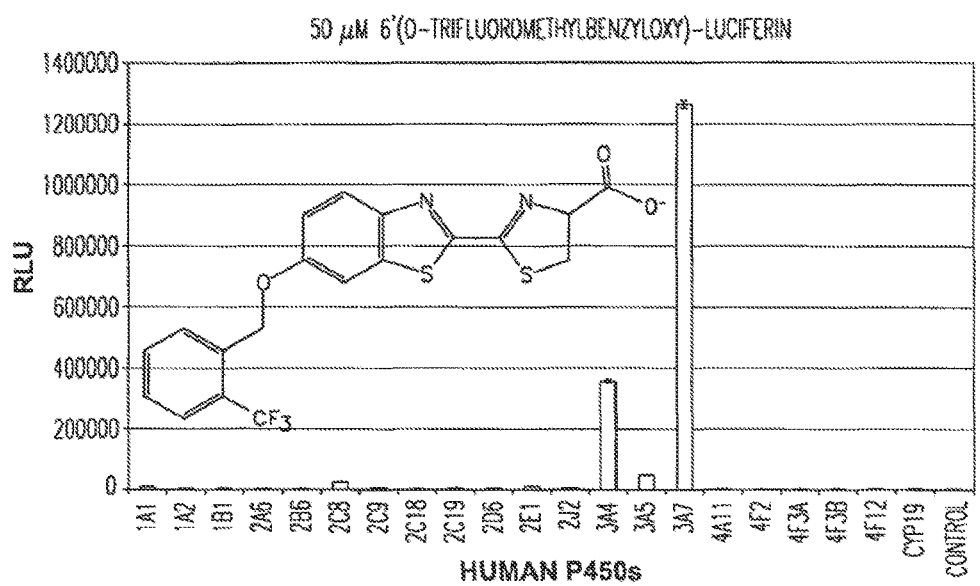
FIG. 43. A graphical representation of RLU for reactions containing one of a panel of P450 enzymes and a luciferin derivative, 6'(o-trifluoromethylbenzyloxy)-luciferin 1 pmol P450 or 5 pmol CYP19.

For FIG. 20, 1 or 5 picomoles of recombinant CYP2D6 or CYP2C19 membrane fractions from an insect cell expression system (Supersomes™, Discovery Labware) were incubated at 37° C. for 60 minutes with 200 μM D-luciferin 6' methyl ether (luciferin-ME) in 50 mM (CYP2C19) or 100 mM (CYP2D6) KPO$_4$ (pH 7.4) with an NADPH regenerating system (as described above) in a volume of 50 μl. At the end of the one hour incubation, P450 reactions were stopped and the detection of P450 generated D-luciferin was initiated by adding 50 μl of luciferin detection reagent. For FIG. 20, the panel of human P450s was screened as described above. The luciferin detection reagent (Promega Corp.) was supplemented with 1 unit per 50 μl of porcine liver esterase. Luminescence was read as relative light units (RLU) 20 minutes after the addition of the luciferin detection reagent with esterase.

Results

Many luciferin derivatives with 6' modifications were tested as substrates for CYP2D6 and 2C19 and for use in luminogenic P450 assays but significant 2D6 or 2C19 activities were not detected with most of these compounds. Luciferin 6-methyl ether did show some activity with these enzymes, however, the activities were modest in that detection required high substrate and enzyme concentrations and a long incubation time (FIG. 20).

The literature suggested that D-luciferin derivatives with a carboxylic acid group and its negative charge at pH 7.4 would indeed be poor CYP2D6 substrates. Models of the CYP2D6 active site include an aspartic acid residue; its negative charge would be expected to repel negatively charged luciferin derivatives (Ellis et al., *J. Biol. Chem.* 270:29055 (1995)). To eliminate the negative charge on luciferin-6-methyl ether, the carboxyl methyl ester of luciferin-ME was prepared. P450s might first catalyze a standard O-dealkylation to remove the 6' methyl group (Guengerich, *Chem. Res. Tox.*, 14:611 (2001)), producing the carboxyl methyl ester of D-luciferin. Though a carboxyl ester of luciferin would not be expected to reset with luciferase to make light, it could be de-esterified by adding an esterase to the luciferin detection reagent used for a standard luminogenic P450 assay. Using this assay strategy, the activity of CYP2D6 with the carboxyl ester of luciferin-ME was found to be substantially increased over its activity with luciferin-ME. The carboxyl ester of luciferin-ME also reacted strongly with several other P450s including CYP2C19 (FIG. 20).

The carboxyl methyl ester of deoxyluciferin (luciferin-H) was screened against the same P450 panel and showed substantial activity with CYP2G19 and strong selectivity for this enzyme over the others tested (line 26 in FIGS. 17-18). The carboxyl methyl esters of luciferin-6-methyl ether and luciferin-H were good substrates for luminogenic P450 assays that include a de-esterification step after the P450 incubation (lines 26 and 33 in FIGS. 17-18). However, both compounds had poor solubility in the aqueous P450 assay buffer. To improve solubility, additional esters of luciferin-6-methyl ether and luciferin-H were prepared. Picolinyl esters showed improved aqueous solubility and a more limited pattern of P450 cross reactivity (lines 27 and 32 in FIGS. 17-18). The carboxyl picolinyl ester of luciferin-6-methyl ether showed a preference for 2D6, 1A1 and 1A2 while the carboxyl picolinyl ester of luciferin-H showed preference for 2C19, 1A1 and 1A2. Both of these compounds had the unexpected property that treatment with an esterase was not required to achieve maximal signals. That is, a substantial difference in signal was not observed when comparing these assays plus and minus esterase.

These results suggest that the substrates may be oxidized by P450 on two sites: the 6' site, as previously suggested, and the methylene of the picolinyl group A hydroxylation at the picolinyl methylene would make an instable compound that would decay to form picolinyl aldehyde and D-luciferin. The sequential oxidation of a given substrate on multiple sites by a single P450 has been described (Cali et al., *J. Biol. Chem.* 266:7774 (1991)). Alternatively, if there were sufficient carboxyl esterases present in the P450 preparation, these could account for the removal of the picolinyl ester group. Experiments with luciferin-6methylether picolinyl ester or luciferin-H picolinyl ester, with purified recombinant CYP2D6 or CYP2C19 preparations that were substantially free of carboxylesterases, clarified the roles of P450 and esterase to remove the picolinyl esters. When 1 unit of porcine esterase was added to the purified P450 reactions a large signal was generated in the 2 step assay format with the thermostable luciferase. In contrast, when the esterase was not added, less than 10% of the plus esterase signal was observed. Thus relatively lower signal was nevertheless higher than signals from reactions that lacked P450 activity altogether (when the essential P450 co-factor NADPH was withheld). Taken together, these results indicate that P450s (CYP2D6 and CYP2C19 in this example) modify the 6' position of the 6'methyl ether and 6' deoxyluciferin picolinyl esters of D-luciferin by hydroxylation or dealkylation, respectively. A second minor reaction, oxidation at the picolinyl methylene is also catalyzed by P450 leading to de-esterification esterification. However, the major de-esterification observed with the recombinant p450s in insect cell membranes (Supersomes™) was catalyzed by non-P450 carboxyl esterase activity present in the membrane preparation. The latter point was confirmed by HPLC analysis of the Supersome™ reactions where accumulation was observed of picolinyl alcohol, the expected product of a carboxyl esterase reaction, whereas picolinyl aldehyde, the expected product of a P450 mediate de-esterification, was not observed (data not shown).

Ethylene glycol esters of luciferin-6-methyl ether and luciferin-H were also prepared. These were reactive with P450s and had greater solubility in aqueous buffer than the methyl and picolinyl esters (lines 24-25 and 36 in FIGS. 17-18). Unlike the picolinyl esters, the ethylene glycol esters required the addition of esterase to achieve maximum signals. Without added esterase diminished signals were observed (lines 24-25 in FIGS. 17-18).

D-luciferin esters were substrates for carboxylesterases in a two step luminescent assay formal similar to that used for P450s. D-luciferin methyl ester, D-luciferin ethyl ester and D-luciferin picolinyl ester were effective in this formal. This was first suggested by results from two of these compounds when screened against the panel of 21 recombinant human P450s. In those experiments, the P450s typically did not give substantially brighter signals than those observed with the control reactions where the recombinant P450 membrane fractions were replaced with a control membrane fraction that lacked P450. Though signals varied between P450 preparations no P450 preparation was much brighter than the control. It seems likely then that the signals were not due to P450 activity in the preparations but rather, variable amounts of carboxyl esterase activities. Methyl, ethyl and picolinyl esters of D-luciferin were also characterized as substrates for a purified preparation of porcine esterase without any p450. In this format each ester linked group was cleaved by the esterase to yield D-luciferin that in turn reacted with luciferase to make light.

There were some compounds that showed substantial light generating activity with aminoluciferin despite the fact that modifications were made to the 6" amine. This was unanticipated because D-luciferins with 6' modifications are typically substantially impaired as light generating substrates for luciferase. A thermostable luciferase reaction with 100 µM dimethyl amino luciferin was only about half as bright as a reaction with 100 µM amino luciferin. This general phenomenon was also true with N,N-benzyl-methyl-aminoluciferin, N,N-benzyl-ethyl-aminoluciferin and isopropyl amino luciferin. Other compounds such as N,N bisbenzyl amino luciferin that react with luciferase to produce substantial amounts of light without prior reaction with a non-luciferase enzyme may also be good substrates for luciferase. Aminoluciferin derivatives that are good substrates for luciferase on their own can be used as scaffolds for further derivatization in the interest of making substrates for nonluciferase enzymes for the luminogenic style of reactions described herein. In this case the luminogenic leaving group would be an aminoluciferin derivative such as dimethylaminoluciferin.

Thus, some luciferin derivatives with an ester group are useful as carboxyl esterase substrates and those derivatives are not necessarily substrates for P450 enzymes. Other luciferin derivatives with an ester group and a P450 substrate are useful as P450 substrates including those where the corresponding derivative which lacks the ester group is not a substrate, or a poor substrate, of at least some P450 enzymes. Moreover, for some luciferin derivatives, e.g., picolinyl luciferin-ME and picolinyl luciferin-H, an exogenous esterase may not be needed to detect P450 activity in samples with endogenous esterase activity.

D. CYP3A Induction Assay in Human Hepatocytes

Figures 52, 53:
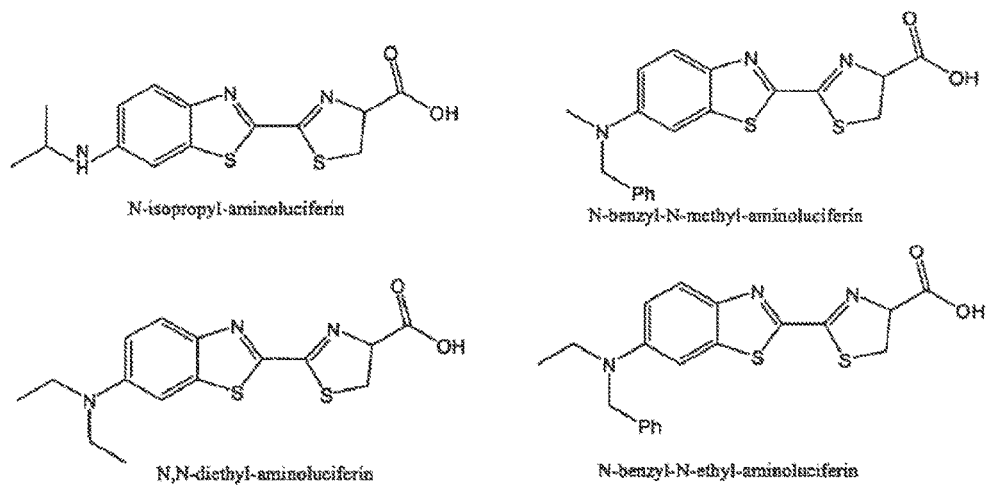
FIG. 52. CYP3A4 activity in human hepatocytes after treatment with rifampicin, ketoconazole, or rifampicin and ketoconazole, in a reaction with luciferin-$F_5$BE.
FIG. 53. Luciferin derivatives which may be luciferase substrates: N-isopropyl aminoluciferin bisethyl aminoluciferin; and benzylaminoluciferin.
Figure 55:
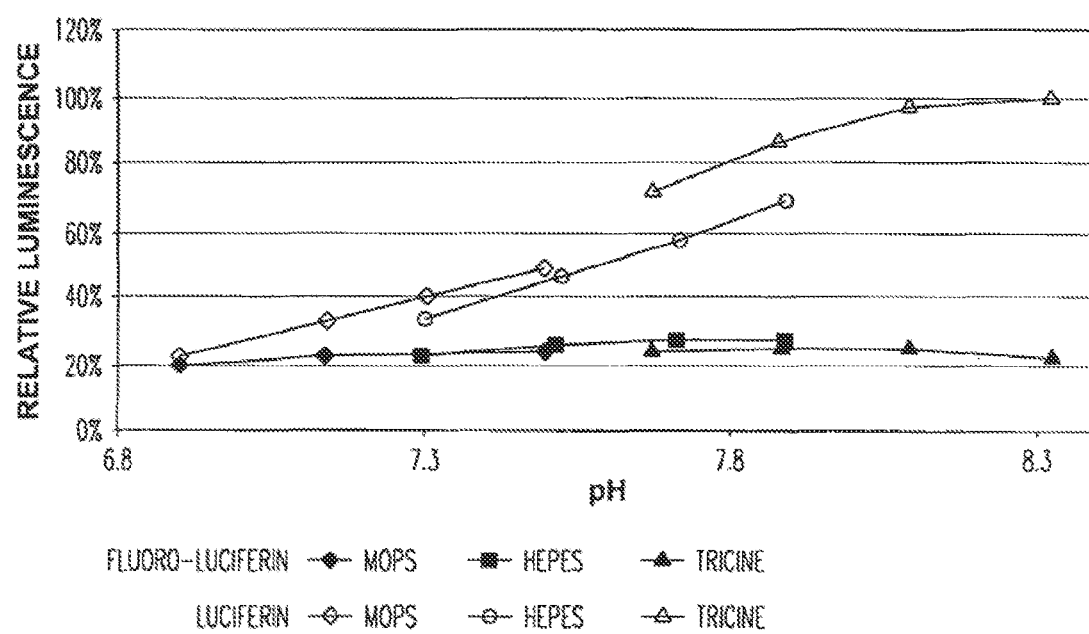
FIG. 55. A graphical representation of RLU for luciferin or 5-fluoroluciferin in luciferase reactions at different pHs.

Certain compounds induce transcription of CYP3A gene expression resulting in increased levels of CYP3A enzyme activity. It is therefore desirable to have probes for detecting such inductions at the level of P450 enzyme activity in cells such as hepatocytes (Madan et al., *Drug Metab. Dispos.*, 31:421 (2003)). 6-(2,3,4,5,6 pentafluorobenzyloxy)-luciferin and 6-phenylpiperizinexylyl-luciferin were tested as probes for detecting CYP3A induction in hepatocytes (FIGS. 51-52). The results from screening a panel of P450 enzymes representing most of those expressed in hepatocytes suggested that these substrates would only react to a substantial extent with CYP3A enzymes (FIGS. 17-18).

Rifampicin is a prototypical CYP3A4 gene inducer and was used to determine whether luminogenic P450 substrates could be used to detect induction in a non-disruptive cell-based assay of human hepatocytes. The luminogenic P450 substrates 6-(2,3,4,5,6 pentafluorobenzyloxy)-luciferin and 6-phenylpiperizinexylyl-luciferin were added to the medium of cultured hepatocytes with the expectation that they would enter cells and react with endogenous P450s to produce D-luciferin. The D-luciferin was in turn expected to exit cells and accumulate in the culture medium. The medium was then sampled and combined with a luciferase reaction mixture to generate light in proportion to the amount of D-luciferin produced by CYP3A enzymes.

Human hepatocytes were used to test the proposed CYP3A4 cell based assay approach (FIGS. 51-52). Freshly plated human hepatocytes on collagen-coated 96 well plates were obtained from Cambrex Bio Science (Walkerville, Md.). Cells were from a male donor and provided alive at near confluence in 96-well plates at ambient temperature. Upon arrival, a plastic adhesive seal was removed from plates and the cells were incubated in a 5% $CO_2$, 37° C. incubator (or 2 hours in the shipping media. After 2 hours, shipping media was removed and replaced with 0.1 mL per well Hepatocyte Culture Medium (HCM, Cambrex) pre-warmed to 37° C. Plates were returned to the incubator for 1 hour. After 1 hour, an additional 0.1 mL cold HCM that had been supplemented with 0.25 mg/mL Matrigel (BD Biosciences, Bedford, Mass.) was added to each well or tap of the existing 0.1 mL HCM. Plates were then returned to the incubator overnight. The next day culture medium was removed and replaced with 0.1 mL fresh medium without Matrigel that included 10 µM rifampicin (the CYP3A inducing compound) or vehicle alone (0.02% DMSO) Rifampicin and vehicle containing medium was changed the next day so that cells were exposed to test compound for a total of 2 days. Vehicle controls were used for measuring basal CYP450 activity. After 2 days of exposure to rifampicin or vehicle medium was removed and replaced with 0.1 mL HCM supplemented with 50 µM of 6-(2,3,4,5,6pentafluorobenzyloxy)-luciferin or 6-phenylpiperizineylyl-luciferin or these substrates plus the CYP3A4 inhibitor ketoconazole. For background luminescence determinations, each luminogenic substrate was added to a set of four empty wells (no cells). For basal CYP450 activity measurements, each luminogenic substrate was added to a set of four vehicle control wells. For rifampicin-treated/induced CYP450 activity measurements, each luminogenic substrate was added to four wells treated with the CYP3A4 inducer, rifampicin. For inhibition of basal or rifampicin-induced CYP450 activity measurements, each luminogenic substrate plus the CYP3A4 inhibitor ketoconazole was added to four wells treated with vehicle alone and to four wells treated with the CYP3A4 inducer, rifampicin.

Samples were then incubated for 4 hours with the luminogenic substrates or luminogenic substrate plus inhibitor. At the end of the 4 hour incubation period with luminogenic substrates, 0.1 mL of medium was removed from each well to a 96 well opaque white luminometer plate at room temperature and combined with 0.1 mL of a luciferin detection reagent (from Promega Corporation). Luminescence was read on a plate reading luminometer (Veritas, Turner BioSystems) 20 minutes after combining medium and luciferin detection reagent. The average luminescence values of background wells were subtracted from rifampicin-treated and untreated (vehicle control) values to give net CYP3A-dependent luminescence.

A basal level of luminescence was found in the vehicle control wells, apparently reflecting basal CYP3A activity and the induction of this activity by rifampicin was reflected as an increase in luminescence over controls with both substrates (FIGS. 51-52), The inhibition by ketoconazole of both basal and rifampicin-induced activity with both luminogenic substrates by the CYP3A4 inhibitor is consistent with the interpretation that the basal and induced luminescence is a consequence a CYP3A reaction with luminogenic substrates. The fold induction measured with 6-(2,3,4,5,6 pentafluorobenzyloxy)-luciferin was greater than that measured with 6-phenylpiperizinexylyl-luciferin. This may be due to improved selectivity of the former substrate for rifampicin-inducible P340s or to better access to the P450s in the hepatocytes. The results demonstrate that both substrates are useful probes for detecting CYP3A gene induction at the level of P450 enzyme activity. The approach has the advantage of leaving the hepatocytes intact so they could be subjected to additional analysis, for example, to test for cytotoxicity of a test compound with a cell viability assay.

Example 6

Luciferase Substrates

A. Firefly Luciferase

Firefly luciferase was shown to utilize luciferin derivatives that were modified such that they formed ethers at rates comparable to the rate with which luciferase uses natural luciferin as a substrate. Such compounds were not known to be able to be utilized by luciferase and in fact one of the compounds was reported to not be a substrate for the enzyme. In addition, the data indicated that the utilization of such derivatives can lead to: 1) inactivation of the luciferase, and 2) fluorescent labeling of the luciferase, but that certain compounds can increase light production.

Materials and Methods

Gel and HPLC stop solution. Solid EDTA (free acid) was placed in a beaker with water and the pH of the solution adjusted to pH 7.0. The solution was then adjusted in volume to produce a solution 400 mM in EDTA.

Enzyme stop solution. A solution was prepared containing 20 mM Bis Tris, pH 6.5, 2 mM EDTA and 1 mg/ml bovine serum albumin.

Reaction buffer (2×). A solution was made containing 100 mM HEPES buffer, pH 8.0; 10 mM $MgCl_2$.

DTT stock. Solid DTT (dithiothreatol) was dissolved in water and then adjusted to pH 8.0 with solid sodium hydroxide. The solution was then adjusted in volume to produce a solution 1 M in DTT.

Results

TABLE 37

| Reaction | Reaction Buffer (2×) | 1M DTT | 20 mM Coenzyme A | Gel/HPLC Stop Sol'n | 10 mM ATP | Luciferin |
|---|---|---|---|---|---|---|
| 1 | 500 µl | 0 µl | 0 µl | 0 µl | 10 µl | 10 µl 5 mM Luciferin BE |
| 2 | 500 µl | 0 µl | 50 µl | 0 µl | 10 µl | 10 µl 5 mM Luciferin BE |
| 3 | 500 µl | 100 µl | 0 µl | 0 µl | 10 µl | 10 µl 5 mM Luciferin BE |
| 4 | 500 µl | 0 µl | 0 µl | 100 µl | 10 µl | 10 µl 5 mM Luciferin BE |
| 5 | 500 µl | 0 µl | 0 µl | 0 µl | 0 µl | 10 µl 5 mM Luciferin BE |
| 6 | 500 µl | 0 µl | 0 µl | 0 µl | 10 µl | 10 µl 5 mM Luciferin ME |
| 7 | 500 µl | 0 µl | 50 µl | 0 µl | 10 µl | 10 µl 5 mM Luciferin ME |
| 8 | 500 µl | 100 µl | 0 µl | 0 µl | 10 µl | 10 µl 5 mM Luciferin ME |
| 9 | 500 µl | 0 µl | 0 µl | 100 µl | 10 µl | 10 µl 5 mM Luciferin ME |
| 10 | 500 µl | 0 µl | 0 µl | 0 µl | 0 µl | 10 µl 5 mM Luciferin ME |

After producing the solutions in Table 37, the volume of all reactions was adjusted to 990 µl with water. Reactions were started by addition of 10 µl of QuantiLum Luciferase (Promega Corp.: 14.9 mg/ml) to a reaction, mixing, removing 100 µl to a luminometer tube and reading the light produced by the reaction. While the light reading was being taken, a 10 µl sample of the reaction was diluted to 500 µl with enzyme stop solution (cooled on ice to 4° C.) mixed and placed on ice and a second sample of 90 µl of reaction was added to 10 µl of Gel/HPLC stop and the tube placed at −20° C. A timer was started with the start of the first reaction and the start times of the remaining reactions was noted. At 15, 30, 45 and 60 minutes, each reaction was sampled as above and the light produced in the luminometer tubes was measured. At 7 and 22 minutes, the light produced in the luminometer tubes was read, but the reactions were not sampled.

After all samples were taken, 50 µl of the sample diluted into enzyme stop solution was mixed with 50 µl of Steady Glo Luciferase Reagent (Promega) and the light produced measured after incubating at room temperature for 10 minutes. This measured the active luciferase in the initial reaction.

Samples of the materials given Gel/HPLC stop solution and frozen were thawed and analyzed by HPLC in addition, selected samples were mixed with SDS PAGE loading buffer and fractionated on 4-20% SDS PAGE gels and visualized on a Typhoon Phosphoimager.

Results

The following readings for light emission from the reactions were obtained (Table 38).

TABLE 38

| | | | Light reading at time | | | | | | |
|---|---|---|---|---|---|---|---|---|---|
| Reaction | Substrate | Addition | 0 min | 7 min | 15 min | 22 min | 30 min | 45 min | 60 min |
| 1 | Luc'in BE | No addition | 135.2 | 22.61 | 12.79 | 9.256 | 6.928 | 4.879 | 3.311 |
| 2 | | +Co A | 139.5 | 11.92 | 10.99 | 9.941 | 7.379 | 7.284 | 6.433 |
| 3 | | +DTT | 948 | 532.8 | 417 | 369.5 | 331.6 | 273.5 | 226.9 |
| 4 | | +EDTA | 1.004 | 0.771 | 0.639 | 0.562 | 0.461 | 0.425 | 0.354 |
| 5 | | w/o ATP | 0.015 | 0 | 0.008 | 0.005 | 0 | 0 | 0.01 |
| 6 | Luc'in ME | No addition | 23.46 | 3.144 | 1.767 | 1.317 | 1.22 | 0.982 | 0.851 |
| 7 | | +Co A | 18.31 | 2.276 | 1.239 | 1.178 | 1.145 | 0.916 | 0.714 |
| 8 | | +DTT | 38.69 | 6.42 | 4.073 | 3.31 | 2.708 | 2.202 | 1.996 |
| 9 | | +EDTA | 1.067 | 0.117 | 0.058 | 0.042 | 0.024 | 0.046 | 0.012 |
| 10 | | w/o ATP | 0 | 0.017 | 0.016 | 0 | 0 | 0.017 | 0.011 |

Analysis of the samples by HPLC indicated that at least 20% of the luciferin derivative was utilized by the time the 15 minute sample was taken except in the reactions where no ATP was added or where EDTA was present in the reaction solution. In those reactions, very little utilization of the derivative was seen under these conditions.

The following readings for light emission from the active enzyme in the samples were obtained (Table 39).

TABLE 39

| Reaction | Substrate | Addition | Light Reading from residual active enzyme at time | | | | |
|---|---|---|---|---|---|---|---|
| | | | 0 min | 15 min | 30 min | 45 min | 60 min |
| 1 | Luc'in BE | No addition | 129.7 | 69.9 | 47.31 | 37.94 | 29.08 |
| 2 | | +Co A | 186.7 | 179.6 | 179.4 | 157.9 | 161.8 |
| 3 | | +DTT | 194 | 233.7 | 224.7 | 219.5 | 226.4 |
| 4 | | +EDTA | 170 | 142.7 | 140.4 | 141.7 | 135.4 |
| 5 | | w/o ATP | 168.3 | 174.1 | 171.7 | 172.9 | 164 |
| 6 | Luc'in ME | No addition | 141.7 | 35.4 | 91.82 | 85.72 | 81.76 |
| 7 | | +Co A | 163.3 | 161.8 | 147.7 | 144.7 | 145.6 |
| 8 | | +DTT | 170 | 172.3 | 164.3 | 161.6 | 167.6 |
| 9 | | +EDTA | 150.5 | 150 | 152.1 | 152.8 | 151 |
| 10 | | w/o ATP | 170 | 168.9 | 175.6 | 181.9 | 173.6 |

As seen from the data in the residual active enzyme table above, little change was seen in the residual enzyme levels in the reactions above except for the reactions without additive. The reactions without additive show a time dependent drop with the magnitudes of the drop dependent upon the derivative present in the reaction.

SDS-PAGE analysis of samples of these reactions followed by visualization of the image of the gel using a Typhoon imager demonstrated that the protein in reactions given no addition did become fluorescently labeled in a note dependent manner.

Thus, substantial and time dependent depletion of the luciferin derivative was seen under conditions where luciferin is highly active (reactions above with no addition, or coenzyme A or DTT addition), light production was seen in reactions with the derivative, and enzyme inactivation and protein labeling were seen in these reactions under some conditions. Accordingly, this enzyme can utilize these luciferin derivatives. As mentioned above, derivatives where the oxygen of luciferin is in an ether linkage had been reported in the literature not to be substrates for luciferin, and thus the fact that these materials are effective substrates is surprising.

After producing the solutions in Table 40, the volume of all reactions was adjusted to 990 μl with water. Reactions were started by addition of 10 μl of QuantiLum Luciferase (Promega Corp.; 14.9 mg/ml) to a reaction, mixing, removing 100 μl to a luminometer tube and reading the light produced by the reaction. While the light reading was being taken, a 10 μl sample of the reaction was diluted to 500 μl with enzyme stop solution (cooled on ice to 4° C.) mixed and placed on ice and a second sample of 90 μl of reaction was added to 10 μl of Gel/HPLC stop and the tube placed at −20° C. A timer was started with the start of the first reaction and the start times of the remaining reactions was noted. At 15, 30, 45 and 60 minutes, each reaction was sampled as above and the light produced in the luminometer tubes was measured. At 7 and 22 minutes, the light produced in the luminometer tubes was read, but the reactions were not sampled.

TABLE 40

| Reaction | Reaction Buffer (2×) | 1M DTT | 20 mM Co-enzyme A | 10 mM ATP | Luciferin |
|---|---|---|---|---|---|
| 3A | 500 μl | 0 μl | 0 μl | 10 μl | 10 μl 5 mM Luciferin |
| 3B | 500 μl | 0 μl | 50 μl | 10 μl | 10 μl 5 mM Luciferin |
| 3C | 500 μl | 100 μl | 0 μl | 10 μl | 10 μl 5 mM Luciferin |
| 3D | 500 μl | 0 μl | 0 μl | 0 μl | 10 μl 5 mM Luciferin |
| 4A | 500 μl | 0 μl | 0 μl | 10 μl | 10 μl 5 mM 2OHETox Luciferin |
| 4B | 500 μl | 0 μl | 50 μl | 10 μl | 10 μl 5 mM 2OHETox Luciferin |
| 4C | 500 μl | 100 μl | 0 μl | 10 μl | 10 μl 5 mM 2OHETox Luciferin |
| 4D | 500 μl | 0 μl | 0 μl | 0 μl | 10 μl 5 mM 2OHETox Luciferin |

The following light readings were collected on a Turner 20/20 (Tables 41 and 42).

TABLE 41

Native Luciferin Data

| Rx | Rx. Type | Time | | | | | | |
|---|---|---|---|---|---|---|---|---|
| | | 0 | 7 | 15 | 22 | 30 | 45 | 60 |
| 3A | No Additive | off scale | off scale | 1,920,967,552 | 1,340,545,280 | 1,080,656,384 | 689,897,920 | 507,915,488 |
| 3B | +Co A | off scale | off scale | 1,817,884,672 | 1,207,508,736 | 1,075,446,272 | 727,134,016 | 516,780,608 |
| 3C | +DTT | off scale | off scale | off scale | 1,828,845,952 | 1,369,086,080 | 882,840,768 | 640,560,896 |
| 3D | no ATP | 1,013,266 | 7,266 | 2,253 | 248,151 | 194,980 | 27,586 | 22,270 |

TABLE 42

2 Hydroxy EthoxyEther Luciferin

| Rx | Rx. Type | 0 | 7 | 15 | 22 | 30 | 45 | 60 |
|---|---|---|---|---|---|---|---|---|
| 4A | No Additive | 749,597 | 114,541 | 63,691 | 259,945 | 233,600 | 51,233 | 44,782 |
| 4B | +Co A | 810,864 | 125,718 | 61,287 | 326,424 | 169,972 | 78,909 | 45,156 |
| 4C | +DTT | 2,515,513 | 294,885 | 146,849 | 335,031 | 237,487 | | 67,064 |
| 4D | no ATP | 87 | 106 | 387,497 | 218,745 | | 11,499 | 20,100 |

The HPLC profiles from the reunions indicated that the peak representing the unreacted luciferin substrates in these reactions was declining at a very similar rate except for the reactions not given ATP. This rate was very similar to the rate seen for utilization of Luciferin BE and Luciferin ME.

The following readings for light emission from the active enzyme in the samples were obtained (Table 43).

TABLE 43

| | Sample Time [min] | | | | |
|---|---|---|---|---|---|
| Reaction | 0 | 15 | 30 | 45 | 60 |
| 3A | 183.6 | 170.7 | 175.6 | 164.6 | 146.5 |
| 3B | 243.6 | 218.2 | 211.1 | 208.2 | 192.1 |
| 3C | 188.7 | 203.9 | 187.9 | 191.5 | 188.7 |
| 3D | 199.9 | 194.2 | 190.4 | 197.4 | 194.2 |
| 4A | 153.2 | 124.8 | 111.6 | 108.4 | 102.5 |
| 4B | 207.7 | 202.5 | 172.8 | 191.3 | 180.8 |
| 4C | 185.6 | 190.8 | 188.1 | 199.7 | 190.6 |
| 4D | 174.3 | 178.3 | 176.2 | 182.2 | 192 |

While the generation of light from transformation of native luciferin by QuantiLum luciferase does not lead to a large loss of luciferase activity (sec reaction A in Table 43), the transformation of the 2 hydroxyethoxyluciferin derivative led to significant and substantial reduction in enzyme activity (see reaction 4A above). This can be prevented to a very large extent by the presence of various compounds, such as DTT (see reaction 4C above). While there have been reports that the rapid turnover of luciferin by the QuantiLum enzyme can lead to some enzyme inactivation, the inactivation rate for reactions using luciferin derivatives appears to be much more rapid. In addition, the inclusion of DTT to reactions using oxygen ether derivatives of luciferin with QuantiLum enzyme increased the light production SDS PAGE analysis of the samples indicated that a faint fluorescent protein band was formed in reactions 3A and 4A but that there was no band formed under the other reaction conditions.

Since the HPLC profiles of these reactions showed about an equal rate of substrate disappearance for the luciferin derivatives as for native luciferin, the rate for the modified substrates and luciferin are approximately the same. Since the light production for the reactions with the derivative is far lower than for native luciferin, turnover of these derivatives by QuantiLum luciferase does not result in as efficient light production as with native luciferin.

B. Scaffolds

In this example, an experiment was performed that demonstrates that light production by some luciferin derivatives may be dependent upon the particular chemical groups attached to the luciferin. However, one general observation that can be made is that aminoluciferin derivatives produce far more light than oxyethers of luciferin. Thus, the aminoluciferin backbone can be used as a scaffold to prepare other luciferin derivatives that are substrates of luciferase or derivatives which are substrates for a nonluciferase enzyme and prosubstrates of luciferase that, after reacting with the nonluciferase enzyme, yield a product that is an aminoluciferin derivative, e.g., dimethyl aminoluciferin or isopropylaminoluciferin.

Materials and Methods

The DTT, Coenzyme A, and QuantiLum stock solutions are the same as those described herein.

An enzyme addition solution was created that contained 400 mM HEPES, pH 8.0, 40 mM $MgCl_2$, 2000 µg/ml BSA, 400 µM ATP and 8 µl of QuantiLum Luciferase (14.9 mg/ml). This solution was diluted 1:1 with water to produce an enzyme solution labeled "No addition." This solution was diluted 1:1 with 400 mM DTT, pH 8.0 to produce a solution labeled +DTT. This solution was diluted 1:1 with 4 mM Coenzyme A to produce a solution labeled +Co A. Finally, this solution was diluted 1:1 with a solution having both 4 mM Coenzyme A and 400 mM DTT to produce a solution labeled +Co A & DTT.

Results

The various luciferin derivatives listed below were diluted from 5 mM stock solutions to produce solutions at 200, 100, 50, 25, 12.5, 6.25 and 3.125 µM derivative. 50 µl samples of these solutions were placed in the wells of luminometer microliter plates, row A to row G, respectively. Row H of the plates was given 50 µl of water.

Reactions in these plates were initiated by addition of 50 µl of solution containing QuantiLum luciferase using a 12 channel micropipette. The solutions added to the rows were: columns 1, 5, and 9—no addition solution; columns 2, 6, and 10—+Co A solution; columns 3, 7, and 11—+DTT solution, and; columns 4, 8, and 12—+Co A and DTT solution. After addition of the enzyme solution to the first row on every plate, a timer was started. After addition of the enzyme solution to the last row on each plate, the plate was sealed and read on a Veritas luminometer. The following light emission values (Tables 44-46) were obtained ("alone" indicates no addition).

TABLE 44

| Plate 1 | dimethylamino luciferin | | | | diethyaminoluciferin | | | | methylbenzylaminoluciferin | | | |
|---|---|---|---|---|---|---|---|---|---|---|---|---|
| Derivative Conc. | Alone | Co A | DTT | Co A + DTT | Alone | Co A | DTT | Co A + DTT | Alone | Co A | DTT | Co A + DTT |
| 100 | 27421864 | 27183208 | 12461676 | 10059717 | 9082149 | 10142081 | 2180983 | 1960750 | 85579872 | 89117784 | 50806656 | 48409604 |
| 50 | 25967878 | 24213794 | 12561822 | 10272291 | 8176569 | 7206157 | 1826771 | 1538668 | 73867336 | 78390592 | 54238960 | 47965140 |

TABLE 44-continued

| Plate 1 | dimethylamino luciferin | | | | diethyaminoluciferin | | | | methylbenzylaminoluciferin | | | |
|---|---|---|---|---|---|---|---|---|---|---|---|---|
| Derivative Conc. | Alone | Co A | DTT | Co A + DTT | Alone | Co A | DTT | Co A + DTT | Alone | Co A | DTT | Co A + DTT |
| 25 | 22309938 | 20845376 | 11892757 | 9925327 | 6763022 | 5623886 | 1304383 | 1067954 | 61572912 | 63598896 | 50632712 | 42613860 |
| 12.5 | 17014016 | 15077778 | 9239960 | 6714299 | 5418990 | 4485779 | 682672 | 645536 | 50528576 | 50418220 | 36663612 | 30367190 |
| 6.25 | 9091842 | 9170130 | 5998175 | 2602679 | 4009797 | 3457051 | 165732 | 261211 | 43052788 | 35730272 | 21756222 | 19738584 |
| 3.13 | 4526705 | 4109624 | 2766839 | 260502 | 2259570 | 1941060 | 47727 | 93423 | 34516960 | 23501282 | 8088743 | 9404429 |
| 1.07 | 304706 | 208370 | 702319 | 7119 | 656110 | 688887 | 5192 | 20592 | 25907602 | 12863007 | 929977 | 2037020 |
| 0 | 786 | 756 | 1135 | 1572 | 1154 | 1188 | 1802 | 4723 | 10614 | 8378 | 4621 | 2959 |

TABLE 45

| Plate 2 | MAO #3 | | | | GST #4 | | | | GST #3 | | | |
|---|---|---|---|---|---|---|---|---|---|---|---|---|
| Derivative Conc. | Alone | Co A | DTT | Co A + DTT | Alone | Co A | DTT | Co A + DTT | Alone | Co A | DTT | Co A + DTT |
| 100 | 348013 | 741882 | 994617 | 1019425 | 2119 | 1853 | 1618 | 1990 | 16388 | 18343 | 21472 | 19129 |
| 50 | 179585 | 444494 | 868903 | 865209 | 1598 | 1366 | 1354 | 1729 | 17409 | 15440 | 22888 | 20009 |
| 25 | 272608 | 588881 | 733675 | 701503 | 1413 | 1026 | 1492 | 1640 | 15957 | 14791 | 21256 | 18145 |
| 12.5 | 252130 | 467021 | 525765 | 509896 | 1692 | 1275 | 1474 | 1891 | 11752 | 10674 | 16587 | 14298 |
| 6.25 | 201597 | 321914 | 348398 | 82531 | 1571 | 1562 | 1633 | 1730 | 7682 | 7149 | 11164 | 10423 |
| 3.13 | 131633 | 176814 | 200074 | 171233 | 1537 | 1635 | 1458 | 2034 | 4913 | 4832 | 9106 | 8826 |
| 1.07 | 94583 | 122510 | 111682 | 52637 | 1146 | 1533 | 1102 | 1714 | 3232 | 3081 | 5953 | 6964 |
| 0 | 528 | 450 | 734 | 1077 | 488 | 463 | 684 | 940 | 450 | 373 | 687 | 1299 |

TABLE 46

| | 2hydroxyethoxyluciferin ether | | | | Luciferin BE | | | | Luciferin ME | | | |
|---|---|---|---|---|---|---|---|---|---|---|---|---|
| Plate 3 | Alone | Co A | DTT | Co A + DTT | Alone | Co A | DTT | Co A + DTT | Alone | Co A | DTT | Co A + DTT |
| 100 | 53804 | 52640 | 128249 | 94724 | 31581 | 33199 | 54592 | 64460 | 3589 | 3389 | 5399 | 4550 |
| 50 | 38444 | 39320 | 98407 | 87170 | 30609 | 38349 | 80001 | 98716 | 2690 | 2704 | 4052 | 3635 |
| 25 | 27356 | 28679 | 76612 | 67303 | 40093 | 53097 | 84034 | 90306 | 2083 | 2224 | 3491 | 2992 |
| 12.5 | 19586 | 21636 | 61882 | 54630 | 40486 | 57996 | 94861 | 97371 | 1563 | 1768 | 2961 | 2510 |
| 6.25 | 14686 | 18532 | 48458 | 42815 | 38838 | 58288 | 100044 | 105912 | 1240 | 1673 | 2844 | 2882 |
| 3.13 | 10769 | 14986 | 36967 | 32555 | 32994 | 55778 | 86445 | 80626 | 1053 | 1360 | 3332 | 2853 |
| 1.07 | 8807 | 13847 | 24491 | 22105 | 29234 | 50144 | 57066 | 51789 | 1197 | 1523 | 3160 | 3180 |
| 0 | 462 | 852 | 952 | 1428 | 856 | 567 | 1294 | 1495 | 753 | 721 | 1378 | 1275 |

An observation made when gathering this data was that the presence of DTT at high concentrations decreased light production from amino derivatives of luciferin while DTT increased light production from oxyether analogs. Thus, these data clearly show that light production can vary up to at least 35,000 fold depending upon the particular concentration of the derivative, and up to at least 12,000 fold depending on the derivative chosen.

B. Thermostable Luciferase

In this example, a second luciferase was demonstrated to utilize luciferin derivatives. Again, the transformation of these substrates led to covalent modification of the protein in such a way that it becomes fluorescently tagged.

Materials and Methods

A thermostable luciferase (see U.S. Pat. No. 6,602,677; Luc 146-1H2) was obtained in pure form at a purified stock protein concentration of 6.8 mg/ml. This stock was used to produce enzyme stock solution having of 200 µg/ml enzyme solution in 1 mg/ml BSA, 200 mM HEPES buffer, pH 8.0, 20 mM MgCl$_2$.

Luciferin BE and Luciferin CEE (Promega Corp.) were diluted with water from an initial concentration of 5 mM to solutions of 400, 80 and 16 µM.

Solutions were made using a 1 M DTT solution, pH adjusted to 8.0, a 20 mM Coenzyme A solution in water (both described in examples above), a 100 mM ATP solution and water to create the following solutions: Sol'A, 100 µM ATP; Sol'B, 100 µM ATP, 4 mM Coenzyme A, Sol'n C, 100 µM ATP, 400 mM DTT. and; Sol'n D, 100 µM ATP, 4 mM Coenzyme A and 400 mM DTT.

The following reactions were prepared (Table 47)

TABLE 47

| Reaction | Luciferin stock, amt. | Water | Sol'A | Sol'B | Sol'C | Sol'D |
|---|---|---|---|---|---|---|
| 1 | 25 µl Luciferin BE, 400 uM | 25 µl | 25 µl | 0 µl | 0 µl | 0 µl |
| 2 | 25 µl Luciferin BE, 400 µM | 25 µl | 0 µl | 25 µl | 0 µl | 0 µl |

TABLE 47-continued

| Reaction | Luciferin stock, amt. | Water | Sol'A | Sol'B | Sol'C | Sol'D |
|---|---|---|---|---|---|---|
| 3 | 25 ul Luciferin BE, 400 μM | 25 μl | 0 μl | 0 μl | 25 μl | 0 μl |
| 4 | 25 ul Luciferin BE, 400 μM | 25 μl | 0 μl | 0 μl | 0 μl | 0 μl |
| 5 | 25 μl Luciferin BE, 20 μM | 25 μl | 25 μl | 0 μl | 0 μl | 0 μl |
| 6 | 25 μl Luciferin BE, 20 μM | 25 μl | 0 μl | 25 μl | 0 μl | 0 μl |
| 7 | 25 μl Luciferin BE, 20 μM | 25 μl | 0 μl | 0 μl | 25 μl | 0 μl |
| 8 | 25 μl Luciferin BE, 20 μM | 25 μl | 0 μl | 0 μl | 0 μl | 0 μl |
| 9 | 25 μl Luciferin BE, 16 μM | 25 μl | 25 μl | 0 μl | 0 μl | 0 μl |
| 10 | 25 μl Luciferin BE, 16 μM | 25 μl | 0 μl | 25 μl | 0 μl | 0 μl |
| 11 | 25 μl Luciferin BE, 16 μM | 25 μl | 0 μl | 0 μl | 25 μl | 0 μl |
| 12 | 25 μl Luciferin BE, 16 μM | 25 μl | 0 μl | 0 μl | 0 μl | 0 μl |
| 13 | 25 μl Luciferin CEE, 400 μM | 25 μl | 25 μl | 0 μl | 0 μl | 0 μl |
| 14 | 25 μl Luciferin CEE, 400 uM | 25 μl | 0 μl | 25 μl | 0 μl | 0 μl |
| 15 | 25 μl Luciferin CEE, 400 μM | 25 μl | 0 μl | 0 μl | 25 μl | 0 μl |
| 16 | 25 μl Luciferin CEE, 400 μM | 25 μl | 0 μl | 0 μl | 0 μl | 0 μl |
| 17 | 25 μl Luciferin CEE, 80 μM | 25 μl | 25 μl | 0 μl | 0 μl | 0 μl |
| 18 | 25 μl Luciferin CEE, 80 μM | 25 μl | 0 μl | 25 μl | 0 μl | 0 μl |
| 19 | 25 μl Luciferin CEE, 80 μM | 25 μl | 0 μl | 0 μl | 25 μl | 0 μl |
| 20 | 25 μl Luciferin CEE, 80 μM | 25 μl | 0 μl | 0 μl | 0 μl | 0 μl |
| 21 | 25 μl Luciferin CEE, 16 μM | 25 μl | 25 μl | 0 μl | 0 μl | 0 μl |
| 22 | 25 μl Luciferin CEE, 16 μM | 25 μl | 0 μl | 25 μl | 0 μl | 0 μl |
| 23 | 25 μl Luciferin CEE, 16 μM | 25 μl | 0 μl | 0 μl | 25 μl | 0 μl |
| 24 | 25 μl Luciferin CEE, 16 μM | 25 μl | 0 μl | 0 μl | 0 μl | 0 μl |
| 25 | 0 μl | 50 μl | 25 μl | 0 μl | 0 μl | 0 μl |

Results

After assembly, the reactions were initialed by addition of 25 μl of the thermostable luciferase stock solution above and mixing the tube contents. A 50 μl sample was immediately removed and placed in a luminometer tube and the light read and the tube then replaced in a tube rack at room temperature. While the light reading was being taken, a 5 μl sample of the remaining reaction (which was kept at room temperature) was diluted into 495 μl of 50 mM BisTris, pH 6.5, 1 mg/ml BSA, 1 mM EDTA prechilled to 4° C. and the tube mixed and placed on ice. The light produced by the samples in the luminometer tubes were re-read at 20, 40, 60, 90 and 120 minutes post enzyme addition. Additional 5 μl samples were taken and diluted as above at 60 and 120 minutes post enzyme addition. Once all these readings and samples were taken, 50 μl of the diluted samples was mixed with 50 μl of Steady Glo in luminometer tubes, the tubes incubated 10 minutes on ice then the light produced was read on a Turner TD 2070 luminometer.

The following light readings from the reaction samples directly placed into luminometer tubes were obtained (Table 48).

TABLE 48

| | | | Time [min] | | | | | |
|---|---|---|---|---|---|---|---|---|
| Reaction | Substrate | Additive | 0 | 20 | 40 | 60 | 90 | 120 |
| 1 | L'in-BE 100 | Alone | 160 | 48.21 | 19.25 | 8.305 | 2.843 | 1.311 |
| 2 | | +Co A | 191.9 | 63.85 | 29.28 | 14.78 | 6.652 | 3.014 |
| 3 | | +DTT | 148.7 | 77.9 | 48.39 | 32.26 | 21.71 | 14.25 |
| 4 | | +Co A & DTT | 140.4 | 71.5 | 45.66 | 29.32 | 19.92 | 13.08 |
| 5 | L'in-BE 25 | Alone | 623.2 | 73.96 | 28.76 | 13.42 | 5.528 | 2.549 |
| 6 | | +Co A | 972.4 | 127.4 | 58.9 | 31.96 | 17.54 | 9.727 |
| 7 | | +DTT | 448.6 | 84.21 | 43.77 | 27.21 | 18.48 | 12.93 |
| 8 | | +Co A & DTT | 402 | 85.37 | 45.87 | 27.94 | 18.94 | 13.13 |
| 9 | L'in-BE 6.26 | Alone | 785.5 | 62.64 | 22.11 | 11.22 | 5.189 | 2.995 |
| 10 | | +Co A | 2575 | 207.1 | 83.73 | 45.54 | 24 | 14.42 |
| 11 | | +DTT | 455.6 | 71.9 | 33.73 | 21.49 | 13.67 | 9.847 |
| 12 | | +Co A & DTT | 436.9 | 80.41 | 38.47 | 22.83 | 16.08 | 12.01 |
| 13 | L'in-CEE 100 | Alone | 20.46 | 1.18 | 0.868 | 0.788 | 0.627 | 0.544 |
| 14 | | +Co A | 97.88 | 10.3 | 7.127 | 5.562 | 3.969 | 2.845 |
| 15 | | +DTT | 22.47 | 2.233 | 1.292 | 1.164 | 1.093 | 0.958 |
| 16 | | +Co A & DTT | 25.41 | 3.278 | 2.027 | 1.666 | 1.27 | 1.157 |
| 17 | L'in-CEE 25 | Alone | 59.87 | 3.176 | 1.919 | 1.305 | 1.178 | 1.03 |

TABLE 48-continued

| Reaction | Substrate | Additive | 0 | 20 | 40 | 60 | 90 | 120 |
|---|---|---|---|---|---|---|---|---|
| | | | | | Time [min] | | | |
| 18 | | +Co A | 489.2 | 45.45 | 25.08 | 16.96 | 11.03 | 7.309 |
| 19 | | +DTT | 56.59 | 3.761 | 2.196 | 1.668 | 1.274 | 1.157 |
| 20 | | +Co A & DTT | 57.98 | 5.721 | 3.272 | 2.192 | 1.379 | 1.174 |
| 21 | L'in-CEE 6.25 | Alone | 121 | 5.884 | 3.316 | 2.352 | 1.569 | 1.154 |
| 22 | | +Co A | 1829 | 114 | 57.82 | 37.53 | 24.66 | 17.02 |
| 23 | | +DTT | 72.52 | 5.903 | 3.073 | 2.089 | 1.431 | 1.125 |
| 24 | | +Co A & DTT | 77.35 | 7.958 | 3.656 | 2.312 | 1.414 | 1.134 |
| 25 | No L'in Con. | ATP Only | 198.8 | 1.177 | 0.123 | 0.119 | 1.101 | 0.089 |

The table below (Table 49) contains the tight values obtained upon addition of the diluted reaction samples into Steady Glo reagent.

TABLE 49

| Reaction | Substrate | Additive | 0 min | 60 min | 120 min |
|---|---|---|---|---|---|
| | | | | Time Sample Taken | |
| 1 | L'in-BE 100 | Alone | 1245 | 156.4 | 61.75 |
| 2 | | +Co A | 1486 | 242.2 | 82.03 |
| 3 | | +DTT | 1762 | 952.1 | 691 |
| 4 | | +Co A & DTT | 1780 | 1016 | 778.7 |
| 5 | L'in-BE 25 | Alone | 1309 | 157.1 | 72.57 |
| 6 | | +Co A | 1610 | 277.8 | 143.2 |
| 7 | | +DTT | 1675 | 910.2 | 738.9 |
| 8 | | +Co A & DTT | 1925 | 1102 | 836.3 |
| 9 | L'in-BE 6.25 | Alone | 2057 | 406.6 | 267.7 |
| 10 | | +Co A | 1841 | 518.6 | 349.1 |
| 11 | | +DTT | 1860 | 1173 | 1067 |
| 12 | | +Co A & DTT | 1943 | 1235 | 1163 |
| 13 | L'in-CEE 100 | Alone | 1262 | 1203 | 1273 |
| 14 | | +Co A | 1127 | 1055 | 770.5 |
| 15 | | +DTT | 1168 | 501.5 | 1478 |
| 16 | | +Co A & DTT | 1745 | 1319 | 1343 |
| 17 | L'in-CEE 25 | Alone | 1345 | 973.4 | 860.3 |
| 18 | | +Co A | 1547 | 777.5 | 588.7 |
| 19 | | +DTT | 1116 | 1372 | 1393 |
| 20 | | +Co A & DTT | 529.6 | 1268 | 1329 |
| 21 | L'in-CEE 6.25 | Alone | 1402 | 1158 | 1073 |
| 22 | | +Co A | 1647 | 976.8 | 921.4 |
| 23 | | +DTT | 1631 | 1544 | 1695 |
| 24 | | +Co A & DTT | 1836 | 1625 | 1622 |
| 25 | No L'in Con. | ATP Only | 1415 | 1685 | 1863 |

These data indicate that the tested thermostable luciferase can utilize these two luciferin derivatives as substrates. With these luciferin derivatives and the tested luciferase, DTT does not appear to have the ability to dramatically stimulate light production as was seen with the QuantiLum enzyme. However, as seen with the QuantiLum Luciferase, utilization of these substrates by the thermostable luciferase resulted in an inactivation of the enzyme that can be reduced by the addition of DTT to the reaction. The addition of coenzyme A increased the level of light production, however, this compound appeared to have differential effects upon the retention of activity of the enzyme with the additive alone, somewhat decreasing the inactivation seen with luciferin BE and enhancing the inactivation with luciferin CEE.

Summary

Figure 7A:
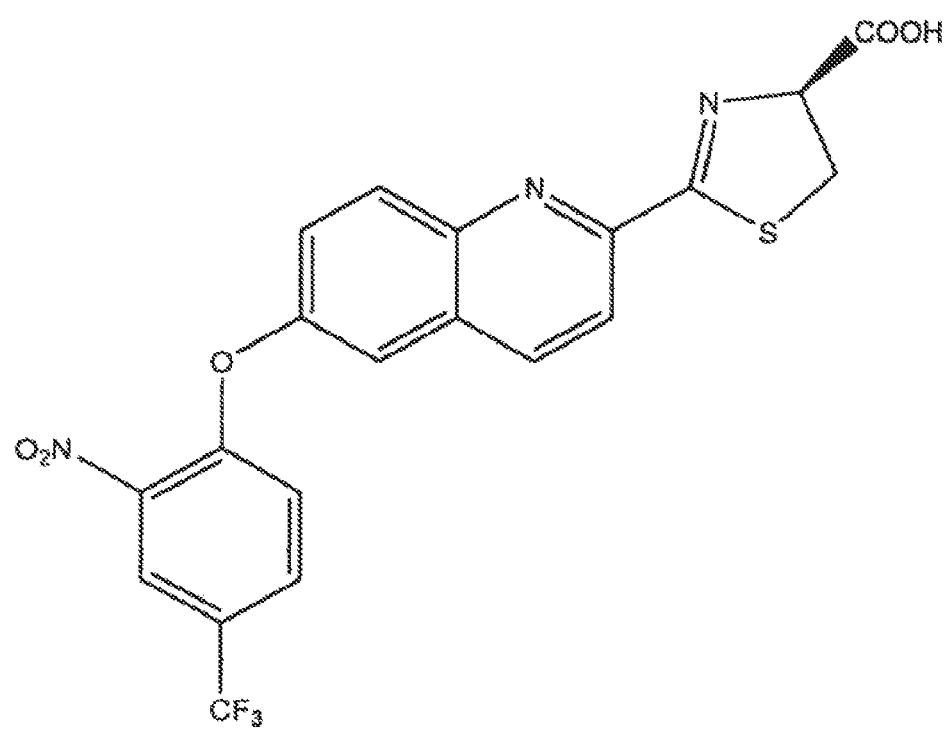
FIGS. 7A-B. Other exemplary derivatives of luciferin.
Figure 7B:
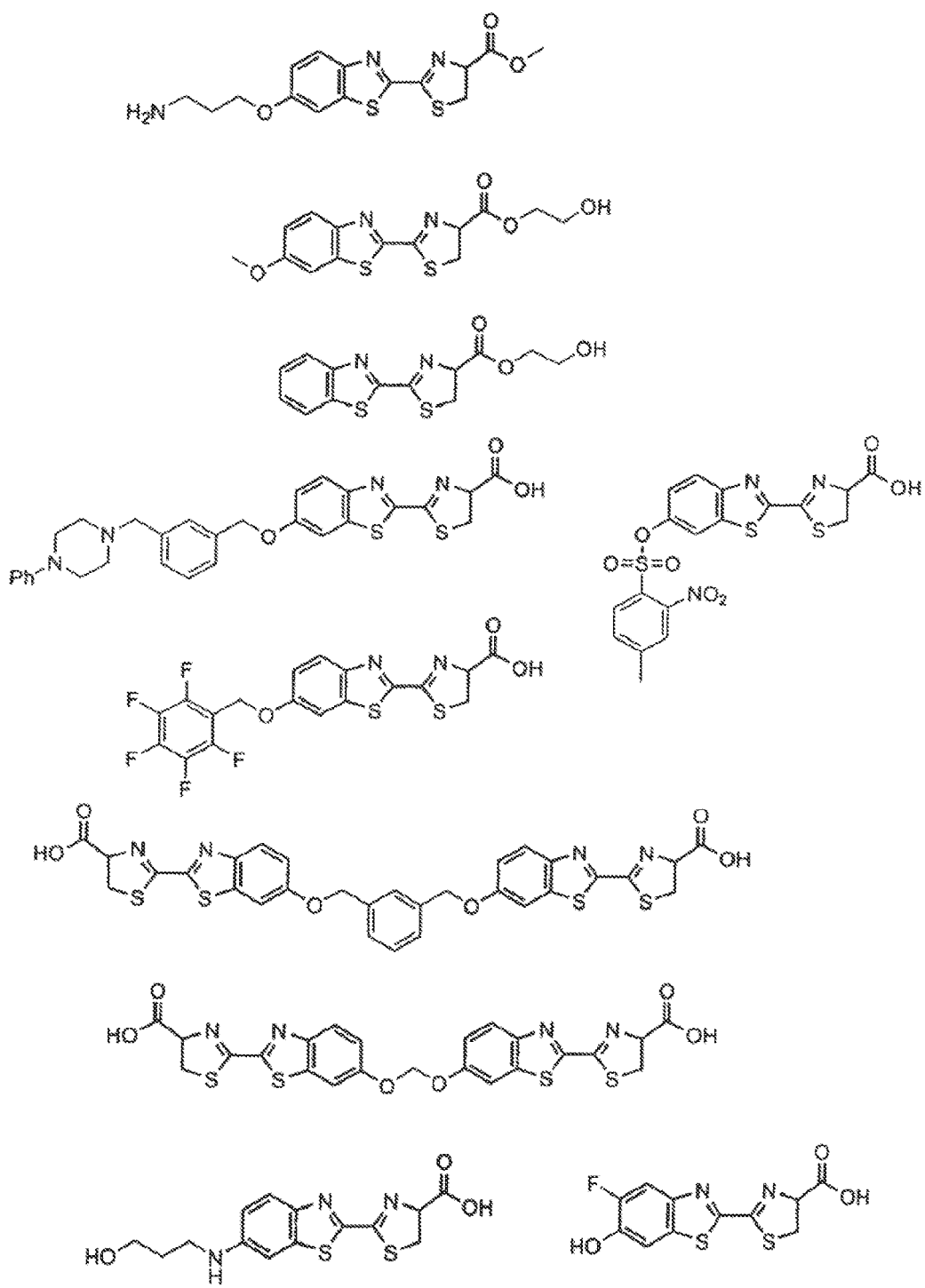
Figure 8A:
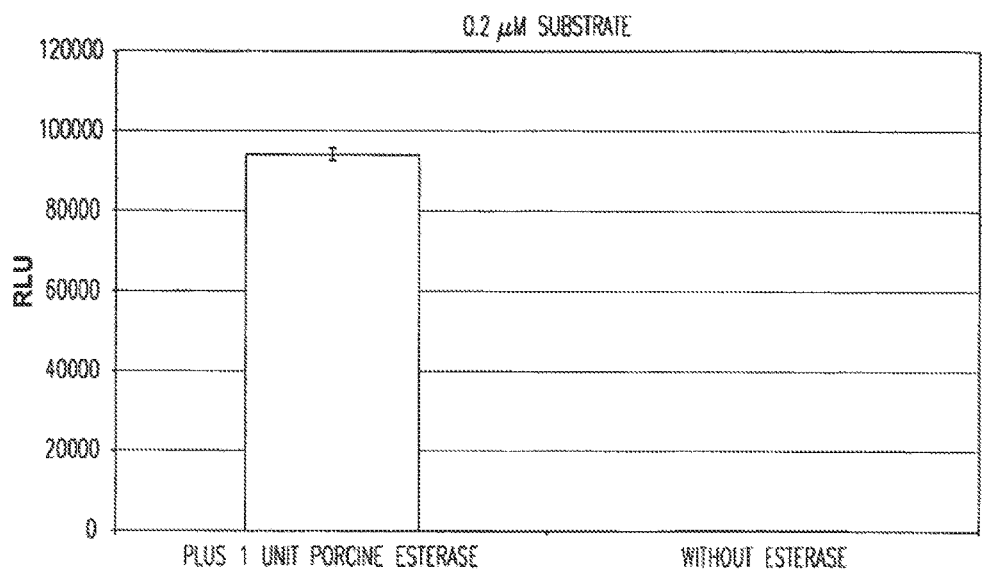
FIG. 8A. A graphical representation of RLU for reactions containing an esterase and a luciferin derivative, luciferin ethyl ester. 20 minute incubation at 37° C.
Figure 8B:
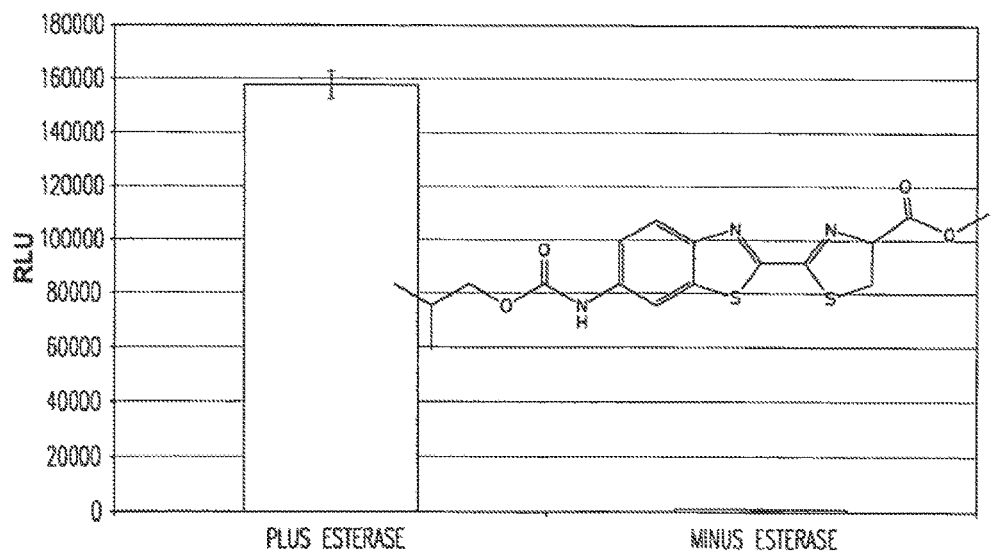
FIG. 8B. A graphical representation of RLU for reactions containing an aminoluciferin derivative (isopropyl urethane aminoluciferin methyl ester; 50 µM), with and without esterase. 20 minute incubation at room temperature.
Figure 9:
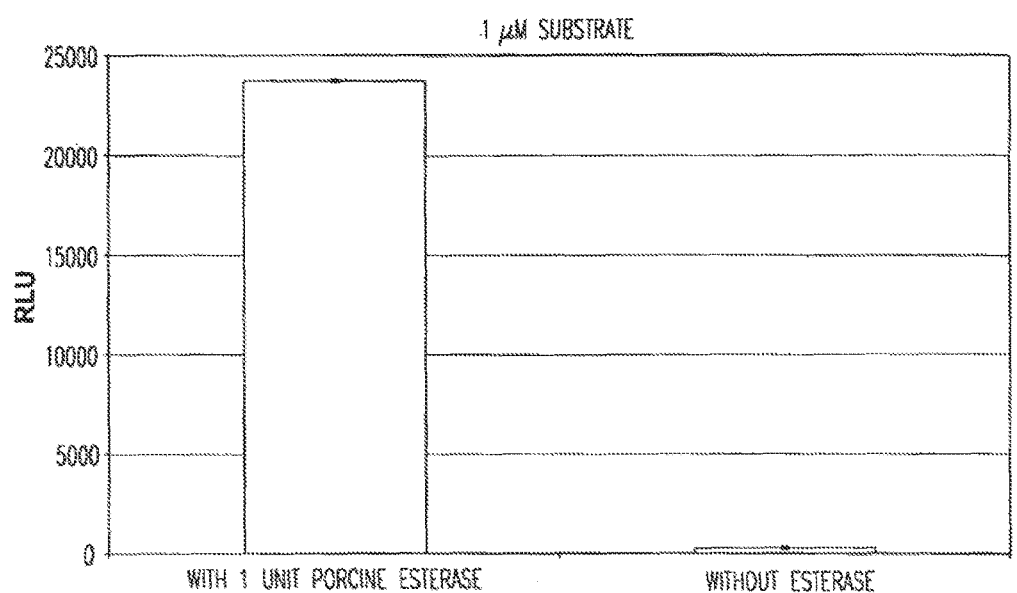
FIG. 9. A graphical representation of RLU for reactions containing an esterase and a luciferin derivative, luciferin methyl ester. 20 minute incubation at 37° C.
Figure 10:
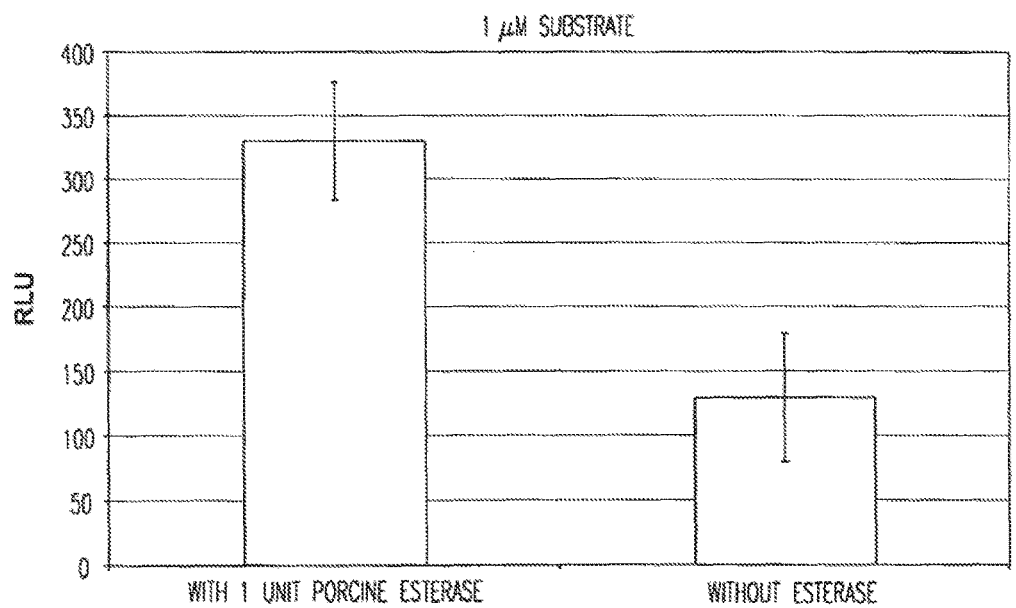
FIG. 10. A graphical representation of RLU for reactions containing an esterase and a luciferin derivative, O-luciferin picolinyl ester. 20 minute incubation at 37° C.

Derivatives that were designed such that the phenolic hydroxyl group on luciferin was modified to be an oxygen ether or a derivatized amine surprisingly were utilized by luciferase. For instance, N-(3-hydroxypropyl)-aminoluciferin (FIG. 7B) is a substrate for luciferase that provides sufficient light output for a luminescence reaction.

The fact that light production from the derivatives varied over several orders of magnitude was also surprising. As described herein, recent data clearly shows that, at least for QuantiLum luciferase, utilization of the derivatives can be as rapid as that seen for native luciferin. However, light production can be over 10,000 fold less than from D-luciferin, indicating that light production may not be an effective means to determine if a derivative is utilized effectively. Thus, the low level of light produced from many of the derivatives could erroneously have been attributed to very low levels of contaminating native luciferin rather than to low level light production from the rapid utilization of the actual derivatives.

For instance, N-(3-hydroxypropyl)-aminoluciferin (FIG. 7B) is a substrate for luciferase that provides sufficient light output for a luminescence reaction.

Further work demonstrated that both the thermostable and QuantiLum luciferases were inactivated in the presence of some of the derivatives and that some compounds, such as DTT, may alter light production. The effect of DTT on light production can result in either no effect on light production, an increase in light production, or a decrease in light production, dependent upon the specific combination of luciferase and derivative employed. Moreover, another compound, coenzyme A, substantially increased light production from a luciferin derivative, however, it may: 1) increase the rate of enzyme inactivation 2) have no apparent effect on enzyme inactivation, or 3) greatly decrease the rate of enzyme inactivation dependent upon the particular combination of luciferase and derivative.

While thiol compounds such as DTT have been shown to prevent inactivation of luciferase during the transformation of native luciferin, and that coenzyme A can stimulate light production, the results with luciferin derivatives on the invention were surprising because the derivatives were unknown and it was unknown whether they were substrates for luciferase, and the phenolic oxygen of luciferin was thought to be crucial for luciferin to act as a substrate, and so at least some of the derivatives, would not be expected to be substrates. If the derivatives were likely not to be substrates, there would be no reason to expect that their biotransformation by luciferase would lead to inactivation of the enzyme. Moreover, since the derivatives were not known to inactivate the enzyme, there would be no expectation that DTT could alter light production in reactions with certain derivatives. Therefore, there would be no reason to expect that any particular derivative could substantially increase light output from transformation of the derivative.

These observations suggest particular modifications that are best avoided as they may be effectively utilized by luciferase without transformation, producing a substrate that can give a very high background signal. In addition, knowing that such a derivative may be utilized may identify why some derivatives produce unexpected light signals when used at different concentrations. Moreover, identifying derivatives that can inactivate luciferase is useful in assay development. For example, for an assay that generates a steady light signal over an extended period of time, an agent that prevents inactivation of the enzyme by the unspent derivative that is in the reaction may be employed. Thus, a solution for the measurement of the amount of luciferin derivative transformed by an enzymatic or chemical process that includes an agent to prevent the inactivation of luciferase in the solution is envisioned.

The observations described herein provide for a synthetic strategy. This strategy is based upon the observation that untransformed derivatives produce light and that different derivatives can produce far different light levels. Prior to these observations, it was likely that all substrates that would be useful for assay of an enzyme through the transformation of a luciferin derivative would need to produce a native luciferin moiety. Understanding that light can be produced by luciferins by transformation of a luciferin derivative indicated that the enzymatic transformation need not produce native luciferin to be able to be measured by light production, only that the production have a measurably different level of light production (either higher or lower) than the original derivative. This strategy simplifies potential substrate design and suggests that the substrates that will generate the strongest light signals without generating native luciferin are those that contain an amino group in place of the phenolic oxygen and that the amino group can be a tertiary amine. If so, one of the attached groups likely is no larger than a methyl group while the other can be as large as at least a benzyl group.

Example 7

Luciferase Reactions with Fluoroluciferins are Less pH Sensitive

A. 5'-fluoroluciferin

As shown below, firefly luciferase (QuantiLum™ Luciferase, E170, Promega Corporation, Madison, Wis.) utilized 5-fluoroluciferin (FIG. 24) in a less pH-dependent manner than it utilized luciferin.

Material and Methods

QuantiLum luciferase was diluted to 14.7 ng/ml in Glo Lysis Buffer (part E266B. Promega Corporation) containing 1 mg/ml BSA (part BP1605-100, Fisher Scientific, N.J.).

To test the pH-dependence of the luciferase signal, the luciferase detection reagents contain one of 3 buffers each at one of 4 pHs, and this combination was identical for luciferin and 5'-fluoroluciferin. The luciferase detection reagents were created using a stock solution containing 0.1850 g of DTT (V3155, Promega Corporation), 0.0121 g ATP (part 27-1006-01, Amersham Biosciences, N.J.), 80 μl of 0.5 M CDTA stock, pH 8.0 (AA842, Promega Corporation), and 240 μM of 1 M magnesium sulfate stock (AA319, Promega Corporation) in 24 ml of water. This was split into 2 aliquots and luciferin (E1602, Promega Corporation) or 5-fluoroluciferin (Promega Biosciences Inc. CA) were added to final concentrations, in this solution, of 787.5 μM. Aliquots of these solutions were then placed into tubes and buffers were added to 80 mM. The final luciferin detection reagents therefore contained 80 mM buffer. 30 mM DTT, 500 μM ATP, 1 mM CDTA, 6 mM magnesium sulfate and 630 μM luciferin or 5-fluoroluciferin.

The buffers were tricine at pH 8.327, 8.100, 7.883 and 7.673; HEPES at pH 7.892, 7.720, 7.521, and 7.303; and MOPS at pH 7.499, 7.296, 7.133, 6.900.

Luminescent reactions were initiated by combining 100 μl of the luciferase-containing solution and 100 μl of the luciferase detection reagents. Luminescence was integrated over 1 second per sample using the Veritas plate luminometer (Turner BioSystems). N=3 for each result.

Results

The average luminescence measured for each set of samples is listed in Table 50 (relative standard deviation ≤4.0%) The relative luminescence shown is the avenge luminescence of each triplicate divided by the average luminescence for the luciferin-based luciferase detection reagent at pH 8.3.

TABLE 50

| pH | Buffer | Absolute Luminescence, Luciferin (RLU) | Absolute Luminescence, 5-Fluoroluciferin (RLU) | Relative Luminescence of Luciferin (% of 8.3 Luciferin) | Relative Luminescence of 5-Fluoroluciferin (% of 8.3 Luciferin) |
|---|---|---|---|---|---|
| 8.327 | Tricine | 1,463,179 | 317,030 | 100% | 22% |
| 8.100 | Tricine | 1,422,936 | 357,041 | 97% | 24% |
| 7.883 | Tricine | 1,254,769 | 357,883 | 86% | 24% |
| 7.673 | Tricine | 1,041,115 | 351,411 | 71% | 24% |
| 7.892 | HEPES | 976,654 | 377,498 | 67% | 26% |
| 7.720 | HEPES | 815,317 | 378,927 | 56% | 27% |
| 7.521 | HEPES | 661,829 | 360,308 | 45% | 25% |
| 7.303 | HEPES | 482,253 | 323,456 | 33% | 22% |
| 7.499 | MOPS | 707,832 | 334,288 | 48% | 23% |
| 7.296 | MOPS | 585,743 | 331,515 | 40% | 23% |
| 7.133 | MOPS | 490,814 | 325,337 | 34% | 22% |
| 6.900 | MOPS | 330,277 | 272,127 | 23% | 19% |

These data show that the luminescence increased almost 5-fold over the pH range tested when the luciferase detection reagent contained luciferin, whereas the luminescence changed by only about 40% when the luciferase detection reagent contained 5'-fluoroluciferin. Furthermore, the luciferase detection reagent was less sensitive to the buffer composition when it contained 5-fluoroluciferin than when it contained luciferin. The luciferase luminescence increased by 28% in pH 7.89 reagent when the luciferin-containing buffer was changed from HEPES to tricine, however, the 5'-fluoroluciferin containing reagent only decreased by 6% when these buffers were changed. The pH insensitivity of the luciferase detection reagent containing 5'-fluoroluciferin could be beneficial if luciferase reactions are run at low pH, especially those below approximately 6.9, or where pH shifts between different samples may occur (for example, if the sample to be measured is highly buffered but not all samples are the same pH). Therefore, the 5'-fluoroluciferin scaffold may be modified to include a site for nonluciferase enzyme activity or chemical activity which derivative could be used to monitor luciferase activity, a nonluciferase enzyme activity, or a chemical activity.

Other Fluoroluciferins
Methods and Methods

Reactions were assembled to compare the spectrum generated by 5'-fluoroluciferin, 7'-fluoroluciferin and luciferin. Reagent was created containing 200 mM HEPES, 200 mM PIPES, 1 mM CDTA, 0.5% Tergitol NP-9, 0.03% Benzyl dodecyldimethyl ammonium bromide, 30 mM thiourea, 3 mM ATP, 6 mM magnesium sulfate, and 0.5 mM luciferin or fluoroluciferin. pH of the reagent was 7.4. All compounds except fluoroluciferin and ATP were purchased from Sigma Chemical ATP was purchased from Amersham/Invitrogen. Luciferin and both fluoroluciferins were made at Promega Biosciences, Inc. Reactions were initiated by adding equal volumes (0.5 ml) of reagent and DMEM medium (Gibco/Invitrogen) containing 0.1% Prionex® (Pentapharm) and $2.94 \times 10^{-2}$ mg/ml QuantiLum™ Luciferase (Promega Corporation).

Spectra were measured using 0.5 s integration with 1 nm increments on a Spex Fluorolog.

For pH titrations, reagent was created containing 100 mM HEPES, 100 mM PIPES, 100 mM Tricine, 1 mM CDTA, 0.5% Tergitol NP-9, 0.03% Benzyl dodecyldimethyl ammonium bromide, 30 mM thiourea, 3 mM ATP, 6 mM magnesium sulfate, and 0.15 mM 7'-fluoroluciferin. All compounds except fluoroluciferin and ATP were purchased from Sigma Chemical. APT was purchased from Amersham/Invitrogen. The pH of solution was adjusted within the range of 8.5 to 6.4. Reactions were initiated by adding equal volumes (0.1 ml) of reagent and DMEM medium (Gibco/Invitrogen) containing 0.1% Prionex® (Pentapharm) and $1.4 \times 10-5$ mg/ml OuantiLum™ Luciferase (Promega Corporation).

Luminescence was measured for 0.5 seconds per well using Turner Biosystems Veritas.

For ATP titrations for luciferin and 5' fluoroluciferin, reagent was created containing 100 mM HEPES pH 7.5, 0.5 mM CDTA, 30 mM DTT, 6 mM magnesium sulfate, and 0.5 mM 5'-fluoroluciferin or luciferin. All compounds except 5'-fluoroluciferin and DTT were purchased from Sigma Chemical. To some of this reagent 5 mM ATP (Amersham/Invitrogen) was added, then serially diluted by half-logs to 0.05 mM. Reactions were initialed by adding equal volumes (0.1 ml) of reagent and DMEM medium (Gibco/Invitrogen) containing 0.1% Prionex® (Pentapharm) and $1.4 \times 10-5$ mg/ml QuantiLum™ Luciferase (Promega Corporation).

For ATP titrations for 7'-fluoroluciferin, reagent was created containing 200 mM HEPES, 200 mM PIPES, 1 mM CDTA, 0.5% Tergitol NP-9, 0.03% Benzyl dodecyldimethyl ammonium bromide, 30 mM thiourea, 10 mM magnesium sulfate, and 0.15 mM 7'-fluoroluciferin. This solution was separated into 3 parts and pH of the reagents were 7.4, 7.2 and 6.7. To some of this reagent, 10 mM ATP (Amersham/Invitrogen) was added. The ATP was serially diluted by quarter-logs from 10 mM to 0.32 mM.

Reaction were initiated by adding equal volumes (0.03 ml) of reagent and DMEM medium (Gibco-Invitrogen) containing 0.1% Prionex® (Pentapharm) and $1.4 \times 10-5$ mg/ml QuantiLum™ Luciferase (Promega Corporation).

Luminescence was measured for 0.5 seconds per well using Berthold Orion luminometer.

Results

Figure 56:
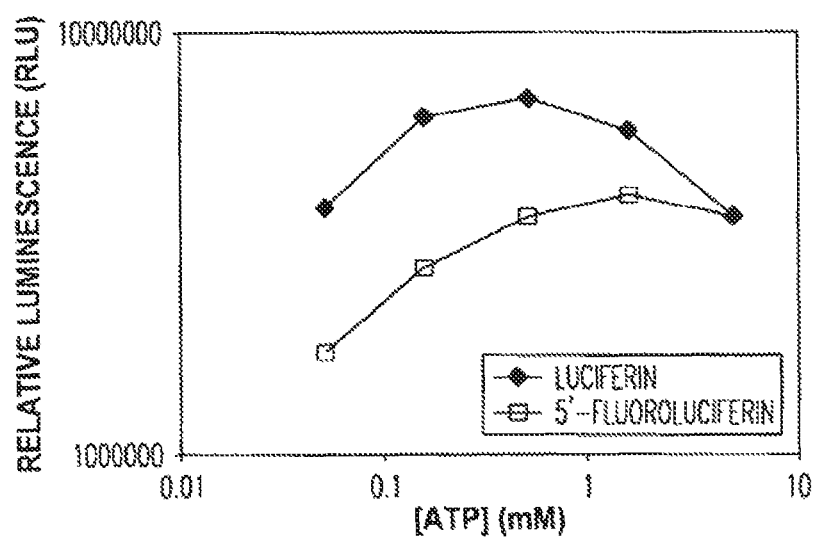
FIG. 56. ATP titration of a 5'fluoroluciferin and luciferin.

The luciferase reaction using 5'-fluoroluciferin saturated with ATP at a higher concentration than the reaction using luciferin (FIG. 56). Luciferase reactions containing 5'-fluoroluciferin could be used to measure ATP levels that exceed the linear range of reactions containing luciferin.

Figure 57:
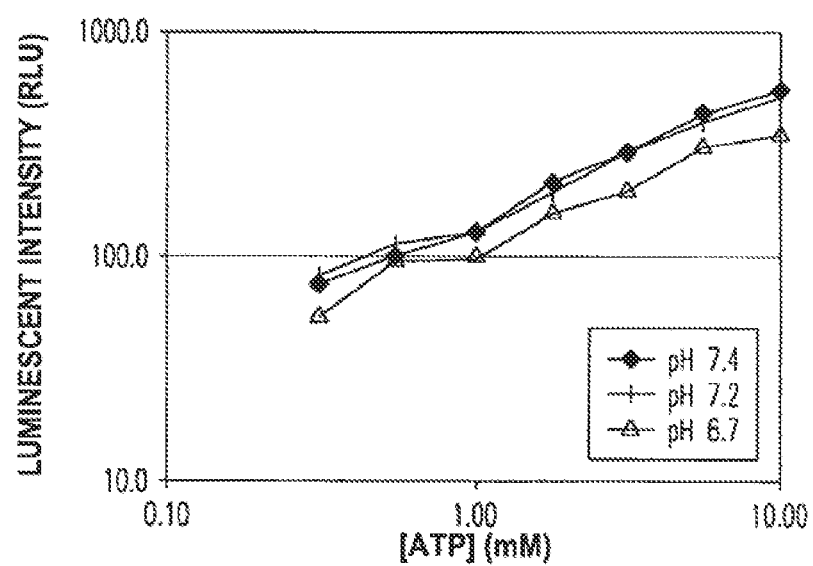
FIG. 57. ATP titration of a 7'fluoroluciferin.

For the other fluoroluciferins, the intensity of luminescence increases with ATP (FIG. 57). Unexpectedly, the requirement for ATP is much higher in firefly luciferase reactions containing 7'-fluoroluciferin than in reactions containing luciferin where the Km for ATP is usually below 1 mM. 7'-fluoroluciferin could therefore be used in firefly luciferase reactions to quantitate ATP levels that exceed the linear range of reactions utilizing luciferin.

The 5'-fluoroluciferin generated luminescence with λmax approximately 25 nm blue-shifted from regular luciferin and 7'-fluoroluciferin generated luminescence with λmax approximately 21 nm red-shifted from regular luciferin. The pH optima for the firefly luciferase reaction using 7'-fluoroluciferin was approximately pH 7.5, much lower than luciferin where the pH optima is approximately 8.2. The firefly luciferase reaction also maintained high comparative intensity at pH below 7.0.

Figure 58:
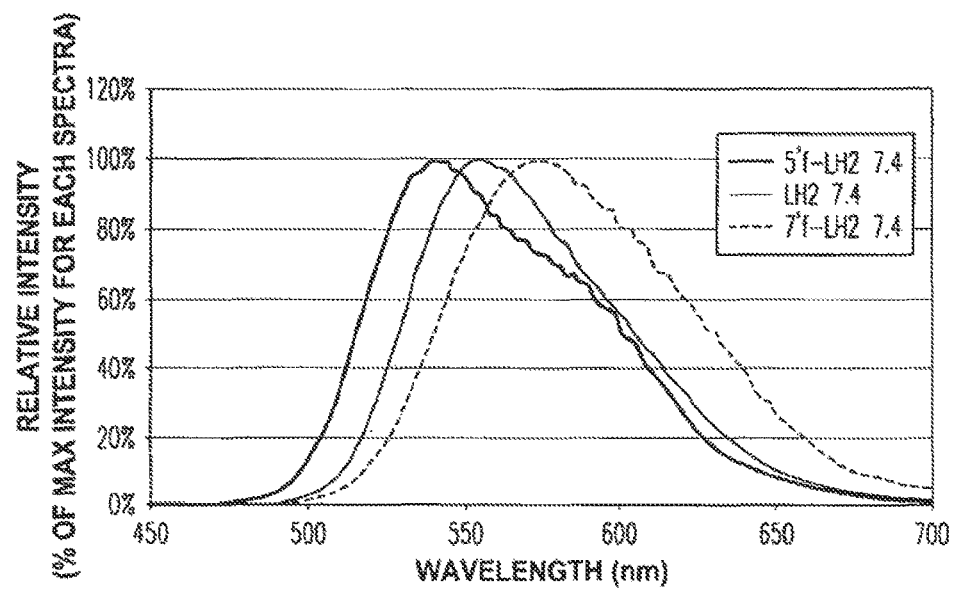
FIG. 58. Spectra of various fluoroluciferins.
Figure 59:
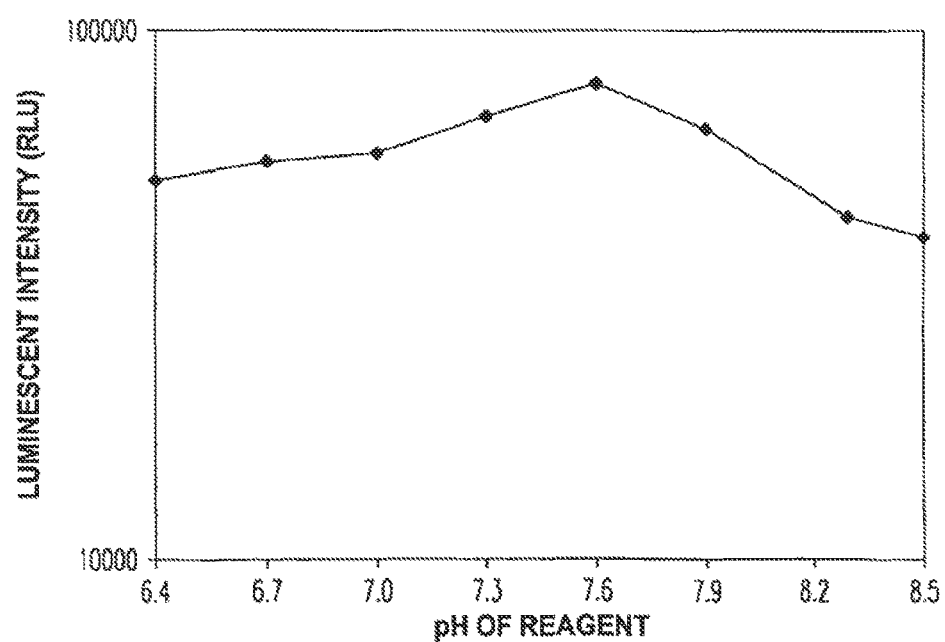
FIG. 59. pH titration of a 7'fluoroluciferin.
Figure 60:
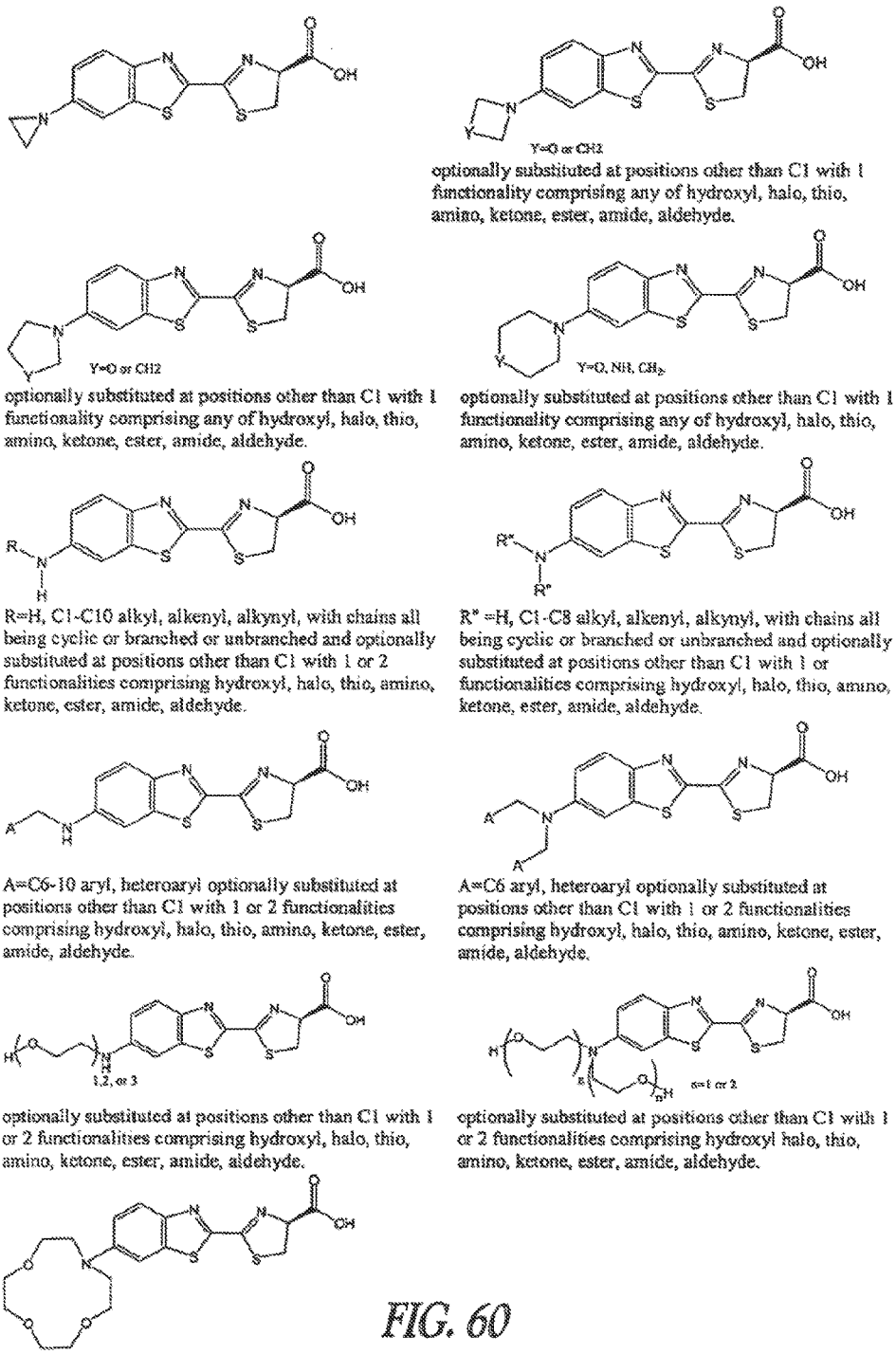
FIG. 60. Luciferin derivatives useful as luciferase substrates and scaffolds for luciferin derivatives useful as non-luciferase substrates.

Thus, 5' fluoroluciferin has a lower pH optima (FIG. 59) and a spectral shift of about 10 nm more blue (FIG. 58) and 7' fluoroluciferin lower pH optima and a spectral shift of about 20 to 30 nm more red. It would be expected that 5' fluoroaminoluciferin, 7'fluoroaminoluciferin and 7',7' fluoroaminoluciferin, would have similar characteristics to their luciferin counterpart.

Running reactions at lower pH increases liability of thiols and luciferin in a formulation, increasing overall reagent stability. Moreover, running reactions at lower pH may permit a coupled enzyme reaction to generate higher light at low pH, and may permit a target enzyme reaction to perform at a higher activity. Further, the reactions may result in higher luminescent intensities at lower pH (and may be used to reduce other enzyme activities, like ATPases of proteases). In addition, the spectral shift allows for better spectral separation in multiplexing. For 7' fluoroluciferin and 7',7' fluoroaminoluciferin, the spectral shift allows for increased measurable luminescence with PMT-based luminometers. 5',7' difluoroluciferin may have similar properties. For 7' fluoroluciferin, the requirement for ATP is very high for the luminescence reaction and so it may be employed in reactions where there is a high Km for ATP without further reagent modification.

Summary

In summary, whereas light production from native luciferin changes dramatically over a pH range of pH 6.5 to 8.5, much less change was seen with fluoroluciferin over these same pH values. This effect resulted in native luciferin generating more light at higher pH values but fluoroluciferin generating at least as much light if not more light at lower pH values, therefore, those compounds are particularly useful where extra signal is important in a reaction that must be performed at lowered pH values.

Moreover, some derivatives, including those with halogen modification, can be utilized to generate light directly, and different derivatives within the broad scope of the luciferin derivatives of the invention, can vary in light production by several orders in magnitude Luciferins modified with fluorine that have lower pH optima are useful in reporter gene measurements, ATP-dependent assays, kinase assays, or other assays such as coupled assays, e.g, assays including caspase assays such as caspase-3/7, caspase-8 or caspase-9 assays, or cathepsin B, cathepsin L or calpain assays, and as luciferase sensors, for example, with derivatives that also have a protease site for a protease with an activity maxima lower than about pH 7.2.

Luciferins modified with fluorine that have a spectral shift of about 10 nm or more blue are useful in all luminescent assays, and in particular in in situ or in vivo luminescent measurements (live cells in culture or live animal imaging), reporter gene assays, and assays that use luciferase as a sensor.

Luciferins modified with fluorine that have a spectral shift of about 20 to 30 nm or more red are useful to improve color quenching in 2 step dual measurement assays, e.g., of a Renilla luciferase signal, or other dual reporter gene assays, or in a multiplex assay for a nonluciferase enzyme, such as a protease, with one or more reporter gene assays, or in other luminescent assays, such as in in situ or in vivo luminescent measurements (live cells in culture or live animal imaging), reporter gene assays, and assays that use luciferase as a sensor.

Example 8

Luciferin Derivative for Beta-Gluronidase

Luciferin 6'-glucuronide was designed as a substrate for beta-glucuronidase (GUS). The Km value of this compound in 50 mM MES, pH 6.3, was 180+/−30 uM; this is reasonably similar to that of 4-methylumbelliferyl glucuronide, a fluorescent substrate for GUS with a Km value of 59+/−8 uM. The luminescent substrate is more sensitive than the fluorescent substrate with a limit-of-detection of 0.28 ng/ml vs 2.01 ng/ml, respectively. The source of the human enzyme was Sigma-Aldrich. GUS was incubated with the substrate in 50 mM MES, pH 6.3, for 15 minutes. An equal volume of the P450-Glo luciferin detection reagent was then added and the luminescence was measured at 2 minutes (Tables 51-52).

TABLE 51

| [substrate] (μM) | +GUS | no GUS |
|---|---|---|
| 2548.0 | 1,335,243 | 209,219 |
| 849.3 | 994,977 | 91,975 |
| 283.1 | 696,778 | 34,127 |
| 94.4 | 423,619 | 13,091 |
| 31.5 | 232,533 | 5,068 |
| 10.5 | 107,502 | 2,190 |
| 3.5 | 46,210 | 1,108 |
| 0.0 | 612 | 451 |

TABLE 52

| [GUS] (ng/ml) | signal-to-noise | |
|---|---|---|
|  | luminescence | fluorescence |
| 277.5 | 7300 | 861.4 |
| 138.8 | 3104 | 376.8 |
| 69.4 | 1411 | 164.6 |

TABLE 52-continued

| [GUS] (ng/ml) | signal-to-noise | |
|---|---|---|
|  | luminescence | fluorescence |
| 34.7 | 649 | 76.5 |
| 17.3 | 296 | 34.7 |
| 8.7 | 133 | 15.6 |
| 4.3 | 68 | 7.5 |

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A compound according to formula IIA:

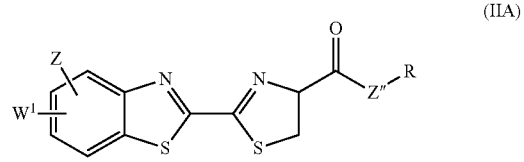

wherein
Z is $OR^1$;
Z" is O;
R is H, $(C_{1-6})$alkyl, saccharide, or $M^+$ wherein M is an alkali metal;
$R^1$ is $(C_{6-30})$aryl, heteroaryl, piperidinyl, $(C_{1-20})$alkylthio, $(C_{1-20})$alkyl-S(O)—, $(C_{1-20})$alkyl-$SO_2$—, $(C_{1-20})$alkyl-$SO_3$—, $(C_{1-20})$alkylphosphate, $(C_{1-20})$alkylphosphonate, $(C_{6-30})$arylthio, $(C_{6-30})$aryl-S(O)—, $(C_{6-30})$aryl-$SO_2$—, $(C_{6-30})$aryl-$SO_3$—, $(C_{6-30})$arylphosphate, $(C_{6-30})$arylphosphonate, or $(C_{1-20})$alkyl substituted by $R^2$;
$R^2$ is $(C_{3-20})$cycloalkyl, $(C_{1-20})$alkoxyl, $(C_{1-20})$alkylcarbonyl, $(C_{1-20})$alkylcarboxyl, hydroxyl, —$COOR^x$, —$SO_3R^x$, $(C_{1-20})$alkylthio, $(C_{6-30})$arylthio, $(C_{1-20})$alkyl-S(O)—, $(C_{1-20})$alkyl-$S(O)_2$—, nitro, amino, $NH(C_{1-6})$alkyl, $NH(C_{1-6})$alkynyl, $N((C_{1-6})$alkyl$)_2$, $N((C_{1-6})$alkynyl$)_2$, mercapto, saccharide, or trifluoromethyl;
$W^1$ is H, halo, hydroxyl, $(C_{1-6})$ alkyl or $(C_{1-6})$ alkoxy;
wherein any alkyl, alkenyl, cycloalkyl, alkoxy, amino, aryl, heteroaryl or heterocycle group is optionally substituted with 1, 2, 3, 4, or 5 substituents selected from the group consisting of $(C_{1-6})$alkyl, phenyl, halo, hydroxyl, —$COOR^x$, —$SO_2R^x$, —$SO_3R^x$, nitro, amino, $NH(C_{1-6})$alkyl, $NH(C_{1-6})$alkynyl, $N((C_{1-6})$alkyl$)_2$, $N((C_{1-6})$alkynyl$)_2$, and mercapto;
$R^x$ is H or $(C_{1-6})$alkyl;
or formula IIA is optionally a dimer connected at Z via a linker comprising a $(C_{1-12})$alkyl diradical that is optionally interrupted by one to four O atoms, N atoms, or an optionally substituted aryl, heteroaryl or heterocycle group to form a bridge between the dimer of formula IIA, and the $R^1$ group of each Z group connecting the dimer for formula IIA is replaced by the linker;

or a salt thereof, provided that the compound is not

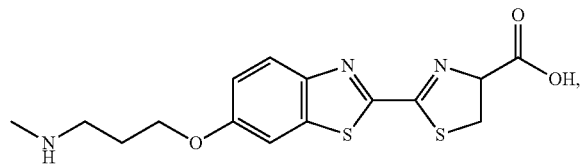

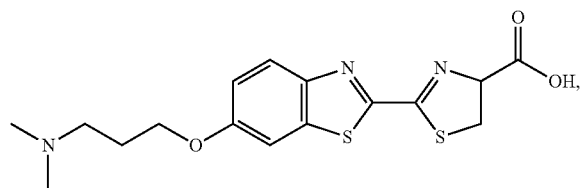

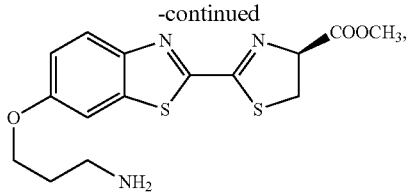

or or a salt thereof.

2. A compound according to claim 1, wherein R is H or methyl.

3. A compound according to claim 2, wherein $R^1$ is $(C_{1-20})$ alkyl substituted by $R^2$.

4. A compound according to claim 3, wherein $R^2$ is amino.

5. A compound according to claim 1, wherein $R^1$ is selected from the group consisting of —$SO_2(C_{6-30})$aryl and —$S(O)_3(C_{6-30})$aryl, wherein the aryl in —$SO_2(C_{6-30})$aryl and —$S(O)_3(C_{6-30})$aryl is optionally substituted.

6. A compound according to claim 5, wherein the aryl in —$SO_2(C_{6-30})$ a and —$S(O)_3(C_{6-30})$aryl is substituted with one or more substituents.

7. A compound according to claim 6, wherein the one or more substituents are selected from the group consisting of nitro, phenyl and $(C_{1-6})$alkyl.

8. A compound selected from the group consisting of:

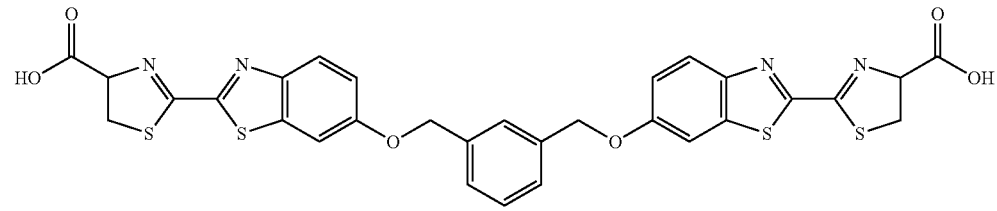

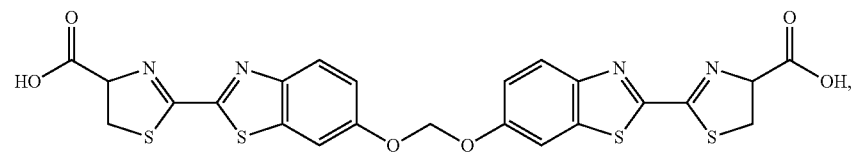

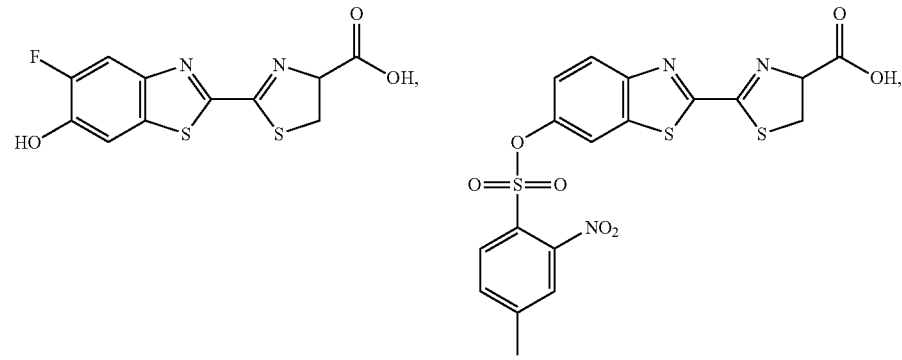

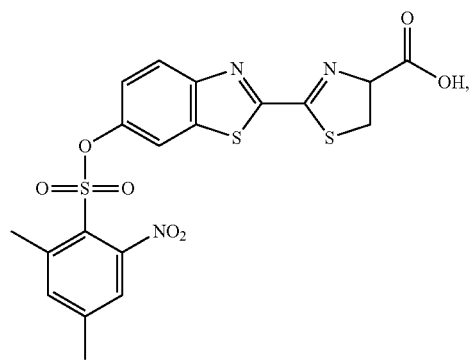
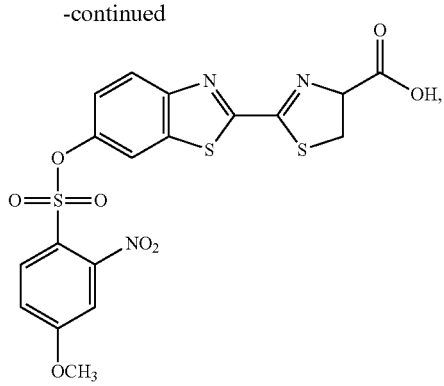
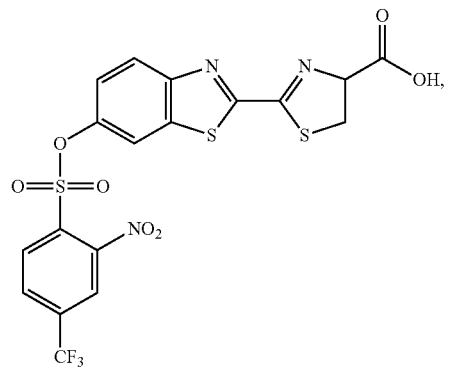
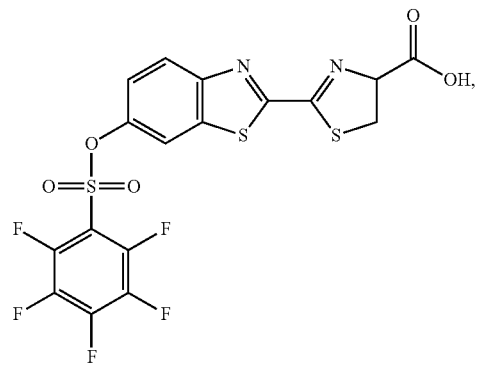
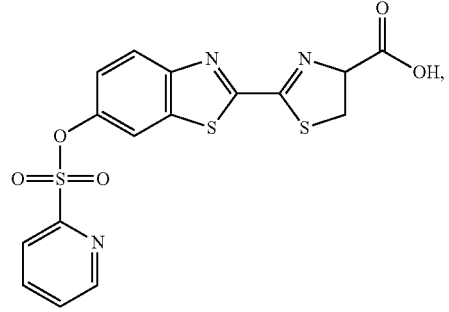
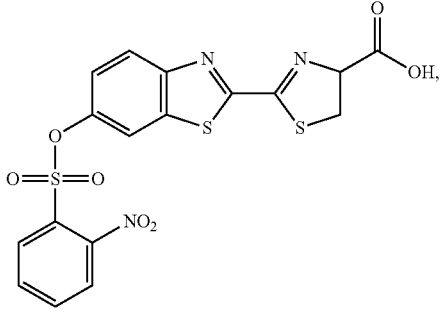
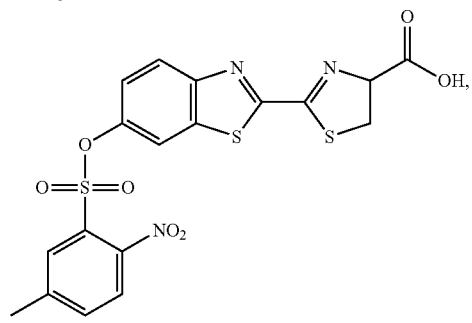
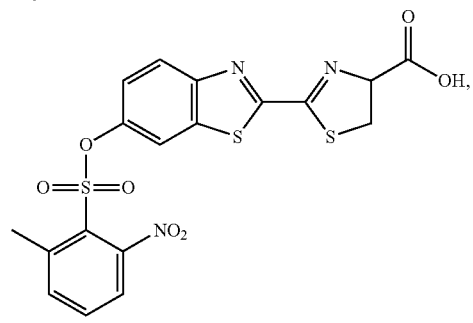
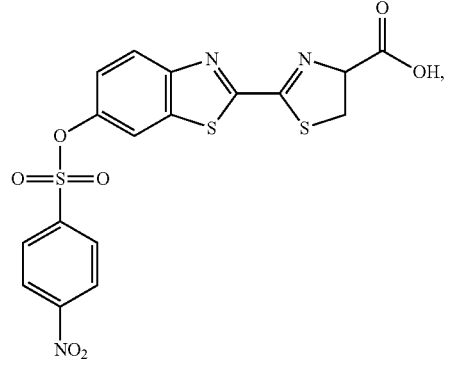
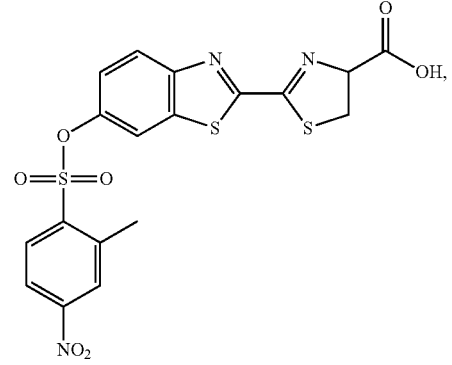

211
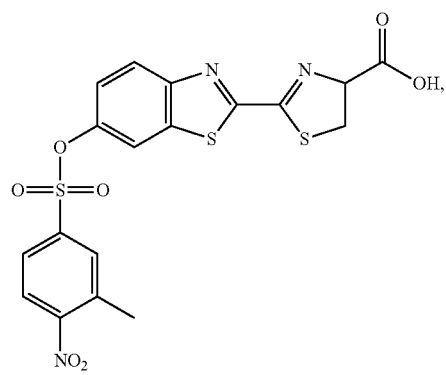
212
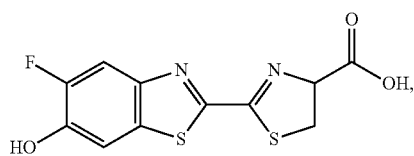
-continued
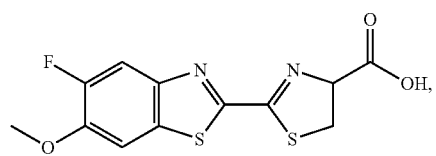
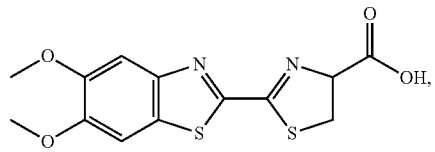
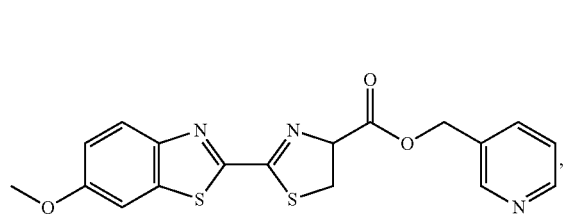
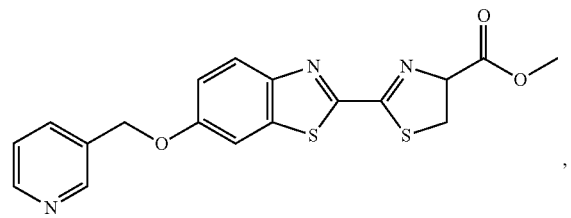
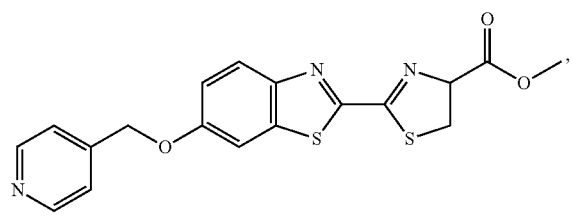
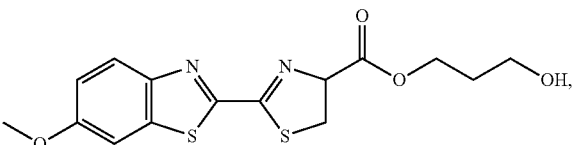
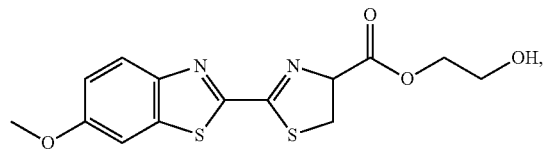
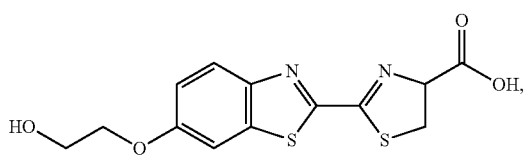
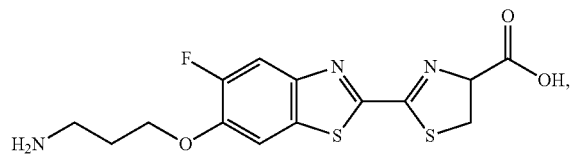
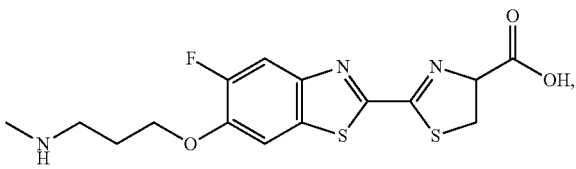
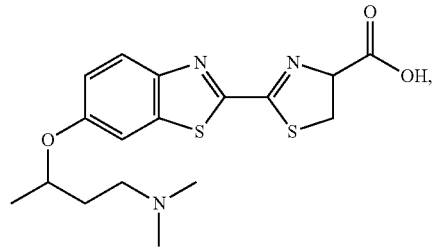
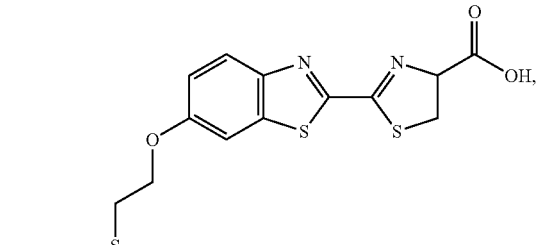
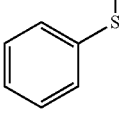

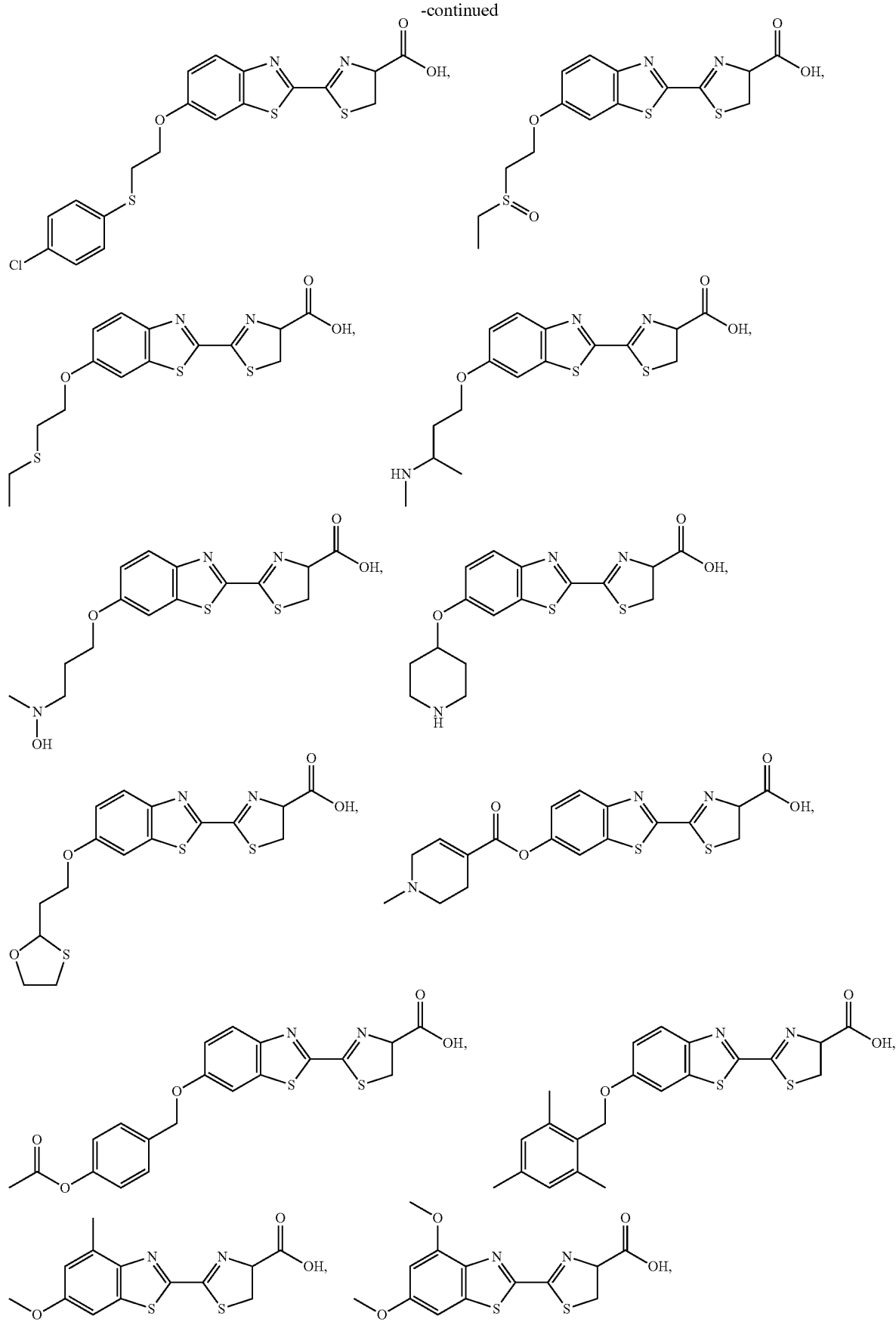

-continued

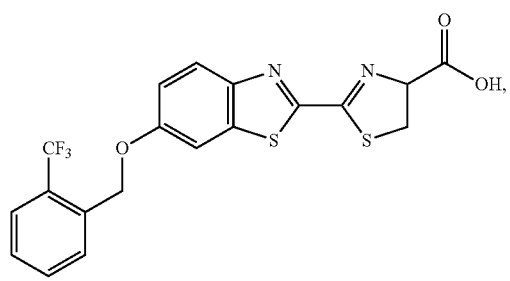

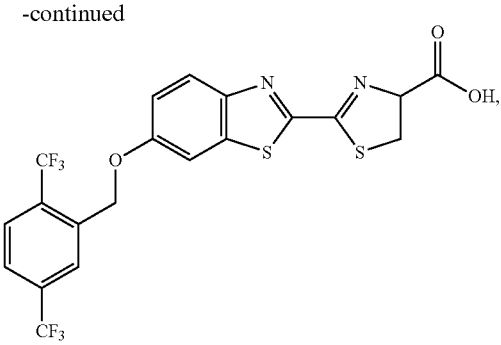

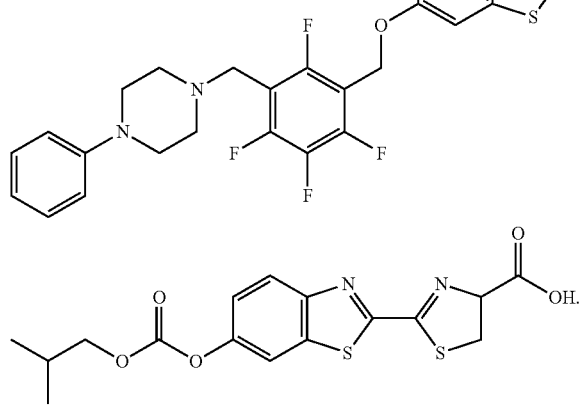

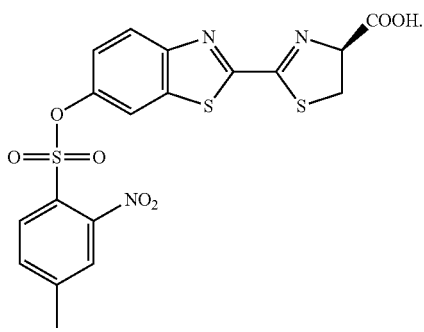 [SMILES: Cc1ccc(S(=O)(=O)Oc2ccc3nc(C4=N[C@@H](C(=O)O)CS4)sc3c2)c([N+](=O)[O-])c1]

9. A compound of claim 8, wherein the compound is

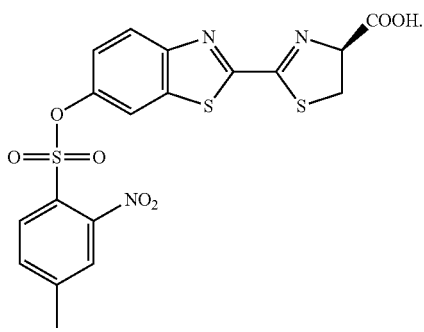 [SMILES: Cc1ccc(S(=O)(=O)Oc2ccc3nc(C4=N[C@@H](C(=O)O)CS4)sc3c2)c([N+](=O)[O-])c1]

10. The compound claim 1, wherein $R^1$ is $(C_{6-30})$aryl, heteroaryl, piperidinyl, $(C_{1-20})$alkylthio, $(C_{1-20})$alkyl-S(O)—, $(C_{1-20})$alkyl-SO$_2$—, $(C_{1-20})$alkyl-SO$_3$—, $(C_{1-20})$alkylphosphate, $(C_{1-20})$alkylphosphonate, $(C_{6-30})$arylthio, $(C_{6-3-0})$aryl-S(O)—, $(C_{6-30})$aryl-SO$_2$—, $(C_{6-30})$aryl-SO$_3$—, $(C_{6-30})$arylphosphate, or $(C_{6-30})$arylphosphonate.

11. The compound of claim 3, wherein $R^2$ is $(C_{3-20})$cycloalkyl, $(C_{1-20})$alkoxyl, $(C_{1-20})$alkylcarbonyl, $(C_{1-20})$alkylcarboxyl, hydroxyl, —COOR$^x$, —SO$_3$R$^x$, $(C_{1-20})$alkylthio, $(C_{6-30})$arylthio, $(C_{1-20})$alkyl-S(O)—, $(C_{1-20})$alkyl-S(O)$_2$—, nitro, NH(C$_{1-6}$)alkynyl, N((C$_{1-6}$)alkynyl)$_2$, mercapto, saccharide, or trifluoromethyl.

12. A compound of formula (VI), or a salt thereof,

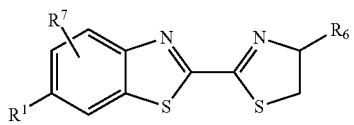

(VI)

wherein $R^1$ is —OCH$_2$CH$_2$CH$_2$—NR$^a$R$^b$, wherein $R^a$ and $R^b$ are independently H or C$_{1-20}$alkyl;

$R^6$ is —COR$^{11}$, wherein $R^{11}$ is H, OH, C$_{1-20}$ alkoxy, C$_{2-20}$ alkenyl, or NR$^{12}$R$^{13}$, wherein $R^{12}$ and $R^{13}$ are independently H or C$_{1-20}$alkyl; and $R^7$ is H, halo, (C$_{1-6}$) alkyl, (C$_{1-6}$) alkoxy, or C$_{2-20}$ alkenyl.

13. The compound of claim 12, or a salt thereof, wherein $R^{11}$ is OH or C$_{1-20}$ alkoxy.

14. The compound of claim 12, wherein the compound is

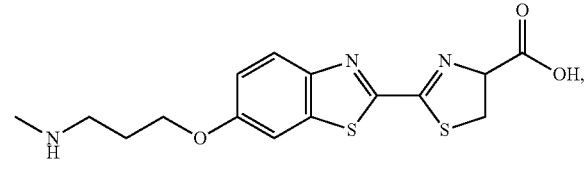

-continued

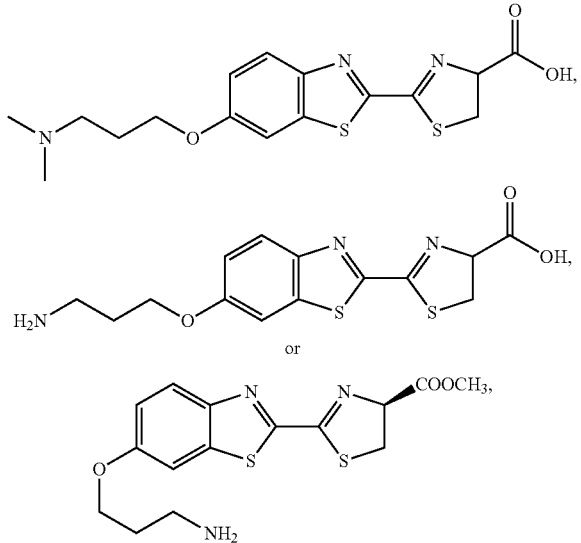

or a salt thereof.

15. The compound of claim 1, wherein in formula IIA
Z is OR;
Z" is O;
R is H, $(C_{1-6})$alkyl, saccharide, or $M^+$ wherein M is an alkali metal;
$R^1$ is $(C_{6-30})$aryl, heteroaryl, piperidinyl, $(C_{1-20})$alkylthio, $(C_{1-20})$alkyl-S(O)—, $(C_{1-20})$alkyl-SO$_2$—, $(C_{1-20})$alkyl-SO$_3$—, $(C_{1-20})$alkylphosphate, $(C_{1-20})$alkylphosphonate, $(C_{6-30})$arylthio, $(C_{6-30})$aryl-S(O)—, $(C_{6-30})$aryl-SO$_2$—, $(C_{6-30})$aryl-SO$_3$—, $(C_{6-30})$arylphosphate, $(C_{6-30})$arylphosphonate, or $(C_{1-20})$alkyl substituted by $R^2$;
$R^2$ is $(C_{3-20})$cycloalkyl, $(C_{1-20})$alkoxyl, $(C_{1-20})$alkylcarbonyl, $(C_{1-20})$alkylcarboxyl, hydroxyl, —COOR$^x$, —SO$_3$R$^x$, $(C_{1-20})$alkylthio, $(C_{6-30})$arylthio, $(C_{1-20})$alkyl-S(O)—, $(C_{1-20})$alkyl-S(O)$_2$—, nitro, amino, NH$(C_{1-6})$alkyl, NH$(C_{1-6})$alkynyl, N(($C_{1-6}$)alkyl)$_2$, N(($C_{1-6}$)alkynyl)$_2$, mercapto, saccharide, or trifluoromethyl;
$W^1$ is H, halo, hydroxyl, $(C_{1-6})$ alkyl or $(C_{1-6})$ alkoxy;
wherein any alkyl, alkenyl, cycloalkyl, alkoxy, amino, aryl, heteroaryl or heterocycle group is optionally substituted with 1, 2, 3, 4, or 5 substituents selected from the group consisting of (C 1-6)alkyl, phenyl, halo, hydroxyl, —COOR$^x$, —SO$_2$R$^x$, —SO$_3$R$^x$, nitro, amino, NH$(C_{1-6})$alkyl, NH$(C_{1-6})$alkynyl, N(($C_{1-6}$)alkyl)$_2$, N(($C_{1-6}$)alkynyl)$_2$, and mercapto; and
$R^x$ is H or $(C_{1-6})$alkyl,
or a salt thereof.

16. The compound of claim 1, wherein formula IIA is a dimer connected at Z via a linker comprising a $(C_{1-12})$alkyl diradical that is optionally interrupted by one to four O atoms, N atoms, or an optionally substituted aryl, heteroaryl or heterocycle group to form a bridge between the dimer of formula IIA, and the $R^1$ group of each Z group connecting the dimer for formula IIA is replaced by the linker, or a salt thereof.

* * * * *